(12) United States Patent
Johnson

(10) Patent No.: US 10,071,970 B2
(45) Date of Patent: **\*Sep. 11, 2018**

(54) CHLORO-PYRAZINE CARBOXAMIDE DERIVATIVES WITH EPITHELIAL SODIUM CHANNEL BLOCKING ACTIVITY

(71) Applicant: Parion Sciences, Inc., Durham, NC (US)

(72) Inventor: Michael R. Johnson, Chapel Hill, NC (US)

(73) Assignee: Parion Sciences, Inc., Durham, NC (US)

( \* ) Notice: Subject to any disclaimer, the term of this patent is extended or adjusted under 35 U.S.C. 154(b) by 0 days.

This patent is subject to a terminal disclaimer.

(21) Appl. No.: 15/452,387

(22) Filed: Mar. 7, 2017

(65) Prior Publication Data

US 2017/0327472 A1    Nov. 16, 2017

Related U.S. Application Data

(63) Continuation of application No. 14/106,125, filed on Dec. 13, 2013, now Pat. No. 9,593,084.

(60) Provisional application No. 61/738,248, filed on Dec. 17, 2012.

(51) Int. Cl.
| | | |
|---|---|---|
| C07D 241/28 | (2006.01) |
| A61K 31/047 | (2006.01) |
| A61K 31/4965 | (2006.01) |
| A61K 33/14 | (2006.01) |
| A61K 45/06 | (2006.01) |
| C07D 241/26 | (2006.01) |

(52) U.S. Cl.
CPC .......... *C07D 241/28* (2013.01); *A61K 31/047* (2013.01); *A61K 31/4965* (2013.01); *A61K 33/14* (2013.01); *A61K 45/06* (2013.01); *C07D 241/26* (2013.01)

(58) Field of Classification Search
CPC .................................................... C07D 241/28
See application file for complete search history.

(56) References Cited

U.S. PATENT DOCUMENTS

| | | |
|---|---|---|
| 3,240,780 A | 3/1966 | Cragoe, Jr. et al. |
| 3,249,610 A | 5/1966 | Cragoe, Jr. et al. |
| 3,268,406 A | 8/1966 | Cragoe, Jr. et al. |
| 3,274,191 A | 9/1966 | Cragoe, Jr. et al. |
| 3,274,192 A | 9/1966 | Cragoe, Jr. et al. |
| 3,290,311 A | 12/1966 | Cragoe, Jr. et al. |
| 3,299,063 A | 1/1967 | Cragoe, Jr. et al. |
| 3,300,494 A | 1/1967 | Cragoe, Jr. et al. |
| 3,305,552 A | 2/1967 | Cragoe, Jr. et al. |
| 3,313,813 A | 4/1967 | Cragoe |
| 3,316,266 A | 4/1967 | Tull et al. |
| 3,325,494 A | 6/1967 | Weinstock et al. |
| 3,341,540 A | 9/1967 | Cragoe, Jr. et al. |
| 3,359,269 A | 12/1967 | Cragoe, Jr. et al. |
| 3,360,517 A | 12/1967 | Cragoe, Jr. et al. |
| 3,361,748 A | 1/1968 | Cragoe, Jr. et al. |
| 3,461,123 A | 8/1969 | Jones et al. |
| 3,472,848 A | 10/1969 | Cragoe, Jr. et al. |
| 3,487,082 A | 12/1969 | Cragoe, Jr. et al. |
| 3,491,094 A | 1/1970 | Cragoe, Jr. et al. |
| 3,503,973 A | 3/1970 | Cragoe, Jr. et al. |
| 3,506,662 A | 4/1970 | Cragoe, Jr. et al. |
| 3,507,865 A | 4/1970 | Jones et al. |
| 3,507,866 A | 4/1970 | Jones et al. |
| 3,515,723 A | 6/1970 | Cragoe, Jr. et al. |
| 3,527,758 A | 9/1970 | Cragoe, Jr. et al. |
| 3,531,484 A | 9/1970 | Bicking et al. |
| 3,539,569 A | 11/1970 | Tull et al. |
| 3,544,568 A | 12/1970 | Cragoe, Jr. et al. |
| 3,544,571 A | 12/1970 | Cragoe, Jr. et al. |

(Continued)

FOREIGN PATENT DOCUMENTS

| | | |
|---|---|---|
| CN | 101534813 A | 9/2009 |
| EA | 005975 B1 | 8/2005 |

(Continued)

OTHER PUBLICATIONS

International Search Report and Written Opinion, dated Apr. 15, 2005, in connection with Application No. PCT/US2004/026808.
International Search Report and Written Opinion, dated Aug. 31, 2005, in connection with Application No. PCT/US2005/017740.
International Search Report and Written Opinion, dated Mar. 27, 2008, in connection with Application No. PCT/US2007/077907.
International Search Report and Written Opinion, dated Sep. 15, 2008, in connection with Application No. PCT/US2007/077880.
International Search Report and Written Opinion, dated Dec. 6, 2007, in connection with Application No. PCT/US2007/070857.

(Continued)

*Primary Examiner* — Brian E McDowell
(74) *Attorney, Agent, or Firm* — Wolf, Greenfield & Sacks, P.C.

(57) ABSTRACT

This invention provides compounds of the formula I:

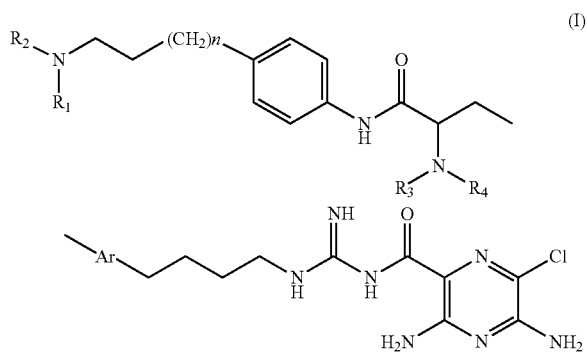

and their pharmaceutically acceptable salts, useful as sodium channel blockers, compositions containing the same, therapeutic methods and uses for the same and processes for preparing the same.

21 Claims, 14 Drawing Sheets

(56) References Cited

U.S. PATENT DOCUMENTS

| | | |
|---|---|---|
| 3,555,023 A | 1/1971 | Cragoe, Jr. et al. |
| 3,555,024 A | 1/1971 | Cragoe, Jr. et al. |
| 3,573,305 A | 3/1971 | Cragoe, Jr. et al. |
| 3,573,306 A | 3/1971 | Shepard et al. |
| 3,575,975 A | 4/1971 | Cragoe, Jr. et al. |
| 3,577,418 A | 5/1971 | Cragoe, Jr. et al. |
| 3,586,688 A | 6/1971 | Cragoe, Jr. et al. |
| 3,625,950 A | 12/1971 | Cragoe, Jr. et al. |
| 3,660,397 A | 5/1972 | Jones et al. |
| 3,660,400 A | 5/1972 | Cragoe, Jr. et al. |
| 3,668,241 A | 6/1972 | Cragoe, Jr. et al. |
| 3,794,734 A | 2/1974 | Cragoe, Jr. et al. |
| 3,864,401 A | 2/1975 | Schultz et al. |
| 3,894,065 A | 7/1975 | Cragoe, Jr. et al. |
| 3,894,085 A | 7/1975 | Eschenmoser |
| 3,914,253 A | 10/1975 | Cragoe, Jr. et al. |
| 3,928,624 A | 12/1975 | Cragoe, Jr. et al. |
| 3,929,872 A | 12/1975 | Cragoe, Jr. et al. |
| 3,931,239 A | 1/1976 | Cragoe, Jr. et al. |
| 3,935,313 A | 1/1976 | Aron-Samuel et al. |
| 3,948,895 A | 4/1976 | Donald |
| 3,953,476 A | 4/1976 | Cragoe, Jr. et al. |
| 3,956,374 A | 5/1976 | Shepard et al. |
| 3,958,004 A | 5/1976 | Cragoe, Jr. et al. |
| 3,966,966 A | 6/1976 | Cragoe, Jr. et al. |
| 3,974,212 A | 8/1976 | Cragoe, Jr. et al. |
| 3,976,681 A | 8/1976 | Cragoe, Jr. et al. |
| 3,976,686 A | 8/1976 | Cragoe, Jr. et al. |
| 3,979,361 A | 9/1976 | Schultz et al. |
| 3,984,465 A | 10/1976 | Cragoe, Jr. et al. |
| 3,984,552 A | 10/1976 | Cragoe, Jr. et al. |
| 3,987,091 A | 10/1976 | Cragoe, Jr. et al. |
| 3,989,749 A | 11/1976 | Cragoe, Jr. et al. |
| 3,991,087 A | 11/1976 | Cragoe, Jr. et al. |
| 3,991,106 A | 11/1976 | Cragoe, Jr. et al. |
| 4,003,927 A | 1/1977 | Woltersdorf, Jr. et al. |
| 4,006,180 A | 2/1977 | Cragoe, Jr. et al. |
| 4,012,524 A | 3/1977 | Cragoe, Jr. et al. |
| 4,018,802 A | 4/1977 | Cragoe, Jr. et al. |
| 4,020,177 A | 4/1977 | Cragoe, Jr. et al. |
| 4,022,794 A | 5/1977 | Smith et al. |
| 4,025,625 A | 5/1977 | Rooney et al. |
| 4,029,803 A | 6/1977 | Hunter et al. |
| 4,029,816 A | 6/1977 | Cragoe, Jr. et al. |
| 4,033,996 A | 7/1977 | Cragoe, Jr. et al. |
| 4,044,153 A | 8/1977 | Schultz et al. |
| 4,054,652 A | 10/1977 | Rooney et al. |
| 4,055,596 A | 10/1977 | Cragoe, Jr. et al. |
| 4,055,597 A | 10/1977 | Cragoe, Jr. et al. |
| 4,059,087 A | 11/1977 | Tanigami et al. |
| 4,059,601 A | 11/1977 | Cragoe, Jr. et al. |
| 4,059,602 A | 11/1977 | Cragoe, Jr. et al. |
| 4,061,643 A | 12/1977 | Cragoe, Jr. et al. |
| 4,066,675 A | 1/1978 | Cragoe, Jr. et al. |
| 4,066,692 A | 1/1978 | Cragoe, Jr. et al. |
| 4,067,980 A | 1/1978 | Cragoe, Jr. et al. |
| 4,070,464 A | 1/1978 | Cragoe, Jr. et al. |
| 4,070,539 A | 1/1978 | Cragoe, Jr. et al. |
| 4,081,554 A | 3/1978 | Cragoe, Jr. et al. |
| 4,085,117 A | 4/1978 | Cragoe, Jr. et al. |
| 4,085,125 A | 4/1978 | Cragoe, Jr. et al. |
| 4,085,211 A | 4/1978 | Cragoe, Jr. et al. |
| 4,085,219 A | 4/1978 | Cragoe, Jr. et al. |
| 4,087,435 A | 5/1978 | Cragoe, Jr. et al. |
| 4,087,526 A | 5/1978 | Cragoe, Jr. et al. |
| 4,087,542 A | 5/1978 | Cragoe, Jr. et al. |
| 4,091,015 A | 5/1978 | Strike |
| 4,091,105 A | 5/1978 | Rokach et al. |
| 4,091,107 A | 5/1978 | Cragoe, Jr. et al. |
| 4,092,356 A | 5/1978 | Cragoe, Jr. et al. |
| 4,092,414 A | 5/1978 | Cragoe, Jr. et al. |
| 4,096,267 A | 6/1978 | Cragoe, Jr. et al. |
| 4,097,504 A | 6/1978 | Cragoe, Jr. et al. |
| 4,100,294 A | 7/1978 | Cragoe, Jr. et al. |
| 4,102,888 A | 7/1978 | Smith et al. |
| 4,105,769 A | 8/1978 | Rooney et al. |
| 4,108,859 A | 8/1978 | Tong |
| 4,111,877 A | 9/1978 | Dixon et al. |
| 4,112,236 A | 9/1978 | Bicking et al. |
| 4,115,402 A | 9/1978 | Cragoe, Jr. et al. |
| 4,115,573 A | 9/1978 | Cragoe, Jr. et al. |
| 4,126,629 A | 11/1978 | Cragoe, Jr. et al. |
| 4,127,584 A | 11/1978 | Rokach et al. |
| 4,127,587 A | 11/1978 | Wade et al. |
| 4,128,564 A | 12/1978 | Cragoe, Jr. et al. |
| 4,133,885 A | 1/1979 | Bolhofer et al. |
| 4,140,776 A | 2/1979 | Cragoe, Jr. et al. |
| 4,140,861 A | 2/1979 | Cragoe, Jr. et al. |
| 4,145,551 A | 3/1979 | Cragoe, Jr. et al. |
| 4,150,235 A | 4/1979 | Cragoe, Jr. et al. |
| 4,154,742 A | 5/1979 | Cragoe, Jr. et al. |
| 4,155,908 A | 5/1979 | Cragoe, Jr. et al. |
| 4,156,005 A | 5/1979 | Stokker et al. |
| 4,159,279 A | 6/1979 | Smith et al. |
| 4,163,781 A | 8/1979 | Cragoe, Jr. et al. |
| 4,163,794 A | 8/1979 | Cragoe, Jr. et al. |
| 4,166,177 A | 8/1979 | Cragoe, Jr. et al. |
| 4,175,203 A | 11/1979 | Cragoe, Jr. et al. |
| 4,177,285 A | 12/1979 | Cragoe, Jr. et al. |
| 4,178,386 A | 12/1979 | Williams et al. |
| 4,181,661 A | 1/1980 | Rooney et al. |
| 4,181,727 A | 1/1980 | Cragoe, Jr. et al. |
| 4,182,764 A | 1/1980 | Cragoe, Jr. et al. |
| 4,187,315 A | 2/1980 | Cragoe, Jr. et al. |
| 4,189,496 A | 2/1980 | Cragoe, Jr. et al. |
| 4,190,655 A | 2/1980 | DeMarco et al. |
| 4,196,292 A | 4/1980 | Woltersdorf, Jr. et al. |
| 4,203,988 A | 5/1980 | Bolhofer et al. |
| 4,207,329 A | 6/1980 | Williams et al. |
| 4,208,413 A | 6/1980 | Cragoe, Jr. et al. |
| 4,220,654 A | 9/1980 | Bolhofer et al. |
| 4,221,790 A | 9/1980 | Cragoe, Jr. et al. |
| 4,224,447 A | 9/1980 | Woltersdorf, Jr. et al. |
| 4,225,609 A | 9/1980 | Cragoe, Jr. et al. |
| 4,226,867 A | 10/1980 | Cragoe, Jr. et al. |
| 4,229,456 A | 10/1980 | Bolhofer et al. |
| 4,233,452 A | 11/1980 | Williams et al. |
| 4,237,130 A | 12/1980 | Cragoe, Jr. et al. |
| 4,237,144 A | 12/1980 | Cragoe, Jr. et al. |
| 4,246,406 A | 1/1981 | Cragoe, Jr. et al. |
| 4,249,021 A | 2/1981 | Cragoe, Jr. et al. |
| 4,256,758 A | 3/1981 | Cragoe, Jr. et al. |
| 4,260,771 A | 4/1981 | Cragoe, Jr. et al. |
| 4,263,207 A | 4/1981 | Rokach et al. |
| 4,267,341 A | 5/1981 | Rokach et al. |
| 4,272,537 A | 6/1981 | Woltersdorf, Jr. et al. |
| 4,277,602 A | 7/1981 | Woltersdorf et al. |
| 4,282,365 A | 8/1981 | Rokach et al. |
| 4,291,050 A | 9/1981 | Woltersdorf, Jr. et al. |
| 4,292,430 A | 9/1981 | Rokach et al. |
| 4,294,829 A | 10/1981 | Suzuki et al. |
| 4,296,122 A | 10/1981 | Cragoe, Jr. et al. |
| 4,296,237 A | 10/1981 | Cragoe, Jr. et al. |
| 4,298,743 A | 11/1981 | Cragoe, Jr. et al. |
| 4,309,540 A | 1/1982 | Bock et al. |
| 4,316,043 A | 2/1982 | Cragoe, Jr. et al. |
| 4,317,822 A | 3/1982 | Woltersdorf, Jr. et al. |
| 4,317,922 A | 3/1982 | Cragoe, Jr. et al. |
| 4,336,397 A | 6/1982 | Cragoe, Jr. et al. |
| 4,337,258 A | 6/1982 | Rooney et al. |
| 4,337,354 A | 6/1982 | Cragoe, Jr. et al. |
| 4,342,776 A | 8/1982 | Cragoe, Jr. et al. |
| 4,342,782 A | 8/1982 | Cragoe, Jr. |
| 4,349,561 A | 9/1982 | Cragoe, Jr. et al. |
| 4,356,313 A | 10/1982 | Cragoe, Jr. et al. |
| 4,356,314 A | 10/1982 | Cragoe, Jr. et al. |
| 4,362,724 A | 12/1982 | Bock et al. |
| 4,375,475 A | 3/1983 | Willard et al. |
| 4,377,588 A | 3/1983 | Cragoe, Jr. et al. |
| 4,379,791 A | 4/1983 | Cragoe, Jr. et al. |
| 4,389,393 A | 6/1983 | Schor et al. |
| 4,389,417 A | 6/1983 | Bourke et al. |
| 4,390,537 A | 6/1983 | Cragoe, Jr. |
| 4,394,385 A | 7/1983 | Cragoe, Jr. |

(56) References Cited

U.S. PATENT DOCUMENTS

| | | |
|---|---|---|
| 4,394,515 A | 7/1983 | Rokach et al. |
| 4,401,669 A | 8/1983 | Cragoe, Jr. et al. |
| 4,420,615 A | 12/1983 | Bolhofer et al. |
| 4,425,337 A | 1/1984 | Alexander et al. |
| 4,428,956 A | 1/1984 | Cragoe, Jr. et al. |
| 4,428,959 A | 1/1984 | Cragoe, Jr. et al. |
| 4,431,652 A | 2/1984 | Cragoe, Jr. et al. |
| 4,431,660 A | 2/1984 | Cragoe, Jr. et al. |
| 4,432,992 A | 2/1984 | Cragoe, Jr. et al. |
| 4,440,740 A | 4/1984 | Fix et al. |
| 4,448,786 A | 5/1984 | Cragoe, Jr. et al. |
| 4,454,132 A | 6/1984 | Bock et al. |
| 4,459,422 A | 7/1984 | Willard et al. |
| 4,463,208 A | 7/1984 | Cragoe, Jr. et al. |
| 4,464,363 A | 8/1984 | Higuchi et al. |
| 4,465,850 A | 8/1984 | Cragoe, Jr. et al. |
| 4,501,729 A | 2/1985 | Boucher et al. |
| 4,510,322 A | 4/1985 | Blaine et al. |
| 4,536,507 A | 8/1985 | Rokach et al. |
| 4,537,902 A | 8/1985 | Cragoe, Jr. et al. |
| 4,567,289 A | 1/1986 | Willard et al. |
| 4,579,869 A | 4/1986 | Cragoe, Jr. et al. |
| 4,582,842 A | 4/1986 | Cragoe, Jr. et al. |
| 4,594,349 A | 6/1986 | Beyer, Jr. |
| 4,596,821 A | 6/1986 | Cragoe, Jr. et al. |
| 4,604,394 A | 8/1986 | Kaczorowski et al. |
| 4,604,396 A | 8/1986 | Cragoe, Jr. et al. |
| 4,604,403 A | 8/1986 | Cragoe, Jr. et al. |
| 4,605,663 A | 8/1986 | Cragoe, Jr. et al. |
| 4,605,664 A | 8/1986 | Cragoe, Jr. et al. |
| 4,625,047 A | 11/1986 | Cragoe, Jr. et al. |
| 4,634,717 A | 1/1987 | Cragoe, Jr. et al. |
| 4,654,365 A | 3/1987 | Cragoe, Jr. et al. |
| 4,663,322 A | 5/1987 | Beyer, Jr. |
| 4,675,341 A | 6/1987 | Cragoe, Jr. |
| 4,680,414 A | 7/1987 | Cragoe, Jr. et al. |
| 4,699,917 A | 10/1987 | Cragoe, Jr. et al. |
| 4,699,926 A | 10/1987 | Abraham et al. |
| 4,710,513 A | 12/1987 | Willard et al. |
| 4,719,310 A | 1/1988 | Pietruszkiewicz et al. |
| 4,731,381 A | 3/1988 | Abraham et al. |
| 4,731,470 A | 3/1988 | Pietruszkiewicz et al. |
| 4,731,471 A | 3/1988 | Cragoe, Jr. et al. |
| 4,731,472 A | 3/1988 | Pietruszkiewicz et al. |
| 4,731,473 A | 3/1988 | Abraham et al. |
| 4,751,244 A | 6/1988 | Abraham et al. |
| 4,754,061 A | 6/1988 | Cragoe, Jr. et al. |
| 4,769,370 A | 9/1988 | Woltersdorf, Jr. et al. |
| 4,771,076 A | 9/1988 | Cragoe, Jr. et al. |
| 4,775,695 A | 10/1988 | Cragoe, Jr. et al. |
| 4,777,281 A | 10/1988 | Woltersdorf, Jr. et al. |
| 4,778,897 A | 10/1988 | Cragoe, Jr. et al. |
| 4,782,073 A | 11/1988 | Cragoe, Jr. |
| 4,797,391 A | 1/1989 | Woltersdorf, Jr. et al. |
| 4,835,142 A | 5/1989 | Suzuki et al. |
| 4,835,313 A | 5/1989 | Pietruszkiewicz et al. |
| 4,894,376 A | 1/1990 | Morad et al. |
| 4,923,874 A | 5/1990 | McMahon et al. |
| 4,937,232 A | 6/1990 | Bell et al. |
| 4,952,582 A | 8/1990 | Beyer, Jr. |
| 5,132,296 A | 7/1992 | Cherksey |
| 5,182,299 A | 1/1993 | Gullans et al. |
| 5,215,991 A | 6/1993 | Burke |
| 5,242,947 A | 9/1993 | Cherksey et al. |
| 5,292,498 A | 3/1994 | Boucher, Jr. |
| 5,312,820 A | 5/1994 | Ashton et al. |
| 5,384,128 A | 1/1995 | Meezan et al. |
| 5,420,116 A | 5/1995 | Puchelle et al. |
| 5,449,682 A | 9/1995 | Greenlee et al. |
| 5,512,269 A | 4/1996 | Molina y Vedia et al. |
| 5,538,991 A | 7/1996 | Ashton et al. |
| 5,618,557 A | 4/1997 | Wille et al. |
| 5,628,984 A | 5/1997 | Boucher, Jr. |
| 5,635,160 A | 6/1997 | Stutts, III et al. |
| 5,651,957 A | 7/1997 | Molina y Vedia et al. |
| 5,656,256 A | 8/1997 | Boucher et al. |
| 5,683,675 A | 11/1997 | Molina y Vedia et al. |
| 5,707,644 A | 1/1998 | Illum |
| 5,716,931 A | 2/1998 | Molina y Vedia et al. |
| 5,725,842 A | 3/1998 | Boucher, Jr. et al. |
| 5,750,697 A | 5/1998 | Cherksey |
| 5,817,028 A | 10/1998 | Anderson |
| 5,849,706 A | 12/1998 | Molina y Vedia et al. |
| 5,866,610 A | 2/1999 | Lang et al. |
| 5,876,700 A | 3/1999 | Boucher, Jr. et al. |
| 5,902,567 A | 5/1999 | Boucher, Jr. |
| 5,908,611 A | 6/1999 | Gottlieb et al. |
| 5,935,555 A | 8/1999 | Stutts, III et al. |
| 5,955,100 A | 9/1999 | Bosslet et al. |
| 5,962,477 A | 10/1999 | Mak |
| 5,994,336 A | 11/1999 | Zasloff et al. |
| 6,015,828 A | 1/2000 | Cuppoletti |
| 6,022,527 A | 2/2000 | Boucher, Jr. et al. |
| 6,033,688 A | 3/2000 | Mrsny et al. |
| 6,051,576 A | 4/2000 | Ashton et al. |
| 6,071,910 A | 6/2000 | Gleich et al. |
| 6,133,247 A | 10/2000 | Boucher, Jr. |
| 6,136,294 A | 10/2000 | Adjei et al. |
| 6,143,279 A | 11/2000 | Boucher, Jr. et al. |
| 6,153,187 A | 11/2000 | Yacoby-Zeevi |
| 6,159,968 A | 12/2000 | Cuppoletti |
| 6,190,691 B1 | 2/2001 | Mak |
| 6,204,270 B1 | 3/2001 | Ron et al. |
| 6,214,536 B1 | 4/2001 | Boucher, Jr. |
| 6,235,266 B1 | 5/2001 | Stutts, III et al. |
| 6,264,975 B1 | 7/2001 | Boucher, Jr. |
| 6,294,188 B1 | 9/2001 | Ragavan et al. |
| 6,297,226 B1 | 10/2001 | Glasky |
| 6,300,350 B1 | 10/2001 | Belloni et al. |
| 6,323,187 B1 | 11/2001 | Yerxa et al. |
| 6,331,529 B1 | 12/2001 | Yerxa et al. |
| 6,344,475 B1 | 2/2002 | Caplan et al. |
| 6,399,585 B1 | 6/2002 | Larson et al. |
| 6,403,633 B2 | 6/2002 | Illig et al. |
| 6,451,288 B1 | 9/2002 | Boucher, Jr. et al. |
| 6,458,338 B1 | 10/2002 | Adjei et al. |
| 6,475,467 B1 | 11/2002 | Keller et al. |
| 6,475,509 B1 | 11/2002 | Boucher, Jr. |
| 6,476,048 B1 | 11/2002 | Szabo et al. |
| 6,607,741 B2 | 8/2003 | Boucher, Jr. |
| 6,613,345 B2 | 9/2003 | Boucher, Jr. |
| 6,739,172 B2 | 5/2004 | Wagner |
| 6,753,164 B2 | 6/2004 | Ni et al. |
| 6,858,614 B2 | 2/2005 | Johnson |
| 6,858,615 B2 | 2/2005 | Johnson |
| 6,903,105 B2 | 6/2005 | Johnson |
| 6,926,911 B1 | 8/2005 | Boucher, Jr. |
| 6,995,160 B2 | 2/2006 | Johnson |
| 7,026,325 B2 | 4/2006 | Johnson |
| 7,030,117 B2 | 4/2006 | Johnson |
| 7,056,524 B2 | 6/2006 | Boucher, Jr. |
| 7,064,129 B2 | 6/2006 | Johnson et al. |
| 7,186,833 B2 | 3/2007 | Johnson |
| 7,189,719 B2 | 3/2007 | Johnson |
| 7,192,958 B2 | 3/2007 | Johnson |
| 7,192,959 B2 | 3/2007 | Johnson |
| 7,192,960 B2 | 3/2007 | Johnson |
| 7,241,766 B2 | 7/2007 | Johnson |
| 7,247,636 B2 | 7/2007 | Johnson |
| 7,247,637 B2 | 7/2007 | Johnson et al. |
| 7,317,013 B2 | 1/2008 | Johnson |
| 7,332,496 B2 | 2/2008 | Johnson |
| 7,345,044 B2 | 3/2008 | Johnson |
| 7,368,447 B2 | 5/2008 | Johnson et al. |
| 7,368,450 B2 | 5/2008 | Johnson |
| 7,368,451 B2 | 5/2008 | Johnson et al. |
| 7,375,102 B2 | 5/2008 | Fu et al. |
| 7,375,107 B2 | 5/2008 | Johnson |
| 7,388,013 B2 | 6/2008 | Johnson et al. |
| 7,399,766 B2 | 7/2008 | Johnson |
| 7,410,968 B2 | 8/2008 | Johnson et al. |
| 7,553,855 B2 | 6/2009 | Young et al. |
| 7,745,442 B2 | 6/2010 | Johnson et al. |
| 7,807,834 B2 | 10/2010 | Johnson et al. |

(56) References Cited

U.S. PATENT DOCUMENTS

| | | |
|---|---|---|
| 7,820,678 B2 | 10/2010 | Johnson |
| 7,842,697 B2 | 11/2010 | Johnson |
| 7,868,010 B2 | 1/2011 | Johnson et al. |
| 7,875,619 B2 | 1/2011 | Johnson |
| 7,956,059 B2 | 6/2011 | Johnson |
| 7,981,898 B2 | 7/2011 | Johnson et al. |
| 8,008,494 B2 | 8/2011 | Johnson |
| 8,022,210 B2 | 9/2011 | Johnson |
| 8,058,278 B2 | 11/2011 | Johnson et al. |
| 8,124,607 B2 | 2/2012 | Johnson |
| 8,143,256 B2 | 3/2012 | Johnson |
| 8,163,758 B2 | 4/2012 | Johnson et al. |
| 8,198,286 B2 | 6/2012 | Johnson |
| 8,211,895 B2 | 7/2012 | Johnson et al. |
| 8,227,474 B2 | 7/2012 | Johnson |
| 8,261,047 B2 | 9/2012 | Moyer |
| 8,288,391 B2 | 10/2012 | Johnson et al. |
| 8,314,105 B2 | 11/2012 | Johnson |
| 8,324,218 B2 | 12/2012 | Johnson |
| 8,431,579 B2 | 4/2013 | Johnson et al. |
| 8,507,497 B2 | 8/2013 | Johnson et al. |
| 8,551,534 B2 | 10/2013 | Boucher et al. |
| 8,575,176 B2 | 11/2013 | Johnson |
| 8,669,262 B2 | 3/2014 | Johnson |
| 8,846,688 B2 | 9/2014 | Johnson |
| 8,980,898 B2 | 3/2015 | Johnson et al. |
| 9,029,382 B2 | 5/2015 | Johnson |
| 9,072,738 B2 | 7/2015 | Johnson |
| 9,102,633 B2 | 8/2015 | Johnson |
| 9,260,398 B2 | 2/2016 | Johnson et al. |
| 9,586,910 B2 | 3/2017 | Johnson |
| 9,586,911 B2 | 3/2017 | Johnson |
| 9,593,084 B2 | 3/2017 | Johnson |
| 9,695,134 B2 | 7/2017 | Johnson |
| 2003/0135716 A1 | 7/2003 | Vinitzky |
| 2003/0195160 A1 | 10/2003 | Johnson |
| 2003/0199456 A1 | 10/2003 | Johnson |
| 2004/0116415 A1 | 6/2004 | Sun et al. |
| 2004/0162296 A1 | 8/2004 | Johnson |
| 2004/0195160 A1 | 10/2004 | Max et al. |
| 2004/0198744 A1 | 10/2004 | Johnson |
| 2004/0198745 A1 | 10/2004 | Johnson |
| 2004/0198746 A1 | 10/2004 | Johnson |
| 2004/0198747 A1 | 10/2004 | Johnson |
| 2004/0198748 A1 | 10/2004 | Johnson |
| 2004/0198749 A1 | 10/2004 | Johnson |
| 2004/0199456 A1 | 10/2004 | Flint et al. |
| 2004/0204424 A1 | 10/2004 | Johnson |
| 2004/0204425 A1 | 10/2004 | Johnson |
| 2004/0229884 A1 | 11/2004 | Johnson |
| 2005/0059676 A1 | 3/2005 | Johnson |
| 2005/0080091 A1 | 4/2005 | Johnson et al. |
| 2005/0080092 A1 | 4/2005 | Johnson |
| 2005/0080093 A1 | 4/2005 | Johnson et al. |
| 2005/0090505 A1 | 4/2005 | Johnson et al. |
| 2005/0113388 A1 | 5/2005 | Johnson |
| 2005/0113389 A1 | 5/2005 | Johnson |
| 2005/0113390 A1 | 5/2005 | Johnson |
| 2005/0228182 A1 | 10/2005 | Johnson et al. |
| 2005/0234072 A1 | 10/2005 | Johnson et al. |
| 2006/0040954 A1 | 2/2006 | Johnson |
| 2006/0052394 A1 | 3/2006 | Johnson et al. |
| 2006/0052395 A1 | 3/2006 | Johnson et al. |
| 2006/0063780 A1 | 3/2006 | Johnson |
| 2006/0142306 A1 | 6/2006 | Johnson |
| 2006/0142581 A1 | 6/2006 | Johnson |
| 2006/0205738 A1 | 9/2006 | Johnson et al. |
| 2007/0018640 A1 | 1/2007 | Guzik et al. |
| 2007/0021439 A1 | 1/2007 | Johnson |
| 2007/0032509 A1 | 2/2007 | Johnson et al. |
| 2007/0265280 A1 | 11/2007 | Johnson |
| 2008/0076782 A1 | 3/2008 | Johnson |
| 2008/0090841 A1 | 4/2008 | Johnson et al. |
| 2008/0096896 A1 | 4/2008 | Johnson |
| 2008/0103148 A1 | 5/2008 | Johnson |
| 2008/0167466 A1 | 7/2008 | Johnson et al. |
| 2008/0171879 A1 | 7/2008 | Johnson |
| 2008/0171880 A1 | 7/2008 | Johnson et al. |
| 2008/0176863 A1 | 7/2008 | Johnson et al. |
| 2008/0177072 A1 | 7/2008 | Johnson |
| 2008/0200476 A1 | 8/2008 | Johnson |
| 2008/0249109 A1 | 10/2008 | Johnson et al. |
| 2008/0293740 A1 | 11/2008 | Johnson et al. |
| 2009/0018144 A1 | 1/2009 | Johnson et al. |
| 2009/0062308 A1 | 3/2009 | Johnson |
| 2009/0076273 A1 | 3/2009 | Johnson |
| 2009/0082287 A1 | 3/2009 | Johnson et al. |
| 2009/0104272 A1 | 4/2009 | Boucher et al. |
| 2009/0214444 A1 | 8/2009 | Johnson |
| 2009/0227530 A1 | 9/2009 | Johnson |
| 2009/0227594 A1 | 9/2009 | Johnson |
| 2009/0253714 A1 | 10/2009 | Johnson et al. |
| 2009/0324724 A1 | 12/2009 | Johnson |
| 2010/0074881 A1 | 3/2010 | Boucher et al. |
| 2010/0130547 A1 | 5/2010 | Zhang et al. |
| 2010/0144661 A1 | 6/2010 | Johnson |
| 2010/0267746 A1 | 10/2010 | Johnson |
| 2011/0003832 A1 | 1/2011 | Johnson et al. |
| 2011/0008268 A1 | 1/2011 | Johnson et al. |
| 2011/0046158 A1 | 2/2011 | Johnson et al. |
| 2011/0144338 A1 | 6/2011 | Johnson et al. |
| 2011/0195973 A1 | 8/2011 | Johnson |
| 2011/0230483 A1 | 9/2011 | Baettig et al. |
| 2012/0044272 A1 | 2/2012 | Han et al. |
| 2012/0116083 A1 | 5/2012 | Johnson |
| 2012/0220606 A1 | 8/2012 | Johnson et al. |
| 2013/0012692 A1 | 1/2013 | Johnson |
| 2013/0060034 A1 | 3/2013 | Johnson |
| 2013/0178482 A1 | 7/2013 | Johnson |
| 2013/0324559 A1 | 12/2013 | Johnson et al. |
| 2014/0031371 A1 | 1/2014 | Johnson |
| 2014/0096765 A1 | 4/2014 | Boucher et al. |
| 2014/0107133 A1 | 4/2014 | Johnson |
| 2014/0142118 A1 | 5/2014 | Johnson |
| 2014/0170244 A1 | 6/2014 | Johnson |
| 2014/0171447 A1 | 6/2014 | Johnson |
| 2014/0179625 A1 | 6/2014 | Johnson |
| 2015/0056305 A1 | 2/2015 | Johnson et al. |
| 2015/0166487 A1 | 6/2015 | Johnson |
| 2015/0166488 A1 | 6/2015 | Johnson |
| 2015/0290189 A1 | 10/2015 | Johnson |
| 2015/0299142 A1 | 10/2015 | Johnson |
| 2015/0307530 A1 | 10/2015 | Johnson et al. |
| 2015/0376145 A1 | 12/2015 | Johnson et al. |
| 2015/0376146 A1 | 12/2015 | Johnson et al. |
| 2017/0267650 A1 | 9/2017 | Johnson |
| 2017/0305868 A1 | 10/2017 | Johnson |
| 2017/0334864 A1 | 11/2017 | Johnson |
| 2017/0362187 A1 | 12/2017 | Johnson |

FOREIGN PATENT DOCUMENTS

| | | |
|---|---|---|
| FR | 1 525 670 A | 5/1968 |
| FR | 1 525 671 A | 5/1968 |
| GB | 1145934 A1 | 6/1967 |
| GB | 1158399 A1 | 6/1967 |
| JP | 2005/530692 A | 10/2005 |
| JP | 2006/518389 A | 8/2006 |
| JP | 2007/517764 A | 7/2007 |
| JP | 2010/502738 A | 1/2010 |
| JP | 4557550 B2 | 6/2010 |
| WO | WO 00/23023 A1 | 4/2000 |
| WO | WO 01/05773 A1 | 1/2001 |
| WO | WO 01/28584 A1 | 4/2001 |
| WO | WO 02/40457 A1 | 5/2002 |
| WO | WO 03/070182 A3 | 8/2003 |
| WO | WO 03/070184 A2 | 8/2003 |
| WO | WO 2004/073629 A2 | 9/2004 |
| WO | WO 2005/016879 A2 | 2/2005 |
| WO | WO 2005/018560 A2 | 3/2005 |
| WO | WO 2005/018644 A1 | 3/2005 |
| WO | WO 2005/025496 A2 | 3/2005 |
| WO | WO 2005/034847 A2 | 4/2005 |
| WO | WO 2005/044180 A2 | 5/2005 |

(56) References Cited

FOREIGN PATENT DOCUMENTS

| | | |
|---|---|---|
| WO | WO 2006/022935 A1 | 3/2006 |
| WO | WO 2006/023573 A2 | 3/2006 |
| WO | WO 2006/023617 A2 | 3/2006 |
| WO | WO 2007/018640 A1 | 2/2007 |
| WO | WO 2007/071396 A2 | 6/2007 |
| WO | WO 2007/071400 A1 | 6/2007 |
| WO | WO 2007/146867 A2 | 12/2007 |
| WO | WO 2007/146869 A1 | 12/2007 |
| WO | WO 2007/146870 A1 | 12/2007 |
| WO | WO 2008/030217 A2 | 3/2008 |
| WO | WO 2008/031028 A2 | 3/2008 |
| WO | WO 2008/031048 A2 | 3/2008 |
| WO | WO 2008/124491 A1 | 10/2008 |
| WO | WO 2008/124496 A1 | 10/2008 |
| WO | WO 2008/135557 A1 | 11/2008 |
| WO | WO 2009/049159 A1 | 4/2009 |
| WO | WO 2009/074575 A2 | 6/2009 |
| WO | WO 2009/138378 A1 | 11/2009 |
| WO | WO 2009/139948 A1 | 11/2009 |
| WO | WO 2009/150137 A2 | 12/2009 |
| WO | WO 2011/156355 A1 | 12/2011 |
| WO | WO 2013/003386 A1 | 1/2013 |
| WO | WO 2013/003444 A1 | 1/2013 |
| WO | WO 2014/076091 A1 | 5/2014 |

OTHER PUBLICATIONS

International Search Report and Written Opinion, dated Nov. 21, 2007, in connection with Application No. PCT/US/2007/070861.
International Search Report and Written Opinion, dated Feb. 17, 2014, in connection with Application No. PCT/US2013/075244.
International Search Report and Written Opinion, dated Mar. 3, 2014, in connection with Application No. PCT/US2013/075093.
International Search Report, dated May 10, 2004, in connection with Application No. PCT/US2003/004823.
International Search Report and Written Opinion, dated Aug. 27, 2004, in connection with Application No. PCT/US2004/004451.
International Search Report and Written Opinion, dated Apr. 15, 2005, in connection with Application No. PCT/US2004/026880.
International Search Report and Written Opinion, dated Oct. 21, 2009, in connection with Application No. PCT/US2009/035286.
International Search Report and Written Opinion, dated Jan. 31, 2005, in connection with Application No. PCT/US2004/026885.
International Search Report and Written Opinion, dated Oct. 5, 2006, in connection with Application No. PCT/US2006/015957.
International Search Report and Written Opinion, dated Mar. 21, 2006, in connection with Application No. PCT/US2005/029345.
International Search Report and Written Opinion, dated Feb. 6, 2014, in connection with Application No. PCT/US2013/075108.
International Search Report and Written Opinion, dated Sep. 20, 2012, in connection with Application No. PCT/US2012/044272.
International Search Report, dated Aug. 21, 2003, in connection with Application No. PCT/US2003/004817.
[No Author Listed] Deterministic effects and stochastic effects. Hong Kong Observatory. Last accessed on Mar. 21, 2016 at http://www.hko.gov.hk/education/dbcp/rad_health/eng/r4_1.htm. 2 pages.
[No Author Listed] http://www.biology-online.org/dictionary/Oligosaccharide. Last accessed on Mar. 20, 2008.
[No Author Listed] http://www.faqs.org/health/topics/96/Bronchodilators.html.Llast accessed on Nov. 22, 2009.
Barbry et al., [3H]phenamil binding protein of the renal epithelium Na+ channel. Purification, affinity labeling, and functional reconstitution. Biochemistry. Jan. 30, 1990;29(4):1039-45.
Barbry et al., Biochemical identification of two types of phenamil binding sites associated with amiloride-sensitive Na+ channels. Biochemistry. May 2, 1989;28(9):3744-9.
Barrett et al., Chloride secretion by the intestinal epithelium: molecular basis and regulatory aspects. Annu Rev Physiol. 2000;62:535-72.

Bennett et al., Effect of uridine 5'-triphosphate plus amiloride on mucociliary clearance in adult cystic fibrosis. Am J Respir Crit Care Med. Jun. 1996;153(6 Pt 1):1796-801.
Bicking et al., Pyrazine Diuretics. I. N-Amidino-3-amino-6-halopyrazinecarboxamides. J. Med. Chem. 1965; 8(5):638-42.
Borisy et al., Systematic discovery of multicomponent therapeutics. Proc Natl Acad Sci U S A. Jun. 24, 2003;100(13):7977-82. Epub Jun. 10, 2003.
Boucher, Airway surface dehydration in cystic fibrosis: pathogenesis and therapy. Annu Rev Med. 2007;58:157-70.
Boucher, Cystic fibrosis: a disease of vulnerability to airway surface dehydration. Trends Mol Med. Jun. 2007;13(6):231-40. Epub May 23, 2007.
Boucher, Evidence for airway surface dehydration as the initiating event in CF airway disease. J Intern Med. Jan. 2007;261(1):5-16.
Cantiello et al., Alpha 2-adrenergic receptors and the Na+/H+ exchanger in the intestinal epithelial cell line, HT-29. J Biol Chem. Sep. 25, 1989;264(27):16000-7.
Chawla et al., Curr. Res. & Info. Pharm. Sci. CRIPS. 2004; 5(1): 9-12.
Cline et al., Predicting the quality of powders for inhalation from surface energy and area. Pharm Res. Sep. 2002;19(9):1274-7.
Clunes et al., Front-runners for pharmacotherapeutic correction of the airway ion transport defect in cystic fibrosis. Curr Opin Pharmacol. Jun. 2008;8(3):292-9. doi: 10.1016/j.coph.2008.04.006. Epub May 28, 2008. Author Manuscript.
Cocks et al., Amiloride analogues cause endothelium-dependent relaxation in the canine coronary artery in vitro: possible role of Na+/Ca2+ exchange. Br J Pharmacol. Sep. 1988; 95(1): 67-76.
Cohn et al., in vitro activity of amiloride combined with tobramycin against Pseudomonas isolates from patients with cystic fibrosis. Antimicrob Agents Chemother. Mar. 1988;32(3):395-6.
Cohn et al., In vitro antimicrobial activity of amiloride analogs against Pseudomonas. Chemotherapy. 1992;38(4):232-7.
Collard et al., Prevention of ventilator-associated pneumonia: an evidence-based systematic review. Ann Intern Med. Mar. 18, 2003;138(6):494-e506.
Cragoe et al., Chapter 2: An Overview of the Structure-Activity Relations in the Amiloride Series. Amiloride and its Analogs. 1992; 9-24.
Cragoe et al., Chapter 3. The Synthesis of Amiloride and its Analogs. 1992; 24-38.
Cragoe et al., Chapter 7: Diuretic Agents. Annual Reports in Medicinal Chemistry. 1965; 67-77.
Cragoe et al., Chapter 7: Diuretic Agents. Annual Reports in Medicinal Chemistry. 1966; 59-68.
Cragoe et al., Pyrazine diuretics. II. N-amidino-3-amino-5-substituted 6-halopyrazinecarboxamides. J Med Chem. Jan. 1967;10(1):66-75.
Cragoe et al., Structure-Activity Relationships in the Amiloride Series. Merck Sharp and Dohme Research Laboratories. 1979; 1-20.
Donaldson et al., Mucociliary clearance as an outcome measure for cystic fibrosis clinical research. Proc Am Thorac Soc. Aug. 1, 2007;4(4):399-405.
Donaldson et al., Mucus clearance and lung function in cystic fibrosis with hypertonic saline. N Engl J Med. Jan. 19, 2006;354(3):241-50.
Dorwald, Side Reactions in Organic Synthesis: A Guide to Successful Synthesis Design. Weinheim: Wiley-VCH Verlag GmbH & Co. KGaA, 2005, Preface.
Elkins et al., A controlled trial of long-term inhaled hypertonic saline in patients with cystic fibrosis. N Engl J Med. Jan. 19, 2006;354(3):229-40.
Epand et al., Reversal of intrinsic multidrug resistance in Chinese hamster ovary cells by amiloride analogs. Br J Cancer. Feb. 1991;63(2):247-51.
Giannakou et al., Characterization of the Drosophila melanogaster alkali-metal/proton exchanger (NHE) gene family. J Exp Biol. Nov. 2001;204(Pt 21):3703-16.
Giunta et al., Amiloride, a diuretic with in vitro antimicrobial activity. Pharmacol Res Commun. Aug. 1984;16(8):821-9.

(56) References Cited

OTHER PUBLICATIONS

Goralski et al., Osmolytes and ion transport modulators: new strategies for airway surface rehydration. Curr Opin Pharmacol. Jun. 2010;10(3):294-9. doi: 10.1016/j.coph.2010.04.003. Epub May 1, 2010.

Gowen et al., Increased nasal potential difference and amiloride sensitivity in neonates with cystic fibrosis. J Pediatr. Apr. 1986;108(4):517-21.

Hackam et al., Translation of research evidence from animals to humans JAMA. Oct. 11, 2006;296(14):1731-2.

Hirsh et al., Design, synthesis, and structure-activity relationships of novel 2-substituted pyrazinoylguanidine epithelial sodium channel blockers: drugs for cystic fibrosis and chronic bronchitis. J Med Chem. Jul. 13, 2006;49(14):4098-115. .

Hirsh et al., Evaluation of second generation amiloride analogs as therapy for cystic fibrosis lung disease. J Pharmacol Exp Ther. Dec. 2004;311(3):929-38. Epub Jul. 23, 2004.

Hirsh et al., Pharmacological properties of N-(3,5-diamino-6-chloropyrazine-2-carbonyl)-N'-4-[4-(2,3-dihydroxypropoxy)phenyl]butyl-guanidine methanesulfonate (552-02), a novel epithelial sodium channel blocker with potential clinical efficacy for cystic fibrosis lung disease. J Pharmacol Exp Ther. Apr. 2008;325(1):77-88. doi: 10.1124/jpet.107.130443. Epub Jan. 24, 2008.

Hoffman et al., Effects of Topically Delivered Benzamil and Amiloride on Nasal Potential Difference in Cystic Fibrosis. Am, J, Resp. Crit. Care Med. 1998; 157:1844-9.

Jones et al., Pharmacokinetics of amiloride after inhalation and oral administration in adolescents and adults with cystic fibrosis. Pharmacotherapy. Mar.-Apr. 1997;17(2):263-70.

Jordan, Nature Reviews:Drug Discovery. 2003; 2:205-13.

Kellerman, P2Y(2) receptor agonists: a new class of medication targeted at improved mucociliary clearance. Chest. May 2002;121(5 Suppl):201S-205S.

Kleyman et al., Amiloride and its analogs as tools in the study of ion transport. J Membr Biol. Oct. 1988;105(1):1-21.

Kleyman et al., Distinct epitopes on amiloride. II. Variably restricted epitopes defined by monoclonal anti-amiloride antibodies. Am J Physiol. Feb. 1991;260(2 Pt 1):C271-6.

Kleyman et al., New amiloride analogue as hapten to raise anti-amiloride antibodies. Am J Physiol. Jan. 1986;250(1 Pt 1):C165-70.

Kleyman et al., The cellular pool of Na+ channels in the amphibian cell line A6 is not altered by mineralocorticoids. Analysis using a new photoactive amiloride analog in combination with anti-amiloride antibodies. J Biol Chem. Jul. 15, 1989;264(20):11995-2000.

Knowles et al, A pilot study of aerosolized amiloride for the treatment of lung disease in cystic fibrosis. N Engl J Med. Apr. 26, 1990;322(17):1189-94.

Knowles et al., Aerosolized amiloride as treatment of cystic fibrosis lung disease: a pilot study. Adv Exp Med Biol. 1991;290:119-28; discussion 129-32.

Knowles et al., Chapter 20. Amiloride in Cystic Fibrosis: Safety, Pharmacokinetics, and Efficacy in the Treatment of Pulmonary Disease. 1992; 301-16.

Kyle et al., Sodium channel blockers. J Med Chem. May 31, 2007;50(11):2583-8. Epub May 10, 2007.

Lammas et al., ATP-induced killing of mycobacteria by human macrophages is mediated by purinergic P2Z(P2X7) receptors. Immunity Sep. 1997;7(3):433-44.

Li et al., Stereoselective blockade of amphibian epithelial sodium channels by amiloride analogs. J Pharmacol Exp Ther. Dec. 1993;267(3):1081-4.

Mastronarde et al., Amiloride inhibits cytokine production in epithelium infected with respiratory syncytial virus. Am J Physiol. Aug. 1996;271(2 Pt 1):L201-7.

Mentz et al., Deposition, clearance, and effects of aerosolized amiloride in sheep airways. Am Rev Respir Dis. Nov. 1986;134(5):938-43.

Olivier et al., Acute safety and effects on mucociliary clearance of aerosolized uridine 5'- triphosphate +/31 amiloride in normal human adults. Am J Respir Crit Care Med. Jul. 1996;154(1):217-23.

O'Neil et al., The Merck Index. An Encyclopedia of Chemicals, Drugs, and Biologicals. 2006; 69-70.

Padmanabhan et al., Solution-phase, parallel synthesis and pharmacological evaluation of acylguanidine derivatives as potential sodium channel blockers. Bioorg Med Chem Lett. Dec. 17, 2001;11(24):3151-5.

Paisley et al., Regulation of airway mucosal hydration. Expert Rev Clin Pharmacol. May. 2010;3(3):361-9. doi: 10.1586/ecp.10.19.

Rogister et al., Novel inhibitors of the sodium-calcium exchanger: benzene ring analogues of N-guanidino substituted amiloride derivatives. Eur J Med Chem. Jul.-Aug. 2001;36(7-8):597-614.

Sabater et al., Aerosolization of P2Y(2)-receptor agonists enhances mucociliary clearance inسheep. J Appl Physiol (1985). Dec. 1999;87(6):2191-6.

Shah, Chapter 7, Progress in the Treatment of Pulmonary Disease in Cystic Fibrosis Annual Reports in Medicinal Chemistry. 2001; 36:67-78.

Shryock et al., Adenosine and adenosine receptors in the cardiovascular system: biochemistry, physiology, and pharmacology. Am J Cardiol. Jun. 19, 1997;79(12A):2-10. Abstract only.

Simchowitz et al., Chapter 2. An Overview of the Structure Activity Relations in the Amiloride Series. 1992; 9-25.

Smith et al., Chapter 7. Diuretics, Annual Reports in Medicinal Chemistry. 1978; 13:61-70.

Smith et al., Chapter 8. Diuretics, Annual Reports in Medicinal Chemistry. 1976; 11:71-9.

Sood et al., Increasing concentration of inhaled saline with or without amiloride: effect on mucociliary clearance in normal subjects. Am J Respir Crit Care Med. Jan. 15, 2003;167(2):158-63. Epub Oct. 31, 2002.

Strader et al., Structural basis of beta-adrenergic receptor function. FASEB J. May 1989;3(7):1825-32.

Strosberg et al., Structure and function of the beta 3-adrenergic receptor. Annu Rev Pharmacol Toxicol. 1997;37:421-50.

Tarran et al., Rationale for hypertonic saline therapy for cystic fibrosis lung disease. Semin Respir Crit Care Med. Jun. 2007;28(3):295-302.

Tarran et al., The CF salt controversy: in vivo observations and therapeutic approaches. Mol Cell. Jul. 2001;8(1):149-58.

Taylor et al., A Facile Route to "Open Chain" Analogues of DDATHF. Heterocycles. 1989; 28(2). 1169-78.

Thelin et al., The epithelium as a target for therapy in cystic fibrosis. Curr Opin Pharmacol. Jun. 2007;7(3):290-5. Epub May 1, 2007.

Tomkiewicz et al., Amiloride inhalation therapy in cystic fibrosis. Influence on ion content, hydration, and rheology of sputum. Am Rev Respir Dis. Oct. 1993;148(4 Pt 1):1002-7.

Van Goor et al., Correction of the F508del-CFTR protein processing defect in vitro by the investigational drug VX-809. Proc Natl Acad Sci U S A. Nov. 15, 2011;108(46):18843-8. doi: 10.1073/pnas.1105787108. Epub Oct. 5, 2011.

Velly et al., Effects of amiloride and its analogues on [3H]batrachotoxinin-A 20-alpha benzoate binding, [3H]tetracaine binding and 22Na influx. Eur J Pharmacol. Apr. 27, 1988;149(1-2):97-105.

Wark et al., Nebulised hypertonic saline for cystic fibrosis. The Cochrane Collaboration, the Cochrane Library. 2008; 4:1-35.

Windscheif et al., Substituted Dipyridlethenes and -ethynes and Key Pyridine Building Blocks. Synthesis. 1994; 87-92.

Wolff, Über Diazoanhydride (1,2,3-Oxydiazole oder Diazoxyde) and Diazoketone. Justus Liebigs Annalen der Chemie. 1913; 394: 23-59.

Worlitzsch et al., Effects of reduced mucus oxygen concentration in airway Pseudomonas infections of cystic fibrosis patients. J Clin Invest. Feb. 2002;109(3):317-36.

Yin et al., Conversion of the 2,2,6,6-tetramethylpiperidine moiety to a 2,2-dimethylpyrrolidine by cytochrome P450: evidence for a mechanism involving nitroxide radicals and heme iron. Biochemistry. May 11, 2004;43(18):5455-66.

Zhou et al., Preventive but not late amiloride therapy reduces morbidity and mortality of lung disease in betaENaC-

(56) References Cited

OTHER PUBLICATIONS overexpressing mice. Am J Respir Crit Care Med. Dec. 15, 2008;178(12):1245-56. doi: 10.1164/rccm.200803-442OC. Epub Oct. 10, 2008.
U.S. Appl. No. 10/920,418, filed Aug. 18, 2004, Johnson.
U.S. Appl. No. 12/098,581, filed Apr. 7, 2008, Johnson.
U.S. Appl. No. 10/920,391, filed Aug. 18, 2004, Johnson.
U.S. Appl. No. 11/573,421, filed Jun. 10, 2009, Johnson.
U.S. Appl. No. 12/049,993, filed Mar. 17, 2008, Johnson.
U.S. Appl. No. 12/050,010, filed Mar. 17, 2008, Johnson.
U.S. Appl. No. 12/050,019, filed Mar. 17, 2008, Johnson.
U.S. Appl. No. 11/852,003, filed Sep. 7, 2007, Johnson et al.
U.S. Appl. No. 11/851,803, filed Sep. 7, 2007, Johnson et al.
U.S. Appl. No. 12/304,040, filed Jun. 23, 2010, Johnson.
U.S. Appl. No. 13/669,822, filed Nov. 6, 2012, Johnson.
U.S. Appl. No. 12/304,006, filed Dec. 9, 2008, Johnson et al.
U.S. Appl. No. 14/106,156, filed Dec. 13, 2013, Johnson.
U.S. Appl. No. 14/577,098, filed Dec. 19, 2014, Johnson.
U.S. Appl. No. 15/446,852, filed Mar. 1, 2017, Johnson.
U.S. Appl. No. 14/106,098, filed Dec. 13, 2013, Johnson.
U.S. Appl. No. 14/592,480, filed Jan. 8, 2015, Johnson.
U.S. Appl. No. 15/638,175, filed Jun. 29, 2017, Johnson.
U.S. Appl. No. 10/076,551, filed Feb. 19, 2002, Johnson.
U.S. Appl. No. 10/828,235, filed Apr. 21, 2004, Johnson.
U.S. Appl. No. 10/828,278, filed Apr. 21, 2004, Johnson.
U.S. Appl. No. 10/828,329, filed Apr. 21, 2004, Johnson.
U.S. Appl. No. 10/828,353, filed Apr. 21, 2004, Johnson.
U.S. Appl. No. 10/828,354, filed Apr. 21, 2004, Johnson.
U.S. Appl. No. 11/696,003, filed Apr. 3, 2007, Johnson.
U.S. Appl. No. 10/367,947, filed Feb. 19, 2003, Johnson.
U.S. Appl. No. 10/545,083, filed Aug. 9, 2005, Johnson.
U.S. Appl. No. 10/973,474, filed Oct. 27, 2004, Johnson.
U.S. Appl. No. 11/261,734, filed Oct. 31, 2005, Johnson.
U.S. Appl. No. 11/950,674, filed Dec. 5, 2007, Johnson.
U.S. Appl. No. 10/973,447, filed Oct. 27, 2004, Johnson.
U.S. Appl. No. 10/973,473, filed Oct. 27, 2004, Johnson.
U.S. Appl. No. 10/920,353, filed Aug. 18, 2004, Johnson.
U.S. Appl. No. 11/960,989, filed Dec. 20, 2007, Johnson.
U.S. Appl. No. 12/393,252, filed Feb. 26, 2009, Johnson.
U.S. Appl. No. 13/353,018, filed Jan. 18, 2012, Johnson.
U.S. Appl. No. 14/043,223, filed Oct. 1, 2013, Johnson.
U.S. Appl. No. 10/920,410, filed Aug. 18, 2004, Johnson et al.
U.S. Appl. No. 11/131,262, filed May 18, 2005, Johnson et al.
U.S. Appl. No. 11/138,280, filed May 27, 2005, Johnson et al.
U.S. Appl. No. 11/211,422, filed Aug. 26, 2005, Johnson et al.
U.S. Appl. No. 11/211,660, filed Aug. 26, 2005, Johnson et al.
U.S. Appl. No. 11/211,707, filed Aug. 26, 2005, Johnson et al.
U.S. Appl. No. 12/049,894, filed Mar. 17, 2008, Johnson et al.
U.S. Appl. No. 12/049,946, filed Mar. 17, 2008, Johnson et al.
U.S. Appl. No. 12/049,968, filed Mar. 17, 2008, Johnson et al.
U.S. Appl. No. 12/171,814, filed Jul. 11, 2008, Johnson et al.
U.S. Appl. No. 12/171,867, filed Jul. 11, 2008, Johnson et al.
U.S. Appl. No. 12/171,897, filed Jul. 11, 2008, Johnson et al.
U.S. Appl. No. 12/939,579, filed Nov. 4, 2010, Johnson et al.
U.S. Appl. No. 11/195,758, filed Aug. 3, 2005, Johnson et al.
U.S. Appl. No. 12/876,615, filed Sep. 7, 2010, Johnson et al.
U.S. Appl. No. 13/467,618, filed May 9, 2012, Johnson et al.
U.S. Appl. No. 11/573,693, filed Feb. 14, 2007, Johnson.
U.S. Appl. No. 14/106,125, filed Dec. 13, 2013, Johnson.
U.S. Appl. No. 13/533,911, filed Jun. 26, 2012, Johnson.
U.S. Appl. No. 14/132,194, filed Dec. 18, 2013, Johnson.
U.S. Appl. No. 15/446,877, filed Mar. 1, 2017, Johnson.
U.S. Appl. No. 10/076,571, filed Feb. 19, 2002, Johnson.
U.S. Appl. No. 10/532,110, filed Apr. 21, 2005, Johnson.
U.S. Appl. No. 12/179,353, filed Jul. 24, 2008, Johnson.
U.S. Appl. No. 13/492,711, filed Jun. 8, 2012, Johnson.
U.S. Appl. No. 14/158,441, filed Jan. 17, 2014, Johnson.
U.S. Appl. No. 14/727,189, filed Jun. 1, 2015, Johnson.
U.S. Appl. No. 10/828,171, filed Apr. 21, 2004, Johnson.
U.S. Appl. No. 10/828,352, filed Apr. 21, 2004, Johnson.
U.S. Appl. No. 10/828,466, filed Apr. 21, 2004, Johnson.
U.S. Appl. No. 10/828,479, filed Apr. 21, 2004, Johnson.
U.S. Appl. No. 11/695,936, filed Apr. 3, 2007, Johnson.
U.S. Appl. No. 12/190,022, filed Aug. 12, 2008, Johnson.
U.S. Appl. No. 12/703,441, filed Feb. 10, 2010, Johnson.
U.S. Appl. No. 15/336,574, filed Oct. 27, 2016, Johnson.
U.S. Appl. No. 15/945,572, filed Apr. 4, 2018, Johnson.

CHLORO-PYRAZINE CARBOXAMIDE DERIVATIVES WITH EPITHELIAL SODIUM CHANNEL BLOCKING ACTIVITY

RELATED APPLICATIONS

This application is a continuation of and claims priority under 35 U.S.C. § 120 to U.S. patent application Ser. No. 14/106,125, filed Dec. 13, 2013, now issued U.S. Pat. No. 9,593,084, which claims priority under 35 U.S.C. § 119(e) to U.S. provisional patent application Ser. No. 61/738,248, filed Dec. 17, 2012; each of which is incorporated herein by reference.

FIELD OF THE INVENTION

The present invention relates to novel compounds, including 3,5-diamino-N—(N-(4-(4-((S)-2-amino-3-(4-(3-(bis((2S,3R,4R,5R)-2,3,4,5,6-pentahydroxyhexyl)amino)propyl) phenylamino)-3-oxopropyl)naphthalen-1-yl)butyl) carbamimidoyl)-6-chloropyrazine-2-carboxamide and related compounds and their pharmaceutically acceptable salts, useful as sodium channel blockers, compositions containing the same, therapeutic methods and uses for the same and processes for preparing the same.

BACKGROUND OF THE INVENTION

The mucosal surfaces at the interface between the environment and the body have evolved a number of "innate defense", i.e., protective mechanisms. A principal form of such innate defense is to cleanse these surfaces with liquid. Typically, the quantity of the liquid layer on a mucosal surface reflects the balance between epithelial liquid secretion, often reflecting anion ($Cl^-$ and/or $HCO_3^-$) secretion coupled with water (and a cation counter-ion), and epithelial liquid absorption, often reflecting $Na^+$ absorption, coupled with water and counter anion ($Cl^-$ and/or $HCO_3^-$). Many diseases of mucosal surfaces are caused by too little protective liquid on those mucosal surfaces created by an imbalance between secretion (too little) and absorption (relatively too much). The defective salt transport processes that characterize these mucosal dysfunctions reside in the epithelial layer of the mucosal surface.

One approach to replenish the protective liquid layer on mucosal surfaces is to "re-balance" the system by blocking $Na^+$ channel and liquid absorption. The epithelial protein that mediates the rate-limiting step of $Na^+$ and liquid absorption is the epithelial $Na^+$ channel ("ENaC"). ENaC is positioned on the apical surface of the epithelium, i.e. the mucosal surface-environmental interface. Ideally, to inhibit ENaC mediated $Na^+$ and liquid absorption, an ENaC blocker of the amiloride class will be delivered to the mucosal surface and maintained at this site to achieve maximum therapeutic benefit.

The use of ENaC blockers has been reported for a variety of diseases which are ameliorated by increased mucosal hydration. In particular, the use of ENaC blockers in the treatment of respiratory diseases such as chronic bronchitis (CB), cystic fibrosis (CF), and COPD, which reflect the body's failure to clear mucus normally from the lungs and ultimately result in chronic airway infection has been reported. See, *Evidence for airway surface dehydration as the initiating event in CF airway disease*, R. C. Boucher, Journal of Internal Medicine, Vol. 261, Issue 1, January 2007, pages 5-16; and *Cystic fibrosis: a disease of vulnerability to airway surface dehydration*, R. C. Boucher, Trends in Molecular Medicine, Vol. 13, Issue 6, June 2007, pages 231-240.

Data indicate that the initiating problem in both chronic bronchitis and cystic fibrosis is the failure to clear mucus from airway surfaces. The failure to clear mucus reflects an imbalance in the quantities of mucus as airway surface liquid (ASL) on airway surfaces. This imbalance results in a relative reduction in ASL which leads to mucus concentration, reduction in the lubricant activity of the periciliary liquid (PCL), mucus adherence to the airway surface, and failure to clear mucus via ciliary activity to the mouth. The reduction in mucus clearance leads to chronic bacterial colonization of mucus adherent to airway surfaces. The chronic retention of bacteria, inability of local antimicrobial substances to kill mucus-entrapped bacteria on a chronic basis, and the consequent chronic inflammatory response to this type of surface infection, are manifest in chronic bronchitis and cystic fibrosis.

There is currently a large, unmet medical need for products that specifically treat the variety of diseases which are ameliorated by increased mucosal hydration, including chronic bronchitis, COPD and cystic fibrosis, among others. The current therapies for chronic bronchitis, COPD and cystic fibrosis focus on treating the symptoms and/or the late effects of these diseases. However, none of these therapies treat effectively the fundamental problem of the failure to clear mucus from the lung.

R. C. Boucher, in U.S. Pat. No. 6,264,975, describes the use of pyrazinoylguanidine sodium channel blockers for hydrating mucosal surfaces typified by the well-known diuretics amiloride, benzamil, and phenamil. However, these compounds are relatively impotent, considering the limited mass of drug that can be inhaled to the lung; (2) rapidly absorbed, and thereby exhibiting undesirably short half-life on the mucosal surface; and (3) are freely dissociable from ENaC. More potent drugs with longer half-lives on the mucosal surface are needed.

Too little protective surface liquid on other mucosal surfaces is a common pathophysiology of a number of diseases. For example, in xerostomia (dry mouth) the oral cavity is depleted of liquid due to a failure of the parotid sublingual and submandibular glands to secrete liquid despite continued $Na^+$ (ENaC) transport mediated liquid absorption from the oral cavity. Keratoconjunctivitis sira (dry eye) is caused by failure of lacrimal glands to secrete liquid in the face of continued $Na^+$ dependent liquid absorption on conjunctival surfaces. In rhinosinusitis, there is an imbalance between mucin secretion and relative ASL depletion. Failure to secrete Cl— (and liquid) in the proximal small intestine, combined with increased $Na^+$ (and liquid) absorption in the terminal ileum leads to the distal intestinal obstruction syndrome (DIOS). In older patients excessive $Na^+$ (and volume) absorption in the descending colon produces constipation and diverticulitis.

The published literature includes number of patent applications and granted patents to Parion Sciences Inc., directed toward pyrazinoylguanidine analogs as sodium channel blockers. Examples of such publications include PCT Publication Nos. WO2003/070182, WO2003/070184, WO2004/073629, WO2005/025496, WO2005/016879, WO2005/018644, WO2006/022935, WO2006/023573, WO2006/023617, WO2007/018640, WO2007/146869, WO2008/031028, WO2008/031048, and U.S. Pat. Nos. 6,858,614, 6,858,615, 6,903,105, 7,064,129, 7,186,833, 7,189,719, 7,192,958, 7,192,959, 7,192,960, 7,241,766, 7,247,636, 7,247,637, 7,317,013, 7,332,496, 7,368,447, 7,368,450, 7,368,451, 7,375,102, 7,388,013, 7,399,766, 7,410,968, 7,807,834, 7,842,697, and 7,868,010.

There remains a need for novel sodium channel blocking compounds with enhanced potency and effectiveness on mucosal tissues. There also remains the need for novel sodium channel blocking compounds that provide therapeutic effect, but minimize or eliminate the onset or progression of hyperkalemia in recipients.

SUMMARY OF THE INVENTION

This invention provides compounds of the formula I:

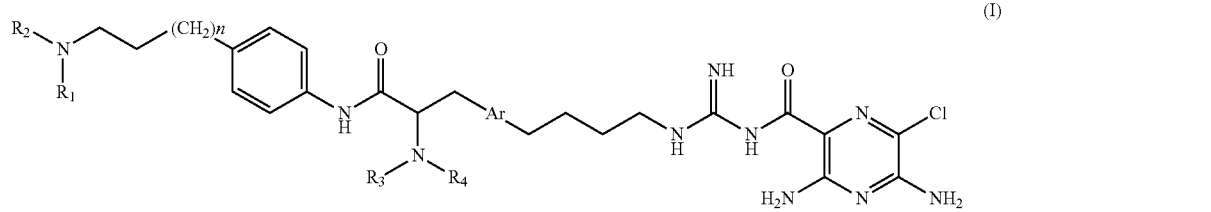

wherein:

Ar is selected from the group of:

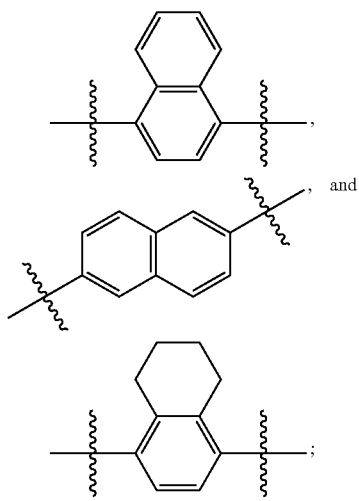

n is an integer selected from 0, 1, 2, 3, 4, 5, or 6;

$R^1$ is selected from hydrogen, $C_1$-$C_8$ alkyl, and a polyhydroxylated alkyl group having from 3 to 8 carbon atoms;

$R^2$ is hydrogen or a polyhydroxylated alkyl group having from 3 to 8 carbon atoms;

$R^3$ and $R^4$ are each, independently, hydrogen or $C_1$-$C_3$ alkyl;

or a pharmaceutically acceptable salt thereof.

This invention also provides solvates and hydrates, individual stereoisomers, including optical isomers (enantiomers and diastereomers) and geometric isomers (cis-/trans-isomerism), mixtures of stereoisomers, and tautomers of compounds of the formula (I), or a pharmaceutically acceptable salt thereof, as well as pharmaceutical compositions comprising the compounds, or a pharmaceutically acceptable salts thereof, their use in methods of treatment, and methods for their preparation.

This invention also provides the compound 3,5-diamino-N—(N-(4-(4-(((S)-2-amino-3-(4-(3-(bis((2S,3R,4R,5R)-2,3,4,5,6-pentahydroxyhexyl)amino)propyl)phenylamino)-3-oxopropyl) naphthalen-1-yl)butyl)carbamimidoyl)-6-chloropyrazine-2-carboxamide, or a pharmaceutically acceptable salt thereof, as well as optical isomers (enantiomers and diastereomers) and geometric isomers (cis-/trans-isomerism), mixtures of stereoisomers, and tautomers thereof, as well as pharmaceutical compositions comprising the compound, or a pharmaceutically acceptable salt thereof, its use in methods of treatment, and methods for its preparation.

BRIEF DESCRIPTION OF THE DRAWINGS

A more complete appreciation of the invention and many of the advantages thereof may be readily obtained by reference to the information herein in conjunction with the following figures.

DETAILED DESCRIPTION OF THE INVENTION

Figure 1:
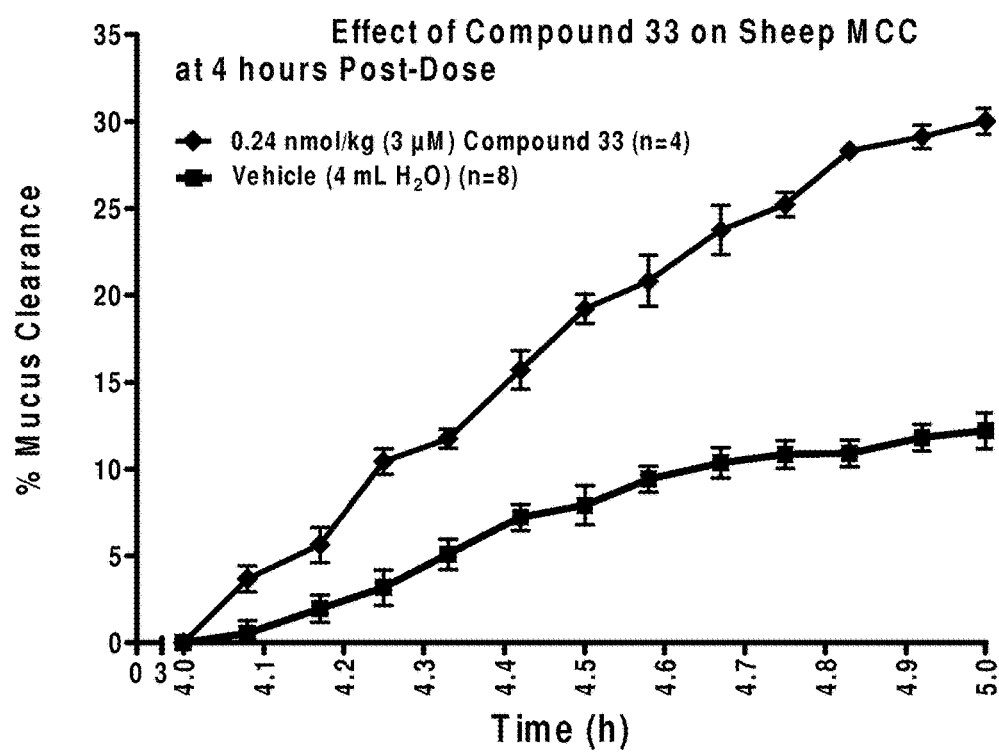
FIG. 1 is a plot of the effect of Compound 33 on Sheep MCC at 4 hours post-dose.

As used herein, the following terms are defined as indicated.

"A compound of the invention" means a compound of Formula I or a salt, particularly a pharmaceutically acceptable salt thereof.

"A compound of Formula I" means a compound having the structural formula designated herein as Formula I. Compounds of Formula I include solvates and hydrates (i.e., adducts of a compound of Formula I with a solvent). In those embodiments wherein a compound of Formula I includes one or more chiral centers, the phrase is intended to encompass each individual stereoisomer including optical isomers (enantiomers and diastereomers) and geometric isomers (cis-/trans-isomerism) and mixtures of stereoisomers. In addition, compounds of Formula I also include tautomers of the depicted formula(s).

Throughout the description and examples, compounds are named using standard IUPAC naming principles, where possible, including the use of the ChemDraw Ultra 11.0 software program for naming compounds, sold by CambridgeSoft Corp./PerkinElmer.

In some chemical structure representations where carbon atoms do not have a sufficient number of attached variables depicted to produce a valence of four, the remaining carbon substituents needed to provide a valence of four should be assumed to be hydrogen. Similarly, in some chemical structures where a bond is drawn without specifying the terminal group, such bond is indicative of a methyl (Me, —CH$_3$) group, as is conventional in the art.

In one embodiment, the compound of Formula (I) is 3,5-diamino-N—(N-(4-(4-(2-amino-3-(4-(3-(bis(2,3,4,5,6-pentahydroxyhexyl)amino)propyl)phenylamino)-3-oxopropyl)naphthalen-1-yl)butyl)carbamimidoyl)-6-chloropyrazine-2-carboxamide, having the structure:

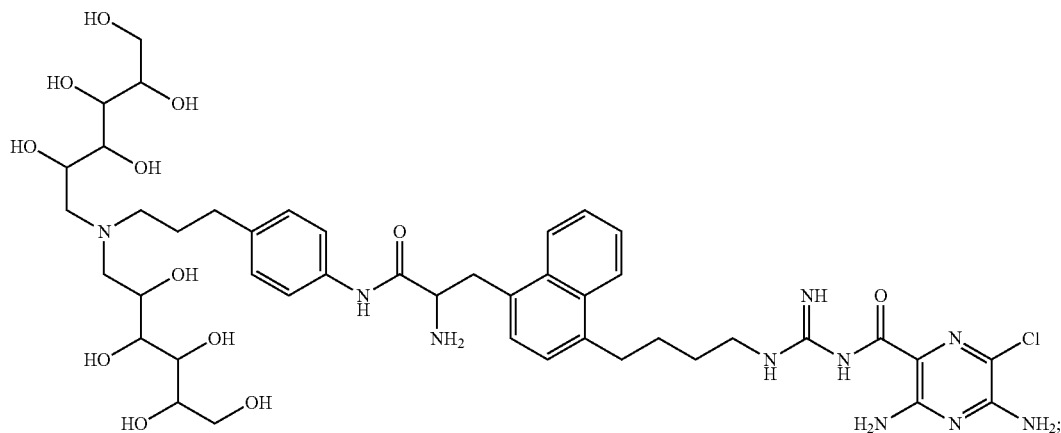 [SMILES: N=C(NCCCCc1ccc(CC(N)C(=O)Nc2ccc(CCCN(CC(O)C(O)C(O)C(O)CO)CC(O)C(O)C(O)C(O)CO)cc2)c2ccccc12)NC(=O)c1nc(Cl)c(N)nc1N]

or a pharmaceutically acceptable salt thereof.

In another embodiment, the compound of Formula (I) is 3,5-diamino-N—(N-(4-(4-(2-amino-3-(4-(3-(bis(2,3,4,5,6-pentahydroxyhexyl)amino)propyl)phenylamino)-3-oxopropyl)-5,6,7,8-tetrahydronaphthalen-1-yl)butyl)carbamimidoyl)-6-chloropyrazine-2-carboxamide, having the structure:

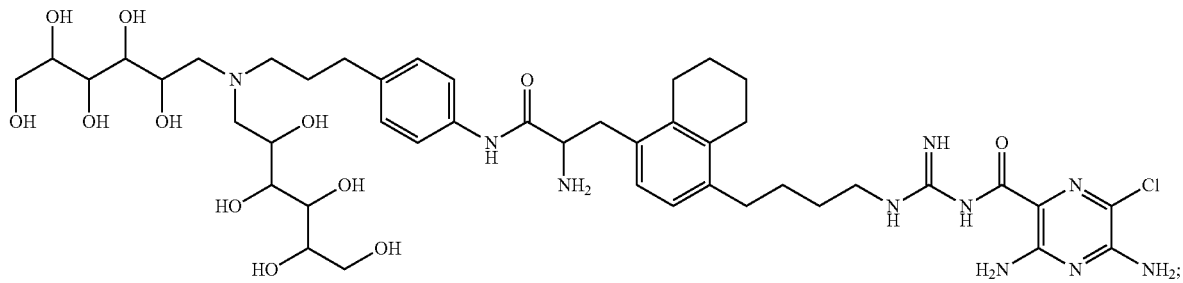 [SMILES: N=C(NCCCCc1ccc(CC(N)C(=O)Nc2ccc(CCCN(CC(O)C(O)C(O)C(O)CO)CC(O)C(O)C(O)C(O)CO)cc2)c2c1CCCC2)NC(=O)c1nc(Cl)c(N)nc1N]

or a pharmaceutically acceptable salt thereof.

In a further embodiment the compound of Formula (I) is 3,5-diamino-N—(N-(4-(6-(2-amino-3-(4-(3-(bis(2,3,4,5,6-pentahydroxyhexyl)amino)propyl)phenylamino)-3-oxopropyl)naphthalen-2-yl)butyl)carbamimidoyl)-6-chloropyrazine-2-carboxamide, having the structure:

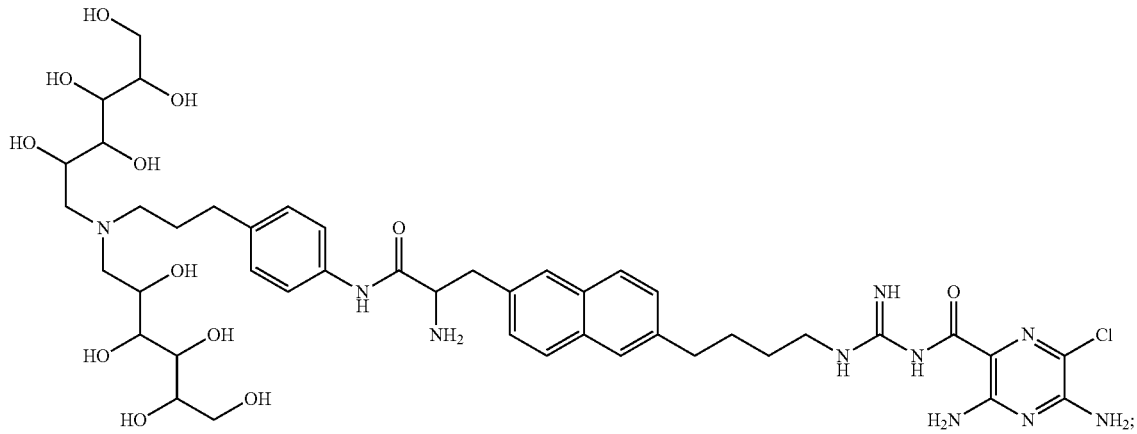 [SMILES: N=C(NCCCCc1ccc2cc(CC(N)C(=O)Nc3ccc(CCCN(CC(O)C(O)C(O)C(O)CO)CC(O)C(O)C(O)C(O)CO)cc3)ccc2c1)NC(=O)c1nc(Cl)c(N)nc1N]

or a pharmaceutically acceptable salt thereof.

In another embodiment, the compound of Formula (I) is 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide, having the formula:

(Ia)

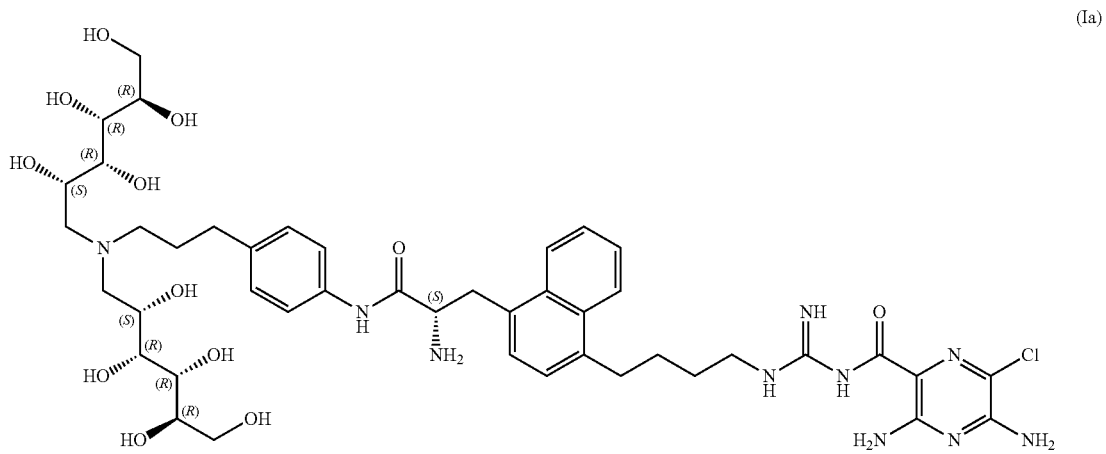

or a pharmaceutically acceptable salt thereof.

Three independent embodiments comprise compounds of Formula (II), Formula (III), and Formula (IV), respectively:

(II)

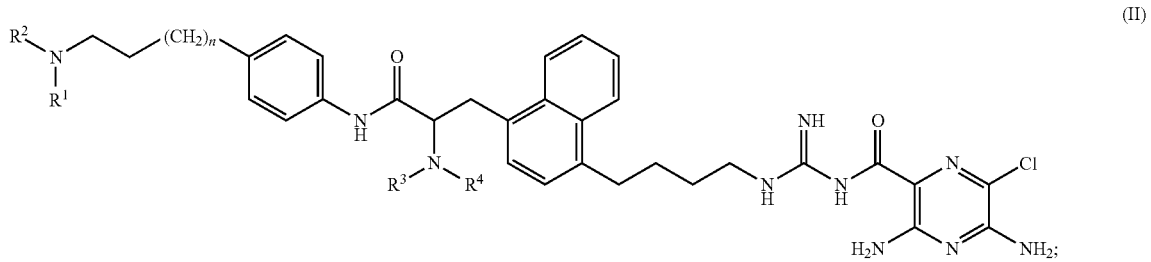

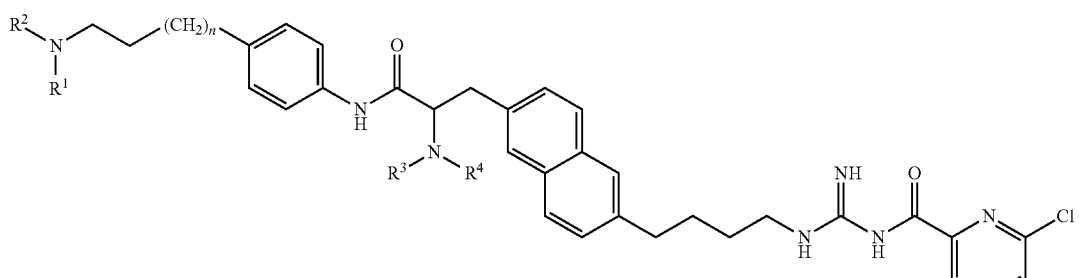

(III)

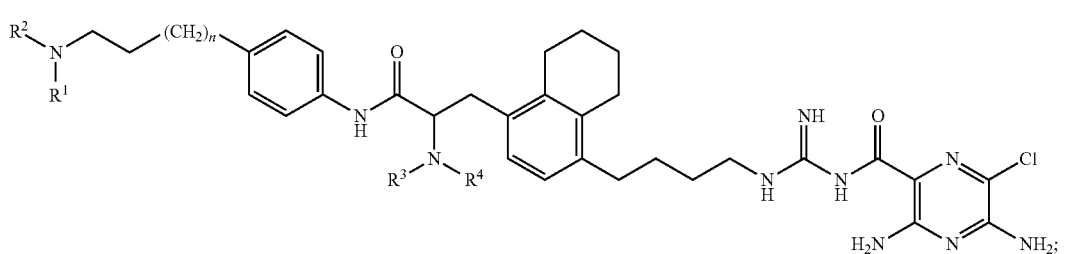

(IV)

wherein:
n is an integer selected from 0, 1, 2, 3, 4, 5, or 6;
$R^1$ is selected from hydrogen, $C_1$-$C_8$ alkyl, and a polyhydroxylated alkyl group having from 3 to 8 carbon atoms;
$R^2$ is hydrogen or a polyhydroxylated alkyl group having from 3 to 8 carbon atoms;
$R^3$ and $R^4$ are each, independently, hydrogen or $C_1$-$C_3$ alkyl;
or a pharmaceutically acceptable salt thereof.

Within each group of compounds independently represented by Formulas (I), (II), (III), and (IV), there is a further embodiment wherein:
n is an integer selected from 1, 2, 3, 4, 5, or 6;
$R^1$ is selected from hydrogen, $C_1$-$C_8$ alkyl, and a polyhydroxylated alkyl group having from 3 to 8 carbon atoms;
$R^2$ is hydrogen or a polyhydroxylated alkyl group having from 3 to 8 carbon atoms;
$R^3$ and $R^4$ are each, independently, hydrogen or $C_1$-$C_3$ alkyl;
or a pharmaceutically acceptable salt thereof.

Within each group of compounds independently represented by Formulas (I), (II), (III), and (IV), there is a further embodiment wherein:
n is an integer selected from 1, 2, 3, 4, 5, or 6;
$R^1$ is selected from hydrogen and $C_1$-$C_8$ alkyl;
$R^2$ is hydrogen or a polyhydroxylated alkyl group having from 3 to 8 carbon atoms;
$R^3$ and $R^4$ are each, independently, hydrogen or $C_1$-$C_3$ alkyl;
or a pharmaceutically acceptable salt thereof.

Within each group of compounds independently represented by Formulas (I), (II), (III), and (IV), there is another embodiment wherein:
n is an integer selected from 1, 2, 3, 4, 5, or 6;
$R^1$ is selected from hydrogen and $C_1$-$C_8$ alkyl;
$R^2$ is hydrogen;
$R^3$ and $R^4$ are each, independently, hydrogen or $C_1$-$C_3$ alkyl;
or a pharmaceutically acceptable salt thereof.

Within each group of compounds independently represented by Formulas (I), (II), (III), and (IV), there is still another embodiment wherein:
n is an integer selected from 1, 2, 3, 4, 5, or 6;
$R^1$ and $R^2$ are each, independently, a polyhydroxylated alkyl group having from 3 to 8 carbon atoms;
$R^3$ and $R^4$ are each, independently, hydrogen or $C_1$-$C_3$ alkyl;
or a pharmaceutically acceptable salt thereof.

Within each group of compounds independently represented by Formulas (I), (II), (III), and (IV), there exists another embodiment wherein:
n is an integer selected from 1, 2, 3, 4, 5, or 6;
$R^1$ and $R^2$ are each, independently, a polyhydroxylated alkyl group having from 3 to 8 carbon atoms;
$R^3$ and $R^4$ are hydrogen;
or a pharmaceutically acceptable salt thereof.

Within each group of compounds independently represented by Formulas (I), (II), (III), and (IV), there is another embodiment wherein:
n is an integer selected from 1, 2, 3, 4, 5, or 6;
$R^1$ and $R^2$ are each, independently, a polyhydroxylated alkyl group having from 3 to 8 carbon atoms;
$R^3$ and $R^4$ are each, independently, $C_1$-$C_3$ alkyl;
or a pharmaceutically acceptable salt thereof.

Within each group of compounds independently represented by Formulas (I), (II), (III), and (IV), there is an additional embodiment wherein:
n is an integer selected from 1, 2, 3, 4, 5, or 6;
$R^1$ and $R^2$ are each, independently, a polyhydroxylated alkyl group having from 3 to 8 carbon atoms;
$R^3$ is hydrogen; and
$R^4$ is $C_1$-$C_3$ alkyl;
or a pharmaceutically acceptable salt thereof.

Polyhydroxylated alkyl groups of this invention are those in which an alkyl chain of from 3 to 8 carbon atoms substituted by two or more hydroxyl groups. Examples of polyhydroxylated alkyl groups are butane-1,4-diol; butane-1,2,2-triol; butane-1,1,2,3,-tetraol; pentane-1,2,3,4-tetraol; hexane-1,2,3,4,5-pentaol; heptane-1,2,3,4,5,6-hexaol; and octane-1,2,3,4,5,6,7-heptaol.

One embodiment within each group of compounds described herein are those compounds in which the polyhydroxylated alkyl group has the formula —$CH_2$—

(CHR⁵)ₙ—H, wherein n is an integer selected from 2, 3, 4, 5, 6, or 7, and R⁵ is independently in each instance H or OH, with the proviso that at least two of the R⁵ groups are OH.

Another embodiment within each group of compounds described herein are those compounds in which the polyhydroxylated alkyl group has the formula —CH₂—CHOH—(CHR⁶)ₘ—H, wherein m is an integer selected from 1, 2, 3, 4, 5, or 6, and R⁶ is independently in each instance H or OH, with the proviso that at least one of the R⁶ groups is OH.

A further embodiment within each group of compounds described herein comprises compounds in which the polyhydroxylated alkyl group has the formula —CH₂—(CHOH)ₙ—CH₂OH, wherein n is an integer selected from 1, 2, 3, 4, 5, or 6. Another embodiment within each group of compounds described herein comprises compounds in which n is an integer selected from 2, 3, 4, or 5. Another embodiment within each group comprises compounds in which n is an integer selected from 3, 4, or 5.

In another embodiment within each group of compounds described herein, the chain represented by the formula —CH₂—(CHOH)ₙ—CH₂OH is 2,3,4,5,6-pentahydroxyhexane, having the formula:

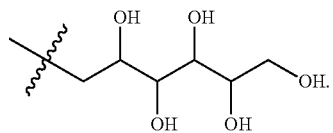 [SMILES: *CC(O)C(O)C(O)C(O)CO]

In a further embodiment within each group of compounds described herein, the chain represented by the formula —CH₂—(CHOH)ₙ—CH₂OH is of the formula:

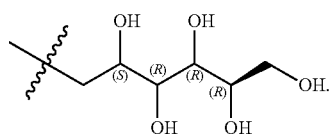

Three further independent embodiments include compounds of Formula (V), Formula (VI), and Formula (VII), respectively:

(V)

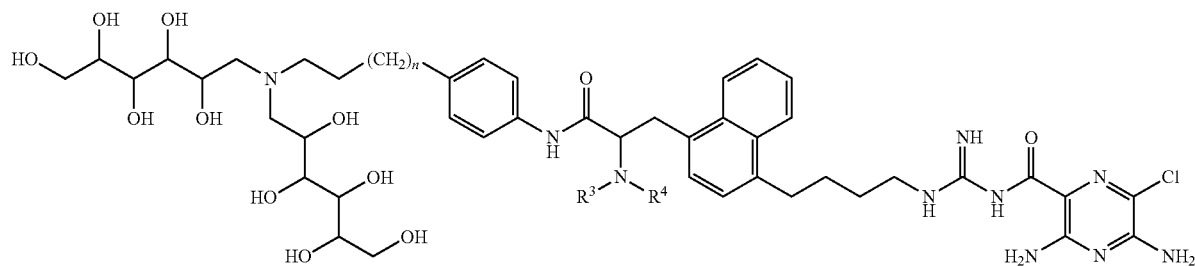

(VI)

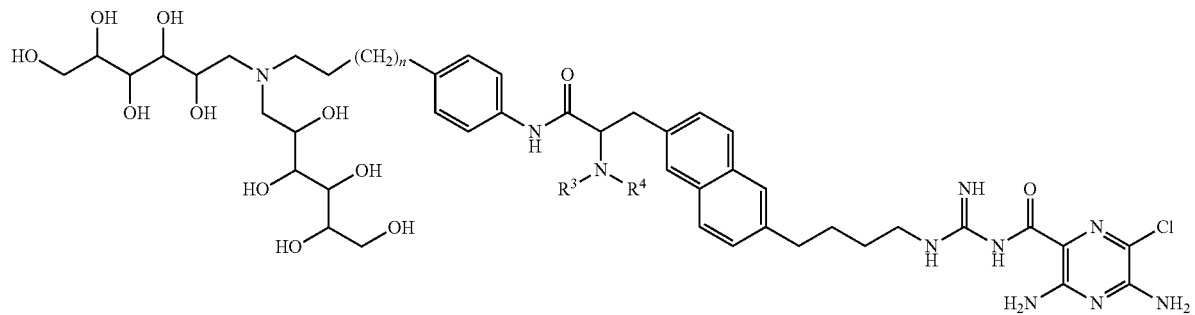

(VII)

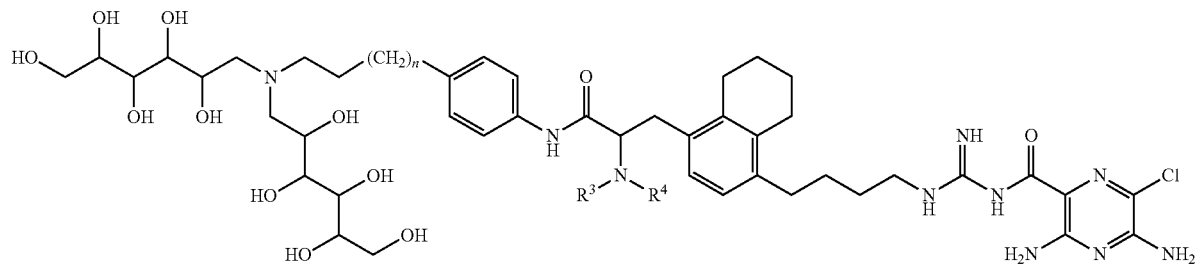

wherein:
n is an integer selected from 1, 2, 3, 4, 5, or 6; and
R³ and R⁴ are each, independently, hydrogen or $C_1$-$C_3$ alkyl;
or a pharmaceutically acceptable salt thereof.

Within each embodiment represented by Formulas (V), (VI), and (VII) there is a further embodiment wherein n is an integer selected from 1, 2, 3, 4, 5, or 6; and R³ and R⁴ are each hydrogen; or a pharmaceutically acceptable salt thereof. Within each embodiment represented by Formulas (V), (VI), and (VII) there is another embodiment wherein n is an integer selected from 1, 2, 3, 4, 5, or 6; and R³ and R⁴ are each $C_1$-$C_3$ alkyl; or a pharmaceutically acceptable salt thereof.

Within each of the embodiments described herein, there is a further embodiment wherein n is an integer selected from 1, 2, or 3. Within each of the embodiments described herein, there is a further embodiment wherein n is an integer selected from 4, 5, or 6. Within each of the embodiments described herein, there are six further independent embodiments wherein n is an integer of, respectively, 1, 2, 3, 4, 5, and 6.

The compounds herein, including those of of Formulas (I), (Ia), (II), (III), (IV), (V), (VI), and (VII), may be in the form of a free base or a salt, particularly a pharmaceutically acceptable salt. For a review of pharmaceutically acceptable salts see Berge et al., *J. Pharma Sci.* (1977) 66:1-19.

Pharmaceutically acceptable salts formed from inorganic or organic acids include for example, hydrochloride, hydrobromide, hydroiodide, sulfate, bisulfate, nitrate, sulfamate, phosphate, hydrogen phosphate, acetate, trifluoroacetate, maleate, malate, fumarate, lactate, tartrate, citrate, formate, gluconate, succinate, pyruvate, tannate, ascorbate, palmitate, salicylate, stearate, phthalate, alginate, polyglutamate, oxalate, oxaloacetate, saccharate, benzoate, alkyl or aryl sulfonates (e.g., methanesulfonate, ethanesulfonate, benzenesulfonate, p-toluenesulfonate or naphthalenesulfonate) and isothionate; complexes formed with amino acids such as lysine, arginine, glutamic acid, glycine, serine, threonine, alanine, isoleucine, leucine and the like. The compounds of the invention may also be in the form of salts formed from elemental anions such as chlorine, bromine or iodine.

For therapeutic use, salts of active ingredients of the compounds of Formula I will be pharmaceutically acceptable, i.e. they will be salts derived from a pharmaceutically acceptable acid. However, salts of acids which are not pharmaceutically acceptable may also find use, for example, in the preparation or purification of a pharmaceutically acceptable compound. Trifluoroacetate salts, for example, may find such use. All salts, whether or not derived from a pharmaceutically acceptable acid, are within the scope of the present invention.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space. "Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography. "Enantiomers" refer to two stereoisomers of a compound which are non-superimposable mirror images of one another.

Stereochemical definitions and conventions used herein generally follow S. P. Parker, Ed., MCGRAW-HILL DICTIONARY OF CHEMICAL TERMS (1984) McGraw-Hill Book Company, New York; and Eliel, E. and Wilen, S., STEREOCHEMISTRY OF ORGANIC COMPOUNDS (1994) John Wiley & Sons, Inc., New York.

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species.

The term "tautomers" refers to a type of stereoisomer in which migration of a hydrogen atom results in two or more structures. The compounds of Formula I may exist in different tautomeric forms. One skilled in the art will recognize that amidines, amides, guanidines, ureas, thioureas, heterocycles and the like can exist in tautomeric forms. By way of example and not by way of limitation, compounds of Formula I can exist in various tautomeric forms as shown below:

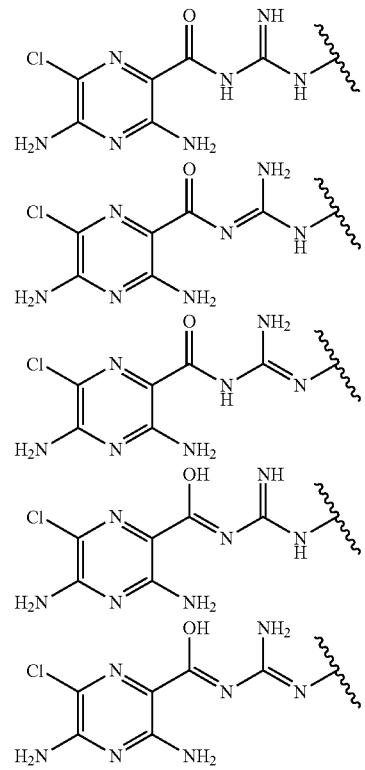

All possible tautomeric forms of the amidines, amides, guanidines, ureas, thioureas, heterocycles and the like of all of the embodiments of Formula I are within the scope of the instant invention. Tautomers exist in equilibrium and thus the depiction of a single tautomer in the formulas provided will be understood by those skilled in the art to refer equally to all possible tautomers.

It is to be noted that all enantiomers, diastereomers, and racemic mixtures, tautomers, polymorphs, pseudopolymorphs of compounds within the scope of Formula I and pharmaceutically acceptable salts thereof are embraced by the present invention. All mixtures of such enantiomers and diastereomers, including enantiomerically enriched mixtures and diastereomerically enriched mixtures are within the scope of the present invention. Enantiomerically enriched mixtures are mixtures of enantiomers wherein the ratio of the specified enantiomer to the alternative enantiomer is greater than 50:50. More particularly, an enantiomerically enriched mixture comprises at least about 75% of the specified enantiomer, and preferably at least about 85% of the specified enantiomer. In one embodiment, the enantiomerically enriched mixture is substantially free of the other enantiomer. Similarly, diastereomerically enriched mixtures are mixtures of diastereomers wherein amount of the specified diastereomer is greater than the amount of each alternative diastereomer. More particularly, a diastereomerically enriched mixture comprises at least about 75% of the specified diastereomer, and preferably at least about 85% of the specified diastereomer. In one embodiment, the diastereomerically enriched mixture is substantially free of all other diastereomers. The term "substantially free of" will be understood by those skilled in the art to indicate less than a 5% presence of other diastereomers, preferably less than 1%, more preferably less than 0.1%. In other embodiments no other diastereomers will be present or the amount of any other diastereomers present will be below the level of detection. Stereoisomers may be separated by techniques known in the art, including high performance liquid chromatography (HPLC) and crystallization of chiral salts.

A single stereoisomer, e.g. an enantiomer, substantially free of its stereoisomer may be obtained by resolution of the racemic mixture using a method such as formation of diastereomers using optically active resolving agents ("Stereochemistry of Carbon Compounds," (1962) by E. L. Eliel, McGraw Hill; Lochmuller, C. H., (1975) *J. Chromatogr.*, 113:(3) 283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

In one embodiment, the present invention provides an enantiomerically enriched mixture or composition comprising 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide, or a pharmaceutically acceptable salt thereof, as the predominant isomer.

Other embodiments comprise the enantiomerically enriched mixtures or compositions comprising, respectively, the compounds of Formulas (I), (Ia), (II), (III), (IV), (V), (VI), and (VII), or a pharmaceutically acceptable salt thereof, as the predominant isomer in each of their respective mixtures.

In another embodiment, the present invention provides an enantiomerically enriched mixture or composition 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide, or a pharmaceutically acceptable salt thereof, substantially free of other isomers.

Four other embodiments comprise the enantiomerically enriched mixtures or compositions comprising, respectively, the compounds of Formulas (I), (Ia), (II), (III), (IV), (V), (VI), and (VII), or a pharmaceutically acceptable salt thereof, substantially free of other isomers in each of their respective mixtures.

Also provided herein is each of the compounds and groups of compounds described herein, including those of Formulas (I), (Ia), (II), (III), (IV), (V), (VI), and (VII), or a pharmaceutically acceptable salt thereof, for use as a medicament.

A compound of Formula I and pharmaceutically acceptable salts thereof may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism also includes the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I and pharmaceutically acceptable salts thereof.

A compound of Formula I and pharmaceutically acceptable salts thereof may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention, including all pharmaceutical compositions, methods of treatment, combination products, and uses thereof described herein, comprises all amorphous forms of the compounds of Formula I and pharmaceutically acceptable salts thereof.

Uses

The compounds of the invention exhibit activity as sodium channel blockers. Without being bound by any particular theory, it is believed that the compounds of the invention may function in vivo by blocking epithelial sodium channels present in mucosal surfaces and thereby reduce the absorption of water by the mucosal surfaces. This effect increases the volume of protective liquids on mucosal surfaces, and rebalances the system.

As a consequence, the compounds of the invention are useful as medicaments, particularly for the treatment of clinical conditions for which a sodium channel blocker may be indicated. Such conditions include pulmonary conditions such as diseases associated with reversible or irreversible airway obstruction, chronic obstructive pulmonary disease (COPD), including acute exacerbations of COPD, asthma, bronchiectasis (including bronchiectasis due to conditions other than cystic fibrosis), acute bronchitis, chronic bronchitis, post-viral cough, cystic fibrosis, emphysema, pneumonia, panbronchiolitis, and transplant-associated bronchiolitis, including lung- and bone marrow-transplant associated bronchiolitis, in a human in need thereof. The compounds of the invention may also be useful for treating ventilator-associated tracheobronchitis and/or preventing ventilator-associated pneumonia in ventilated patients. The present invention comprises methods for treating each of the conditions described herein in a mammal in need thereof, preferably in a human in need thereof, each method comprising administering to said mammal a pharmaceutically effective amount of a compound of the present invention, or a pharmaceutically acceptable salt thereof. Also provided are (a) a method for reducing exacerbations of COPD in a mammal in need thereof; (b) a method for reducing exacerbations of CF in a mammal in need thereof; (c) a method of improving lung function (FEV1) in a mammal in need thereof, (d) a method of improving lung function (FEV1) in a mammal experiencing COPD, (e) a method of improving lung function (FEV1) in a mammal experiencing CF, (f) a method of reducing airway infections in a mammal in need thereof.

Also provided is a method of stimulating, enhancing or improving mucociliary clearance in a mammal, the method comprising administering to a mammal in need thereof a pharmaceutically effective amount of a compound of formula (I), or a pharmaceutically acceptable salt thereof. Mucociliary clearance will be understood to include the natural mucociliary actions involved in the transfer or clearance of mucus in the airways, including the self-clearing mechanisms of the bronchi. Therefore, also provided is a method of improving mucus clearance in the airways of a mammal in need thereof.

Additionally, sodium channel blockers may be indicated for the treatment of conditions which are ameliorated by increased mucosal hydration in mucosal surfaces other than pulmonary mucosal surfaces. Examples of such conditions include dry mouth (xerostomia), dry skin, vaginal dryness, sinusitis, rhinosinusitis, nasal dehydration, including nasal dehydration brought on by administering dry oxygen, dry eye, Sjogren's disease, otitis media, primary ciliary dyskinesia, distal intestinal obstruction syndrome, esophagitis, constipation, and chronic diverticulitis. The compounds of the invention can also be used for promoting ocular or corneal hydration.

The compounds of the present invention may also be useful in methods for obtaining a sputum sample from a human. The method may be carried out by administering an effective amount of a compound of the invention to at least one lung of the patient, and then inducing and collecting a sputum sample from that human.

Accordingly, in one aspect, the present invention provides a method for the treatment of a condition in a mammal, such as a human, for which a sodium channel blocker is indicated.

In other embodiments, the present invention provides each of the methods described herein with the additional benefit of minimizing or eliminating hyperkalemia in the recipient of the method. Also provided are embodiments comprising each of the methods described herein wherein an improved therapeutic index is achieved.

The terms "treat", "treating" and "treatment", as used herein refers to reversing, alleviating, inhibiting the progress of, or preventing the disorder or condition or one or more symptoms of such disorder or condition.

All therapeutic methods described herein are carried out by administering an effective amount of a compound of the invention, a compound of Formula I or a pharmaceutically acceptable salt thereof, to a subject (typically mammal and preferably human) in need of treatment.

In one embodiment the invention provides a method for the treatment of a condition which is ameliorated by increased mucosal hydration in a mammal, particularly a human in need thereof. In one embodiment the invention provides a method for the treatment of a disease associated with reversible or irreversible airway obstruction in a mammal, particularly a human, in need thereof. In one particular embodiment the present invention provides a method for the treatment of chronic obstructive pulmonary disease (COPD) in a mammal, particularly a human in need thereof. In one particular embodiment the present invention provides a method for reducing the frequency, severity or duration of acute exacerbation of COPD or for the treatment of one or more symptoms of acute exacerbation of COPD in a mammal, particularly a human in need thereof. In one embodiment the invention provides a method for the treatment of asthma in a mammal, particularly a human, in need thereof. In one embodiment the invention provides a method for the treatment of bronchiectasis (including bronchiectasis due to conditions other than cystic fibrosis) in a mammal, particularly a human, in need thereof. In one embodiment the invention provides a method for the treatment of bronchitis, including acute and chronic bronchitis in a mammal, particularly a human, in need thereof. In one embodiment the invention provides a method for the treatment of post-viral cough in a mammal, particularly a human, in need thereof. In one embodiment the invention provides a method for the treatment of cystic fibrosis in a mammal, particularly a human, in need thereof. In one embodiment the invention provides a method for the treatment of emphysema in a mammal, particularly a human in need thereof. In one embodiment the invention provides a method for the treatment of pneumonia in a mammal, particularly a human in need thereof. In one embodiment the invention provides a method for the treatment of panbronchiolitis in a mammal, particularly a human in need thereof. In one embodiment the invention provides a method for the treatment of transplant-associated bronchiolitis, including lung- and bone marrow-transplant associated bronchiolitis in a mammal, particularly a human in need thereof. In one embodiment the invention provides a method for treating ventilator-associated tracheobronchitis and/or preventing ventilator-associated pneumonia in a ventilated human in need thereof.

This invention provides specific methods for treating a disease selected from the group of reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia in a human in need thereof, each method comprising administering to said human an effective amount of a compound of formula 1(a), or a pharmaceutically acceptable salt thereof. In further embodiments for each method of treatment, the pharmaceutically acceptable salt form is a hydrochloride salt or a hydroxynaphthoate salt of the compound of formula (1a). In another embodiment within each method of treatment, the freebase of the compound of formula (1a) is used.

In one embodiment the invention provides a method for the treatment of dry mouth (xerostomia) in a mammal, particularly a human in need thereof. In one embodiment the invention provides a method for the treatment of dry skin in a mammal, particularly a human in need thereof. In one embodiment the invention provides a method for the treatment of vaginal dryness in a mammal, particularly a human in need thereof. In one embodiment the invention provides a method for the treatment of sinusitis, rhinosinusitis, or nasal dehydration, including nasal dehydration brought on by administering dry oxygen, in a mammal, particularly a human in need thereof. In one embodiment the invention provides a method for the treatment of dry eye, or Sjogren's disease, or promoting ocular or corneal hydration in a mammal, particularly a human in need thereof. In one embodiment the invention provides a method for the treatment of otitis media in a mammal, particularly a human in need thereof. In one embodiment the invention provides a method for the treatment of primary ciliary dyskinesia, in a mammal, particularly a human in need thereof. In one embodiment the invention provides a method for the treatment of distal intestinal obstruction syndrome, esophagitis, constipation, or chronic diverticulitis in a mammal, particularly a human in need thereof.

There is also provided a compound of the invention for use in medical therapy, particularly for use in the treatment of condition in a mammal, such as a human, for which a sodium channel blocker is indicated. All therapeutic uses described herein are carried out by administering an effective amount of a compound of the invention to the subject in need of treatment. In one embodiment there is provided a compound of the invention for use in the treatment of a pulmonary condition such as a disease associated with reversible or irreversible airway obstruction in a mammal, particularly a human, in need thereof. In one particular embodiment there is provided a compound of the invention for use in the treatment of chronic obstructive pulmonary disease (COPD) in a mammal, particularly a human in need thereof. In one embodiment, there is provided a compound of the invention for use in reducing the frequency, severity or duration of acute exacerbation of COPD or for the treatment of one or more symptoms of acute exacerbation of COPD, in a mammal, particularly a human, in need thereof. In one embodiment there is provided a compound of the invention for use in the treatment of asthma in a mammal, particularly a human, in need thereof. In one embodiment there is provided a compound for use in the treatment of bronchiectasis, including bronchiectasis due to conditions other than cystic fibrosis, or bronchitis, including acute bronchitis and chronic bronchitis, in a mammal, particularly a human, in need thereof. In one embodiment there is provided a compound for use in the treatment of post-viral cough, in a mammal, particularly a human, in need thereof. In one embodiment there is provided a compound for use in the treatment of cystic fibrosis in a mammal, particularly a human in need thereof. In one embodiment there is provided a compound of the invention for use in the treatment of emphysema in a mammal, particularly a human, in need thereof. In one embodiment there is provided a compound of the invention for use in the treatment of pneumonia in a mammal, particularly a human, in need thereof. In one embodiment there is provided a compound of the invention for use in the treatment of panbronchiolitis or transplant-associated bronchiolitis, including lung- and bone marrow-transplant associated bronchiolitis in a mammal, particularly a human, in need thereof. In one embodiment there is provided a compound of the invention for use in the treatment of ventilator-associated tracheobronchitis or preventing ventilator-associated pneumonia in a ventilated human in need thereof.

In one embodiment there is provided a compound of the invention for use in the treatment of a condition ameliorated by increased mucosal hydration in mucosal surfaces of a mammal, particularly a human, in need thereof. In one embodiment there is provided a compound for use in the treatment of dry mouth (xerostomia) in a mammal, particularly a human, in need thereof. In one embodiment there is provided a compound for use in the treatment of dry skin in a mammal, particularly a human, in need thereof. In one embodiment there is provided a compound for use in the treatment of vaginal dryness in a mammal, particularly a human in need thereof. In one embodiment there is provided a compound of the invention for use in the treatment of sinusitis, rhinosinusitis, or nasal dehydration, including nasal dehydration brought on by administering dry oxygen in a mammal, particularly a human, in need thereof. In one embodiment there is provided a compound of the invention for use in the treatment of dry eye, or Sjogren's disease or promoting ocular or corneal hydration in a mammal, particularly a human, in need thereof. In one embodiment there is provided a compound of the invention for use in the treatment of otitis media in a mammal, particularly a human, in need thereof. In one embodiment there is provided a compound of the invention for use in the treatment of primary ciliary dyskinesia in a mammal, particularly a human, in need thereof. In one embodiment there is provided a compound of the invention for use in the treatment of distal intestinal obstruction syndrome, esophagitis, constipation, or chronic diverticulitis in a mammal, particularly a human, in need thereof.

The present invention also provides the use of a compound of the invention in the manufacture of a medicament for the treatment of a condition in a mammal, such as a human, for which a sodium channel blocker is indicated. In one embodiment is provided the use of a compound of the invention in the manufacture of a medicament for the treatment of diseases associated with reversible or irreversible airway obstruction, chronic obstructive pulmonary disease (COPD), acute exacerbations of COPD, asthma, bronchiectasis (including bronchiectasis due to conditions other than cystic fibrosis), bronchitis (including acute bronchitis and chronic bronchitis), post-viral cough, cystic fibrosis, emphysema, pneumonia, panbronchiolitis, transplant-associated bronchiolitis, (including lung- and bone marrow-transplant associated bronchiolitis), ventilator-associated tracheobronchitis or preventing ventilator-associated pneumonia.

In one particular embodiment is provided the use of a compound of the invention in the manufacture of a medicament for the treatment of a condition ameliorated by increased mucosal hydration in mucosal surfaces, treatment of dry mouth (xerostomia), dry skin, vaginal dryness, sinusitis, rhinosinusitis, nasal dehydration, including nasal dehydration brought on by administering dry oxygen, treatment of dry eye, Sjogren's disease, promoting ocular or corneal hydration, treatment of otitis media, primary ciliary dyskinesia, distal intestinal obstruction syndrome, esophagitis, constipation, or chronic diverticulitis The terms "effective amount", "pharmaceutically effective amount", "effective dose", and "pharmaceutically effective dose" as used herein, refer to an amount of compound of the invention which is sufficient in the subject to which it is administered, to elicit the biological or medical response of a cell culture, tissue, system, or mammal (including human) that is being sought, for instance by a researcher or clinician. The term also includes within its scope, amounts effective to enhance normal physiological function. In one embodiment, the effective amount is the amount needed to provide a desired level of drug in the secretions and tissues of the airways and lungs, or alternatively, in the bloodstream of a subject to be treated to give an anticipated physiological response or desired biological effect when such a composition is administered by inhalation. For example an effective amount of a compound of the invention for the treatment of a condition for which a sodium channel blocker is indicated is sufficient in the subject to which it is administered to treat the particular condition. In one embodiment an effective amount is an amount of a compound of the invention which is sufficient for the treatment of COPD or cystic fibrosis in a human.

The precise effective amount of the compounds of the invention will depend on a number of factors including but not limited to the species, age and weight of the subject being treated, the precise condition requiring treatment and its severity, the bioavailability, potency, and other properties of the specific compound being administered, the nature of the formulation, the route of administration, and the delivery device, and will ultimately be at the discretion of the attendant physician or veterinarian. Further guidance with respect to appropriate dose may be found in considering conventional dosing of other sodium channel blockers, such as amiloride, with due consideration also being given to any differences in potency between amiloride and the compounds of the present invention.

A pharmaceutically effective dose administered topically to the airway surfaces of a subject (e.g., by inhalation) of a compound of the invention for treatment of a 70 kg human may be in the range of from about 10 ng to about 10 mg. In another embodiment, the pharmaceutically effective dose may be from about 0.1 to about 1000 µg. Typically, the daily dose administered topically to the airway surfaces will be an amount sufficient to achieve dissolved concentration of active agent on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter. The selection of the specific dose for a patient will be determined by the attendant physician, clinician or veterinarian of ordinary skill in the art based upon a number of factors including those noted above. In one particular embodiment the dose of a compound of the invention for the treatment of a 70 kg human will be in the range of from about 10 nanograms (ng) to about 10 mg. In another embodiment, the effective dose would be from about 0.1 µg to about 1,000 µg. In one embodiment, the dose of a compound of the invention for the treatment of a 70 kg human will be in the range of from about 0.5 µg to about 0.5 mg. In a further embodiment the dose will be from about 0.5 µg to about 60 µg. In another embodiment, the pharmaceutically effective dose will be from about 1 to about 10 µg. In another embodiment, the pharmaceutically effective dose will be from about 5 µg to about 50 µg. Another embodiment will have an effective dose of from about 10 µg to about 40 µg. In two further embodiments, the pharmaceutically effective dose will be from about 15 µg to about 50 µg from about 15 µg to about 30 µg, respectively. It will be understood that in each of these dose ranges, all incremental doses in the range are included. For instance, the 0.5-50 µg range includes individual doses of: 0.5 µg, 0.6 µg, 0.7 µg, 0.8 µg, 0.9 µg, 1.0 jag, 1.1 µg, 1.2 µg, 1.3 µg, 1.4 jag, 1.5 jag, 1.6 jag, 1.7 µg, 1.8 µg, 1.9 µg, 2.0 jag, 2.1 µg, 2.2 µg, 2.3 µg, 2.4 jag, 2.5 jag, 2.6 jag, 2.7 µg, 2.8 µg, 2.9 µg, 3.0 jag, 3.1 µg, 3.2 µg, 3.3 jag, 3.4 µg, 3.5 µg, 3.6 µg, 3.7 µg, 3.8 µg, 3.9 jag, 4.0 jag, 4.1 µg, 4.2 µg, 4.3 µg, 4.4 jag, 4.5 jag, 4.6 jag, 4.7 µg, 4.8 µg, 4.9 µg, 5.0 µg, 5.1 µg, 5.2 jag, 5.3 µg, 5.4 µg, 5.5 µg, 5.6 µg, 5.7 µg, 5.8 µg, 5.9 jag, 6.0 µg, 6.1 µg, 6.2 µg, 6.3 µg, 6.4 µg, 6.5 jag, 6.6 µg, 6.7 µg, 6.8 µg, 6.9 µg, 7.0 jag, 7.1 µg, 7.2 µg, 7.3 µg, 7.4 µg, 7.5 µg, 7.6 µg, 7.7 µg, 7.8 µg, 7.9 µg, 8.0 µg, 8.1 µg, 8.2 µg, 8.3 µg, 8.4 µg, 8.5 µg, 8.6 µg, 8.7 µg, 8.8 µg, 8.9 µg, 9.0 µg, 9.1 µg, 9.2 µg, 9.3 µg, 9.4 µg, 9.5 µg, 9.6 µg, 9.7 µg, 9.8 µg, 9.9 µg, 10.0 µg, 10.1 µg, 10.2 µg, 10.3 µg, 10.4 µg, 10.5 µg, 10.6 µg, 10.7 µg, 10.8 µg, 10.9 µg, 11.0 µg, 11.1 µg, 11.2 µg, 11.3 µg, 11.4 µg, 11.5 µg, 11.6 µg, 11.7 µg, 11.8 µg, 11.9 µg, 12.0 µg, 12.1 µg, 12.2 µg, 12.3 µg, 12.4 µg, 12.5 µg, 12.6 µg, 12.7 µg, 12.8 µg, 12.9 µg, 13.0 µg, 13.1 µg, 13.2 µg, 13.3 µg, 13.4 µg, 13.5 µg, 13.6 µg, 13.7 µg, 13.8 µg, 13.9 µg, 14.0 µg, 14.1 µg, 14.2 µg, 14.3 µg, 14.4 µg, 14.5 µg, 14.6 µg, 14.7 µg, 14.8 µg, 14.9 µg, 15.0 µg, 15.1 µg, 15.2 µg, 15.3 µg, 15.4 µg, 15.5 µg, 15.6 µg, 15.7 µg, 15.8 µg, 15.9 µg, 16.0 µg, 16.1 µg, 16.2 µg, 16.3 µg, 16.4 µg, 16.5 µg, 16.6 µg, 16.7 µg, 16.8 µg, 16.9 µg, 17.0 µg, 17.1 µg, 17.2 µg, 17.3 µg, 17.4 µg, 17.5 µg, 17.6 µg, 17.7 µg, 17.8 µg, 17.9 µg, 18.0 µg, 18.1 µg, 18.2 µg, 18.3 µg, 18.4 µg, 18.5 µg, 18.6 µg, 18.7 µg, 18.8 µg, 18.9 µg, 19.0 µg, 19.1 µg, 19.2 µg, 19.3 µg, 19.4 µg, 19.5 µg, 19.6 µg, 19.7 µg, 19.8 µg, 19.9 µg, 20.0 µg, 20.1 µg, 20.2 µg, 20.3 µg, 20.4 µg, 20.5 µg, 20.6 µg, 20.7 µg, 20.8 µg, 20.9 µg, 21.0 µg, 21.1 µg, 21.2 µg, 21.3 µg, 21.4 µg, 21.5 µg, 21.6 µg, 21.7 µg, 21.8 µg, 21.9 µg, 22.0 µg, 22.1 µg, 22.2 µg, 22.3 µg, 22.4 µg, 22.5 µg, 22.6 µg, 22.7 µg, 22.8 µg, 22.9 µg, 23.0 µg, 23.1 µg, 23.2 µg, 23.3 µg, 23.4 µg, 23.5 µg, 23.6 µg, 23.7 µg, 23.8 µg, 23.9 µg, 24.0 µg, 24.1 µg, 24.2 µg, 24.3 µg, 24.4 µg, 24.5 µg, 24.6 µg, 24.7 µg, 24.8 µg, 24.9 µg, 25.0 µg, 25.1 µg, 25.2 µg, 25.3 µg, 25.4 µg, 25.5 µg, 25.6 µg, 25.7 µg, 25.8 µg, 25.9 µg, 26.0 µg, 26.1 µg, 26.2 µg, 26.3 µg, 26.4 µg, 26.5 µg, 26.6 µg, 26.7 µg, 26.8 µg, 26.9 µg, 27.0 µg, 27.1 µg, 27.2 µg, 27.3 µg, 27.4 µg, 27.5 µg, 27.6 µg, 27.7 µg, 27.8 µg, 27.9 µg, 28.0 µg, 28.1 µg, 28.2 µg, 28.3 µg, 28.4 µg, 28.5 µg, 28.6 µg, 28.7 µg, 28.8 µg, 28.9 µg, 29.0 µg, 29.1 µg, 29.2 µg, 29.3 µg, 29.4 µg, 29.5 µg, 29.6 µg, 29.7 µg, 29.8 µg, 29.9 µg, 30.0 µg, 30.1 µg, 30.2 µg, 30.3 µg, 30.4 µg, 30.5 µg, 30.6 µg, 30.7 µg, 30.8 µg, 30.9 µg, 31.0 µg, 31.1 µg, 31.2 µg, 31.3 µg, 31.4 µg, 31.5 µg, 31.6 µg, 31.7 µg, 31.8 µg, 31.9 µg, 32.0 µg, 32.1 µg, 32.2 µg, 32.3 µg, 32.4 µg, 32.5 µg, 32.6 µg, 32.7 µg, 32.8 µg, 32.9 µg, 33.0 µg, 33.1 µg, 33.2 µg, 33.3 µg, 33.4 µg, 33.5 µg, 33.6 µg, 33.7 µg, 33.8 µg, 33.9 µg, 34.0 µg, 34.1 µg, 34.2 µg, 34.3 µg, 34.4 µg, 34.5 µg, 34.6 µg, 34.7 µg, 34.8 µg, 34.9 µg, 35.0 µg, 35.1 µg, 35.2 µg, 35.3 µg, 35.4 µg, 35.5 µg, 35.6 µg, 35.7 µg, 35.8 µg, 35.9 µg, 36.0 µg, 36.1 µg, 36.2 µg, 36.3 µg, 36.4 µg, 36.5 µg, 36.6 µg, 36.7 µg, 36.8 µg, 36.9 µg, 37.0 µg, 37.1 µg, 37.2 µg, 37.3 µg, 37.4 µg, 37.5 µg, 37.6 µg, 37.7 µg, 37.8 µg, 37.9 µg, 38.0 µg, 38.1 µg, 38.2 µg, 38.3 µg, 38.4 µg, 38.5 µg, 38.6 µg, 38.7 µg, 38.8 µg, 38.9 µg, 39.0 µg, 39.1 µg, 39.2 µg, 39.3 µg, 39.4 µg, 39.5 µg, 39.6 µg, 39.7 µg, 39.8 µg, 39.9 µg, 40.0 µg, 40.1 µg, 40.2 µg, 40.3 µg, 40.4 µg, 40.5 µg, 40.6 µg, 40.7 µg, 40.8 µg, 40.9 µg, 41.0 µg, 41.1 µg, 41.2 µg, 41.3 µg, 41.4 µg, 41.5 µg, 41.6 µg, 41.7 µg, 41.8 µg, 41.9 µg, 42.0 µg, 42.1 µg, 42.2 µg, 42.3 µg, 42.4 µg, 42.5 µg, 42.6 µg, 42.7 µg, 42.8 µg, 42.9 µg, 43.0 µg, 43.1 µg, 43.2 µg, 43.3 µg, 43.4 µg, 43.5 µg, 43.6 µg, 43.7 µg, 43.8 µg, 43.9 µg, 44.0 µg, 44.1 µg, 44.2 µg, 44.3 µg, 44.4 µg, 44.5 µg, 44.6 µg, 44.7 µg, 44.8 µg, 44.9 µg, 45.0 µg, 45.1 µg, 45.2 µg, 45.3 µg, 45.4 µg, 45.5 µg, 45.6 µg, 45.7 µg, 45.8 µg, 45.9 µg, 46.0 µg, 46.1 µg, 46.2 µg, 46.3 µg, 46.4 µg, 46.5 µg, 46.6 µg, 46.7 µg, 46.8 µg, 46.9 µg, 47.0 µg, 47.1 µg, 47.2 µg, 47.3 µg, 47.4 µg, 47.5 µg, 47.6 µg, 47.7 µg, 47.8 µg, 47.9 µg, 48.0 µg, 48.1 µg, 48.2 µg, 48.3 µg, 48.4 µg, 48.5 µg, 48.6 µg, 48.7 µg, 48.8 µg, 38.9 µg, 49.0 µg, 49.1 µg, 49.2 µg, 49.3 µg, 49.4 µg, 49.5 µg, 49.6 µg, 49.7 µg, 49.8 µg, 39.9 µg, and 50 µg.

The foregoing suggested doses may be adjusted using conventional dose calculations if the compound is administered via a different route. Determination of an appropriate dose for administration by other routes is within the skill of those in the art in light of the foregoing description and the general knowledge in the art.

Delivery of an effective amount of a compound of the invention may entail delivery of a single dosage form or multiple unit doses which may be delivered contemporaneously or separate in time over a designated period, such as 24 hours. A dose of a compound of the invention (alone or in the form of a composition comprising the same) may be administered from one to ten times per day. Typically, a compound of the invention (alone or in the form of a composition comprising the same) will be administered four, three, two, or once per day (24 hours).

The compounds of formula (I) of the present invention are also useful for treating airborne infections. Examples of airborne infections include, for example, RSV. The compounds of formula (I) of the present invention are also useful for treating an anthrax infection. The present invention relates to the use of the compounds of formula (I) of the present invention for prophylactic, post-exposure prophylactic, preventive or therapeutic treatment against diseases or conditions caused by pathogens. In a preferred embodiment, the present invention relates to the use of the compounds of formula (I) for prophylactic, post-exposure prophylactic, preventive or therapeutic treatment against diseases or conditions caused by pathogens which may be used in bioterrorism.

In recent years, a variety of research programs and biodefense measures have been put into place to deal with concerns about the use of biological agents in acts of terrorism. These measures are intended to address concerns regarding bioterrorism or the use of microorganisms or biological toxins to kill people, spread fear, and disrupt society. For example, the National Institute of Allergy and Infectious Diseases (NIAID) has developed a Strategic Plan for Biodefense Research which outlines plans for addressing research needs in the broad area of bioterrorism and emerging and reemerging infectious diseases. According to the plan, the deliberate exposure of the civilian population of the United States to *Bacillus anthracis* spores revealed a gap in the nation's overall preparedness against bioterrorism. Moreover, the report details that these attacks uncovered an unmet need for tests to rapidly diagnose, vaccines and immunotherapies to prevent, and drugs and biologics to cure disease caused by agents of bioterrorism.

Much of the focus of the various research efforts has been directed to studying the biology of the pathogens identified as potentially dangerous as bioterrorism agents, studying the host response against such agents, developing vaccines against infectious diseases, evaluating the therapeutics currently available and under investigation against such agents, and developing diagnostics to identify signs and symptoms of threatening agents. Such efforts are laudable but, given the large number of pathogens which have been identified as potentially available for bioterrorism, these efforts have not yet been able to provide satisfactory responses for all possible bioterrorism threats. Additionally, many of the pathogens identified as potentially dangerous as agents of bioterrorism do not provide adequate economic incentives for the development of therapeutic or preventive measures by industry. Moreover, even if preventive measures such as vaccines were available for each pathogen which may be used in bioterrorism, the cost of administering all such vaccines to the general population is prohibitive.

Until convenient and effective treatments are available against every bioterrorism threat, there exists a strong need for preventative, prophylactic or therapeutic treatments which can prevent or reduce the risk of infection from pathogenic agents.

The present invention provides such methods of prophylactic treatment. In one aspect, a prophylactic treatment method is provided comprising administering a prophylactically effective amount of the compounds of formula (I) to an individual in need of prophylactic treatment against infection from one or more airborne pathogens. A particular example of an airborne pathogen is anthrax.

In another aspect, a prophylactic treatment method is provided for reducing the risk of infection from an airborne pathogen which can cause a disease in a human, said method comprising administering an effective amount of the compounds of formula (I) to the lungs of the human who may be at risk of infection from the airborne pathogen but is asymptomatic for the disease, wherein the effective amount of a sodium channel blocker and osmolye are sufficient to reduce the risk of infection in the human. A particular example of an airborne pathogen is anthrax.

In another aspect, a post-exposure prophylactic treatment or therapeutic treatment method is provided for treating infection from an airborne pathogen comprising administering an effective amount of the compounds of formula (I) to the lungs of an individual in need of such treatment against infection from an airborne pathogen. The pathogens which may be protected against by the prophylactic post exposure, rescue and therapeutic treatment methods of the invention include any pathogens which may enter the body through the mouth, nose or nasal airways, thus proceeding into the lungs. Typically, the pathogens will be airborne pathogens, either naturally occurring or by aerosolization. The pathogens may be naturally occurring or may have been introduced into the environment intentionally after aerosolization or other method of introducing the pathogens into the environment. Many pathogens which are not naturally transmitted in the air have been or may be aerosolized for use in bioterrorism. The pathogens for which the treatment of the invention may be useful includes, but is not limited to, category A, B and C priority pathogens as set forth by the NIAID. These categories correspond generally to the lists compiled by the Centers for Disease Control and Prevention (CDC). As set up by the CDC, Category A agents are those that can be easily disseminated or transmitted person-to-person, cause high mortality, with potential for major public health impact. Category B agents are next in priority and include those that are moderately easy to disseminate and cause moderate morbidity and low mortality. Category C consists of emerging pathogens that could be engineered for mass dissemination in the future because of their availability, ease of production and dissemination and potential for high morbidity and mortality. Particular examples of these pathogens are anthrax and plague. Additional pathogens which may be protected against or the infection risk therefrom reduced include influenza viruses, rhinoviruses, adenoviruses and respiratory syncytial viruses, and the like. A further pathogen which may be protected against is the coronavirus which is believed to cause severe acute respiratory syndrome (SARS).

The present invention also relates to the use of sodium channel blockers of Formula I, or a pharmaceutically acceptable salt thereof, for preventing, mitigating, and/or treating deterministic health effects to the respiratory tract caused by exposure to radiological materials, particularly respirable aerosols containing radionuclides from nuclear attacks, such as detonation of radiological dispersal devices (RDD), or accidents, such as nuclear power plant disasters. As such, provided herein is a method for preventing, mitigating, and/or treating deterministic health effects to the respiratory tract and/or other bodily organs caused by respirable aerosols containing radionuclides in a recipient in need thereof, including in a human in need thereof, said method comprising administering to said human an effective amount of a compound of Formula (I), or a pharmaceutically acceptable salt thereof.

A major concern associated with consequence management planning for exposures of members of the public to respirable aerosols containing radionuclides from nuclear attacks, such as detonation of radiological dispersal devices (RDD), or accidents, such as nuclear power plant disasters is how to prevent, mitigate or treat potential deterministic health effects to the respiratory tract, primarily the lung. It is necessary to have drugs, techniques and procedures, and trained personnel prepared to manage and treat such highly internally contaminated individuals.

Research has been conducted to determine ways in which to prevent, mitigate or treat potential damage to the respiratory tract and various organs in the body that is caused by internally deposited radionuclides. To date, most of the research attention has focused on strategies designed to mitigate health effects from internally deposited radionuclides by accelerating their excretion or removal. These strategies have focused on soluble chemical forms that are capable of reaching the blood stream and are deposited at remote systemic sites specific to a given radioelement. Such approaches will not work in cases where the deposited radionuclide is in relatively insoluble form. Studies have shown that many, if not most of the physicochemical forms of dispersed radionuclides from RDDs, will be in relatively insoluble form.

The only method known to effectively reduce the radiation dose to the lungs from inhaled insoluble radioactive aerosols is bronchoalveolar lavage or BAL. This technique, which was adapted from that already in use for the treatment of patients with alveolar proteinosis, has been shown to be a safe, repeatable procedure, even when performed over an extended period of time. Although there are variations in procedure, the basic method for BAL is to anaesthetize the subject, followed by the slow introduction of isotonic saline into a single lobe of the lung until the function residual capacity is reached. Additional volumes are then added and drained by gravity.

The results of studies using BAL on animals indicate that about 40% of the deep lung content can be removed by a reasonable sequence of BALs. In some studies, there was considerable variability among animals in the amount of radionuclide recovered. The reasons for the variability are currently not understood.

Further, based on a study on animals, it is believed that a significant dose reduction from BAL therapy results in mitigation of health effects due to inhalation of insoluble radionuclides. In the study, adult dogs inhaled insoluble $^{144}$Ce-FAP particles. Two groups of dogs were given lung contents of $^{144}$Ce known to cause radiation pneumonitis and pulmonary fibrosis (about 2 MBq/kg body mass), with one group being treated with 10 unilateral lavages between 2 and 56 days after exposure, the other untreated. A third group was exposed at a level of $^{144}$Ce comparable to that seen in the BAL-treated group after treatment (about 1 MBq/kg), but these animals were untreated. All animals were allowed to live their lifespans, which extended to 16 years. Because there is variability in initial lung content of $^{144}$Ce among the dogs in each group, the dose rates and cumulative doses for each group overlap. Nevertheless, the effect of BAL in reducing the risk from pneumonitis/fibrosis was evident from the survival curves. In the untreated dogs with lung contents of 1.5-2.5 MBq/kg, the mean survival time was 370±65 d. For the treated dogs, the mean survival was 1270±240 d, which was statistically significantly different. The third group, which received lung contents of $^{144}$Ce of 0.6-1.4 MBq had a mean survival time of 1800±230, which was not statistically different from the treated group. Equally important to the increased survival, the dogs in the high-dose untreated group died from deterministic effects to lung (pneumonitis/fibrosis) while the treated dogs did not. Instead, the treated dogs, like the dogs in the low-dose untreated group, mostly had lung tumors (hemangiosarcoma or carcinoma). Therefore, the reduction in dose resulting from BAL treatment appears to have produced biological effects in lung that were predictable based on the radiation doses that the lungs received.

Based on these results, it is believed that decreasing the residual radiological dose further by any method or combination of methods for enhancing the clearance of particles from the lung would further decrease the probability of health effects to lung. However, BAL is a procedure that has many drawbacks. BAL is a highly invasive procedure that must be performed at specialized medical centers by trained pulmonologists. As such, a BAL procedure is expensive. Given the drawbacks of BAL, it is not a treatment option that would be readily and immediately available to persons in need of accelerated removal of radioactive particles, for example, in the event of a nuclear attack. In the event of a nuclear attack or a nuclear accident, immediate and relatively easily administered treatment for persons who have been exposed or who are at risk of being exposed is needed. Sodium channel blockers administered as an inhalation aerosol have been shown to restore hydration of airway surfaces. Such hydration of airway surfaces aids in clearing accumulated mucus secretions and associated particulate matter from the lung. As such, without being bound by any particular theory, it is believed that sodium channel blockers can be used to accelerate the removal of radioactive particles from airway passages.

As discussed above, the greatest risk to the lungs following a radiological attack, such as a dirty bomb, results from the inhalation and retention of insoluble radioactive particles. As a result of radioactive particle retention, the cumulative exposure to the lung is significantly increased, ultimately resulting in pulmonary fibrosis/pneumonitis and potentially death. Insoluble particles cannot be systemically cleared by chelating agents because these particles are not in solution. To date, the physical removal of particulate matter through BAL is the only therapeutic regimen shown to be effective at mitigating radiation-induced lung disease. As discussed above, BAL is not a realistic treatment solution for reducing the effects of radioactive particles that have been inhaled into the body. As such, it is desirable to provide a therapeutic regimen that effectively aids in clearing radioactive particles from airway passages and that, unlike BAL, is relatively simple to administer and scalable in a large-scale radiation exposure scenario. In addition, it is also desirable that the therapeutic regimen be readily available to a number of people in a relatively short period of time.

In an aspect of the present invention, a method for preventing, mitigating, and/or treating deterministic health effects to the respiratory tract and/or other bodily organs caused by respirable aerosols containing radionuclides comprises administering an effective amount of a sodium channel blocker of Formula I or a pharmaceutically acceptable salt thereof to an individual in need. In a feature of this aspect, the sodium channel blocker is administered in conjunction with an osmolyte. With further regard to this feature, the osmolyte is hypertonic saline (HS). In a further feature, the sodium channel blocker and the osmolyte are administered in conjunction with an ion transport modulator.

With further regard to this feature, the ion transport modulator may be selected from the group consisting of β-agonists, CFTR potentiators, purinergic receptor agonists, lubiprostones, and protease inhibitors. In another feature of this aspect, the radionuclides are selected from the group consisting of Colbalt-60, Cesium-137, Iridium-192, Radium-226, Phospohrus-32, Strontium-89 and 90, Iodine-125, Thallium-201, Lead-210, Thorium-234, Uranium-238, Plutonium, Cobalt-58, Chromium-51, Americium, and Curium. In a further feature, the radionuclides are from a radioactive disposal device. In yet another feature, the sodium channel blocker or pharmaceutically acceptable salt thereof is administered in an aerosol suspension of respirable particles which the individual inhales. In an additional feature, the sodium channel blocker or a pharmaceutically acceptable salt thereof is administered post-exposure to the radionuclides.

Compositions

While it is possible for a compound of the invention to be administered alone, in some embodiments it is preferable to present it in the form of a composition, particularly a pharmaceutical composition (formulation). Thus, in another aspect, the invention provides compositions, and particularly pharmaceutical compositions (such as an inhalable pharmaceutical composition) comprising a pharmaceutically effective amount of a compound of the invention as an active ingredient, and a pharmaceutically acceptable excipient, diluent or carrier. The term "active ingredient" as employed herein refers to any compound of the invention or combination of two or more compounds of the invention in a pharmaceutical composition. Also provided are specific embodiments in which a pharmaceutical composition comprises a pharmaceutically effective amount of a compound of Formulas (I), (Ia), (II), (III), (IV), (V), (VI), and (VII), or a pharmaceutically acceptable salt thereof, independently or in combination, and a pharmaceutically acceptable excipient, diluent or carrier.

In some embodiments, the pharmaceutical composition comprises a pharmaceutically effective amount of a compound of Formulas (I), (Ia), (II), (III), (IV), (V), (VI), and (VII), or a pharmaceutically acceptable salt thereof, independently or in combination, in a diluent. In separate embodiments, the pharmaceutical composition comprises a pharmaceutically effective amount of a compound of Formulas (I), (Ia), (II), (III), (IV), (V), (VI), and (VII), or a pharmaceutically acceptable salt thereof, in hypertonic saline, sterile water, and hypertonic saline, respectively, wherein the saline concentration can be as described herein. In one embodiment the saline concentration is 0.17% w/v and in another it is 2.8% w/v.

Also provided is a kit comprising i) a pharmaceutically effective amount of a compound of Formula (I), (Ia), (II), (III), (IV), (V), (VI), and (VII), or a pharmaceutically acceptable salt thereof; ii) one or more pharmaceutically acceptable excipients, carriers, or diluents; iii) instructions for administering the compound of group i) and the excipients, carriers, or diluents of group ii) to a subject in need thereof; and; iv) a container. A subject in need thereof includes any subject in need of the methods of treatment described herein, particularly including a human subject in need thereof. Further embodiments also comprise an aerosolization device selected from the group of a nebulizer, including vibrating mesh nebulizers and jet nebulizers, a dry powder inhaler, including active and passive dry powder inhalers, and a metered dose inhaler, including pressurized, dry powder, and soft mist metered dose inhalers.

In one embodiment a kit comprises i) from about 10 ng to about 10 mg of a compound of Formula (I), (Ia), (II), (III), (IV), (V), (VI), and (VII), or a pharmaceutically acceptable salt thereof, per dose; ii) from about 1 to about 5 mL of diluent per dose; iii) instructions for administering the compound of group i) and the diluent of group ii) to a subject in need thereof; and; iv) a container. In a further embodiment, the diluent is from about 1 to about 5 mL of a saline solution, as described herein, per dose. In a further embodiment, the diluent is from about 1 to about 5 mL of a hypotonic saline solution per dose. In another embodiment, the diluent is from about 1 to about 5 mL of a hypertonic saline solution per dose. In a still further embodiment, the diluent is from about 1 to about 5 mL of sterile water per dose.

Also provided is a kit comprising i) a solution comprising a pharmaceutically effective amount of a compound of Formula (I), (Ia), (II), (III), (IV), (V), (VI), and (VII), or a pharmaceutically acceptable salt thereof; dissolved in a pharmaceutically acceptable diluent; iii) instructions for administering the solution of group i) to a subject in need thereof; and iii) a container.

Also provided is a kit comprising i) a solution comprising from about 10 ng to about 10 mg of a compound of Formula (I), (Ia), (II), (III), (IV), (V), (VI), and (VII), or a pharmaceutically acceptable salt thereof; dissolved in a pharmaceutically acceptable diluent; iii) instructions for administering the solution of group i) to a subject in need thereof; and iii) a container. In a further embodiment, the diluent is from about 1 to about 5 mL of a saline solution, as described herein, per dose.

Another embodiment comprises a kit comprising i) a pharmaceutically effective amount of a compound of Formula (I), (Ia), (II), (III), (IV), (V), (VI), and (VII), or a pharmaceutically acceptable salt thereof; in a dry powder formulation suitable for inhalation ii) optionally, one or more pharmaceutically acceptable excipients or carriers suitable for inhalation; iii) instructions for administering the compound of group i) and the excipients or carriers of group ii) to a subject in need thereof; and; iv) a container. In a further embodiment, the kit also comprises a dry powder inhaler suitable for delivering the dry powder formulation to a recipient. The dry powder inhaler may be, in additional embodiments, a single-dose inhaler or a multi-dose inhaler.

Further embodiments of each of the kits described herein includes those in which the concentration of the compound of Formula (I), (Ia), (II), (III), (IV), (V), (VI), and (VII), or a pharmaceutically acceptable salt thereof, per dose, is one of the effective dose ranges described herein, including a) from about 0.1 μg to about 1,000 jag; b) from about 0.5 jag to about 0.5 mg; and c) from about 0.5 jag to about 50 jag.

For each of the kits described above there is an additional embodiment in which the diluent is hypertonic saline of the concentrations described herein. In another embodiment for each kit the diluent is hypotonic saline of the concentrations described herein. In a further embodiment for each kit, the diluent is sterile water suitable for inhalation.

The pharmaceutically acceptable excipient(s), diluent(s) or carrier(s) must be acceptable in the sense of being compatible with the other ingredients of the formulation and not deleterious to the recipient thereof. Generally, the pharmaceutically acceptable excipient(s), diluent(s) or carrier(s) employed in the pharmaceutical formulation are "non-toxic" meaning that it/they is/are deemed safe for consumption in the amount delivered in the formulation and "inert" meaning that it/they does/do not appreciable react with or result in an undesired effect on the therapeutic activity of the active ingredient(s). Pharmaceutically acceptable excipients, diluents and carriers are conventional in the art and may be selected using conventional techniques, based upon the desired route of administration. See, REMINGTON'S, PHARMACEUTICAL SCIENCES, Lippincott Williams & Wilkins; 21$^{st}$ Ed (May 1, 2005). Preferably, the pharmaceutically acceptable excipient(s), diluent(s) or carrier(s) are Generally Regarded As Safe (GRAS) according to the FDA.

Pharmaceutical compositions according to the invention include those suitable for oral administration; parenteral administration, including subcutaneous, intradermal, intramuscular, intravenous and intraarticular; topical administration, including topical administration to the skin, eyes, ears, etc; vaginal or rectal administration; and administration to the respiratory tract, including the nasal cavities and sinuses, oral and extrathoracic airways, and the lungs, including by use of aerosols which may be delivered by means of various types of dry powder inhalers, pressurized metered dose inhalers, softmist inhalers, nebulizers, or insufflators. The most suitable route of administration may depend upon, several factors including the patient and the condition or disorder being treated.

The formulations may be presented in unit dosage form or in bulk form as for example in the case of formulations to be metered by an inhaler and may be prepared by any of the methods well known in the art of pharmacy. Generally, the methods include the step of bringing the active ingredient into association with the carrier, diluent or excipient and optionally one or more accessory ingredients. In general the formulations are prepared by uniformly and intimately bringing into association the active ingredient with one or more liquid carriers, diluents or excipients or finely divided solid carriers, diluents or excipients, or both, and then, if necessary, shaping the product into the desired formulation.

In one preferred embodiment, the composition is an inhalable pharmaceutical composition which is suitable for inhalation and delivery to the endobronchial space. Typically, such composition is in the form of an aerosol comprising particles for delivery using a nebulizer, pressurized metered dose inhaler (MDI), softmist inhaler, or dry powder inhaler (DPI). The aerosol formulation used in the methods of the present invention may be a liquid (e.g., solution) suitable for administration by a nebulizer, softmist inhaler, or MDI, or a dry powder suitable for administration by an MDI or DPI.

Aerosols used to administer medicaments to the respiratory tract are typically polydisperse; that is they are comprised of particles of many different sizes. The particle size distribution is typically described by the Mass Median Aerodynamic Diameter (MMAD) and the Geometric Standard Deviation (GSD). For optimum drug delivery to the endobronchial space the MMAD is in the range from about 1 to about 10 μm and preferably from about 1 to about 5 μm, and the GSD is less than 3, and preferably less than about 2. Aerosols having a MMAD above 10 μm are generally too large when inhaled to reach the lungs. Aerosols with a GSD greater than about 3 are not preferred for lung delivery as they deliver a high percentage of the medicament to the oral cavity. To achieve these particle sizes in powder formulation, the particles of the active ingredient may be size reduced using conventional techniques such as micronisation or spray drying. Non-limiting examples of other processes or techniques that can be used to produce respirable particles include spray drying, precipitation, supercritical fluid, and freeze drying. The desired fraction may be separated out by air classification or sieving. In one embodiment, the particles will be crystalline. For liquid formulations, the particle size is determined by the selection of a particular model of nebulizer, softmist inhaler, or MDI.

Aerosol particle size distributions are determined using devices well known in the art. For example a multi-stage Anderson cascade impactor or other suitable method such as those specifically cited within the US Pharmacopoeia Chapter 601 as characterizing devices for aerosols emitted from metered-dose and dry powder inhalers.

Dry powder compositions for topical delivery to the lung by inhalation may be formulated without excipient or carrier and instead including only the active ingredients in a dry powder form having a suitable particle size for inhalation. Dry powder compositions may also contain a mix of the active ingredient and a suitable powder base (carrier/diluent/excipient substance) such as mono-, di- or poly-saccharides (e.g., lactose or starch). Lactose is typically the preferred excipient for dry powder formulations. When a solid excipient such as lactose is employed, generally the particle size of the excipient will be much greater than the active ingredient to aid the dispersion of the formulation in the inhaler.

Non-limiting examples of dry powder inhalers include reservoir multi-dose inhalers, pre-metered multi-dose inhalers, capsule-based inhalers and single-dose disposable inhalers. A reservoir inhaler contains a large number of doses (e.g. 60) in one container. Prior to inhalation, the patient actuates the inhaler which causes the inhaler to meter one dose of medicament from the reservoir and prepare it for inhalation. Examples of reservoir DPIs include but are not limited to the Turbohaler® by AstraZeneca and the ClickHaler® by Vectura.

In a pre-metered multi-dose inhaler, each individual dose has been manufactured in a separate container, and actuation of the inhaler prior to inhalation causes a new dose of drug to be released from its container and prepared for inhalation. Examples of multidose DPI inhalers include but are not limited to Diskus® by GSK, Gyrohaler® by Vectura, and Prohaler® by Valois. During inhalation, the inspiratory flow of the patient accelerates the powder out of the device and into the oral cavity. For a capsule inhaler, the formulation is in a capsule and stored outside the inhaler. The patient puts a capsule in the inhaler, actuates the inhaler (punctures the capsule), then inhales. Examples include the Rotohaler™ (GlaxoSmithKline), Spinhaler™ (Novartis), HandiHaler™ (IB), TurboSpin™ (PH&T). With single-dose disposable inhalers, the patient actuates the inhaler to prepare it for inhalation, inhales, then disposes of the inhaler and packaging. Examples include the Twincer™ (U Groningen), OneDose™ (GFE), and Manta Inhaler™ (Manta Devices).

Generally, dry powder inhalers utilize turbulent flow characteristics of the powder path to cause the excipient-drug aggregates to disperse, and the particles of active ingredient are deposited in the lungs. However, certain dry powder inhalers utilize a cyclone dispersion chamber to produce particles of the desired respirable size. In a cyclone dispersion chamber, the drug enters a coin shaped dispersion chamber tangentially so that the air path and drug move along the outer circular wall. As the drug formulation moves along this circular wall it bounces around and agglomerates are broken apart by impact forces. The air path spirals towards the center of the chamber exiting vertically. Particles that have small enough aerodynamic sizes can follow the air path and exit the chamber. In effect, the dispersion chamber works like a small jet mill. Depending on the specifics of the formulation, large lactose particles may be added to the formulation to aid in the dispersion through impact with the API particles.

The Twincer™ single-dose disposable inhaler appears to operate using a coin-shaped cyclone dispersion chamber referred to as an "air classifier." See, U.S. Published Patent Application No. 2006/0237010 to Rijksuniversiteit Groningen. Papers published by the University of Groningen, have stated that a 60 mg dose of pure micronized colistin sulfomethate could be effectively delivered as an inhalable dry powder utilizing this technology.

In preferred embodiments, the aerosol formulation is delivered as a dry powder using a dry powder inhaler wherein the particles emitted from the inhaler have an MMAD in the range of about 1 µm to about 5 µm and a GSD about less than 2.

Examples of suitable dry powder inhalers and dry powder dispersion devices for use in the delivery of compounds and compositions according to the present invention include but are not limited to those disclosed in U.S. Pat. No. 7,520,278; U.S. Pat. No. 7,322,354; U.S. Pat. No. 7,246,617; U.S. Pat. No. 7,231,920; U.S. Pat. No. 7,219,665; U.S. Pat. No. 7,207,330; U.S. Pat. No. 6,880,555; U.S. Pat. No. 5,522,385; U.S. Pat. No. 6,845,772; U.S. Pat. No. 6,637,431; U.S. Pat. No. 6,329,034; U.S. Pat. No. 5,458,135; U.S. Pat. No. 4,805,811; and U.S. Published Patent Application No. 2006/0237010.

In one embodiment, the pharmaceutical formulation according to the invention is a dry powder for inhalation which is formulated for delivery by a Diskus®-type device. The Diskus® device comprises an elongate strip formed from a base sheet having a plurality of recesses spaced along its length and a lid sheet hermetically but peelably sealed thereto to define a plurality of containers, each container having therein an inhalable formulation containing a predetermined amount of active ingredient either alone or in admixture with one or more carriers or excipients (e.g., lactose) and/or other therapeutically active agents. Preferably, the strip is sufficiently flexible to be wound into a roll. The lid sheet and base sheet will preferably have leading end portions which are not sealed to one another and at least one of the leading end portions is constructed to be attached to a winding means. Also, preferably the hermetic seal between the base and lid sheets extends over their whole width. To prepare the dose for inhalation, the lid sheet may preferably be peeled from the base sheet in a longitudinal direction from a first end of the base sheet.

In one embodiment, the pharmaceutical formulation according to the invention is a dry powder for inhalation which is formulated for delivery using a single-dose disposable inhaler, and particularly the Twincer™ inhaler. The Twincer™ inhaler comprises a foil laminate blister with one or more recesses and a lid sheet hermetically but peelably sealed thereto to define a plurality of containers. Each container has therein an inhalable formulation containing a predetermined amount of active ingredient(s) either alone or in admixture with one or more carriers or excipients (e.g., lactose). The lid sheet will preferably have a leading end portion which is constructed to project from the body of the inhaler. The patient would operate the device and thereby administer the aerosol formulation by 1) removing the outer packaging overwrap, 2) pulling the foil tab to uncover the drug in the blister and 3) inhaling the drug from the blister.

In another embodiment, the pharmaceutical formulation according to the invention is a dry powder for inhalation wherein the dry powder is formulated into microparticles as described in PCT Publication No. WO2009/015286 or WO2007/114881, both to NexBio. Such microparticles are generally formed by adding a counter ion to a solution containing a compound of the invention in a solvent, adding an antisolvent to the solution; and gradually cooling the solution to a temperature below about 25° C., to form a composition containing microparticles comprising the compound. The microparticles comprising the compound may then be separated from the solution by any suitable means such as sedimentation, filtration or lyophillization. Suitable counterions, solvents and antisolvents for preparing microparticles of the compounds of the invention are described in WO2009/015286.

In another embodiment, a pharmaceutical composition according to the invention is delivered as a dry powder using a metered dose inhaler. Non-limiting examples of metered dose inhalers and devices include those disclosed in U.S. Pat. No. 5,261,538; U.S. Pat. No. 5,544,647; U.S. Pat. No. 5,622,163; U.S. Pat. No. 4,955,371; U.S. Pat. No. 3,565,070; U.S. Pat. No. 3,361,306 and U.S. Pat. No. 6,116,234 and U.S. Pat. No. 7,108,159. In a preferred embodiment, a compound of the invention is delivered as a dry powder using a metered dose inhaler wherein the emitted particles have an MMAD that is in the range of about 1 µm to about 5 µm and a GSD that is less than about 2.

Liquid aerosol formulations for delivery to the endobronchial space or lung by inhalation may for example be formulated as aqueous solutions or suspensions or as aerosols delivered from pressurized packs, such as metered dose inhalers, with the use of suitable liquefied propellants, softmist inhalers, or nebulizers. Such aerosol compositions suitable for inhalation can be either a suspension or a solution and generally contain the active ingredient(s) together with a pharmaceutically acceptable carrier or diluent (e.g., water (distilled or sterile), saline, hypertonic saline, or ethanol) and optionally one or more other therapeutically active agents.

Aerosol compositions for delivery by pressurized metered dose inhalers typically further comprise a pharmaceutically acceptable propellant. Examples of such propellants include fluorocarbon or hydrogen-containing chlorofluorocarbon or mixtures thereof, particularly hydrofluoroalkanes, e.g., dichlorodifluoromethane, trichlorofluoromethane, dichlorotetrafluoroethane, especially 1,1,1,2-tetrafluoroethane, 1,1,1,2,3,3,3,-heptafluoro-n-propane or a mixture thereof. The aerosol composition may be excipient free or may optionally contain additional formulation excipients well known in the art such as surfactants e.g., oleic acid or lecithin and cosolvents e.g., ethanol. Pressurized formulations will generally be retained in a canister (e.g., an aluminum canister) closed with a valve (e.g., a metering valve) and fitted into an actuator provided with a mouthpiece.

In another embodiment, a pharmaceutical composition according to the invention is delivered as a liquid using a metered dose inhaler. Non-limiting examples of metered dose inhalers and devices include those disclosed in U.S. Pat. Nos. 6,253,762, 6,413,497, 7,601,336, 7,481,995, 6,743,413, and 7,105,152. In a preferred embodiment, a compound of the invention is delivered as a dry powder using a metered dose inhaler wherein the emitted particles have an MMAD that is in the range of about 1 µm to about 5 µm and a GSD that is less than about 2.

In one embodiment the aerosol formulation is suitable for aerosolization by a jet nebulizer, or ultrasonic nebulizer including static and vibrating porous plate nebulizers. Liquid aerosol formulations for nebulization may be generated by solubilizing or reconstituting a solid particle formulation or may be formulated with an aqueous vehicle with the addition of agents such as acid or alkali, buffer salts, and isotonicity adjusting agents. They may be sterilized by in-process techniques such as filtration, or terminal processes such as heating in an autoclave or gamma irradiation. They may also be presented in non-sterile form.

Patients can be sensitive to the pH, osmolality, and ionic content of a nebulized solution. Therefore these parameters should be adjusted to be compatible with the active ingredient and tolerable to patients. The most preferred solution or suspension of active ingredient will contain a chloride concentration >30 mM at pH 4.5-7.4, preferably 5.0-5.5, and an osmolality of from about 800-1600 mOsm/kg. The pH of the solution can be controlled by either titration with common acids (hydrochloric acid or sulfuric acid, for example) or bases (sodium hydroxide, for example) or via the use of buffers. Commonly used buffers include citrate buffers, such as citric acid/sodium citrate buffers, acetate buffers, such as acetic acid/sodium acetate buffers, and phosphate buffers. Buffer strengths can range from 2 mM to 50 mM.

Useful acetate, phosphate, and citrate buffers include sodium acetate, sodium acetate trihydrate, ammonium acetate, potassium acetate, sodium phosphate, sodium phosphate dibasic, disodium hydrogen phosphate, potassium dihydrogen phosphate, potassium hydrogen phosphate, potassium phosphate, sodium citrate, and potassium citrate. Other buffers which may be utilized include sodium hydroxide, potassium hydroxide, ammonium hydroxide, aminomethylpropanol, tromethamine, tetrahydroxypropyl ethylenediamine, citric acid, acetic acid, hydroxytricarboxylic acid or a salt thereof, such as a citrate or sodium citrate salt thereof, lactic acid, and salts of lactic acid including sodium lactate, potassium lactate, lithium lactate, calcium lactate, magnesium lactate, barium lactate, aluminum lactate, zinc lactate, silver lactate, copper lactate, iron lactate, manganese lactate, ammonium lactate, monoethanolamine, diethanolamine, triethanolamine, diisopropanolamine, as well as combinations thereof, and the like.

Such formulations may be administered using commercially available nebulizers or other atomizer that can break the formulation into particles or droplets suitable for deposition in the respiratory tract. Non-limiting examples of nebulizers which may be employed for the aerosol delivery of a composition of the invention include pneumatic jet nebulizers, vented or breath-enhanced jet nebulizers, or ultrasonic nebulizers including static or vibrating porous plate nebulizers. Commercially available nebulizers include the Aeroneb® Go nebulizer (Aerogen) and the eFlow nebulizer (Pari Pharma).

A jet nebulizer utilizes a high velocity stream of air blasting up through a column of water to generate droplets. Particles unsuitable for inhalation impact on walls or aerodynamic baffles. A vented or breath enhanced nebulizer works in essentially the same way as a jet nebulizer except that inhaled air passes through the primary droplet generation area to increase the output rate of the nebulizer while the patient inhales.

In an ultrasonic nebulizer, vibration of a piezoelectric crystal creates surface instabilities in the drug reservoir that cause droplets to be formed. In porous plate nebulizers pressure fields generated by sonic energy force liquid through the mesh pores where it breaks into droplets by Rayleigh breakup. The sonic energy may be supplied by a vibrating horn or plate driven by a piezoelectric crystal, or by the mesh itself vibrating. Non-limiting examples of atomizers include any single or twin fluid atomizer or nozzle that produces droplets of an appropriate size. A single fluid atomizer works by forcing a liquid through one or more holes, where the jet of liquid breaks up into droplets. Twin fluid atomizers work by either forcing both a gas and liquid through one or more holes, or by impinging a jet of liquid against another jet of either liquid or gas.

The choice of nebulizer which aerosolizes the aerosol formulation is important in the administration of the active ingredient(s). Different nebulizers have differing efficiencies based their design and operation principle and are sensitive to the physical and chemical properties of the formulation. For example, two formulations with different surface tensions may have different particle size distributions. Additionally, formulation properties such as pH, osmolality, and permeant ion content can affect tolerability of the medication, so preferred embodiments conform to certain ranges of these properties.

In a preferred embodiment, the formulation for nebulization is delivered to the endobronchial space as an aerosol having an MMAD between about 1 μm and about 5 μm and a GSD less than 2 using an appropriate nebulizer. To be optimally effective and to avoid upper respiratory and systemic side effects, the aerosol should not have a MMAD greater than about 5 μm and should not have a GSD greater than about 2. If an aerosol has an MMAD larger than about 5 μm or a GSD greater than about 2 a large percentage of the dose may be deposited in the upper airways decreasing the amount of drug delivered to the desired site in the lower respiratory tract. If the MMAD of the aerosol is smaller than about 1 μm then a large percentage of the particles may remain suspended in the inhaled air and may then be exhaled during expiration.

The compounds of the invention may also be administered by transbronchoscopic lavage.

Formulations suitable for oral administration may be presented as discrete units such as capsules, cachets or tablets, each containing a predetermined amount of the active ingredient; as a powder or granules; as a solution or suspension in an aqueous liquid or a non-aqueous liquid; or as an oil-in-water liquid emulsion or a water-in-oil liquid emulsion. The active ingredient may also be presented as a sachet, bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binders, lubricant, inert diluent, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for topical administration in the mouth, for example buccally or sublingually, include lozenges, comprising the active ingredient in a flavored base such as sucrose and acacia or tragacanth, and pastilles comprising the active ingredient in a base such as gelatin and glycerin or sucrose and acacia.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example saline or water-for-injection, immediately prior to use. Extemporaneous injection solutions and suspensions may be prepared from sterile powders, granules and tablets of the kind previously described.

Oral fluids such as solutions, syrups and elixirs can be prepared in dosage unit form so that a given quantity contains a predetermined amount of the active ingredient. Syrups can be prepared by dissolving the active ingredient in a suitably flavored aqueous solution, while elixirs are prepared through the use of a pharmaceutically acceptable alcoholic vehicle. Suspensions can be formulated by dispersing the active ingredient in a pharmaceutically acceptable vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be incorporated into oral liquid compositions.

Liposome delivery systems such as small unilamellar vesicles, large unilamellar vesicles and multilamellar vesicles may also be employed as delivery means for the compounds of the invention. Liposomes may be formed from a variety of phospholipids such as cholesterol, stearylamine and phosphatidylcholines.

Pharmaceutical compositions for topical administration may be formulated as ointments, creams, suspensions, lotions, powders, solutions, pastes, gels, sprays, aerosols or oils. Compositions designed for the treatment of the eyes or other external tissues, for example the mouth and skin, may be applied as a topical ointment or cream. When formulated as an ointment, the active ingredient may be employed with either a paraffinic or a water-miscible ointment base. Alternatively, the active ingredient may be formulated in a cream with an oil-in-water cream base or a water-in-oil base.

Other compositions designed for topical administration to the eyes or ears include eye drops and ear drops wherein the active ingredient is dissolved or suspended in a suitable carrier, such as for example an aqueous solvent, including saline.

Compositions designed for nasal administration include aerosols, solutions, suspensions, sprays, mists and drops. Aerosolable formulations for nasal administration may be formulated in much the same ways as aerosolable formulations for inhalation with the condition that particles of non-respirable size will be preferred in formulations for nasal administration. Typically, particles of about 5 microns in size, up to the size of visible droplets may be employed. Thus, for nasal administration, a particle size in the range of 10-500 μm may be used to ensure retention in the nasal cavity.

Transdermal patches may also be employed, which are designed to remain in contact with the epidermis of the patient for an extended period of time and promote the absorption of the active ingredient there through.

Compositions for vaginal or rectal administration include ointments, creams, suppositories and enemas, all of which may be formulated using conventional techniques.

In another aspect, the invention provides a method of promoting hydration of mucosal surfaces or restoring mucosal defense in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of: a disease associated with reversible or irreversible airway obstruction, chronic obstructive pulmonary disease (COPD), asthma, bronchiectasis (including bronchiectasis due to conditions other than cystic fibrosis), acute bronchitis, chronic bronchitis, post-viral cough, cystic fibrosis, emphysema, pneumonia, panbronchiolitis, transplant-associate bronchiolitis, and ventilator-associated tracheobronchitis or preventing ventilator-associated pneumonia in a human in need thereof, comprising administering to the human a pharmaceutical composition comprising a compound of the invention, wherein said compound is administered in an effective amount. In one preferred embodiment, the method comprises administering the pharmaceutical composition as an inhalable composition comprising an amount of a compound of the invention that is sufficient to achieve dissolved concentration of the compound on the airway surfaces of from about $10^{-9}$, $10^{-8}$, or $10^{-7}$ to about $10^{-4}$, $10^{-3}$, $10^{-2}$, or $10^{-1}$ Moles/liter, more preferably from about $10^{-9}$ to about $10^{-4}$ Moles/liter.

In another aspect, the invention provides a method of treating any one of dry mouth (xerostomia), dry skin, vaginal dryness, sinusitis, rhinosinusitis, or nasal dehydration, including nasal dehydration brought on by administering dry oxygen, dry eye or Sjogren's disease, promoting ocular or corneal hydration, treating distal intestinal obstruction syndrome, treating otitis media, primary ciliary diskinesia, distal intestinal obstruction syndrome, esophagitis, constipation, or chronic diverticulitis in a human in need thereof, comprising administering to the human a pharmaceutical composition comprising a compound of the invention, wherein said compound is administered in an effective amount.

Preferred unit dosage formulations for the compounds of the invention are those containing an effective amount of the active ingredient or an appropriate fraction thereof.

It should be understood that in addition to the ingredients particularly mentioned above, the formulations of this invention may include other agents conventional in the art having regard to the type of formulation in question for example those suitable for oral administration may include flavoring agents.

The compositions of the present invention may be formulated for immediate, controlled or sustained release as desired for the particular condition being treated and the desired route of administration. For example, a controlled release formulation for oral administration may be desired for the treatment of constipation in order to maximize delivery of the active agent to colon. Such formulations and suitable excipients for the same are well known in the art of pharmacy. Because the free base of the compound is generally less soluble in aqueous solutions than the salt, compositions comprising a free base of a compound of Formula I may be employed to provide more sustained release of active agent delivered by inhalation to the lungs. An active agent present in the lungs in particulate form which has not dissolved into solution is not available to induce a physiological response, but serves as a depot of bioavailable drug which gradually dissolves into solution. As another example, a formulation may employ both a free base and salt form of a compound of the invention to provide both immediate release and sustained release of the active ingredient for dissolution into the mucus secretions of, for example, the nose.

Combinations

The compounds of the invention may be formulated and/or used in combination with other therapeutically active agents. Examples of other therapeutically active agents which may be formulated or used in combination with the compounds of the invention include but are not limited to osmolytes, anti-inflammatory agents, anticholinergic agents, β-agonists (including selective $β_2$-agonists), P2Y2 receptor agonists, peroxisome proliferator-activated receptor (PPAR) delta agonists, other epithelial sodium channel blockers (ENaC receptor blockers), cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants. In addition, for cardiovascular indications, the compounds of the invention may be used in combination with beta blockers, ACE inhibitors, HMGCoA reductase inhibitors, calcium channel blockers and other cardiovascular agents.

The present invention thus provides, as another aspect, a composition comprising an effective amount of a compound of the invention and one or more other therapeutically active agents selected from osmolytes, anti-inflammatory agents, anticholinergic agents, β-agonists (including selective $β_2$-agonists), P2Y2 receptor agonists, PPAR delta agonists, ENaC receptor blockers, cystic fibrosis transmembrane conductance regulator (CFTR) modulators, kinase inhibitors, antiinfective agents, antihistamines, non-antibiotic anti-inflammatory macrolides, elastase and protease inhibitors, and mucus or mucin modifying agents, such as surfactants. The present invention thus provides, as another aspect, a composition comprising an effective amount of a compound of the invention and one or more other therapeutically active agents selected from beta blockers, ACE inhibitors, HMG-CoA reductase inhibitors, and calcium channel blockers. Use of the compounds of the invention in combination with one or more other therapeutically active agents (particularly osmolytes) may lower the dose of the compound of the invention that is required to sufficiently hydrate mucosal surfaces, thereby reducing the potential for undesired side-effects attributable to systemic blocking of sodium channels such as for example in the kidneys.

"Osmolytes" according to the present invention are molecules or compounds that are osmotically active. "Osmotically active" molecules and compounds are membrane-impermeable (i.e., essentially non-absorbable) on the airway or pulmonary epithelial surface. The terms "airway surface" and "pulmonary surface," as used herein, include pulmonary airway surfaces such as the bronchi and bronchioles, alveolar surfaces, and nasal and sinus surfaces. Suitable osmolytes include ionic osmolytes (i.e., salts), and non-ionic osmolytes (i.e., sugars, sugar alcohols, and organic osmolytes). In general, osmolytes (both ionic and non-ionic) used in combination with the compounds of the invention are preferably osmolytes that do not promote, or in fact deter or retard bacterial growth. Osmolytes suitable for use in the present invention may be in racemic form or in the form of an enantiomer, diastereomer, tautomer, polymorph or pseudopolymorph.

Examples of ionic osmolytes useful in the present invention include any salt of a pharmaceutically acceptable anion and a pharmaceutically acceptable cation. Preferably, either (or both) of the anion and cation are osmotically active and not subject to rapid active transport, in relation to the airway surfaces to which they are administered. Such compounds include but are not limited to anions and cations that are contained in FDA approved commercially marketed salts, see, e.g., *Remington: The Science and Practice of Pharmacy*, Vol. II, pg. 1457 ($19^{th}$ Ed. 1995), and can be used in any combination as known in the art.

Specific examples of pharmaceutically acceptable osmotically active anions include but are not limited to, acetate, benzenesulfonate, benzoate, bicarbonate, bitartrate, bromide, calcium edetate, camsylate (camphorsulfonate), carbonate, chloride, citrate, dihydrochloride, edetate, edisylate (1,2-ethanedisulfonate), estolate (lauryl sulfate), esylate (1,2-ethanedisulfonate), fumarate, gluceptate, gluconate, glutamate, glycollylarsanilate (p-glycollamidophenylarsonate), hexylresorcinate, hydrabamine (N,N'-Di(dehydroabietyl)ethylenediamine), hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, nitrite, pamoate (embonate), pantothenate, phosphate or diphosphate, polygalacturonate, salicylate, stearate, subacetate, succinate, sulfate, tannate, tartrate, teoclate (8-chlorotheophyllinate), triethiodide, bicarbonate, etc. Preferred anions include chloride, sulfate, nitrate, gluconate, iodide, bicarbonate, bromide, and phosphate.

Specific examples of pharmaceutically acceptable osmotically active cations include but are not limited to, organic cations such as benzathine (N,N'-dibenzylethylenediamine), chloroprocaine, choline, diethanolamine, ethylenediamine, meglumine (N-methyl D-glucamine), procaine, D-lysine, L-lysine, D-arginine, L-arginine, triethylammonium, N-methyl D-glycerol, and the like; and metallic cations such as aluminum, calcium, lithium, magnesium, potassium, sodium, zinc, iron, ammonium, and the like. Preferred organic cations include 3-carbon, 4-carbon, 5-carbon and 6-carbon organic cations. Preferred cations include sodium, potassium, choline, lithium, meglumine, D-lysine, ammonium, magnesium, and calcium.

Specific examples of ionic osmolytes that may be used in combination with a compound of the invention include but are not limited to, sodium chloride (particularly hypertonic saline), potassium chloride, choline chloride, choline iodide, lithium chloride, meglumine chloride, L-lysine chloride, D-lysine chloride, ammonium chloride, potassium sulfate, potassium nitrate, potassium gluconate, potassium iodide, ferric chloride, ferrous chloride, potassium bromide, and combinations of any two or more of the foregoing. In one embodiment, the present invention provides a combination of a compound of the invention and two different osmotically active salts. When different salts are used, one of the anion or cation may be the same among the differing salts. Hypertonic saline is a preferred ionic osmolyte for use in combination with the compounds of the invention.

Non-ionic osmolytes include sugars, sugar-alcohols, and organic osmolytes. Sugars and sugar-alcohols useful as osmolytes in the present invention include but are not limited to 3-carbon sugars (e.g., glycerol, dihydroxyacetone); 4-carbon sugars (e.g., both the D and L forms of erythrose, threose, and erythrulose); 5-carbon sugars (e.g., both the D and L forms of ribose, arabinose, xylose, lyxose, psicose, fructose, sorbose, and tagatose); and 6-carbon sugars (e.g., both the D and L forms of altose, allose, glucose, mannose, gulose, idose, galactose, and talose, and the D and L forms of allo-heptulose, allo-hepulose, gluco-heptulose, manno-heptulose, gulo-heptulose, ido-heptulose, galacto-heptulose, talo-heptulose). Additional sugars useful in the practice of the present invention include raffinose, raffinose series oligosaccharides, and stachyose. Both the D and L forms of the reduced form of each sugar/sugar alcohol are also suitable for the present invention. For example, glucose, when reduced, becomes sorbitol; an osmolyte within the scope of the invention. Accordingly, sorbitol and other reduced forms of sugar/sugar alcohols (e.g., mannitol, dulcitol, arabitol) are suitable osmolytes for use in the present invention. Mannitol is a preferred non-ionic osmolyte for use in combination with the compounds of the invention.

"Organic osmolytes" is generally used to refer to molecules that control intracellular osmolality in the kidney. See e.g., J. S. Handler et al., *Comp. Biochem. Physiol*, 117, 301-306 (1997); M. Burg, *Am. J. Physiol*. 268, F983-F996 (1995). Organic osmolytes include but are not limited to three major classes of compounds: polyols (polyhydric alcohols), methylamines, and amino acids. Suitable polyol organic osmolytes include but are not limited to, inositol, myo-inositol, and sorbitol. Suitable methylamine organic osmolytes include but are not limited to, choline, betaine, carnitine (L-, D- and DL forms), phosphorylcholine, lysophosphorylcholine, glycerophosphorylcholine, creatine, and creatine phosphate. Suitable amino acid organic osmolytes include but are not limited to, the D- and L-forms of glycine, alanine, glutamine, glutamate, aspartate, proline and taurine. Additional organic osmolytes suitable for use in the present invention include tihulose and sarcosine. Mammalian organic osmolytes are preferred, with human organic osmolytes being most preferred. However, certain organic osmolytes are of bacterial, yeast, and marine animal origin, and these compounds may also be employed in the present invention.

Osmolyte precursors may be used in combination with the compounds of the invention An "osmolyte precursor" as used herein refers to a compound which is converted into an osmolyte by a metabolic step, either catabolic or anabolic. Examples of osmolyte precursors include but are not limited to, glucose, glucose polymers, glycerol, choline, phosphatidylcholine, lyso-phosphatidylcholine and inorganic phosphates, which are precursors of polyols and methylamines. Precursors of amino acid osmolytes include proteins, peptides, and polyamino acids, which are hydrolyzed to yield osmolyte amino acids, and metabolic precursors which can be converted into osmolyte amino acids by a metabolic step such as transamination. For example, a precursor of the amino acid glutamine is poly-L-glutamine, and a precursor of glutamate is poly-L-glutamic acid.

Chemically modified osmolytes or osmolyte precursors may also be employed. Such chemical modifications involve linking the osmolyte (or precursor) to an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., *J. Med. Chem*. 19:113-117 (1976); Bodor, N. et al., *J. Pharm. Sci*. 67:1045-1050 (1978); Bodor, N. et al., *J. Med. Chem*. 26:313-318 (1983); Bodor, N. et al., *J. Pharm. Sci*. 75:29-35 (1986).

Preferred osmolytes for use in combination with the compounds of the invention include sodium chloride, particular hypertonic saline, and mannitol.

For the formulation of 7% and >7% hypertonic saline, formulations containing bicarbonate anions may be particularly useful, especially for respiratory disorders with cystic fibrosis transmembrane conductance regulator (CFTR) dysfunction such as CF or COPD. Recent findings indicate that, although the relative ratio of $HCO_3^-$ conductance/$Cl^-$ conductance is between 0.1 and 0.2 for single CFTR channels activated with cAMP and ATP, the ratio in the sweat duct can range from virtually 0 to almost 1.0, depending on conditions of stimulation. That is, combining cAMP+cGMP+α-ketoglutarate can yield CFTR $HCO_3$ conductance almost equal to that of $Cl^-$ conductance (Quiton et al. Physiology, Vol. 22, No. 3, 212-225, June 2007). Furthermore, formulations of 7% and >7% hypertonic saline containing bicarbonate anions may be particularly useful due to better control of the pH in the airway surface liquid. First, it has shown that that airway acidification occurs in CF (Tate et al. 2002) and that absent CFTR-dependent bicarbonate secretion can lead to an impaired capacity to respond to airway conditions associated with acidification of airway surface liquid layer (Coakley et al. 2003). Second, addition of HS solution without bicarbonate to the surface of the lung may further dilute the bicarbonate concentrations, and potentially reduce the pH or the ability to respond to airway acidification within the airway surface liquid layer. Therefore addition of bicarbonate anions to HS may help maintain or improve the pH of airway surface liquid layer in CF patients.

Due to this evidence, inclusion of bicarbonate anion in the formulation of 7% or >7% hypertonic saline administered by the method of this invention would be particularly useful. Formulations containing up to 30 to 200 mM concentrations of bicarbonate anions are of particular interest for 7% or >7% HS solutions.

Hypertonic saline is understood to have a salt concentration greater than that of normal saline (NS), i.e. greater than 9 g/L or 0.9% w/v, and hypotonic saline has a salt concentration less than that of normal saline, such as from about 1 g or L/0.1% w/v to about 8 g/L or 0.8% w/v. Hypertonic saline solutions useful in the formulations and methods of treatment herein may have a salt concentration from about 1% to about 23.4% (w/v). In one embodiment the hypertonic saline solution has a salt concentration from about 60 g/L (6% w/v) to about 100 g/L (10% w/v). In another embodiment, the saline solution has a salt concentration from about 70 g/L (7% w/v) to about 100 g/L (10% w/v). In further embodiments, the saline solution has salt concentrations of
a) from about 0.5 g/L (0.05% w/v) to about 70 g/L (7% w/v);
b) from about 1 g/L (0.1% w/v) to about 60 g/L (6% w/v);
c) from about 1 g/L (0.1% w/v) to about 50 g/L (5% w/v);
d) from about 1 g/L (0.1% w/v) to about 40 g/L (4% w/v);
e) from about 1 g/L (0.1% w/v) to about 30 g/L (3% w/v);
and f) from about 1 g/L (0.1% w/v) to about 20 g/L (2% w/v).

Specific concentrations of saline solutions useful in the formulations and methods of treatment herein include, independently, those having salt concentrations of 1 g/L (0.1% w/v), 2 g/L (0.2% w/v), 3 g/L (0.3% w/v), 4 g/L (0.4% w/v), 5 g/L (0.5% w/v), 6 g/L (0.6% w/v), 7 g/L (0.7% w/v), 8 g/L (0.8% w/v), 9 g/L (0.9% w/v), 10 g/L (1% w/v), 20 g/L (2% w/v), 30 g/L (3% w/v), 40 g/L (4% w/v), 50 g/L (5% w/v), 60 g/L (6% w/v), 70 g/L (7% w/v), 80 g/L (8% w/v), 90 g/L (9% w/v), 100 g/L (10% w/v), 110 g/L (11% w/v), 120 g/L (12% w/v), 130 g/L (13% w/v), 140 g/L (14% w/v), 150 g/L (15% w/v), 160 g/L (16% w/v), 170 g/L (17% w/v), 180 g/L (18% w/v), 190 g/L (19% w/v), 200 g/L (20% w/v), 210 g/L (21% w/v), 220 g/L (22% w/v), and 230 g/L (23% w/v).

Saline concentrations between each of these listed concentrations/percentages may also be used, such as saline of 1.7 g/L (0.17% w/v), 1.25 g/L (1.25% w/v), 1.5 g/L (1.5% w/v), 25 g/L (2.5% w/v), 28 g/L (2.8% w/v), 35 g/L (3.5% w/v), 45 g/L (4.5% w/v), and 75 g/L (7.5% w/v).

Specific useful concentration of hypotonic saline solutions include those from about 0.12 g/L (0.012% w/v) to about 8.5 g/L (0.85% w/v). Any concentration within this range may be used, such as, on a w/v basis, 0.05%, 0.1%, 0.15%, 0.2%, 0.225% (¼ NS), 0.25%, 0.3% (⅓ NS), 0.35%, 0.4%, 0.45% (½ NS), 0.5%, 0.55%, 0.6% (⅔ NS), 0.65%, 0.675% (¾ NS), 0.7%, 0.75%, and 0.8%.

Each of the ranges and specific concentrations of saline described herein may be used with the formulations, methods of treatment, regimens, and kits described herein.

Also intended within the scope of this invention are chemically modified osmolytes or osmolyte precursors. Such chemical modifications involve linking to the osmolyte (or precursor) an additional chemical group which alters or enhances the effect of the osmolyte or osmolyte precursor (e.g., inhibits degradation of the osmolyte molecule). Such chemical modifications have been utilized with drugs or prodrugs and are known in the art. (See, for example, U.S. Pat. Nos. 4,479,932 and 4,540,564; Shek, E. et al., J. Med. Chem. 19:113-117 (1976); Bodor, N. et al., J. Pharm. Sci. 67:1045-1050 (1978); Bodor, N. et al., J. Med. Chem. 26:313-318 (1983); Bodor, N. et al., J. Pharm. Sci. 75:29-35 (1986), each incorporated herein by reference.

Suitable anti-inflammatory agents for use in combination with the compounds of the invention include corticosteroids and non-steroidal anti-inflammatory drugs (NSAIDs), particularly phosphodiesterase (PDE) inhibitors. Examples of corticosteroids for use in the present invention include oral or inhaled corticosteroids or prodrugs thereof. Specific examples include but are not limited to ciclesonide, desisobutyryl-ciclesonide, budesonide, flunisolide, mometasone and esters thereof (e.g., mometasone furoate), fluticasone propionate, fluticasone furoate, beclomethasone, methyl prednisolone, prednisolone, dexamethasone, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g., the 17-propionate ester or the 17,21-dipropionate ester, fluoromethyl ester, triamcinolone acetonide, rofleponide, or any combination or subset thereof. Preferred corticosteroids for formulation or use in combination with the compounds of the invention are selected from ciclesonide, desisobutyryl-ciclesonide, budesonide, mometasone, fluticasone propionate, and fluticasone furoate, or any combination or subset thereof.

NSAIDs for use in the present invention include but are not limited to sodium cromoglycate, nedocromil sodium, phosphodiesterase (PDE) inhibitors (e.g., theophylline, aminophylline, PDE4 inhibitors, mixed PDE3/PDE4 inhibitors or mixed PDE4/PDE7 inhibitors), leukotriene antagonists, inhibitors of leukotriene synthesis (e.g., 5 LO and FLAP inhibitors), nitric oxide synthase (iNOS) inhibitors, protease inhibitors (e.g., tryptase inhibitors, neutrophil elastase inhibitors, and metalloprotease inhibitors) β2-integrin antagonists and adenosine receptor agonists or antagonists (e.g., adenosine 2a agonists), cytokine antagonists (e.g., chemokine antagonists) or inhibitors of cytokine synthesis (e.g., prostaglandin D2 (CRTh2) receptor antagonists). Examples of leukotriene modifiers suitable for administration by the method of this invention include montelukast, zileuton and zafirlukast.

The PDE4 inhibitor, mixed PDE3/PDE4 inhibitor or mixed PDE4/PDE7 inhibitor may be any compound that is known to inhibit the PDE4 enzyme or which is discovered to act as a PDE4 inhibitor, and which are selective PDE4 inhibitors (i.e., compounds which do not appreciably inhibit other members of the PDE family). Examples of specific PDE4 inhibitors for formulation and use in combination with the compounds of the present invention include but are not limited to roflumilast, pumafentrine, arofylline, cilomilast, tofimilast, oglemilast, tolafentrine, piclamilast, ibudilast, apremilast, 2-[4-[6,7-diethoxy-2,3-bis(hydroxymethyl)-1-naphthalenyl]-2-pyridinyl]-4-(3-pyridinyl)-1(2H)-phthalazinone (T2585), N-(3,5-dichloro-4-pyridinyl)-1-[(4-fluorophenyl)methyl]-5-hydroxy-α-oxo-H-indole-3-acetamide (AWD-12-281, 4-[(2R)-2-[3-(cyclopentyloxy)-4-methoxyphenyl]-2-phenylethyl]-pyridine (CDP-840), 2-[4-[[[[2-(1,3-benzodioxol-5-yloxy)-3-pyridinyl]carbonyl]amino]methyl]-3-fluorophenoxy]-(2R)-propanoic acid (CP-671305), N-(4,6-dimethyl-2-pyrimidinyl)-4-[4,5,6,7-tetrahydro-2-(4-methoxy-3-methylphenyl)-5-(4-methyl-1-piperazinyl)-1H-indol-1-yl]-benzenesulfonamide, (2E)-2-butenedioate (YM-393059), 9-[(2-fluorophenyl)methyl]-N-methyl-2-(trifluoromethyl)-9H-purin-6-amine (NCS-613), N-(2,5-dichloro-3-pyridinyl)-8-methoxy-5-quinolinecarboxamide (D-4418), N-[(3R)-9-amino-3,4,6,7-tetrahydro-4-oxo-1-phenylpyrrolo[3,2,1-i][1,4]benzodiazepin-3-yl]-3H-purin-6-amine (PD-168787), 3-[[3-(cyclopentyloxy)-4-methoxyphenyl]methyl]-N-ethyl-8-(1-methylethyl)-3H-purin-6-amine hydrochloride (V-11294A), N-(3,5-dichloro-1-oxido-4-pyridinyl)-8-methoxy-2-(trifluoromethyl)-5-quinolinecarboxamide (Sch351591), 5-[3-(cyclopentyloxy)-4-methoxyphenyl]-3-[(3-methylphenyl)methyl]-(3S,5S)-2-piperidinone (HT-0712), 5-(2-((1R,4R)-4-amino-1-(3-(cyclopentyloxy)-4-methyoxyphenyl)cyclohexyl) ethynyl)-pyrimidine-2-amine,cis-[4-cyano-4-(3-cyclopropylmethoxy-4-difluoromethoxy phenyl) cyclohexan-1-ol], and 4-[6,7-diethoxy-2,3-bis (hydroxymethyl)-1-naphthalenyl]-1-(2-methoxyethyl)-2 (1H)-pyridinone (T-440), and any combination or subset thereof.

Leukotriene antagonists and inhibitors of leukotriene synthesis include zafirlukast, montelukast sodium, zileuton, and pranlukast.

Anticholinergic agents for formulation or use in combination with the compounds of the invention include but are not limited to muscarinic receptor antagonists, particularly including pan antagonists and antagonists of the $M_3$ receptors. Exemplary compounds include the alkaloids of the belladonna plants, such as atropine, scopolamine, homatropine, hyoscyamine, and the various forms including salts thereof (e.g., anhydrous atropine, atropine sulfate, atropine oxide or HCl, methylatropine nitrate, homatropine hydrobromide, homatropine methyl bromide, hyoscyamine hydrobromide, hyoscyamine sulfate, scopolamine hydrobromide, scopolamine methyl bromide), or any combination or subset thereof.

Additional anticholinergics for formulation and use in combination with the methantheline, propantheline bromide, anisotropine methyl bromide or Valpin 50, aclidinium bromide, glycopyrrolate (Robinul), isopropamide iodide, mepenzolate bromide, tridihexethyl chloride, hexocyclium methylsulfate, cyclopentolate HCl, tropicamide, trihexyphenidyl CCl, pirenzepine, telenzepine, and methoctramine, or any combination or subset thereof.

Preferred anticholinergics for formulation and use in combination with the compounds of the invention include ipratropium (bromide), oxitropium (bromide) and tiotropium (bromide), or any combination or subset thereof.

Examples of β-agonists for formulation and use in combination with the compounds of the invention include but are not limited to salmeterol, R-salmeterol, and xinafoate salts thereof, albuterol or R-albuterol (free base or sulfate), levalbuterol, salbutamol, formoterol (fumarate), fenoterol, procaterol, pirbuterol, metaprterenol, terbutaline and salts thereof, and any combination or subset thereof.

P2Y2 receptor agonists for formulation and use in combination with the compounds of the invention may be employed in an amount effective to stimulate chloride and water secretion by airway surfaces, particularly nasal airway surfaces. Suitable P2Y2 receptor agonists are known in the art and are described for example, in columns 9-10 of U.S. Pat. No. 6,264,975, and also U.S. Pat. Nos. 5,656,256 and 5,292,498.

$P2Y_2$ agonists that can be administered by the methods of this invention include $P2Y_2$ receptor agonists such as ATP, UTP, UTP-.gamma.-S and dinucleotide $P2Y_2$ receptor agonists (e.g. denufosol or diquafosol) or a pharmaceutically acceptable salt thereof. The $P2Y_2$ receptor agonist is typically included in an amount effective to stimulate chloride and water secretion by airway surfaces, particularly nasal airway surfaces. Suitable $P2Y_2$ receptor agonists are described in, but are not limited to, U.S. Pat. No. 6,264,975, U.S. Pat. No. 5,656,256, U.S. Pat. No. 5,292,498, U.S. Pat. No. 6,348,589, U.S. Pat. No. 6,818,629, U.S. Pat. No. 6,977,246, U.S. Pat. No. 7,223,744, U.S. Pat. No. 7,531,525 and U.S. Pat. AP.2009/0306009 each of which is incorporated herein by reference.

Combination therapies and formulations herein can include adenosine 2b (A2b) agonists, also, including BAY 60-6583, NECA (N-ethylcarboxamidoadenosine), (S)-PHP-NECA, LUF-5835 and LUF-5845. A2b agonists that may be used are described by Volpini et al., *Journal of Medicinal Chemistry* 45 (15): 3271-9 (2002); Volpini et al., *Current Pharmaceutical Design* 8 (26): 2285-98 (2002); Baraldi et al., *Journal of Medicinal Chemistry* 47 (6): Cacciari et al., 1434-47 (2004); *Mini Reviews in Medicinal Chemistry* 5 (12): 1053-60 (December 2005); Baraldi et al., *Current Medicinal Chemistry* 13 (28): 3467-82 (2006); Beukers et al., *Medicinal Research Reviews* 26 (5): 667-98 (September 2006); Elzein et al., *Bioorganic & Medicinal Chemistry Letters* 16 (2): 302-6 (January 2006); Carotti, et al., *Journal of Medicinal Chemistry* 49 (1): 282-99 (January 2006); Tabrizi et al., *Bioorganic & Medicinal Chemistry* 16 (5): 2419-30 (March 2008); and Stefanachi, et al., *Bioorganic & Medicinal Chemistry* 16 (6): 2852-69 (March 2008).

Examples of other ENaC receptor blockers for formulation and use in combination with the compounds of the invention include but are not limited to amiloride and derivatives thereof such as those compounds described in U.S. Pat. No. 6,858,615, and PCT Publication Nos. WO2003/070182, WO2004/073629, WO2005/018644, WO2006/022935, WO2007/018640, and WO2007/146869, all to Parion Sciences, Inc.

Small molecule ENaC blockers are capable of directly preventing sodium transport through the ENaC channel pore. ENaC blocker that can be administered in the combinations herein include, but are not limited to, amiloride, benzamil, phenamil, and amiloride analogues as exemplified by U.S. Pat. No. 6,858,614, U.S. Pat. No. 6,858,615, U.S. Pat. No. 6,903,105, U.S. Pat. No. 6,995,160, U.S. Pat. No. 7,026,325, U.S. Pat. No. 7,030,117, U.S. Pat. No. 7,064,129, U.S. Pat. No. 7,186,833, U.S. Pat. No. 7,189,719, U.S. Pat. No. 7,192,958, U.S. Pat. No. 7,192,959, U.S. Pat. No. 7,241,766, U.S. Pat. No. 7,247,636, U.S. Pat. No. 7,247,637, U.S. Pat. No. 7,317,013, U.S. Pat. No. 7,332,496, U.S. Pat. No. 7,345,044, U.S. Pat. No. 7,368,447, U.S. Pat. No. 7,368,450, U.S. Pat. No. 7,368,451, U.S. Pat. No. 7,375,107, U.S. Pat. No. 7,399,766, U.S. Pat. No. 7,410,968, U.S. Pat. No. 7,820,678, U.S. Pat. No. 7,842,697, U.S. Pat. No. 7,868,010, U.S. Pat. No. 7,875,619.

ENaC proteolysis is well described to increase sodium transport through ENaC. Protease inhibitor block the activity of endogenous airway proteases, thereby preventing ENaC cleavage and activation. Protease that cleave ENaC include furin, meprin, matriptase, trypsin, channel associated proteases (CAPs), and neutrophil elastases. Protease inhibitors that can inhibit the proteolytic activity of these proteases that can be administered in the combinations herein include, but are not limited to, camostat, prostasin, furin, aprotinin, leupeptin, and trypsin inhibitors.

Combinations herein may include one or more suitable nucleic acid (or polynucleic acid), including but not limited to antisense oligonucleotide, siRNA, miRNA, miRNA mimic, antagomir, ribozyme, aptamer, and decoy oligonucleotide nucleic acids. See, e.g., US Patent Application Publication No. 20100316628. In general, such nucleic acids may be from 17 or 19 nucleotides in length, up to 23, 25 or 27 nucleotides in length, or more. Examples include, but are not limited to, those described in U.S. Pat. No. 7,517,865 and US Patent Applications Nos. 20100215588; 20100316628; 20110008366; and 20110104255. In general, the siRNAs are from 17 or 19 nucleotides in length, up to 23, 25 or 27 nucleotides in length, or more.

CFTR activity modulating compounds that can be administered in the combinations of this invention include, but are not limited to, compounds described in US 2009/0246137 A1, US 2009/0253736 A1, US 2010/0227888 A1, U.S. Pat. No. 7,645,789, US 2009/0246820 A1, US 2009/0221597 A1, US 2010/0184739 A1, US 2010/0130547 A1, US 2010/0168094 A1 and issued U.S. Pat. No. 7,553,855; U.S. Pat. No. 7,772,259 B2, U.S. Pat. No. 7,405,233 B2, US 2009/0203752, U.S. Pat. No. 7,499,570.

Mucus or mucin modifying agents useful in the combinations and methods herein include reducing agents, surfactants and detergents, expectorants, and deoxyribonuclease agents.

Mucin proteins are organized into high molecular weight polymers via the formation of covalent (disulfide) and non-covalent bonds. Disruption of the covalent bonds with reducing agents is a well-established method to reduce the viscoelastic properties of mucus in vitro and is predicted to minimize mucus adhesiveness and improve clearance in vivo. Reducing agents are well known to decrease mucus viscosity in vitro and commonly used as an aid to processing sputum samples. Examples of reducing agents include sulfide containing molecules or phosphines capable of reducing protein di-sulfide bonds including, but not limited to, N-acetyl cysteine, N-acystelyn, carbocysteine, glutathione, dithiothreitol, thioredoxin containing proteins, and tris (2-carboxyethyl) phosphine.

N-acetyl cysteine (NAC) is approved for use in conjunction with chest physiotherapy to loosen viscid or thickened airway mucus. Clinical studies evaluating the effects of oral or inhaled NAC in CF and COPD have reported improvements in the rheologic properties of mucus and trends toward improvements in lung function and decreases in pulmonary exacerbations[9]. However, the preponderance of clinical data suggests that NAC is at best a marginally effective therapeutic agent for treating airway mucus obstruction when administered orally or by inhalation. A recent Cochrane review of the existing clinical literature on the use of NAC found no evidence to support the efficacy of NAC for CF. The marginal clinical benefit of NAC reflects:

NAC is a relative inefficient reducing agent which is only partially active on the airway surface. Very high concentrations of NAC (200 mM or 3.26%) are required to fully reduce Muc5B, a major gel-forming airway mucin, in vitro. Furthermore, in the pH environment of the airway surface (measured in the range of pH 6.0 to 7.2 in CF and COPD airways), NAC exists only partially in its reactive state as a negatively charge thiolate. Thus, in the clinic, NAC is administered at very high concentrations. However, it is predicted that current aerosol devices will not be able to achieve therapeutic concentrations of even a 20% Mucomyst solution on distal airway surfaces within the relatively short time domains (7.5-15 minutes) typically used.

In non-clinical studies, $^{14}$C-labeled NAC, administered by inhalation, exhibits rapid elimination from the lungs with a half-life ranging from 6 to 36 minutes.

NAC is administered as a highly concentrated, hypertonic inhalation solution (20% or 1.22 molar) and has been reported to cause bronchoconstriction and cough. In many cases, it is recommended that NAC be administered with a bronchodilator to improve the tolerability of this agent.

Thus, reducing agents such as NAC are not well suited for bolus aerosol administration. However, it is anticipated that delivery of reducing agents by pulmonary aerosol infusion would increase the effectiveness, while allowing for a decrease in the concentration of reducing agent in the inhalation solution (predicted to increase tolerability).

Surfactants and detergents are spreading agents shown to decrease mucus viscoelasticity, improving mucus clearability. Examples of surfactants include dipalmitoylphosphatidylcholine (DPPC), PF, palmitic acid, palmitoyl-oleoylphosphatidylglycerol, surfactant-associated proteins (e.g. SP-A, B, or C), or may be animal derived (e.g. from cow or calf lung lavage or extracted from minced pig lung) or combinations thereof. See, e.g., U.S. Pat. Nos. 7,897,577; 5,876,970; 5,614,216; 5,100,806; and 4,312,860. Examples of surfactant products include Exosurfo Neonatal (colfosceril palmitate), Pumactant® (DPPC and egg phosphatidylglycerol), KL-4 surfactant, Venticute® (lusuptide, rSP-C surfactant), Alveofact® (bovactant), Curosurfo (poractant alfa), Infasurfo (calfactant), Newfacten® (modified bovine surfactant), Surface®, Natsurf™ (nonionic alcohol ethoxylate surfactant) and Survanta® (beractant). Examples of detergents include, but are not limited to, Tween-80 and triton-X 100.

Any suitable expectorant can be used, including but not limited to guaifenesin (see, e.g., U.S. Pat. No. 7,345,051). Any suitable deoxyribonuclease can be used, including but not limited to Dornase Alpha. (see, e.g., U.S. Pat. No. 7,482,024).

Examples of kinase inhibitors include inhibitors of NFkB, PI3K (phosphatidylinositol 3-kinase), p38-MAP kinase and Rho kinase.

Antiinfective agents for formulation and use in combination with the compounds of the invention include antivirals and antibiotics. Examples of suitable antivirals include Tamiflu® (oseltamivir) and Relenza® (zanamivir). Examples of suitable antibiotics include but are not limited to aztreonam (arginine or lysine), fosfomycin, and aminoglycosides such as tobramycin, or any combination or subset thereof. Additional antiinfective agents that may be used herein include aminoglycosides, Daptomycin, Fluoroquinolones, Ketolides, Carbapenems, Cephalosporins, Erythromycin, Linezolid, Penicillins, Azithromycin, Clindamycin, Oxazolidinones, Tetracyclines, and Vancomycin.

Examples of useful carbapenam antibiotics are impenam, panipenam, meropenam, biapenam, MK-826 (L-749,345), DA-1131, ER-35786, lenapenam, S-4661, CS-834 (prodrug of R-95867), KR-21056 (prodrug of KR-21012), L-084 (prodrug of LJC 11036) and Ceftolozane (CXA-101).

Antihistamines (i.e., H1-receptor antagonists) for formulation and use in combination with the compounds of the invention include but are not limited to: ethanolamines such as diphenhydramine HCl, carbinoxamine maleate, doxylamine, clemastine fumarate, diphenylhydramine HCl and dimenhydrinate; ethylenediamines such as pyrilamine maleate (metpyramine), tripelennamine HCl, tripelennamine citrate, and antazoline; alkylamines such as pheniramine, chloropheniramine, bromopheniramine, dexchlorpheniramine, triprolidine and acrivastine; pyridines such as methapyrilene, piperazines such as hydroxyzine HCl, hydroxyzine pamoate, cyclizine HCl, cyclizine lactate, meclizine HCl and cetirizine HCl; piperidines such as astemisole, levocabastine HCl, loratadine, descarboethoxyloratadine, terfenadine, and fexofenadine HCl; tri- and tetracyclics such as promethazine, chlorpromethazine trimeprazine and azatadine; and azelastine HCl, or any combination or subset thereof.

Examples of other classes of therapeutic agents suitable for use in the combinations and methods herein include antivirals such as ribavirin, anti-fungal agents such as amphotericin, intraconazol and voriconazol, anti-rejection drugs such as cyclosporine, tacrolimus and sirolimus, bronchodilators including but not limited to anticholinergic agents such as atrovent, siRNAs, gene therapy vectors, aptamers, endothelin-receptor antagonists, alpha-1-antitrypsin and prostacyclins.

In the above-described methods of treatment and uses, a compound of the invention may be employed alone, or in combination with one or more other therapeutically active agents. Typically, any therapeutically active agent that has a therapeutic effect in the disease or condition being treated with the compound of the invention may be utilized in combination with the compounds of the invention, provided that the particular therapeutically active agent is compatible with therapy employing a compound of the invention. Typical therapeutically active agents which are suitable for use in combination with the compounds of the invention include agents described above.

In one preferred embodiment, the compounds of the invention are used in combination with one or more osmolytes, particularly hypertonic saline or mannitol.

In another aspect, the invention provides methods for treatment and uses as described above, which comprise administering an effective amount of a compound of the invention and at least one other therapeutically active agent. The compounds of the invention and at least one additional therapeutically active agent may be employed in combination concomitantly or sequentially in any therapeutically appropriate combination. The administration of a compound of the invention with one or more other therapeutically active agents may be by administration concomitantly in 1) a unitary pharmaceutical composition, such as the compositions described above, or 2) separate pharmaceutical compositions each including one or more of the component active ingredients. The components of the combination may be administered separately in a sequential manner wherein the compound of the invention is administered first and the other therapeutically active agent is administered second or vice versa.

In the embodiments wherein the compound of the invention is administered in combination with one or more osmolytes, the administration of each component is preferably concomitant, and may be in a unitary composition or separate compositions. In one embodiment, the compound of the invention and one or more osmolytes are administered concomitantly by transbronchoscopic lavage. In another embodiment, the compound of the invention and one or more osmolytes are administered concomitantly by inhalation.

When a compound of the invention is used in combination with another therapeutically active agent, the dose of each compound may differ from that when the compound of the invention is used alone. Appropriate doses will be readily determined by one of ordinary skill in the art. The appropriate dose of the compound of the invention, the other therapeutically active agent(s) and the relative timings of administration will be selected in order to achieve the desired combined therapeutic effect, and are within the expertise and discretion of the attendant physician, clinician or veterinarian.

Experimental Procedures

The present invention also provides processes for preparing the compounds of the invention and to the synthetic intermediates useful in such processes, as described in detail below.

| Abbreviation | Meaning |
|---|---|
| AcOH | Acetic Acid |
| AIBN | Azobisisobutyrolnitrile |
| DIAD | Diisopropyl azidocarboxylate |
| DIPEA | N,N-Diisopropylethylamine |
| DCE | dichloroethane |
| DCM | dichloromethane |
| DMF | dimethylformamide |
| Et | Ethyl |
| EtOAc or EA | ethyl acetate |
| EtOH | Ethanol |
| ESI | electrospray ionization |
| HATU | 2-(1H-7-Azabenzotriazol-1-yl)-1,1,3,3-tetramethyl uronium hexafluorophosphate |
| HPLC | High performance liquid chromatography |
| iPrOH | Isopropyl alcohol |
| i.t. or IT | intratracheal |
| Me | Methyl |
| MeOH | methanol |
| m/z or m/e | mass to charge ratio |
| MH$^+$ | mass plus 1 |
| MH$^-$ | mass minus 1 |
| MIC | minimal inhibitory concentration |
| MS or ms | mass spectrum |
| rt or r.t. | room temperature |
| R$_f$ | Retardation factor |
| t-Bu | tert-butyl |
| THF | tetrahydrofuran |
| TLC or tlc | thin layer chromatography |
| δ | parts per million down field from tetramethylsilane |
| Cbz | Benzyloxycarbonyl, i.e. —(CO)O-benzyl |
| AUC | Area under the curve or peak |
| MTBE | Methyl tertiary butyl ether |
| AcOH | Acetic Acid |
| t$_R$ | Retention time |
| GC-MS | Gas chromatography-mass spectrometry |
| wt % | Percent by weight |
| h | Hours |
| min | Minutes |
| MHz | megahertz |
| TFA | Trifluoroacetic acid |
| UV | Ultraviolet |

-continued

| Abbreviation | Meaning |
|---|---|
| Boc | tert-butyloxycarbonyl |
| DIAD | Diisopropyl azodicarboxylate |
| AcOH | Acetic Acid |
| DIPEA | N,N-Diisopropylethylamine or Hünig's base |
| Ph$_3$P | Triphenylphosine |

The compounds of Formula I may be synthesized using techniques known in the art. A representative synthetic procedure is illustrated in Scheme 1 below.

Scheme 1

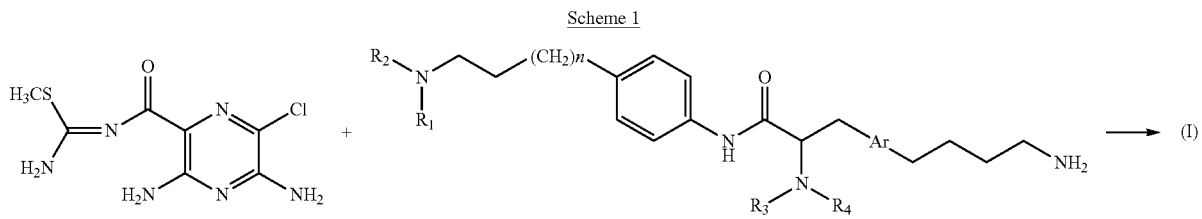

Certain abbreviations and acronyms are used in describing the synthetic processes and experimental details. Although most of these would be understood by one skilled in the art, the following table contains a list of many of these abbreviations and acronyms.

These procedures are described in, for example, E. J. Cragoe, "The Synthesis of Amiloride and Its Analogs" (Chap 3) in Amiloride and Its Analogs, pp. 25-36. Other processes for preparing amiloride analogs are described in, for example, U.S. Pat. No. 3,318,813, to Cragoe, particularly at methods A, B, C, and D of the '813 patent. Still other processes which may be adapted for the preparation of the compounds of the invention are described in PCT Publication Nos. WO2003/07182, WO2005/108644, WO2005/022935, U.S. Pat. No. 7,064,129, U.S. Pat. No. 6,858,615, U.S. Pat. No. 6,903,105, WO 2004/073629, WO 2007/146869, and WO 2007/018640, all assigned to Parion Sciences, Inc.

Preparation of methyl N'-3,5-diamino-6-chloropyrazine-2-carbonylcarbamimido thioate (2) can be seen in WO 2009/074575.

Generally, the compounds of the invention may be conveniently prepared by treating a compound of Formula II with an amine of Formula III. More specifically, compounds of Formula 2 are treated with the amine of Formula 3 in a suitable solvent such as methanol, ethanol, or tetrahydrofuran, and a base such as triethylamine (TEA), or di-isoproylethylamine (DIPEA), with heating to elevated temperature, e.g., 70° C. Further purification, resolution of stereoisomers, crystallization and/or preparation of salt forms may be carried out using conventional techniques.

As will be apparent to those skilled in the art, in certain instances, the starting or intermediate compounds in the synthesis may possess other functional groups which provide alternate reactive sites. Interference with such functional groups may be avoided by utilization of appropriate protecting groups, such as amine or alcohol protecting groups, and where applicable, appropriately prioritizing the synthetic steps. Suitable protecting groups will be apparent to those skilled in the art. Methods are well known in the art for installing and removing such protecting groups and such conventional techniques may be employed in the processes of the instant invention as well.

The following specific examples which are provided herein for purposes of illustration only and do not limit the scope of the invention, which is defined by the claims.

Material and methods. All reagent and solvents were purchased from Aldrich Chemical Corp., Chem-Impex International Inc. and TCI chemical industry Co. Ltd. NMR spectra were obtained on either a Bruker AC 400 ($^1$H NMR at 400 MHz and $^{13}$C NMR at 100 MHz) or a Bruker AC 300

(¹H NMR at 300 MHz and ¹³C NMR at 75 MHz). Proton spectra were referenced to tetramethylsilane as an internal standard and the carbon spectra were referenced to CDCl₃, CD₃OD, or DMSO-d₆ (purchased from Aldrich or Cambridge Isotope Laboratories, unless otherwise specified). Flash chromatography was performed on a Combiflash system (Combiflash Rf, Teledyne Isco) charged with silica gel column (Redi Sep. Rf, Teledyne Isco) or reverse phase column (High performance C18 Gold column). ESI Mass spectra were obtained on a Shimadzu LCMS-2010 E V Mass Spectrometer. HPLC analyses were obtained using a Waters XTerra MS C18 5 µm 4.6×150 mm Analytical Column detected at 220 nm (unless otherwise specified) on a Shimadzu Prominence HPLC system. The following time program was used with a flow rate of 1.0 mL per minute:

| Time (min) | Percent A ($H_2O$ with 0.05% TFA) | Percent B ($CH_3CN$ with 0.05% TFA) |
|---|---|---|
| 2.50 | 90 | 10 |
| 20.00 | 10 | 90 |
| 30.00 | 10 | 90 |
| 32.50 | 90 | 10 |

UPLC analyses were obtained using a Waters ACQUITY UPLC HSS T3 1.8 µm 2.1×100 mm Analytical Column detected at 220 nm (unless otherwise specified) on a Shimadzu Prominence UFLC system. The following time program was used with a flow rate of 0.3 mL per minute:

| Time (min) | Percent A ($H_2O$ with 0.05% $NH_4COOH$ and 0.1% HCOOH) | Percent B ($CH_3CN$/Water 80:20% with 0.05% $NH_4COOH$ and 0.1% HCOOH) |
|---|---|---|
| 1.00 | 90 | 10 |
| 4.00 | 30 | 70 |
| 5.00 | 30 | 70 |
| 5.50 | 90 | 10 |
| 6.50 | 90 | 10 |

1. Preparation of the hydrochloride salt of (S)-2-amino-3-(4-(4-(3-(3,5-diamino-6-chloropyrazine-2-carbonyl)guanidino)butyl)naphthalen-1-yl)propanoic acid (16)

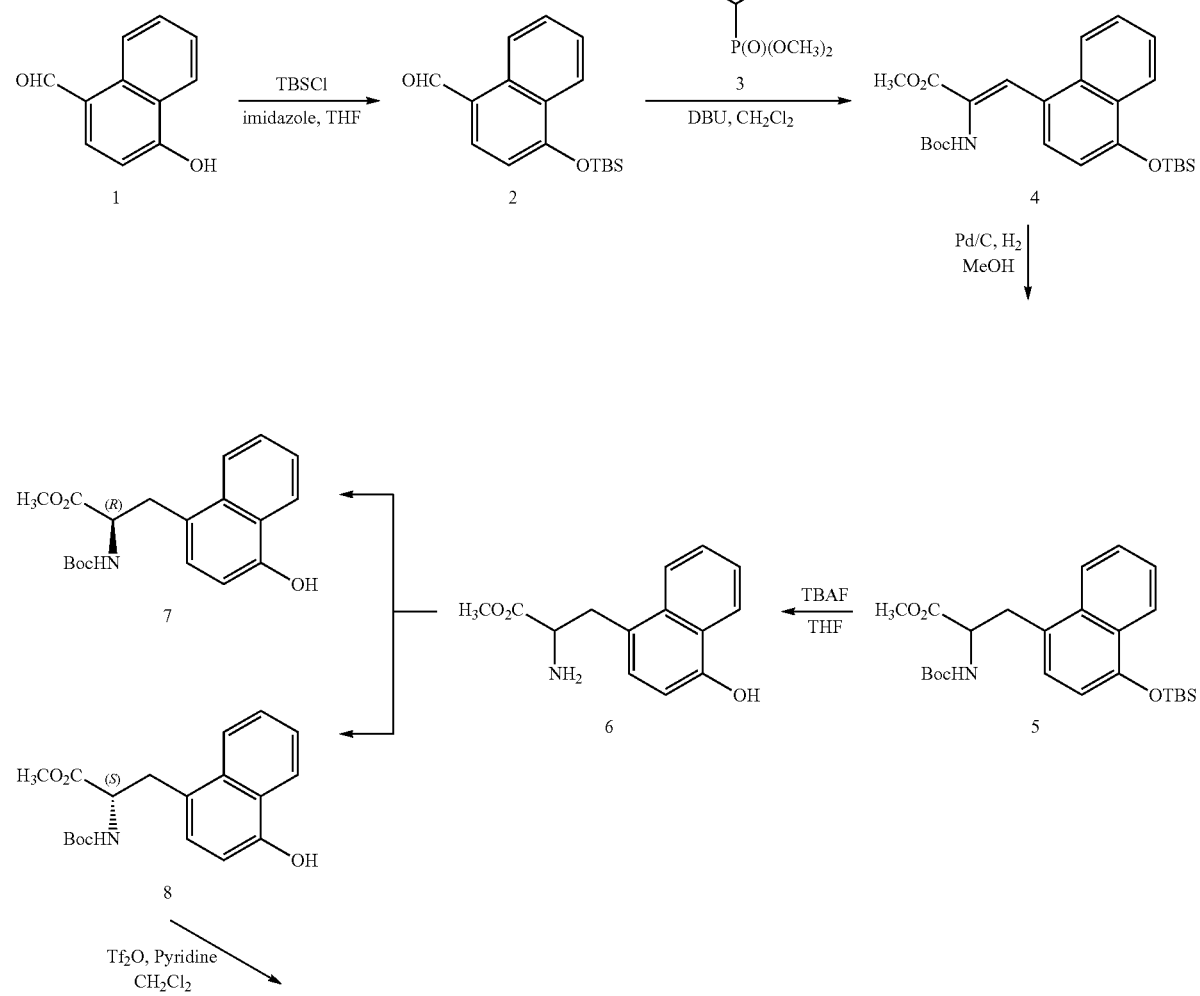

Scheme 2

51                                    52
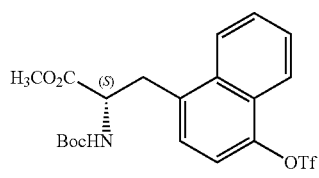
9
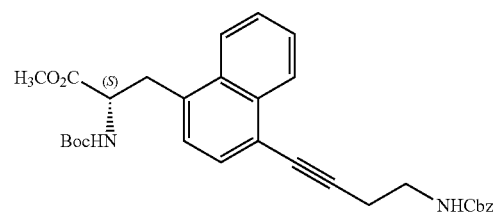
11
Pd/C, H₂, MeOH/AcOH ↓
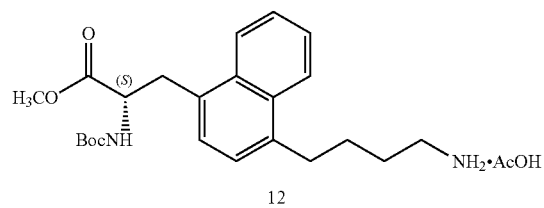
12
DIPEA, EtOH ↓
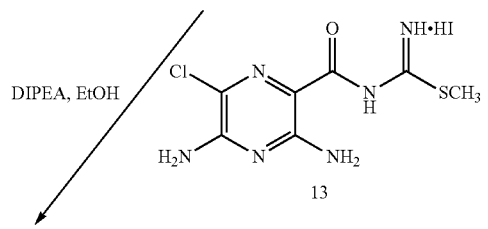
13
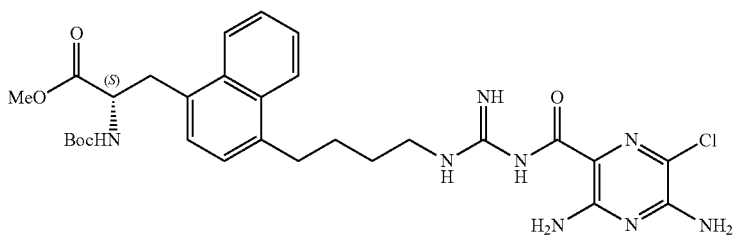
14
LiOH, MeOH/THF/H₂O ↓
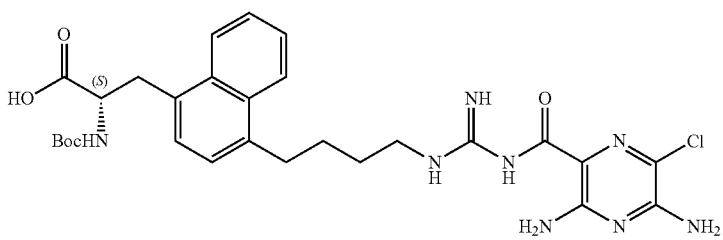
15
4N aq HCl ↓

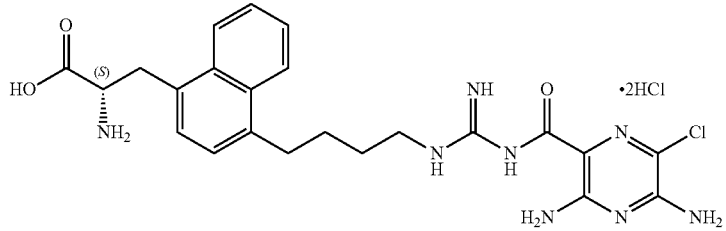

16

Preparation of 4-(tert-Butyldimethylsilyloxy)naphthalene-1-carbaldehyde (2)

A solution of 4-hydroxynaphthalene-1-carbaldehyde (1) (10.0 g, 58.1 mmol) in dry THF (200 mL) was cooled to 0° C., and imidazole (12.0 g, 174 mmol) and tert-butyldimethylsilyl chloride (TBSCl) (13.1 g, 87.1 mmol) were added sequentially. After stirring at room temperature for 16 h the reaction mixture was filtered and the solvent evaporated. The residue was taken up in EtOAc (500 mL), washed with saturated aqueous NH4Cl (100 mL), water (100 mL), and brine (100 mL), and dried over Na$_2$SO$_4$. The solvent was removed under reduced pressure and the residue purified by flash chromatography on silica gel (2% EtOAc/hexane), yielding 2 (14.8 g, 90%) as a pale yellow solid: $^1$H NMR (300 MHz, CDCl$_3$): δ 10.22 (s, 1H), 9.30 (d, J=8.10 Hz, 1H), 8.27 (d, J=8.1 Hz, 1H), 7.86 (d, J=7.8 Hz, 1H), 7.69 (ddd, J=8.4, 7.0, 1.3 Hz, 1H), 7.57 (ddd, J=8.4, 7.0, 1.3 Hz, 1H), 6.95 (d, J=7.5 Hz, 1H), 1.10 (s, 9H), 0.36 (s, 6H)

Preparation of (Z)-Methyl 2-(tert-Butyloxycarbonyl)amino-3-[1-(tert-butyldimethylsilyloxy)naphthalen-4-yl]acrylate (4)

A solution of (MeO)$_2$P(O)CH(NHBoc)CO$_2$Me, 3 (23.0 g, 52.7 mmol) in dry CH$_2$Cl$_2$ (100 mL) was charged with DBU (10.1 mL, 67.3 mmol), and the mixture was stirred for 30 min at 0° C. A solution of 1 (14.8 g, 51.74 mmol) in dry CH$_2$Cl$_2$ (60 mL) was added slowly via syringe, and the reaction mixture was warmed to room temperature over 16 h. After the solvent was removed under reduced pressure, the residue was dissolved in CH$_2$Cl$_2$ (500 mL), quickly washed with saturated aqueous NH$_4$Cl (2×150 mL) and brine (200 mL), and dried over Na$_2$SO$_4$. The solvent was evaporated and the crude product purified by flash chromatography on silica gel (20% EtOAc/hexane with 1% NEt$_3$), yielding 4 (20.0 g, 85%) as a yellow solid: $^1$H NMR (300 MHz, CDCl$_3$): δ 8.23 (dd, J=8.6, 2.1 Hz, 1H), 7.93 (dd, J=8.6, 2.1 Hz, 1H), 7.67 (s, 1H), 7.57 (d, J=8.4 Hz, 1H), 7.53-7.47 (m, 2H), 6.85 (d, J=7.8 Hz, 1H), 6.05 (brs, 1H), 3.88 (s, 3H), 1.30 (s, 9H), 1.09 (s, 9H), 0.30 (s, 6H).

Preparation of Methyl 2-(tert-butoxycarbonylamino)-3-(4-(tert-butyldimethylsilyloxy)naphthalen-1-yl)propanoate(5)

A suspension of 4 (17.2 g, 37.6 mmol) and 10% Pd/C (3.40 g) in EtOH (200 mL) was degassed and subjected to hydrogenation conditions (1 atm, balloon) for 16 h at room temperature. The reaction mixture was filtered through a plug of Celite and the plug was washed with MeOH. The filtrate was concentrated under vacuum to afford 5 (17.0 g, 99%) as a white solid: $^1$H NMR (300 MHz, CDCl$_3$): δ 8.23 (d, J=8.2 Hz, 1H), 7.99 (d, J=8.2 Hz, 1H), 7.57-7.44 (m, 2H), 7.10 (d, J=8.2 Hz, 1H), 6.77 (d, J=8.2 Hz, 1H), 5.07-4.94 (brs, 1H), 4.74-4.61 (m, 1H), 3.66 (s, 3H), 3.55-3.17 (m, 2H), 1.40 (s, 9H), 1.18 (s, 9H), 0.30 (s, 6H).

Preparation of Methyl 2-(tert-butoxycarbonylamino)-3-(4-hydroxynaphthalen-1-yl)propanoate (6)

A solution of 5 (17.0 g, 37.0 mmol) in dry THF (200 mL) at 0° C. was charged with tetrabutylammonium fluoride (48.1 mL, 48.1 mmol). The resulting solution was stirred for 15 min and quenched with saturated aqueous NH$_4$Cl (150 mL). After the solvent was removed under reduced pressure, the residue was dissolved in CH$_2$Cl$_2$ (500 mL), quickly washed with saturated aqueous water (2×150 mL) and brine (200 mL), and dried over Na$_2$SO$_4$. The solvent was evaporated and the crude product purified by flash chromatography on silica gel (25% EtOAc/hexane), yielding rotamer 6 (14.0 g, 94%) as a yellow solid: $^1$H NMR (300 MHz, CDCl3): δ 8.23 (d, J=8.2 Hz, 1H), 7.98 (d, J=8.2 Hz, 1H), 7.57-7.44 (m, 2H), 7.07 (d, J=8.0 Hz, 1H), 6.68 (d, J=7.6 Hz, 1H), 6.55 (brs, 1H), 5.14-4.85 (brs, 1H), 4.77-4.51 (m, 1H), 3.78-3.31 (m, 5H), 1.40 (s, 6H), 1.10 (s, 3H).

Preparation of Compounds 7 and 8

CHIRALPAK AD column 5 cm I.D×50 cm L, particle 20μ was used to separate enantiomers using isocratic system IPA/Heptane (7.5% with 0.4% DEA). 8.0 g of racemic compound 6 was purified by the column to afford S-isomer 8 (3.5 g, 44% yield) as a white solid and R-isomer 7 (2.2 g, 28%) as a white solid.

Preparation of (S)-methyl 2-(tert-butoxycarbonylamino)-3-[4-(trifluoromethylsulfonyloxy)naphthalen-1-yl]propanoate (9)

A solution of compound 8 (1.22 g, 3.53 mmol) in pyridine (20 mL) was charged with triflate (0.9 mL, 5.30 mmol) at 0° C., and the reaction mixture was stirred at room temperature for 2 h. After concentration, the reaction mixture was partitioned between CH$_2$Cl$_2$ (100 mL) and water (50 mL). The aqueous layer was separated and extracted with CH$_2$Cl$_2$ (2×50 mL). The combined organic extracts were washed with brine, dried over Na$_2$SO$_4$, and concentrated to afford compound 9 (1.51 g, 89%) as a brown oil: $^1$H NMR (400 MHz, CDCl$_3$): δ 8.19-8.07 (m, 2H), 7.69-7.64 (m, 2H), 7.38 (d, J=8.1 Hz, 1H), 7.28 (d, J=7.9 Hz, 1H), 5.12-5.06 (brs, 1H), 4.78-4.67 (m, 1H), 3.68-3.46 (m, 5H), 1.39 (s, 8H), 1.25 (s, 1H).

Preparation of (S)-methyl 3-{4-[4-(benzyloxycarbonylamino)but-1-ynyl]naphthalen-1-yl}-2-(tert-butoxycarbonylamino)propanoate (11)

A solution of compound 9 (1.50 g, 3.14 mmol) in anhydrous CH$_3$CN (60 mL) was charged with TEA (1.27 mL, 12.6 mmol), 10% (t-Bu)$_3$P in hexanes (1.27 mL, 0.62 mmol), benzyl but-3-ynylcarbamate (10, 948 mg, 4.71 mmol), and CuI (30 mg, 0.16 mmol) at room temperature. The resulting mixture was degassed with argon for 10 min and Pd(PPh$_3$)$_4$ (363 mg, 0.31 mmol) was charged rapidly in one portion. After degassing with argon for 5 min, the resulting mixture was refluxed for 16 h. The reaction mixture was concentrated under vacuum and the residue was purified by column chromatography (silica gel, 60:40 ethyl acetate/hexanes) to afford compound 11 (1.30 g, 78%) as a brown oil: $^1$H NMR (400 MHz, CDCl$_3$): δ 8.33 (dd, J=7.5, 2.2 Hz, 1H), 8.07 (dd, J=7.5, 2.2 Hz, 1H), 7.58-7.51 (m, 2H), 7.52 (d, J=7.5 Hz, 1H), 7.35-7.29 (m, 5H), 7.19 (d, J=7.5 Hz, 1H), 5.16-5.12 (m, 1H), 5.13 (s, 2H), 5.07-4.99 (m, 1H), 4.74-4.65 (m, 1H), 3.59 (s, 3H), 3.91-3.42 (m, 2H), 3.53 (d, J=6.2 Hz, 2H), 2.79 (t, J=6.4 Hz, 2H), 1.39 (s, 8H), 1.25 (s, 1H).

Preparation of acetic acid salt of (S)-methyl 3-(4-(4-aminobutyl)naphthalen-1-yl)-2-(tert-butoxycarbonylamino)propanoate (12)

A suspension of 11 (1.00 g, 1.88 mmol) and 10% Pd/C (200 mg) in a mixture of MeOH (20 mL) and AcOH (2 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 12 (820 mg, 95%) as a white solid: $^1$H NMR (300 MHz, CD$_3$OD): δ 8.17-8.05 (m, 2H), 7.62-7.48 (m, 2H), 7.27 (brs, 2H), 4.47 (t, J=7.4 Hz, 1H), 3.75-3.51 (m, 5H), 3.13 (t, J=7.5 Hz, 2H), 2.93 (t, J=7.66 Hz, 2H), 1.93 (s, 3H), 1.88-1.65 (m, 4H), 1.34 (s, 7H), 1.01 (s, 2H).

Preparation of (S)-methyl 2-(tert-butoxycarbonylamino)-3-(4-{4-[3-(3,5-diamino-6-chloropyrazine-2-carbonyl)guanidino]butyl}naphthalen-1-yl)propanoate (14)

A solution of amine salt 12 (815 mg, 1.77 mmol) and methyl 3,5-diamino-6-chloropyrazine-2-carbonylcarbamimidothioate (13, 1.1 g, 2.83 mmol) in EtOH (6.0 mL) was charged with DIPEA (2.50 mL, 14.2 mmol) at room temperature. The reaction mixture was heated at 70° C. in a sealed tube for 2 h, cooled to room temperature, and concentrated under vacuum. The residue was purified by column chromatography (silica gel, 80:18:2 CHCl$_3$/CH$_3$OH/NH$_4$OH) to afford guanidine 14 (870 mg, 80%) as a yellow solid: $^1$H NMR (400 MHz, CD$_3$OD): δ 8.17-8.07 (m, 2H), 7.58-7.48 (m, 2H), 7.26 (q, J=7.4 Hz, 2H), 4.56-3.68 (m, 1H), 3.75-3.68 (m, 1H), 3.64 (s, 2H), 3.58-3.43 (m, 2H), 3.13 (t, J=6.7 Hz, 2H), 2.98 (q, J=7.2 Hz, 2H), 1.86-1.70 (m, 4H), 1.33 (s, 7H), 0.98 (s, 2H).

(S)-2-(tert-butoxycarbonylamino)-3-(4-(4-(3-(3,5-diamino-6-chloropyrazine-2-carbonyl)guanidino)butyl)naphthalen-1-yl)propanoic acid (15)

A solution of methyl ester 14 (510 mg, 0.83 mmol) in a mixture of THF (3 mL), methanol (3 mL), and water (1 mL) was charged with solid LiOH (120 mg, 4.99 mmol) and the reaction mixture was stirred at room temperature for 2 h. When TLC of the reaction mixture showed completion of the reaction, the pH of the reaction mixture was brought to 9-10 by addition of 1 N HCl (aqueous) and the organic solvent was removed. The pH of the aqueous part was adjusted to 5-6, and the resulting precipitate was extracted with dichloromethane. The aqueous part was extracted with DCM (2×50 mL). The organic layers were combined, dried over Na$_2$SO$_4$, filtered, and concentrated to afford compound 15 (375 mg, 76%) as a white solid: $^1$H NMR (300 MHz, DMSO-d$_6$): δ 8.22-8.02 (m, 2H), 7.59-7.47 (m, 2H), 7.34-7.22 (m, 2H), 6.82 (brs, 2H), 4.19-4.06 (m, 1H), 3.59-3.46 (m, 1H), 3.25-3.13 (m, 2H), 3.09-2.94 (m, 10H), 1.80-1.55 (m, 4H), 1.28 (s, 7H), 0.93 (s, 2H).

Preparation of the HCl salt of (S)-2-amino-3-(4-(4-(3-(3,5-diamino-6-chloropyrazine-2-carbonyl)guanidino)butyl)naphthalen-1-yl)propanoic acid (16)

4 N HCl in dioxane (8.0 mL) was added to 15 (258 mg, 0.43 mmol) followed by water (4.0 mL) and the reaction mixture was stirred at room temperature for 3 h. The solvent was removed and the residue was lyophilized to give compound 16 (250 mg, 99%) as a yellow solid: $^1$H NMR (400 MHz, DMSO-d$_6$): δ 10.54 (brs, 1H), 9.33 (t, J=5.92 Hz, 1H), 9.03-8.80 (m, 2H), 8.60 (brs, 3H), 8.17 (ddd, J=10.1, 7.6, 4.5 Hz, 2H), 7.59 (ddd, J=9.2, 6.7, 4.5 Hz, 2H), 7.46-7.36 (m, 2H), 7.34 (dd, J=9.9, 7.5 Hz, 2H), 4.13-4.02 (m, 1H), 3.75-3.44 (m, 3H), 3.43-3.33 (m, 2H), 3.09 (t, J=6.4 Hz, 2H), 1.81-1.62 (m, 4H).

2. Preparation of (S)-3,5-diamino-N—(N-(4-(4-(2-amino-3-(4-(3-(dimethylamino)propyl)phenylamino)-3-oxopropyl)naphthalen-1-yl)butyl)carbamimidoyl)-6-chloropyrazine-2-carboxamide (23)

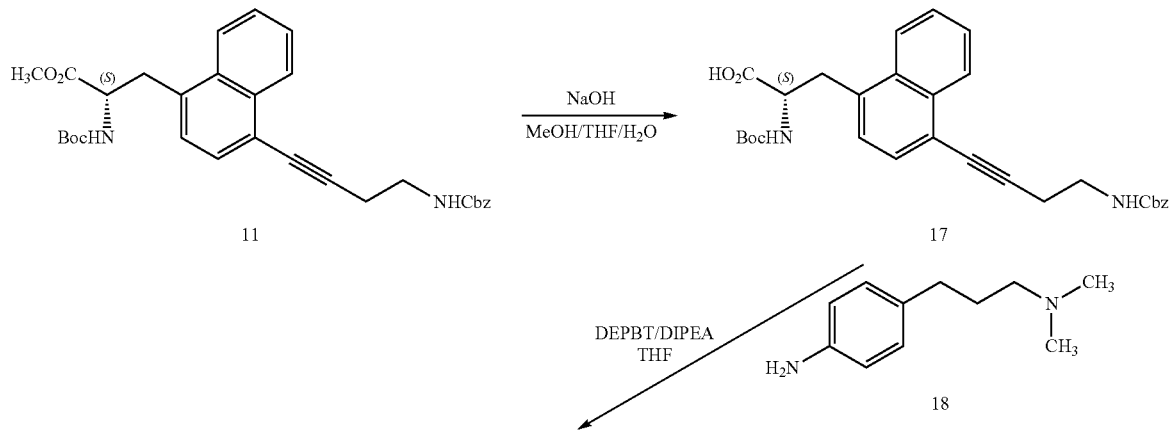

Scheme 3

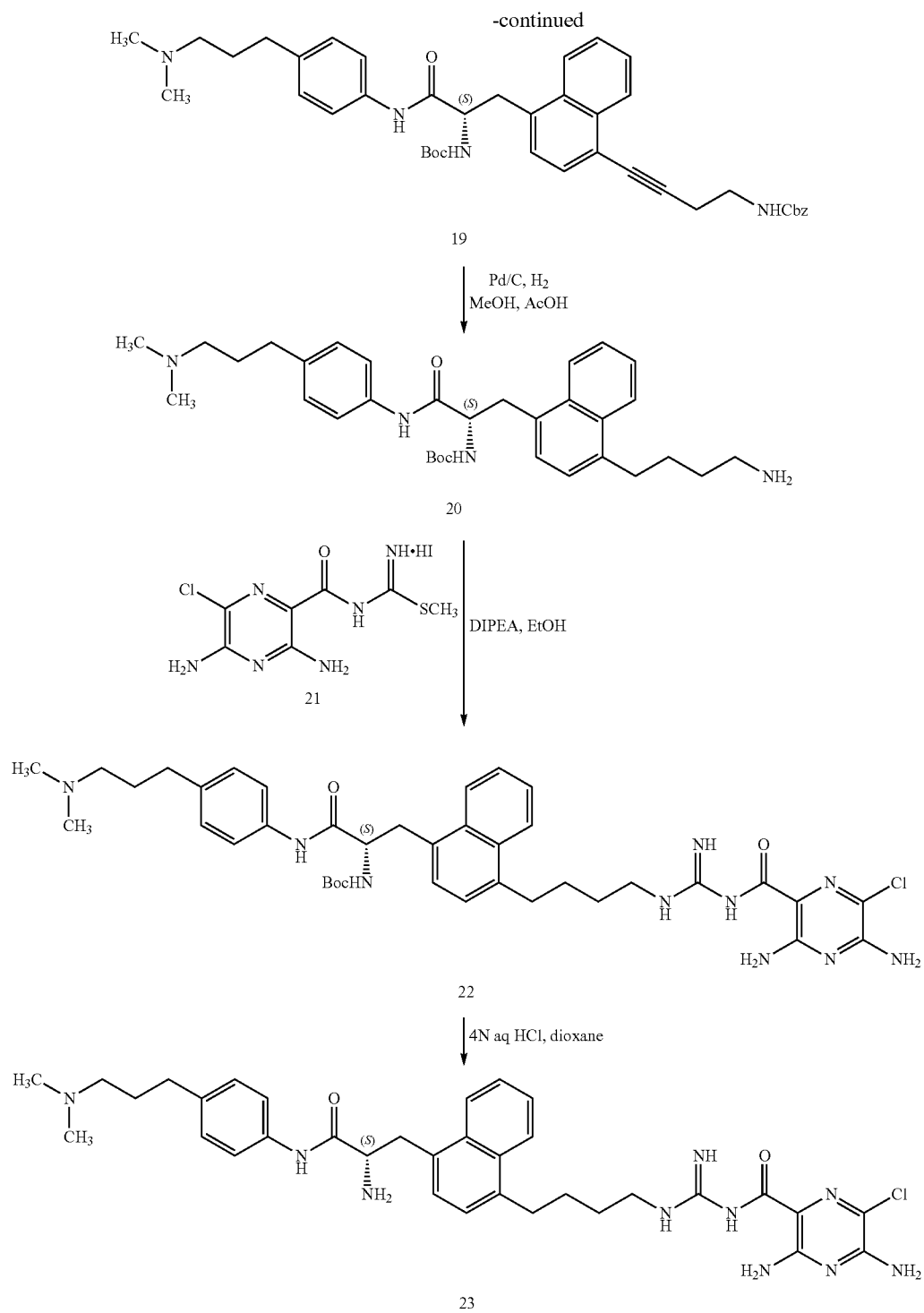

Preparation of (S)-methyl 3-{4-[4-(benzyloxycarbonylamino)but-1-ynyl]naphthalen-1-yl}-2-(tert-butoxycarbonylamino)propanoate (17)

A solution of methyl ester 11 (1.71 g, 3.22 mmol) in a mixture of THF (21 mL), methanol (21 mL), and water (7.0 mL) was charged with solid NaOH (1.29 g, 32.3 mmol) and the reaction mixture was stirred at room temperature for 3 h. When TLC of the reaction mixture showed completion of the reaction, the pH of the reaction mixture was brought to 9-10 by addition of 1 N HCl (aqueous) and the organic solvent was removed. The pH of the aqueous part was adjusted to 5-6, and the resulting precipitate was extracted with dichloromethane. The aqueous part was extracted with $CH_2Cl_2$ (2×50 mL). The organic layers were combined, dried over $Na_2SO_4$, filtered, and concentrated to afford compound 17 (1.55 g, 93%) as a brown solid: $^1$H NMR (400 MHz, DMSO-$d_6$): δ 8.32 (d, J=7.4 Hz, 1H), 8.13-8.05 (m, 1H), 7.58-7.48 (m, 4H), 7.38-7.29 (m, 5H), 5.21-5.15 (m, 1H), 5.12 (s, 2H), 5.07-4.93 (m, 1H), 4.70-4.54 (m, 1H), 3.77-3.62 (m, 1H), 3.57-3.35 (m, 2H), 2.84-2.68 (m, 2H), 1.37 (s, 9H).

Preparation of Compound 19

The compound 18 (100 mg, 0.56 mmol) in THF (2.5 mL) was charged with DEPBT (218 mg, 0.72 mmol), 17 (289 mg, 0.56 mmol), and DIPEA (0.3 mL, 1.68 mmol) successively and stirred at room temperature for 16 h. After the solvent was removed under reduced pressure, the residue was dissolved in $CH_2Cl_2$ (100 mL), quickly washed with saturated aqueous $NaHCO_3$ (2×50 mL) and brine (50 mL), and dried over $Na_2SO_4$. The solvent was evaporated and the crude product purified by flash chromatography on silica gel (8% methanol/$CH_2Cl_2$), yielding amide 19 (250 mg, 66%) as a yellow solid: $^1$H NMR (400 MHz, CDCl3): δ 8.34 (dd, J=8.3, 1.4 Hz, 1H), 8.21 (d, J=8.3 Hz, 1H), 7.61-7.47 (m, 4H), 7.39-7.27 (m, 5H), 7.16 (d, J=8.3 Hz, 2H), 7.05 (d, J=8.3 Hz, 2H), 5.36-5.19 (m, 2H), 5.12 (s, 2H), 4.36-4.53 (m, 1H), 3.66-3.42 (m, 4H), 2.79 (t, J=6.6 Hz, 2H), 2.57 (t, J=7.5 Hz, 2H), 2.40 (t, J=7.5 Hz, 2H), 2.32 (s, 6H), 1.86-1.75 (m, 2H), 1.39 (s, 9H).

Preparation of Compound 20

A suspension of 19 (210 mg, 0.31 mmol) and 10% Pd/C (150 mg) in a mixture of MeOH (3.0 mL) and AcOH (0.3 mL) was degassed and subjected to hydrogenation conditions (1 atm) for 12 h at room temperature. The reaction mixture was filtered through a plug of Celite and the plug was washed with MeOH. The filtrate was concentrated under vacuum to afford amine salt 22 which was neutralized with triethylamine, and the crude product was purified by flash chromatography on silica gel (CMA, 80:18:2) yielding free amine 20 (130 mg, 77%) as a white solid: $^1$H NMR (300 MHz, CD$_3$OD): δ 8.24 (dd, J=8.1, 2.1 Hz, 1H), 8.08 (dd, J=8.2, 1.5 Hz, 1H), 7.58-7.47 (m, 2H), 7.33-7.20 (m, 4H), 7.07-7.05 (m, 2H), 4.53 (t, J=7.2 Hz, 1H), 3.66-3.55 (m, 2H), 3.09 (t, J=7.5 Hz, 2H), 2.82 (t, J=7.4 Hz, 2H), 2.57 (t, J=7.2 Hz, 2H), 2.35 (dd, J=10.5, 7.5 Hz, 2H), 2.24 (s, 6H), 1.84-1.61 (m, 6H), 1.36 (s, 7H), 1.10 (s, 2H).

Preparation of 22

A solution of amine 20 (122 mg, 0.22 mmol) and methyl 3,5-diamino-6-chloropyrazine-2-carbonylcarbamimidothioate (21, 139 mg, 0.35 mmol) in EtOH (4.0 mL) was charged with DIPEA (0.31 mL, 1.76 mmol) at room temperature. The reaction mixture was heated at 70° C. in a sealed tube for 2 h, cooled to room temperature, and concentrated under vacuum. The residue was purified by column chromatography (silica gel, 80:18:2 CHCl$_3$/CH$_3$OH/NH$_4$OH) to afford guanidine 22 (111 mg, 66%) as a yellow solid: $^1$H NMR (400 MHz, CD$_3$OD): δ 8.23 (dd, J=7.5, 2.4 Hz, 1H), 8.10 (d, J=8.1 Hz, 1H), 7.57-7.48 (m, 2H), 7.29 (d, J=7.3 Hz, 2H), 7.24 (d, J=8.0 Hz, 2H), 7.13-7.05 (m, 2H), 4.53 (t, J=8.0 Hz, 1H), 3.60-3.37 (m, 2H), 3.23 (t, J=7.3 Hz, 2H), 3.15-3.03 (m, 2H), 2.55 (t, J=7.3 Hz, 2H), 2.29 (dd, J=9.7, 7.6 Hz, 2H), 2.21 (s, 6H), 1.86-1.64 (m, 6H), 1.36 (s, 7H), 1.12 (s, 2H).

Preparation of the HCl salt of Compound 23 (S)-3,5-diamino-N—(N-(4-(4-(2-amino-3-(4-(3-(dimethylamino)propyl)phenylamino)-3-oxopropyl)naphthalen-1-yl)butyl)carbamimidoyl)-6-chloropyrazine-2-carboxamide 4 N HCl in dioxane (3.0 mL) was added to 22 (100 mg, 0.13 mmol) followed by water (1.0 mL) and the reaction mixture was stirred at room temperature for 3 h. The solvent was removed and neutralized with 1N NaOH (aqueous), the resulting solid was washed with water and again treated with 1 N HCl (aqueous), water was removed, and the residue was lyophilized to afford compound 22 (65 mg, 65%) as a yellow solid: $^1$H NMR (400 MHz, DMSO-d$_6$) 10.50 (s, 1H), 10.48 (s, 1H), 10.46-10.40 (m, 1H), 9.26 (t, J=4.9 Hz, 1H), 9.01-8.74 (m, 2H), 8.61 (brs, 1H), 8.35 (dd, J=6.6, 3.4 Hz, 1H), 8.13 (dd, J=6.5, 3.3 Hz, 1H), 7.58 (ddd, J=9.9, 6.6, 3.6 Hz, 2H), 7.42 (brs, 1H), 7.40 (d, J=7.3 Hz, 2H), 7.34 (d, J=7.3 Hz, 1H), 7.28 (d, J=7.3 Hz, 1H), 7.16 (d, J=8.6 Hz, 2H), 4.29-4.20 (m, 1H), 3.64-3.49 (m, 2H), 3.12-3.03 (m, 2H), 3.02-2.94 (m, 2H), 2.72 (s, 3H), 2.70 (s, 3H), 2.56 (t, J=8.1 Hz, 2H), 1.97-1.88 (m, 2H), 1.79-1.61 (m, 4H).

3. Preparation of 3,5-diamino-N—(N-(4-(4-((S)-2-amino-3-(4-(3-(hexyl((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (28)

Scheme 4

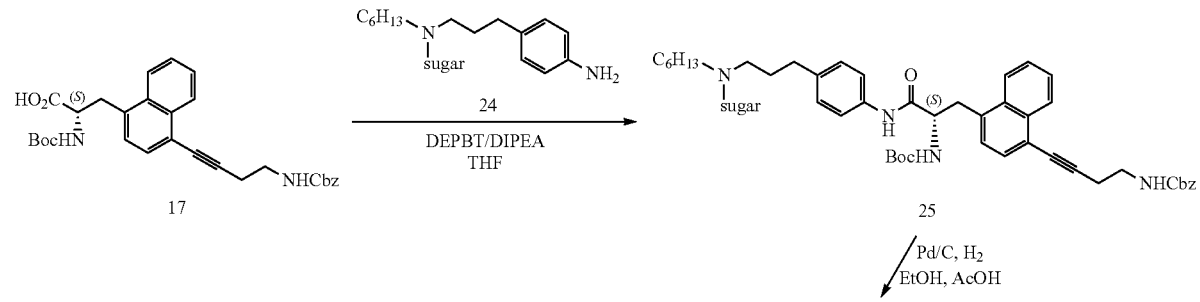

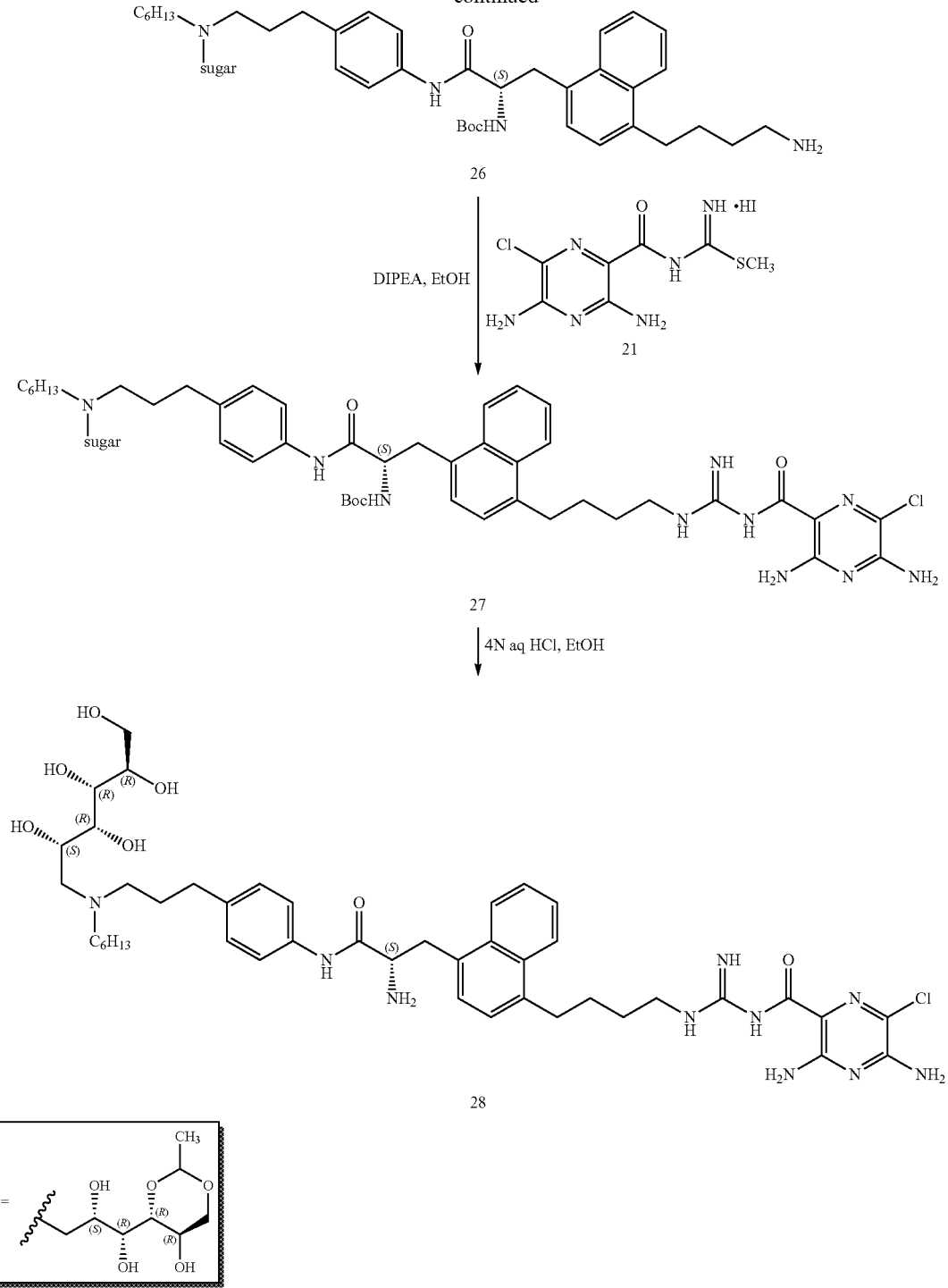

Preparation of Compound 25

The compound 24 (165 mg, 0.38 mmol) in THF (10 mL) was charged with DEPBT (148 mg, 0.48 mmol), 17 (200 mg, 0.38 mmol), and DIPEA (0.2 mL, 1.14 mmol) successively and stirred at room temperature for 16 h. After the solvent was removed under reduced pressure, the residue was dissolved in $CH_2Cl_2$ (100 mL), quickly washed with saturated aqueous $NaHCO_3$ (2×50 mL) and brine (50 mL), and dried over $Na_2SO_4$. The solvent was evaporated and the crude product purified by flash chromatography on silica gel (8% methanol/$CH_2Cl_2$), yielding amide 25 (210 mg, 60%) as a yellow solid: $^1H$ NMR (300 MHz, $CDCl_3$): δ 8.35 (d, J=8.2 Hz, 1H), 8.21 (d, J=8.3 Hz, 1H), 7.63-7.52 (m, 2H), 7.51 (d, J=7.3 Hz, 1H), 7.44-7.39 (m, 1H), 7.37-7.27 (m, 6H), 7.16-7.02 (m, 3H), 5.24-5.16 (m, 1H), 5.13 (s, 2H), 4.68 (ddd, J=11.3, 10.3, 5.1 Hz, 1H), 4.56 (q, J=7.2 Hz, 1H), 4.19-4.09 (m, 1H), 3.90-3.76 (m, 5H), 3.74-3.68 (m, 1H), 3.63-3.46 (m, 5H), 3.45-3.24 (m, 3H), 2.80 (t, J=6.7 Hz, 2H), 2.70-2.35 (m, 8H), 1.81-1.67 (m, 2H), 1.63-1.53 (m, 1H), 1.35-1.20 (m, 6H), 1.21 (s, 9H), 1.31 (d, J=5.1 Hz, 3H), 0.87 (t, J=6.2 Hz, 3H).

Preparation of Compound 26

A suspension of 25 (280 mg, 0.30 mmol) and 10% Pd/C (560 mg) in a mixture of EtOH (9.0 mL) and AcOH (1.0 mL) was degassed and subjected to hydrogenation conditions (1 atm) for 4 h at room temperature. The reaction mixture was filtered through a plug of Celite and the plug was washed with MeOH. The filtrate was concentrated under vacuum to afford amine salt 22, which was neutralized with $NaHCO_3$, and the crude product was purified by flash chromatography on silica gel (CMA, 80:18:2) yielding free amine 26 (160 mg, 67%) as a yellow solid: $^1$H NMR (400 MHz, $CD_3OD$): δ 8.29 (d, J=8.2 Hz, 1H), 8.07 (d, J=8.6 Hz, 1H), 7.60 (t, J=6.9 Hz, 1H), 7.55 (ddd, J=8.2, 6.9, 1.1 Hz, 1H), 7.24 (d, J=7.1 Hz, 1H), 7.18 (d, J=7.1 Hz, 1H), 7.02-7.96 (m, 1H), 7.95-6.88 (m, 2H), 6.77-6.69 (m, 1H), 5.56-5.35 (m, 1H), 4.68 (q, J=5.1 Hz, 1H), 4.61-4.53 (m, 1H), 4.12 (dd, J=10.8, 5.4 Hz, 1H), 3.89-3.80 (m, 2H), 3.74 (t, J=3.3 Hz, 2H), 3.46 (d, J=3.8 Hz, 1H), 3.39 (t, J=10.7 Hz, 2H), 3.18-3.09 (m, 1H), 3.02-2.92 (m, 1H), 2.68 (t, J=7.1 Hz, 2H), 2.61-2.47 (m, 5H), 2.46-2.37 (m, 4H), 1.77-1.63 (m, 4H), 1.33 (d, J=5.1 Hz, 3H), 1.31-1.20 (m, 8H), 1.21 (s, 9H), 0.88 (t, J=6.7 Hz, 3H).

Preparation of Compound 27

A solution of amine 26 (155 mg, 0.20 mmol) and methyl 3,5-diamino-6-chloropyrazine-2-carbonylcarbamimidothioate (21, 123 mg, 0.31 mmol) in EtOH (8.0 mL) was charged with DIPEA (0.28 mL, 1.56 mmol) at room temperature. The reaction mixture was heated at 70° C. in a sealed tube for 2 h, cooled to room temperature, and concentrated under vacuum. The residue was purified by silica-gel column chromatography (80:18:2 $CHCl_3/CH_3OH/NH_4OH$) followed by reverse-phase chromatography (Gold C18) to afford guanidine 27 (100 mg, 51%) as a yellow solid: $^1$H NMR (400 MHz, $CD_3OD$): δ 8.23 (dd, J=8.8, 2.5 Hz, 1H), 8.10 (d, J=8.2 Hz, 1H), 7.56-7.49 (m, 2H), 7.29 (d, J=7.9 Hz, 2H), 7.24 (d, J=7.4 Hz, 2H), 7.08 (d, J=7.9 Hz, 2H), 4.67 (q, J=5.1 Hz, 1H), 4.56-4.50 (m, 1H), 4.04 (dd, J=10.8, 5.4 Hz, 1H), 3.92-3.86 (m, 1H), 3.82-3.74 (m, 2H), 3.51-3.46 (m, 1H), 3.25 (t, J=7.1 Hz, 2H), 3.15-3.06 (m, 2H), 2.71 (dd, J=13.2, 5.2 Hz, 1H), 2.60-2.45 (m, 6H), 1.87-1.63 (m, 6H), 1.48-1.40 (m, 6H), 1.33-1.26 (m, 6H), 1.23 (d, J=5.1 Hz, 3H), 1.20 (s, 9H), 0.89 (t, J=6.7 Hz, 3H).

Preparation of the HCl salt of Compound 28—3,5-diamino-N—(N-(4-(4-((S)-2-amino-3-(4-(3-(hexyl((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide 4 N HCl in water (3.0 mL) was added to 27 (80 mg, 0.08 mmol) in ethanol (0.5 mL) and the reaction mixture was stirred at 40° C. for 6 h. The solvent was removed, an additional 4 N HCl was added, and the mixture was heated at 40° C. for another 4 h. The solvent was removed, water was added, and the residue was lyophilized to afford compound 28 (78 mg, 99%) as a yellow solid: $^1$H NMR (400 MHz, DMSO-$d_6$): δ 10.58 (brs, 1H), 10.56 (brs, 1H), 9.70-9.58 (m, 1H), 9.38-9.31 (m, 1H), 9.04-8.84 (m, 2H), 8.70 (brs, 1H), 8.43-8.34 (m, 1H), 8.16-8.08 (m, 1H), 7.62-7.52 (m, 2H), 7.46-7.37 (m, 4H), 7.34 (d, J=7.1 Hz, 1H), 7.27 (d, J=7.1 Hz, 1H), 7.17 (d, J=8.1 Hz, 2H), 5.52-5.46 (m, 1H), 4.85-4.76 (m, 1H), 4.68-4.52 (m, 2H), 4.49-4.37 (m, 1H), 4.32-4.22 (m, 1H), 4.05-3.97 (m, 1H), 3.72-3.43 (m, 6H), 3.17-2.97 (m, 8H), 2.02-1.90 (m, 2H), 1.77-1.54 (m, 6H), 1.33-1.21 (m, 6H), 0.86 (t, J=6.6 Hz, 3H).

$^1$H NMR (400 MHz, $CD_3OD$): δ 8.23 (d, J=8.3 Hz, 1H), 8.17 (d, J=8.2 Hz, 1H), 7.62-7.53 (m, 2H), 7.41-7.36 (m, 1H), 7.35-7.32 (m, 1H), 7.31-7.25 (m, 2H), 7.21-7.12 (m, 2H), 4.35-4.25 (m, 1H), 4.17-4.02 (m, 1H), 3.86-3.75 (m, 2H), 3.73-3.59 (m, 6H), 3.23-3.08 (m, 9H), 2.73-2.60 (m, 2H), 2.11-1.97 (m, 2H), 1.91-1.75 (m, 4H), 1.74-1.62 (m, 2H), 1.44-1.30 (m, 6H), 0.92 (t, J=6.6 Hz, 3H)

4. Preparation of 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (33)

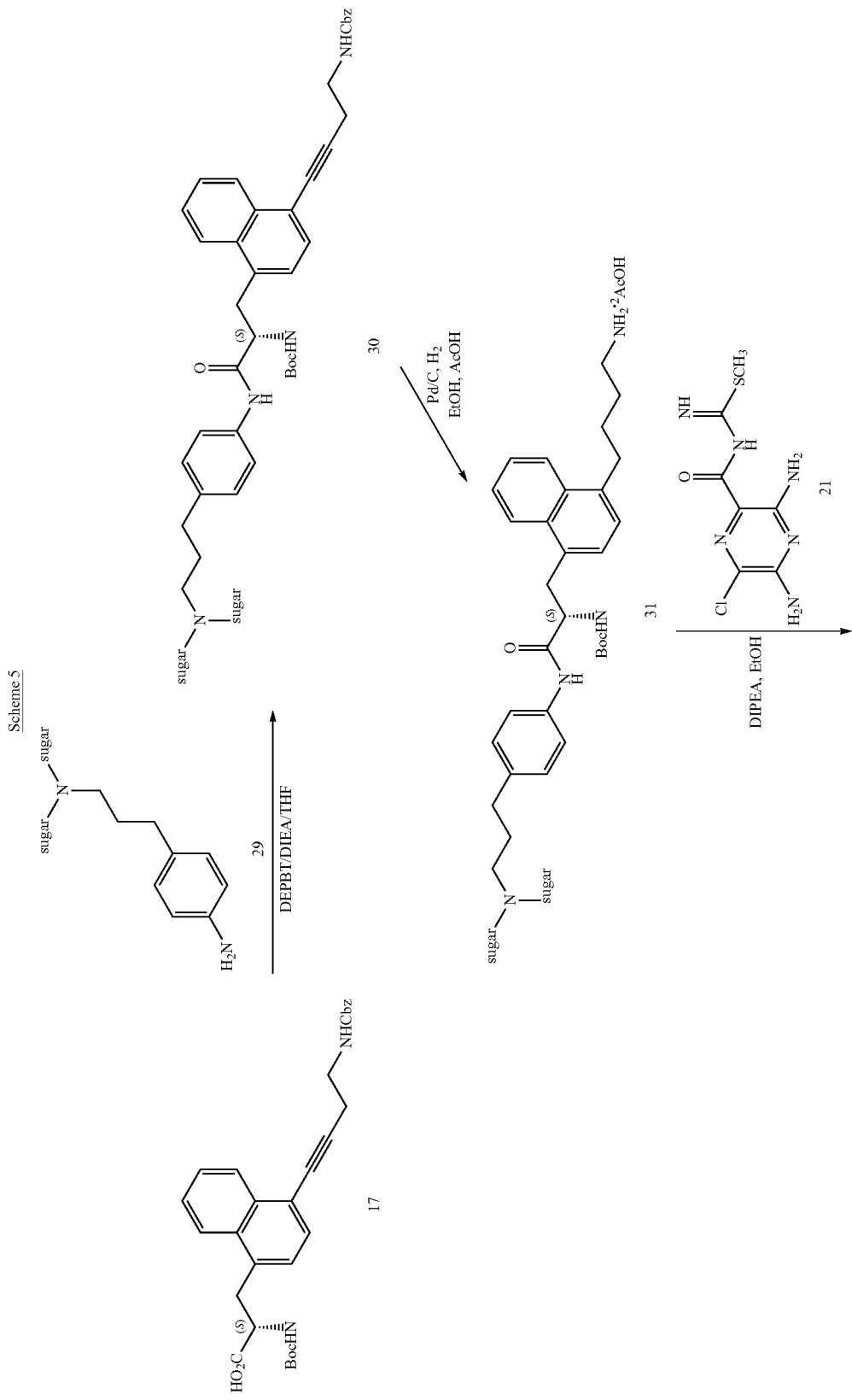
Scheme 5

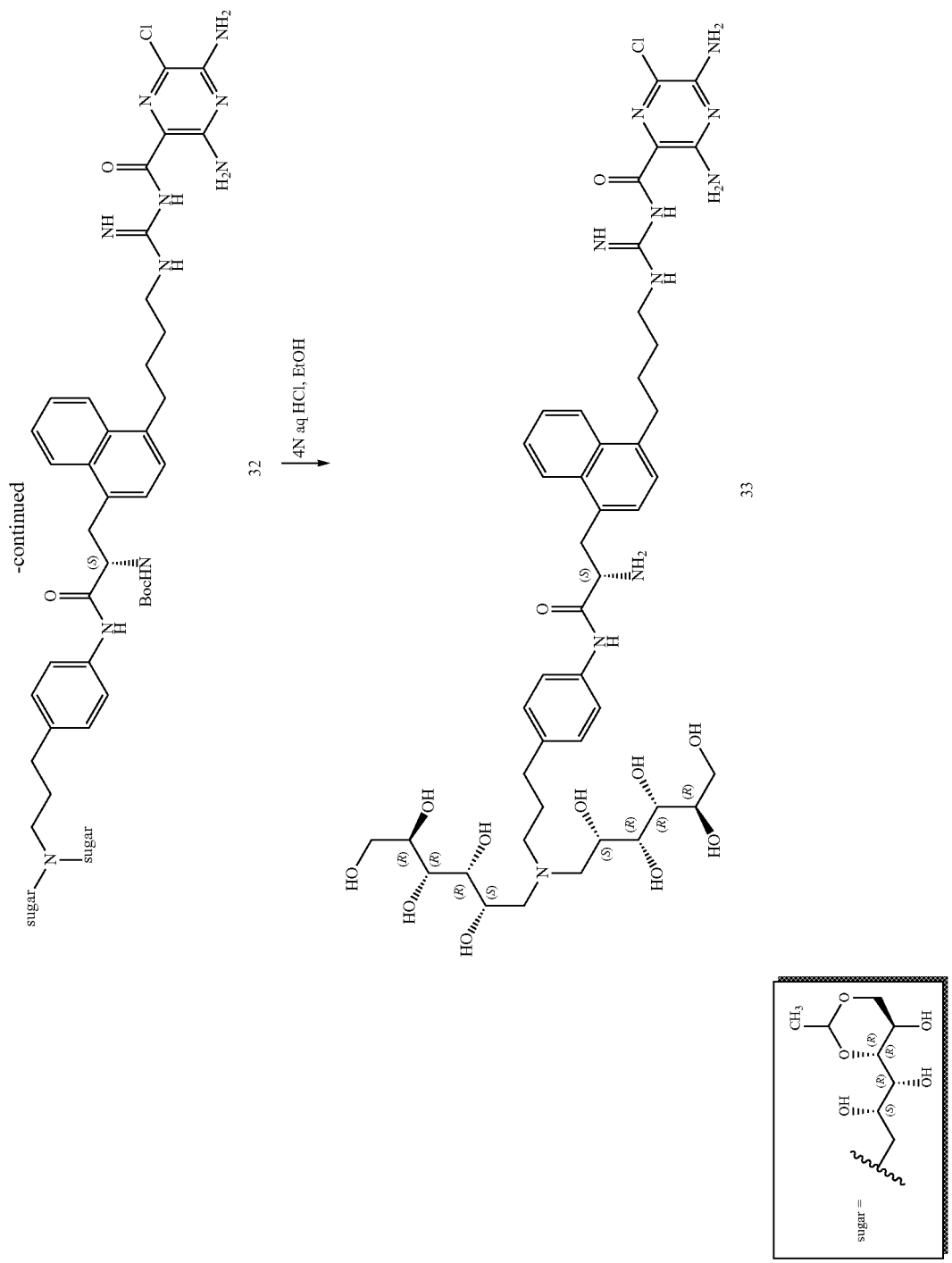

Preparation of Compound 30

Compound 29 (290 mg, 0.54 mmol) in THF (8.0 mL) was charged with DEPBT (210 mg, 0.70 mmol), 17 (311 mg, 0.60 mmol), and DIPEA (0.28 mL, 1.62 mmol) successively and stirred at room temperature for 16 h. After the solvent was removed under reduced pressure, the residue was dissolved in $CH_2Cl_2$ (100 mL), quickly washed with saturated aqueous $NaHCO_3$ (2×50 mL) and brine (50 mL), and dried over $Na_2SO_4$. The solvent was evaporated and the crude product purified by flash chromatography on silica gel (8% methanol/$CH_2Cl_2$), yielding amide 30 (400 mg, 72%) as a yellow solid: $^1$H NMR (400 MHz, $CDCl_3$): δ 8.36-8.26 (m, 1H), 8.20-8.09 (m, 1H), 8.03-7.85 (m, 1H), 7.61-7.46 (m, 1H), 7.49 (d, J=7.2 Hz, 2H), 7.38-7.28 (m, 5H), 7.18-6.96 (m, 4H), 5.51-5.36 (m, 1H), 5.32-5.21 (m, 1H), 5.12 (s, 2H), 4.67 (q, J=5.1 Hz, 2H), 4.66-4.53 (m, 1H), 4.11 (dd, J=10.4, 5.2 Hz, 2H), 4.06-3.96 (m, 2H), 3.93-3.86 (m, 2H), 3.86-3.77 (m, 2H), 3.68-3.56 (m, 2H), 3.56-3.44 (m, 6H), 3.39 (t, J=10.4 Hz, 2H), 3.05 (q, J=7.6 Hz, 2H), 2.96-2.88 (m, 2H), 2.79 (t, J=6.1 Hz, 2H), 2.64-2.61 (m, 4H), 1.93-1.72 (m, 4H), 1.48-1.40 (m, 2H), 1.35 (s, 9H), 1.29 (d, J=5.1 Hz, 6H).

Preparation of Compound 31

A suspension of 30 (400 mg, 0.39 mmol) and 10% Pd/C (210 mg) in a mixture of EtOH (54 mL) and AcOH (6.0 mL) was degassed and subjected to hydrogenation conditions (1 atm) for 4 h at room temperature. The reaction mixture was filtered through a plug of Celite and the plug was washed with MeOH. The filtrate was concentrated under vacuum to afford amine salt 31 (333 mg, 84%) as a yellow solid: $^1$H NMR (400 MHz, $CD_3OD$): δ 8.25 (dd, J=7.5, 2.5 Hz, 1H), 8.10 (d, J=7.3 Hz, 1H), 7.60-7.51 (m, 2H), 7.36-7.32 (m, 1H), 7.31 (d, J=7.2 Hz, 2H), 7.26 (d, J=7.8 Hz, 1H), 7.15 (d, J=7.8 Hz, 2H), 4.70 (q, J=4.9 Hz, 2H), 4.54 (d, J=7.3 Hz, 1H), 4.18-4.10 (m, 2H), 4.06 (dd, J=10.6, 5.3 Hz, 2H), 3.87-3.82 (m, 2H), 3.81-3.68 (m, 3H), 3.53 (dd, J=9.5, 1.8 Hz, 2H), 3.39 (t, J=9.2 Hz, 3H), 3.35-3.30 (m, 2H), 3.15-3.08 (m, 2H), 2.92 (t, J=8.0 Hz, 2H), 2.09-2.00 (m, 4H), 2.77-2.58 (m, 2H), 1.95 (s, 6H), 1.88-1.60 (m, 4H), 1.36 (s, 9H), 1.25 (d, J=4.9 Hz, 6H).

Preparation of 32

A solution of 31 (370 mg, 0.36 mmol) and methyl 3,5-diamino-6-chloropyrazine-2-carbonylcarbamimidothioate (21, 226 mg, 0.58 mmol) in EtOH (12 mL) was charged with DIPEA (0.51 mL, 2.88 mmol) at room temperature. The reaction mixture was heated at 70° C. in a sealed tube for 2 h, cooled to room temperature, and concentrated under vacuum. The residue was purified by silica-gel column chromatography (80:18:2 $CHCl_3$/$CH_3OH$/$NH_4OH$) to afford guanidine 32 (250 mg, 63%) as a yellow solid: $^1$H NMR (400 MHz, $CD_3OD$): δ 8.23 (d, J=8.6 Hz, 1H), 8.13-8.03 (m, 1H), 7.54-7.49 (m, 2H), 7.30-7.20 (m, 4H), 7.13-7.04 (m, 2H), 4.67 (q, J=4.9 Hz, 2H), 4.54-4.49 (m, 1H), 4.03 (dd, J=10.8, 5.4 Hz, 2H), 3.91-3.84 (m, 2H), 3.82-3.72 (m, 5H), 3.48-3.43 (m, 5H), 3.41-3.34 (m, 2H), 3.13-3.10 (m, 2H), 2.68-2.50 (m, 8H), 1.87-1.67 (m, 6H), 1.36 (s, 9H), 1.23 (d, J=4.9 Hz, 6H).

Preparation of the HCl Salt of 33—3,5-diamino-N—(N-(4-(4-(((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide 4 N HCl in water (6.0 mL) was added to 32 (200 mg, 0.18 mmol) in ethanol (2.0 mL) and the reaction mixture was stirred at 40° C. for 8 h. The solvent was removed, an additional 4N HCl was added, and the mixture was heated at 40° C. for another 6 h. The solvent was removed, the mixture was purified by reverse-phase chromatography (Gold column), and the residue was lyophilized to afford compound 33 (138 mg, 59%) as a yellow solid: $^1$H NMR (400 MHz, DMSO-$d_6$): δ 10.48 (brs, 1H), 10.45-10.41 (m, 1H), 9.25-9.19 (m, 1H), 8.95-8.85 (m, 1H), 8.81-8.69 (m, 1H), 8.64-8.46 (m, 4H), 8.36-8.29 (m, 1H), 8.18-8.10 (m, 1H), 7.62-7.55 (m, 2H), 7.46-7.38 (m, 4H), 7.34 (d, J=7.5 Hz, 1H), 7.28 (d, J=7.3 Hz, 1H), 7.18 (d, J=8.7 Hz, 2H), 5.48-5.39 (m, 2H), 4.87-4.75 (m, 2H), 4.68-4.33 (m, 4H), 4.28-4.17 (m, 1H), 4.05-3.93 (m, 2H), 3.72-3.65 (m, 2H), 3.62-3.53 (m, 4H), 3.52-3.35 (m, 8H), 3.27-3.13 (m, 6H), 3.3.10-3.00 (m, 2H), 2.62-2.48 (m, 4H), 2.03-1.90 (m, 2H), 1.78-1.61 (m, 4H).
$^1$H NMR (400 MHz, $CD_3OD$): δ 8.24-8.20 (m, 1H), 8.18-8.15 (m, 1H), 7.57 (td, J=4.6, 1.5 Hz, 2H), 7.38 (d, J=7.4 Hz, 1H), 7.33 (d, J=7.4 Hz, 1H), 7.28 (dd, J=8.4, 2.6 Hz, 2H), 7.16 (dd, J=8.4, 2.0 Hz, 2H), 4.28 (t, J=6.9 Hz, 1H), 4.19-4.13 (m, 1H), 4.12-4.07 (m, 1H), 3.85-3.79 (m, 2H), 3.77 (dd, J=10.4, 5.2 Hz, 2H), 3.73-3.60 (m, 6H), 3.49-3.45 (m, 2H), 3.42-3.34 (m, 6H), 3.26-3.23 (m, 1H), 3.19-3.13 (m, 2H), 3.14-3.11 (m, 1H), 2.74-2.59 (m, 2H), 2.14-2.00 (m, 2H), 1.90-1.72 (m, 4H).

5. Preparation of 3,5-diamino-N—(N-(4-(4-(((S)-2-amino-3-oxo-3-(4-(3-((2S,3R,4R,5R)-2,3,4,5,6-pentahydroxyhexylamino)propyl)phenylamino)propyl)naphthalen-1-yl)butyl)carbamimidoyl)-6-chloropyrazine-2-carboxamide (38)

Scheme 6

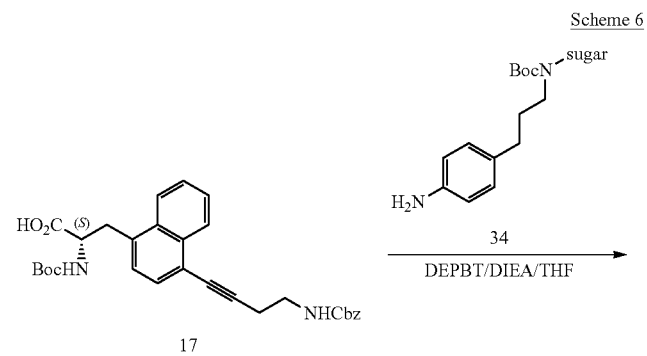

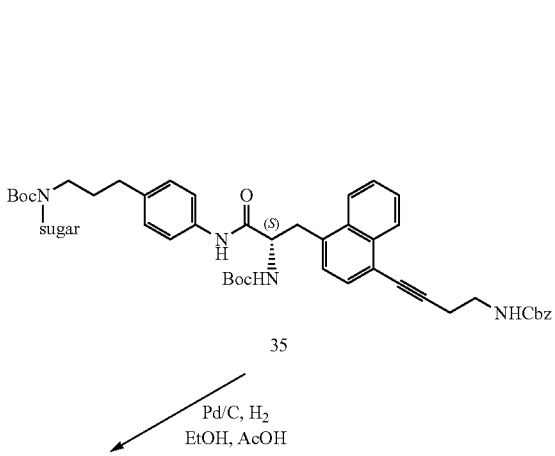

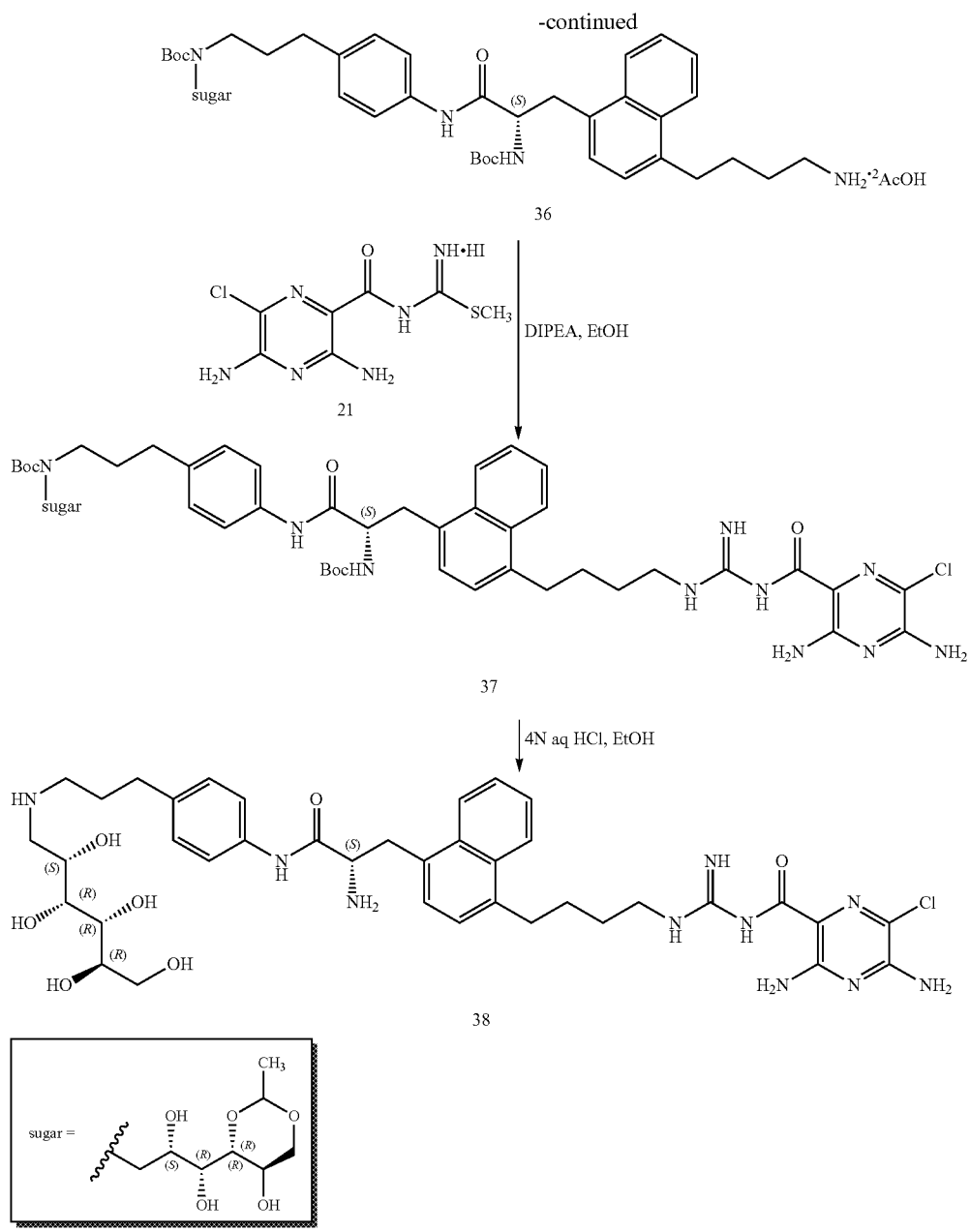

Preparation of Compound 35

Compound 34 (400 mg, 0.91 mmol) in THF (15 mL) was charged with DEPBT (389 mg, 1.30 mmol), 17 (516 mg, 1.00 mmol), and DIPEA (0.52 mL, 3.00 mmol) successively and stirred at room temperature for 16 h. After the solvent was removed under reduced pressure, the residue was dissolved in $CH_2Cl_2$ (100 mL), quickly washed with saturated aqueous $NaHCO_3$ (2×50 mL) and brine (50 mL), and dried over $Na_2SO_4$. The solvent was evaporated and the crude product purified by flash chromatography on silica gel (8% methanol/$CH_2Cl_2$), yielding amide 35 (700 mg, 83%) as a yellow solid: $^1$H NMR (400 MHz, $CDCl_3$): δ 8.35 (dd, J=8.2, 1.5 Hz, 1H), 8.22 (d, J=8.1 Hz, 1H), 7.64-7.35 (m, 4H), 7.38-7.26 (m, 5H), 7.06 (d, J=7.8 Hz, 2H), 7.17-7.09 (m, 2H), 5.21-5.13 (m, 2H), 5.12 (s, 2H), 4.69 (q, J=5.1 Hz, 1H), 4.55 (q, J=7.25 Hz, 1H), 4.15 (dd, J=11.4, 5.6 Hz, 1H), 4.11-4.02 (m, 1H), 4.07-3.92 (m, 1H), 3.88-3.77 (m, 1H), 3.73-3.67 (m, 1H), 3.64-3.49 (m, 5H), 3.41 (d, J=10.6 Hz, 2H), 3.37-3.30 (m, 2H), 3.29-3.20 (m, 3H), 2.80 (t, J=6.2 Hz, 2H), 2.52 (t, J=7.8 Hz, 2H), 1.90-1.76 (m, 3H), 1.42 (s, 18H), 1.32 (d, J=5.2 Hz, 3H).

Preparation of Compound 36

A suspension of 35 (700 mg, 0.74 mmol) and 10% Pd/C (400 mg) in a mixture of EtOH (90 mL) and AcOH (10 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 36 (650 mg, 95%) as a yellow solid: $^1$H NMR (400 MHz, $CDCl_3$): δ 8.20 (d, J=8.4 Hz, 1H), 7.96 (d, J=7.3 Hz, 1H), 7.86-7.71 (m, 1H), 7.70-7.63 (m, 1H), 7.58-7.43 (m, 2H), 7.36-7.26 (m, 2H), 7.02-6.91 (m, 2H), 4.70-4.63 (m, 1H), 4.61-4.54 (m, 1H), 4.20-4.05 (m, 2H), 4.04-3.90 (m, 1H), 3.89-3.68 (m, 3H), 3.67-3.46 (m, 3H), 3.45-3.27 (m, 5H), 3.29-3.21 (m, 4H), 3.11-2.91 (m, 4H), 2.90-2.76 (m, 2H), 2.48 (d, J=7.3 Hz, 2H), 2.08 (s, 6H), 1.86-1.61 (m, 6H), 1.41 (s, 15H), 1.32 (d, J=5.1 Hz, 3H), 1.25 (s, 3H).

Preparation of 37

A solution of 36 (650 mg, 0.70 mmol) and methyl 3,5-diamino-6-chloropyrazine-2-carbonylcarbamimidothioate (21, 436 mg, 1.13 mmol) in EtOH (12 mL) was charged with DIPEA (0.90 mL, 5.60 mmol) at room temperature. The reaction mixture was heated at 70° C. in a sealed tube for 2 h, cooled to room temperature, and concentrated under vacuum. The residue was purified by silica-gel column chromatography (80:18:2 CHCl$_3$/CH$_3$OH/NH$_4$OH) to afford guanidine 37 (444 mg, 62%) as a yellow solid: H NMR (400 MHz, CD$_3$OD): δ 8.23 (dd, J=7.7, 2.2 Hz, 1H), 8.10 (d, J=8.1 Hz, 1H), 7.57-7.47 (m, 2H), 7.33-7.21 (m, 4H), 7.08 (d, J=8.1 Hz, 2H), 4.68 (q, J=5.0 Hz, 1H), 4.53 (t, J=7.2 Hz, 1H), 4.04 (dd, J=10.8, 5.4 Hz, 1H), 4.03-3.93 (m, 1H), 3.25 (ddd, J=10.3, 9.2, 5.2 Hz, H), 3.71-3.65 (m, 1H), 3.58-3.37 (m, 4H), 3.27-3.20 (m, 4H), 3.20-3.15 (m, 1H), 3.14-3.05 (m, 2H), 2.66 (q, J=7.5 Hz, 1H), 2.53 (t, J=7.2 Hz, 2H), 1.89-1.76 (m, 4H), 1.76-1.64 (m, 2H), 1.36 (s, 6H), 1.42 (s, 9H), 1.25 (d, J=5.0 Hz, 3H), 1.11 (s, 3H).

Preparation of the HCl Salt of 38

4 N HCl in water (6.0 mL) was added to 37 (240 mg, 0.23 mmol) in ethanol (3.0 mL) and the reaction mixture was stirred at 40° C. for 8 h. The solvent was removed, an additional 4N HCl was added, and the mixture was heated at 40° C. for another 8 h. The solvent was removed, the mixture was purified by reverse-phase chromatography (Gold column), and the residue was lyophilized to afford compound 38 (251 mg, 64%) as a yellow solid: $^1$H NMR (400 MHz, DMSO-d$_6$): δ 10.50 (brs, 1H), 9.28 (t, J=5.7 Hz, 1H), 9.02-8.87 (m, 1H), 8.86-8.75 (m, 1H), 8.72-8.55 (m, 4H), 8.39-8.33 (m, 1H), 8.16-8.10 (m, 1H), 7.61-7.55 (m, 2H), 7.45-7.40 (m, 1H), 7.40 (d, J=7.4 Hz, 2H), 7.34 (d, J=7.3 Hz, 1H), 7.28 (d, J=7.4 Hz, 1H), 7.14 (d, J=8.5 Hz, 2H), 5.38 (d, J=4.3 Hz, 1H), 4.74 (d, J=4.9 Hz, 1H), 4.64-4.51 (m, 2H), 4.49-4.35 (m, 1H), 4.30-4.20 (m, 2H), 3.94-3.86 (m, 1H), 3.70-3.64 (m, 1H), 3.63-3.52 (m, 3H), 3.51-3.34 (m, 6H), 3.15-2.98 (m, 3H), 2.98-2.81 (m, 3H), 2.58 (t, J=7.6 Hz, 2H), 1.96-1.85 (m, 2H), 1.79-1.61 (m, 4H).

$^1$H NMR (400 MHz, CD$_3$OD): δ 8.26-8.20 (m, 1H), 8.19-8.14 (m, 1H), 7.60-7.53 (m, 2H), 7.38 (d, J=7.2 Hz, 1H), 7.33 (d, J=8.4 Hz, 1H), 7.28 (dd, J=8.4, 2.0 Hz, 2H), 7.14 (d, J=8.4 Hz, 2H), 4.29 (t, J=8.3 Hz, 1H), 4.07-4.00 (m, 1H), 3.83 (dd, J=9.8, 1.5 Hz, 1H), 3.77 (dd, J=9.8, 2.6 Hz, 1H), 3.73-3.64 (m, 5H), 3.37 (t, J=7.2 Hz, 2H), 3.21-3.11 (m, 4H), 3.06-2.96 (m, 2H), 2.66 (t, J=7.7 Hz, 2H), 2.03-1.94 (m, 2H), 1.90-1.75 (m, 4H).

6. Preparation of (S)-3,5-diamino-N—(N-(4-(4-(2-amino-3-(4-(6-(dimethylamino)hexyl)phenylamino)-3-oxopropyl)naphthalen-1-yl)butyl)carbamimidoyl)-6-chloropyrazine-2-carboxamide (43)

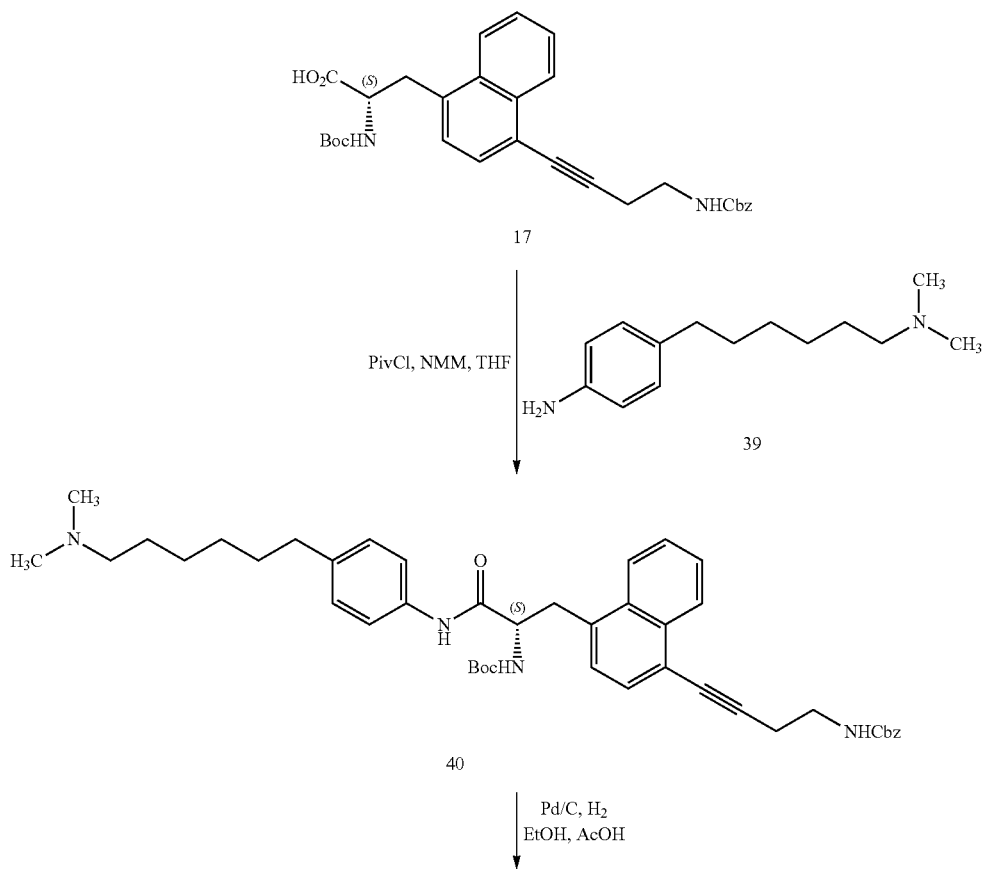

Scheme 7

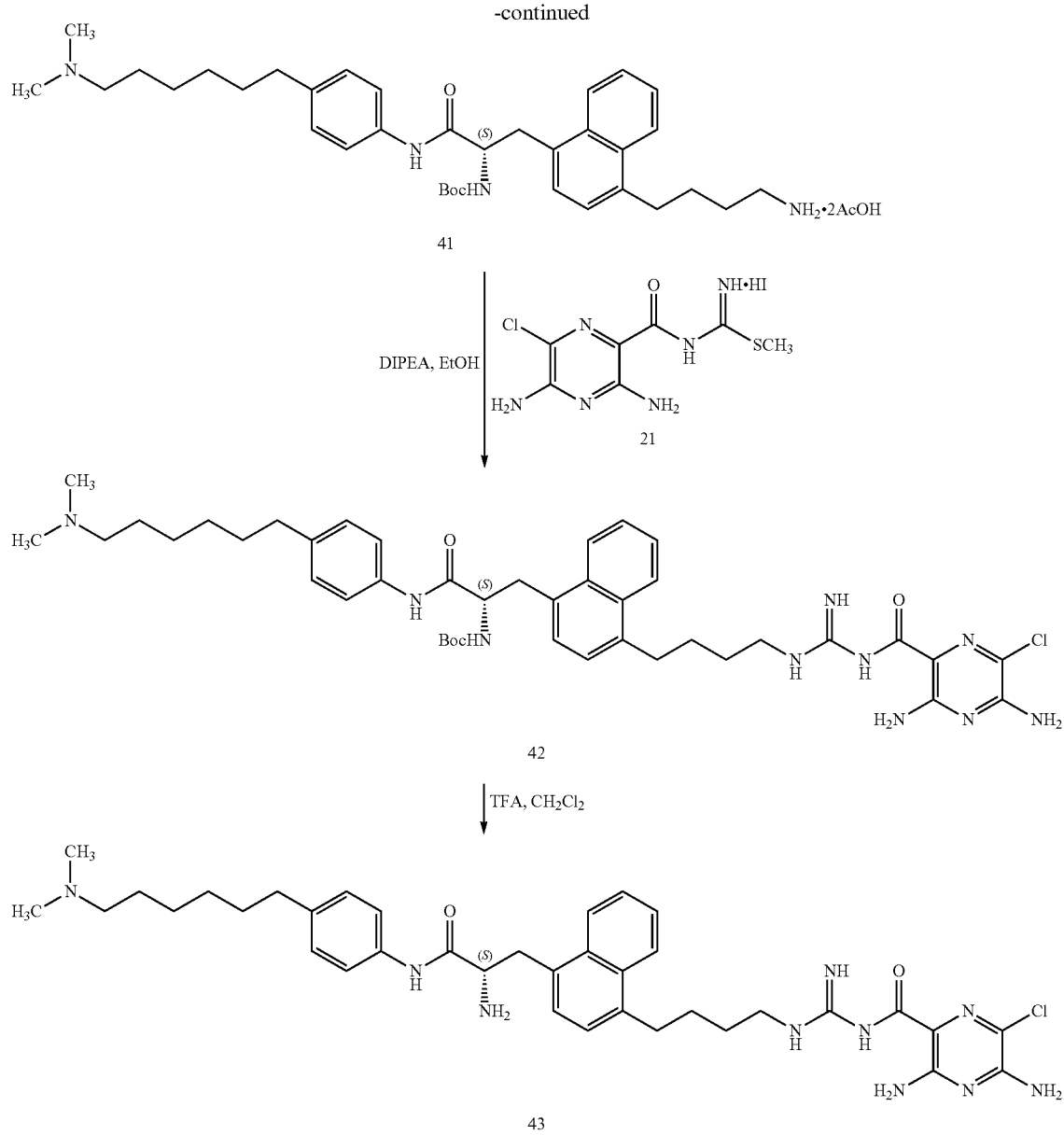

Preparation of Compound 40

A solution of acid 17 (880 mg, 1.70 mmol) in THF (30 mL) was cooled to 0° C. in an ice bath. NMM (0.37 mL, 3.40 mmol) was added, followed by PivCl (0.20 mL, 1.70 mmol), and the reaction mixture was stirred at the same temperature for 2 h. 39 (375 mg, 1.70 mmol, 15 mL THF) was added and the reaction mixture was stirred at the same temperature for a further 10 min. The reaction mixture was brought to room temperature and stirred for 16 h. The organic solvent was removed. The residue was charged with water and extracted with $CH_2Cl_2$ (3×100 mL). The organic layers were combined, dried over $Na_2SO_4$, filtered, and concentrated. The residue was purified by column chromatography (4% methanol in chloroform) to afford amide 40 (719 mg, 59%) as a light yellow solid: [M+H]$^+$ 720.

Preparation of Compound 41

A suspension of 40 (719 mg, 1.00 mmol) and 10% Pd/C (300 mg) in a mixture of EtOH (110 mL) and AcOH (20 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 41 as a yellow solid (660 mg, 93%): [M+H]$^+$ 589.

Preparation of Compound 42

A solution of amine 41 (660 mg, 0.93 mmol) and methyl 3,5-diamino-6-chloropyrazine-2-carbonylcarbamimidothioate (21, 650 mg, 1.67 mmol) in EtOH (10 mL) was charged with DIPEA (1.66 mL, 9.3 mmol) at room temperature. The reaction mixture was heated at 70° C. in a sealed tube for 2 h, cooled to room temperature, and concentrated under vacuum. The residue was purified by silica-gel column chromatography (80:18:2 CHCl$_3$/CH$_3$OH/NH$_4$OH) to afford guanidine 42 (370 mg, 50%) as a yellow solid: [M+H]$^+$ 801.

Preparation of the HCl salt of Compound 43 (S)-3, 5-diamino-N—(N-(4-(4-(2-amino-3-(4-(6-(dimethyl-amino)hexyl)phenylamino)-3-oxopropyl)naphthalen-1-yl)butyl)carbamimidoyl)-6-chloropyrazine-2-carboxamide TFA (10 mL) was added to 42 (370 mg, 0.46 mmol) in CH$_2$Cl$_2$ (10 mL) and the reaction mixture was stirred at room temperature for 2 h. The solvent was removed, an additional 1N HCl was added, and solvent was removed. The mixture was purified by reverse-phase chromatography (Gold column) and the residue was lyophilized to afford compound 43 (290 mg, 92%) as a yellow solid: $^1$H NMR (400 MHz, DMSO-d$_6$): δ 10.39 (brs, 2H), 9.25 (brs, 1H), 9.02-8.87 (m, 1H), 8.86-8.73 (m, 2H), 8.71-8.44 (m, 2H), 8.35 (brs, 1H), 8.13 (dd, J=6.8, 3.8 Hz, 1H), 7.58 (dd, J=6.5, 3.2 Hz, 2H), 7.42 (brs, 2H), 7.35 (d, J=8.6 Hz, 2H), 7.33 (d, J=7.8 Hz, 1H), 7.27 (d, J=7.3 Hz, 1H), 7.11 (d, J=8.4 Hz, 2H), 4.26-4.18 (m, 1H), 3.65-3.48 (m, 2H), 3.39-3.32 (m, 3H), 3.06 (t, J=6.5 Hz, 2H), 2.99-2.91 (m, 2H), 2.69 (s, 6H), 1.77-1.56 (m, 6H), 1.52 (t, J=8.2 Hz, 2H), 1.34-1.21 (m, 4H).

$^1$H NMR (400 MHz, CD$_3$OD): δ 8.22-8.17 (m, 1H), 8.16-8.12 (m, 1H), 7.58-7.51 (m, 2H), 7.36 (d, J=7.2 Hz, 1H), 7.30 (d, J=7.4 Hz, 1H), 7.19 (d, J=8.04 Hz, 2H), 7.05 (d, J=8.3 Hz, 1H), 4.24 (t, J=8.2 Hz, 1H), 3.70-3.58 (m, 2H), 3.33 (t, J=6.9 Hz, 2H), 3.14 (t, J=7.4 Hz, 2H), 3.09-3.03 (m, 2H), 2.84 (s, 6H), 2.53 (t, J=8.6 Hz, 2H), 1.88-1.73 (m, 4H), 1.72-1.63 (m, 2H), 1.61-1.52 (m, 2H), 1.41-1.32 (m, 4H).

7. Preparation of 3,5-diamino-N—(N-(4-(4-((S)-2-amino-3-(4-(6-(bis((2S,3R,4R,5R)-2,3,4,5,6-penta-hydroxyhexyl)amino)hexyl)phenylamino)-3-oxopropyl)naphthalen-1-yl)butyl)carbamimidoyl)-6-chloropyrazine-2-carboxamide

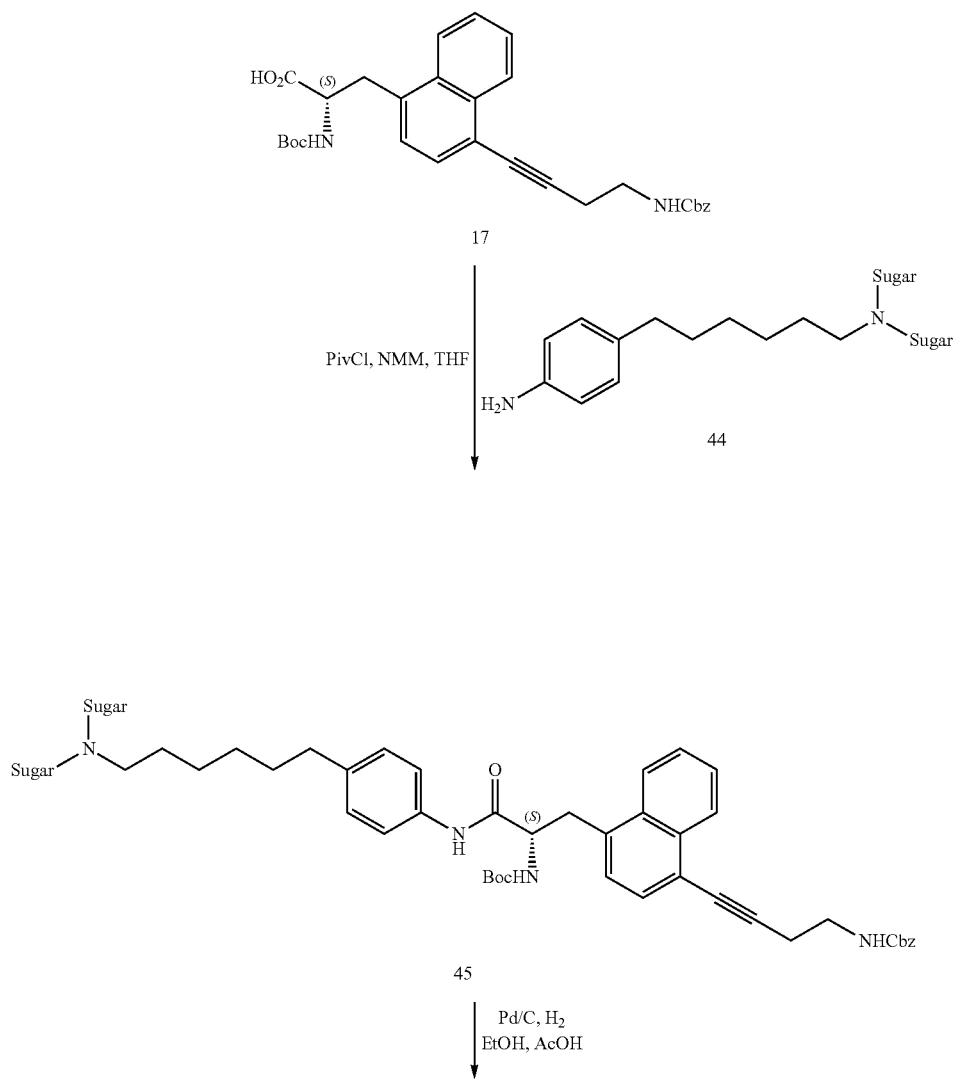

Scheme 8

-continued
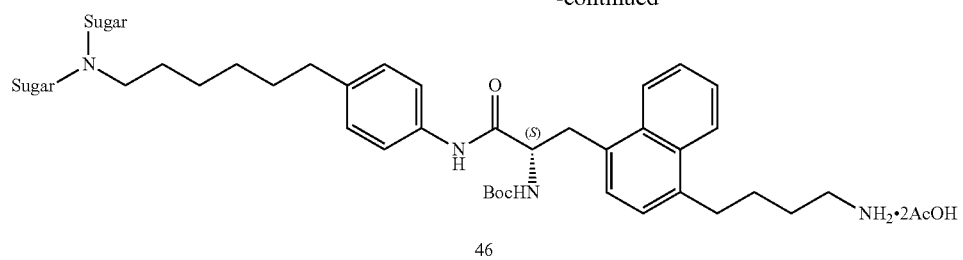
46
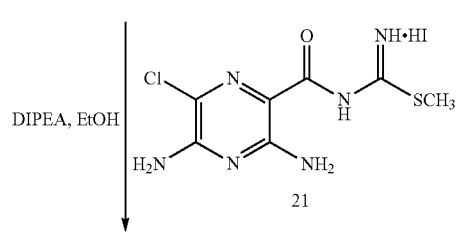
21
DIPEA, EtOH
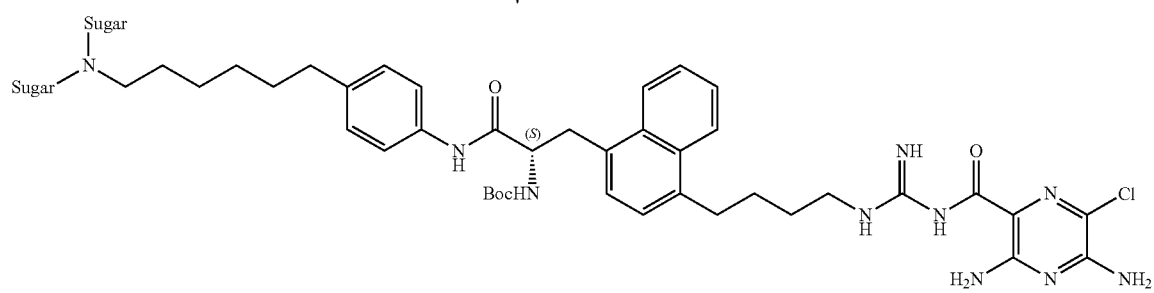
47
4N aq HCl, EtOH
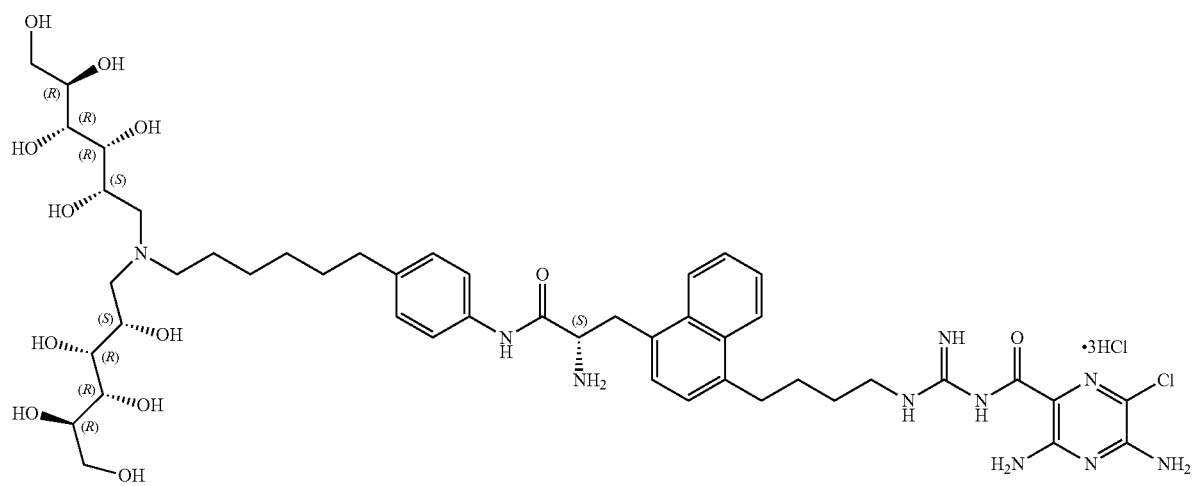
48
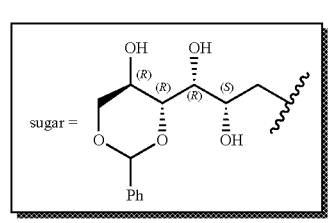

Preparation of Compound 45

A solution of acid 17 (900 mg, 1.74 mmol) in THF (40 mL) was cooled to 0° C. in an ice bath. NMM (0.38 mL, 3.48 mmol) was added, followed by PivCl (0.21 mL, 1.74 mmol), and the reaction mixture was stirred at the same temperature for 2 h. 44 (1.21 g, 1.74 mmol, 20 mL THF) was added and the reaction mixture was stirred at the same temperature for a further 10 min. The reaction mixture was brought to room temperature and stirred for 16 h. The organic solvent was removed. The residue was charged with water and extracted with $CH_2Cl_2$ (3×100 mL). The organic layers were combined, dried over $Na_2SO_4$, filtered, and concentrated. The residue was purified by column chromatography (4% methanol in chloroform) to afford amide 45 (2.00 g, impure) as a light yellow solid: $[M+H]^+$ 1196.

Preparation of Compound 46

A suspension of 45 (2.00 g, impure) and 10% Pd/C (400 mg) in a mixture of EtOH (120 mL) and AcOH (20 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 46, which was neutralized with $NaHCO_3$, and the crude product was purified by flash chromatography on silica gel (CMA, 80:18:2) yielding free amine 46 as a yellow solid (500 mg, 27% over two steps): $[M+H]^+$ 1067.

Preparation of Compound 47

A solution of amine 46 (500 mg, 0.47 mmol) and methyl 3,5-diamino-6-chloropyrazine-2-carbonylcarbamimidothioate (21, 330 mg, 0.84 mmol) in EtOH (20 mL) was charged with DIPEA (0.84 mL, 94.70 mmol) at room temperature. The reaction mixture was heated at 70° C. in a sealed tube for 2 h, cooled to room temperature, and concentrated under vacuum. The residue was purified by silica-gel column chromatography (80:18:2 $CHCl_3/CH_3OH/NH_4OH$) to afford guanidine 47 (325 mg, 55%) as a yellow solid: $[M+H]^+$ 1278.

Preparation of the HCl Salt Compound 48 3,5-diamino-N—(N-(4-(4-((S)-2-amino-3-(4-(6-(bis((2S,3R,4R,5R)-2,3,4,5,6-pentahydroxyhexyl)amino)hexyl)phenylamino)-3-oxopropyl)naphthalen-1-yl)butyl)carbamimidoyl)-6-chloropyrazine-2-carboxamide 4 N HCl in water (20 mL) was added to 47 (325 mg, 0.25 mmol) in EtOH (2.0 mL) and the reaction mixture was stirred at room temperature for 2 h. The solvent was removed, the mixture was purified by reverse-phase chromatography (Gold column), and the residue was lyophilized to afford compound 48 (165 mg, 60%) as a yellow solid: $^1H$ NMR (400 MHz, DMSO-$d_6$): δ 10.52 (brs, 1H), 10.44 (brs, 1H), 9.28 (t, J=5.2 Hz, 1H), 9.00-8.88 (m, 1H), 8.87-8.75 (m, 1H), 8.63 (brs, 2H), 8.60-8.50 (m, 1H), 8.39-8.33 (m, 1H), 8.17-8.11 (m, 1H), 7.58 (dd, J=6.5, 3.3 Hz, 2H), 7.47-7.35 (m, 2H), 7.36 (d, J=8.7 Hz, 2H), 7.33 (d, J=6.8 hz, 1H), 7.27 (d, J=3.6 Hz, 1H), 7.11 (d, J=8.8 Hz, 2H), 3.72-3.66 (m, 3H), 3.60 (d, J=3.6 Hz, 1H), 3.57 (d, J=2.8 Hz, 1H), 3.53-3.46 (m, 3H), 3.45-3.38 (m, 3H), 3.37-3.27 (m, 4H), 3.26-3.12 (m, 4H), 3.06 (t, J=8.5 Hz, 2H), 1.76-1.60 (m, 6H), 1.58-1.47 (m, 2H), 1.35-1.23 (m, 4H).

$^1H$ NMR (400 MHz, $CD_3OD$): δ 8.23-8.18 (m, 1H), 8.17-8.12 (m, 1H), 7.59-7.52 (m, 2H), 7.36 (d, J=7.8 Hz, 1H), 7.31 (d, J=7.2 Hz, 1H), 7.18 (d, J=8.2 Hz, 2H), 7.04 (d, J=8.2 Hz, 2H), 4.25 (t, J=7.8 Hz, 1H), 4.18-4.10 (m, 2H), 3.83-3.79 (m, 2H), 3.77 (d, J=3.1 Hz, 1H), 3.74 (d, J=3.5 Hz, 1H), 3.71-3.60 (m, 8H), 3.49-3.41 (m, 2H), 3.40-3.33 (m, 4H), 3.32-3.30 (m, 1H), 3.25-3.19 (m, 1H), 3.18-3.10 (m, 2H), 2.52 (t, J=7.4 Hz, 2H), 1.88-1.69 (m, 6H), 1.62-1.53 (m, 2H), 1.44-1.30 (m, 4H).

8. Preparation of 3,5-diamino-N—(N-(4-(4-((S)-2-amino-3-oxo-3-(4-(6-((2S,3R,4R,5R)-2,3,4,5,6-pentahydroxyhexylamino)hexyl)phenylamino)propyl)naphthalen-1-yl)butyl)carbamimidoyl)-6-chloropyrazine-2-carboxamide

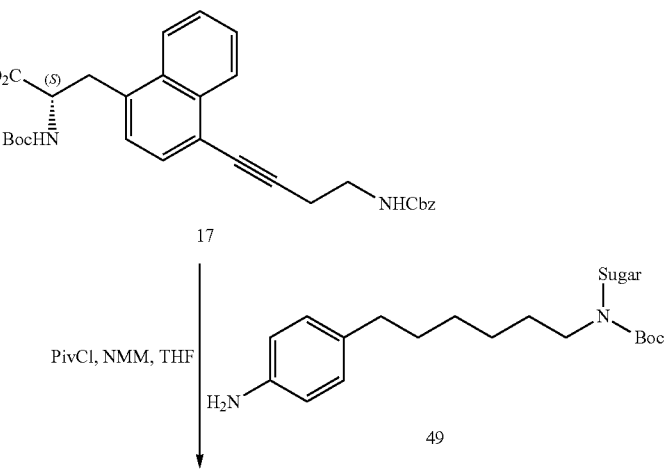

Scheme 9

-continued
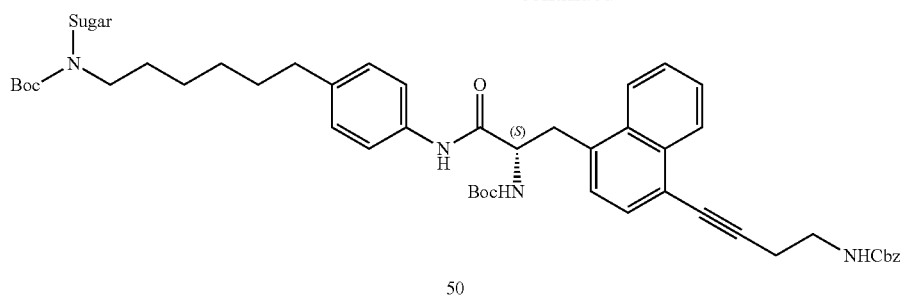
50
↓ Pd/C, H₂
EtOH, AcOH
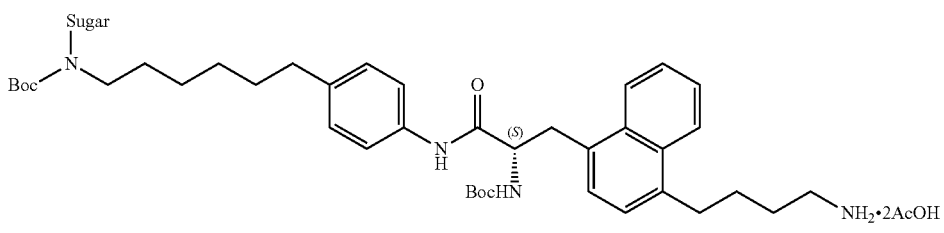
51
↓ DIPEA, EtOH
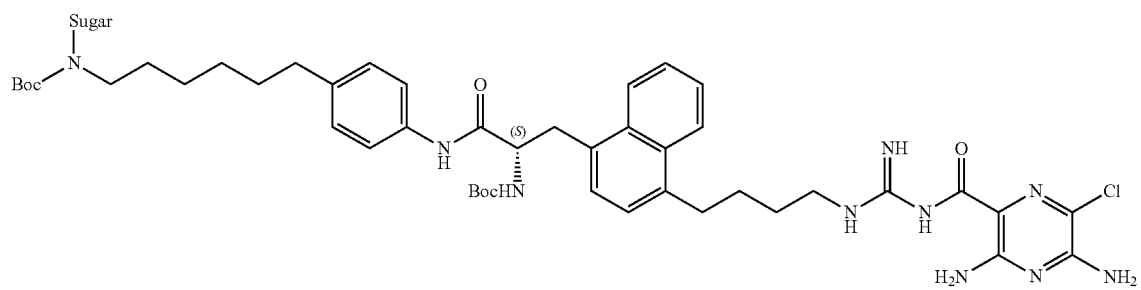
52
↓ 4N aq HCl, EtOH

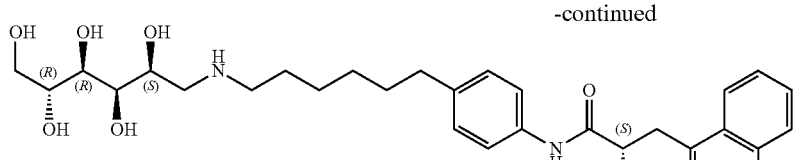
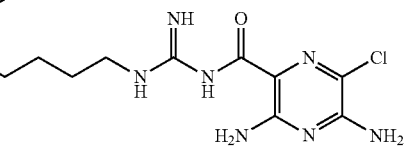

53

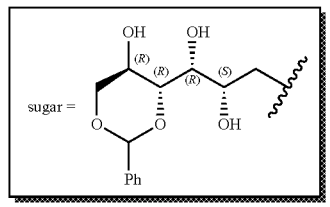

Preparation of Compound 50

A solution of acid 17 (950 mg, 1.84 mmol) in THF (30 mL) was cooled to 0° C. in an ice bath. NMM (0.40 mL, 3.68 mmol) was added, followed by PivCl (0.23 mL, 1.84 mmol), and the reaction mixture was stirred at the same temperature for 2 h. 49 (800 mg, 1.47 mmol, 10 mL THF) was added and the reaction mixture was stirred at the same temperature for a further 10 min. The reaction mixture was brought to room temperature and stirred for 16 h. The organic solvent was removed. The residue was charged with water and extracted with $CH_2Cl_2$ (3×100 mL). The organic layers were combined, dried over $Na_2SO_4$, filtered, and concentrated. The residue was purified by column chromatography (4% methanol in chloroform) to afford amide 50 (1.40 g, impure) as a light yellow solid: $[M+H]^+$ 1043.

Preparation of Compound 51

A suspension of 50 (1.40 g, impure) and 10% Pd/C (400 mg) in a mixture of EtOH (120 mL) and AcOH (20 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 51, directly used in the next step (1.20 g, crude): [M+H]+ 913.

Preparation of Compound 52

A solution of amine 51 (1.20 g, 0.47 mmol, crude) and methyl 3,5-diamino-6-chloropyrazine-2-carbonylcarbamimidothioate (21, 723 mg, 1.86 mmol) in EtOH (20 mL) was charged with DIPEA (2.00 mL, 11.6 mmol) at room temperature. The reaction mixture was heated at 70° C. in a sealed tube for 2 h, cooled to room temperature, and concentrated under vacuum. The residue was purified by silica-gel column chromatography (80:18:2 $CHCl_3/CH_3OH/$ $NH_4OH$) to afford guanidine 52 (500 mg, 24% over three steps) as a yellow solid: [M+H]+ 1125.

Preparation of the HCl Salt of Compound 53 3,5-diamino-N—(N-(4-(4-((S)-2-amino-3-oxo-3-(4-(6-((2S,3R,4R,5R)-2,3,4,5,6-pentahydroxyhexylamino) hexyl)phenylamino)propyl) naphthalen-1-yl)butyl) carbamimidoyl)-6-chloropyrazine-2-carboxamide 4 N HCl in water (25 mL) was added to 52 (500 mg, 0.44 mmol) in EtOH (5.0 mL) and the reaction mixture was stirred at room temperature for 2 h. The solvent was removed, the mixture purified by reverse-phase chromatography (Gold column), and the residue was lyophilized to afford compound 53 (170 mg, 41%) as a yellow solid: $^1H$ NMR (400 MHz, DMSO-$d_6$): δ 10.52 (brs, 1H), 10.45-10.41 (m, 1H), 9.31-9.24 (m, 1H), 9.02-8.89 (m, 1H), 8.88-8.76 (m, 1H), 8.70-8.58 (m, 3H), 8.57-8.46 (m, 2H), 8.40-8.31 (m, 1H), 8.17-8.10 (m, 1H), 7.62-7.54 (m, 2H), 7.42 (brs, 2H), 7.36 (d, J=8.7 Hz, 2H), 7.33 (d, J=6.7 Hz, 1H), 7.27 (d, J=7.5 Hz, 1H), 7.11 (d, J=8.7 Hz, 2H), 5.41-5.35 (m, 1H), 4.79-4.72 (m, 1H), 4.62-4.53 (m, 2H), 4.47-4.38 (m, 1H), 4.29-4.19 (m, 1H), 3.94-3.87 (m, 1H), 3.63-3.52 (m, 3H), 3.50-3.39 (m, 3H), 3.38-3.32 (m, 2H), 3.12-2.96 (m, 3H), 2.97-2.90 (m, 1H), 2.89-2.80 (m, 2H), 1.77-1.56 (m, 6H), 1.54-1.45 (m, 2H), 1.35-1.20 (m, 4H).

$^1H$ NMR (400 MHz, $CD_3OD$): δ 8.24-8.20 (m, 1H), 8.19-8.14 (m, 1H), 7.60-7.53 (m, 2H), 7.38 (d, J=7.6 Hz, 1H), 7.33 (d, J=7.2 Hz, 1H), 7.24-7.18 (m, 2H), 7.07 (d, J=8.1 Hz, 2H), 4.31-4.22 (m, 1H), 4.08-4.01 (m, 1H), 3.84 (dd, J=4.8, 1.3 Hz, 1H), 3.77 (dd, J=10.1, 2.5 Hz, 1H), 3.71-3.62 (m, 5H), 3.36 (t, J=7.2 Hz, 2H), 3.19-3.12 (m, 4H), 3.03-2.96 (m, 2H), 2.55 (t, J=7.7 Hz, 2H), 1.90-1.74 (m, 4H), 1.73-1.64 (m, 2H), 1.63-1.53 (m, 2H), 1.45-1.31 (m, 4H).

9. Preparation of 3,5-diamino-N—(N-(4-(4-((S)-2-amino-3-(4-(6-(hexyl((2S,3R,4R,5R)-2,3,4,5,6-pentahydroxyhexyl)amino)hexyl)phenylamino)-3-oxo-propyl)naphthalen-1-yl)butyl)carbamimidoyl)-6-chloropyrazine-2-carboxamide
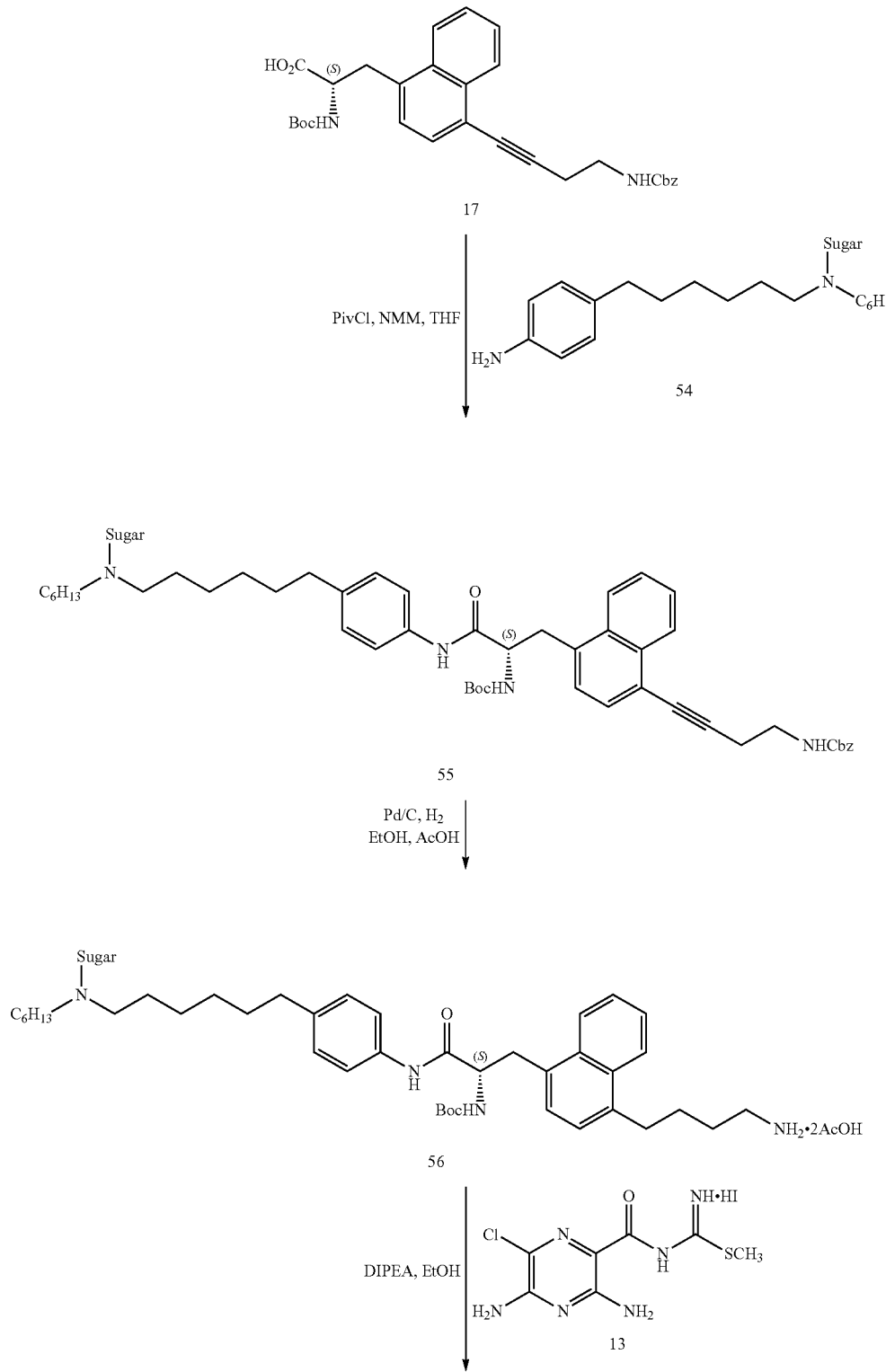

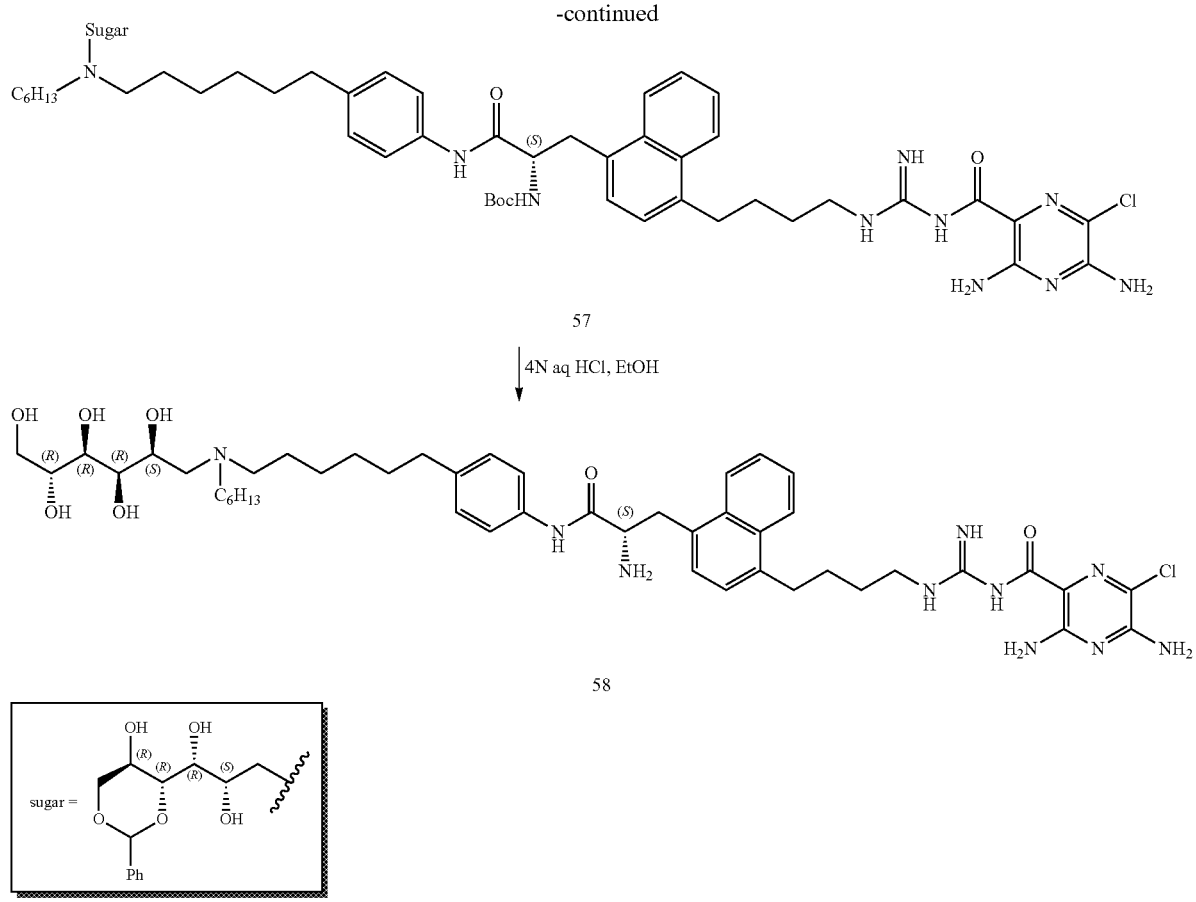

Preparation of Compound 55

Compound 54 (770 mg, 1.45 mmol) in THF (50 mL) was charged with DEPBT (564 mg, 1.88 mmol), 17 (752 mg, 1.45 mmol), and DIPEA (0.77 mL, 4.35 mmol) successively and stirred at room temperature for 16 h. After the solvent was removed under reduced pressure, the residue was dissolved in $CH_2Cl_2$ (100 mL), quickly washed with saturated aqueous $NaHCO_3$ (2×100 mL) and brine (50 mL), and dried over $Na_2SO_4$. The solvent was evaporated and the crude product purified by flash chromatography on silica gel (5% methanol/$CH_2Cl_2$) and by reverse-phase chromatography (Gold column), yielding amide 55 as a yellow solid (800 mg, 54%): $[M+H]^+$ 1027.

Preparation of Compound 56

A suspension of 55 (800 mg, 0.78 mmol) and 10% Pd/C (400 mg) in a mixture of EtOH (120 mL) and AcOH (30 mL) was degassed and subjected to hydrogenation conditions (1 atm) for 16 h at room temperature. The reaction mixture was filtered through a plug of Celite and the plug was washed with MeOH. The filtrate was concentrated under vacuum to afford amine salt 56 as a yellow solid (780 mg, 99%): $[M+H]^+$ 897.

Preparation of Compound 57

A solution of amine salt 56 (780 mg, 0.75 mmol) and methyl 3,5-diamino-6-chloropyrazine-2-carbonylcarbamimidothioate (21, 466 mg, 1.20 mmol) in EtOH (20 mL) was charged with DIPEA (1.37 mL, 7.67 mmol) at room temperature. The reaction mixture was heated at 70° C. in a sealed tube for 2 h, cooled to room temperature, and concentrated under vacuum. The residue was purified by silica-gel column chromatography (80:18:2 $CHCl_3/CH_3OH/NH_4OH$) to afford guanidine 57 (455 mg, 55%) as a yellow solid: $[M+H]^+$ 1110.

Preparation of the HCl Salt of Compound 58 3,5-diamino-N—(N-(4-(4-((S)-2-amino-3-(4-(6-(hexyl((2S,3R,4R,5R)-2,3,4,5,6-pentahydroxyhexyl) amino)hexyl)phenylamino)-3-oxopropyl)naphthalen-1-yl)butyl)carbamimidoyl)-6-chloropyrazine-2-carboxamide 4 N HCl in water (25 mL) was added to 57 (455 mg, 0.41 mmol) in ethanol (10 mL) and the reaction mixture was stirred at room temperature for 2 h. The mixture was purified by reverse-phase chromatography (Gold column) and the residue was lyophilized to afford compound 58 (230 mg, 55%) as a yellow solid: H NMR (400 MHz, DMSO-$d_6$): δ 10.45 (brs, 1H), 9.30 (brs, 1H), 9.09-8.49 (m, 3H), 8.41-8.32 (m, 1H), 8.16-8.08 (m, 1H), 7.62-7.52 (m, 2H), 7.42 (brs, 2H), 7.37 (t, J=8.4 Hz, 2H), 7.32 (d, J=7.8 Hz, 1H), 7.27 (d, J=7.2 Hz, 1H), 7.10 (d, J=8.1 Hz, 2H), 5.52-5.36 (m, 1H), 4.87-4.70 (m, 1H), 4.63-4.51 (m, 2H), 4.47-4.38 (m, 1H), 4.23 (t, J=6.7 Hz, 1H), 4.03-3.94 (m, 1H), 3.71-3.66 (m, 1H), 3.65-3.52 (m, 2H), 3.50-3.34 (m, 5H), 3.21 (d, J=3.2 Hz, 1H), 3.12 (d, J=3.2 Hz, 1H), 3.09-2.96 (m, 6H), 1.77-1.58 (m, 8H), 1.57-1.46 (m, 2H), 1.35-1.21 (m, 10H), 0.86 (t, J=6.4 Hz, 3H).

¹H NMR (400 MHz, CD₃OD): δ 8.26-8.20 (m, 1H), 8.19-8.12 (m, 1H), 7.60-7.51 (m, 2H), 7.38 (d, J=7.2 Hz, 1H), 7.32 (d, J=7.4 Hz, 1H), 7.21 (d, J=8.3 Hz, 2H), 7.06 (d, J=8.5 Hz, 2H), 4.26 (t, J=7.4 Hz, 1H), 4.16-4.09 (m, 1H), 3.82 (dd, J=5.0, 1.5 Hz, 1H), 3.78 (dd, J=11.3, 3.2 Hz, 1H), 3.72-3.61 (m, 6H), 3.35 (t, J=6.7 Hz, 2H), 3.24-3.11 (m, 7H), 2.54 (t, J=7.4 Hz, 2H), 1.90-1.67 (m, 8H), 1.64-1.54 (m, 2H), 1.44-1.30 (m, 10H), 0.92 (t, J=6.7 Hz, 3H).
10. Preparation of (S)-2-amino-3-(6-(4-(3-(3,5-diamino-6-chloropyrazine-2-carbonyl)guanidino)butyl)naphthalen-2-yl)propanoic acid (80)
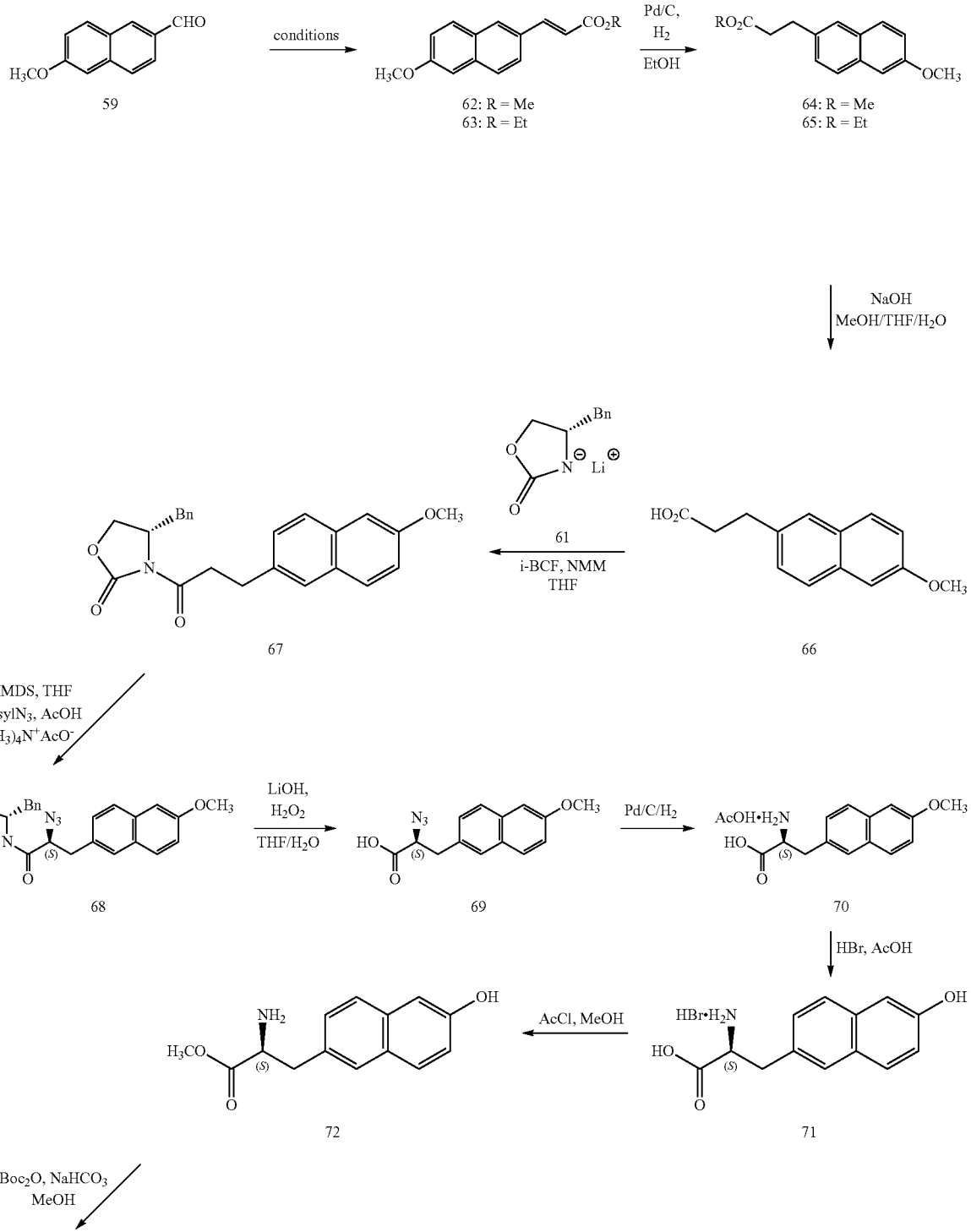

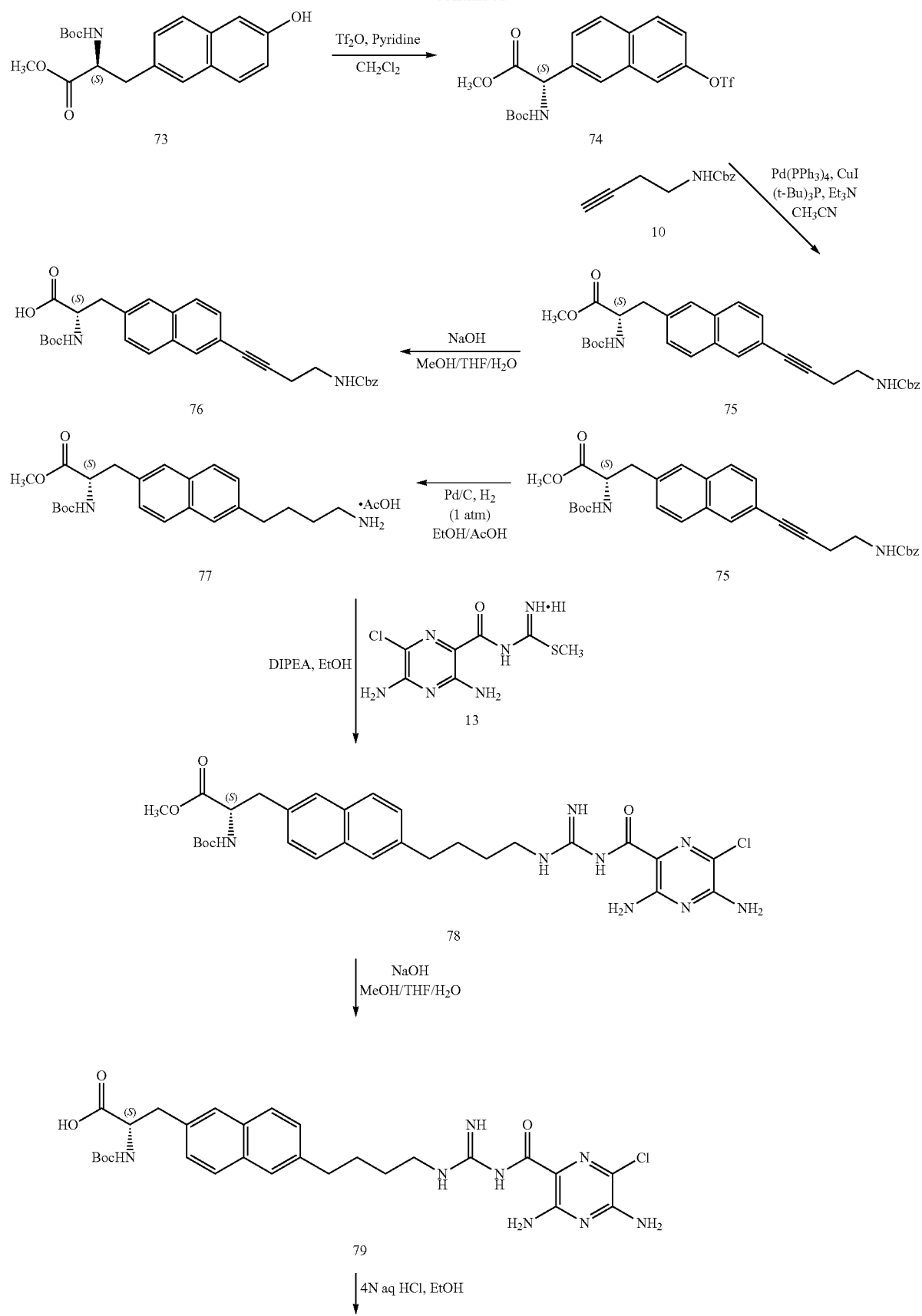

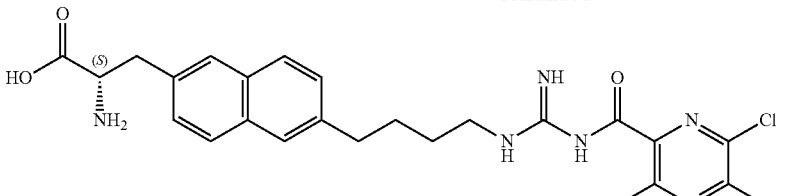

80

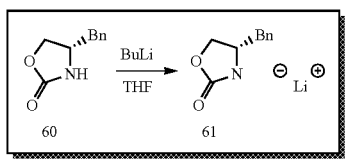

Preparation of Compound 62

The stable Wittig ylide carbomthoxymethylenetriphenyl-phosphorane (Ph₃PCHCO₂Me, 43.0 g, 129 mmol) was added to a solution of the aldehyde 59 (20.0 g, 107 mmol) in CH₂Cl₂ (200 mL) under nitrogen atmosphere and the reaction mixture was stirred 16 h at ambient temperature. TLC monitored the completion of the reaction (16 h). CH₂Cl₂ was removed under reduced pressure and FCC using 10% ethyl acetate-hexanes gave the corresponding trans-α,β-unsaturated ester 62 (24.0 g, 92%) as a white solid: $^1$H NMR (400 MHz, CDCl₃) δ 7.88-7.82 (m, 1H), 8.81 (d, J=15.8 Hz, 1H), 7.73 (d, J=9.0 Hz, 1H), 7.70 (d, J=8.8 Hz, 1H), 7.61 (dd, J=8.8, 2.2 Hz, 1H), 7.15 (dd, J=9.2, 2.2 Hz, 1H), 7.11 (d, J=2.2 Hz, 1H), 6.49 (d, J=15.8 Hz, 1H), 3.82 (s, 3H), 3.82 (s, 3H).

Preparation of Compound 62 (Additional Route)

To the Trimethyl phosphonoacetate (55.6 mL, 381 mmol) in 250 mL anhydrous CH₂Cl₂ cooled to 0° C. was added DBU (48.8 mL, 322 mmol) and the mixture was stirred for 15 min. Aldehyde 59 (40.0 g, 215 mmol) in 50 mL CH₂Cl₂ was added dropwise. The temperature of the reaction mixture brought to rt and resulting reaction mixture was stirred at rt for 16 h, and then quenched with 100 mL of Water. The mixture was partitioned, and the aq. layer was extracted with CH₂Cl₂ (3×150 mL). The combined organics were washed with brine, dried (Na2SO4), filtered, concentrated and the residue was purified by silica gel column chromatography (10:1 hexanes/ethyl acetate) to give the desired trans-α,β-unsaturated ester 62 (48.0 g, 92%) as a white solid.

Preparation of Compound 64

A suspension of compound 62 (48.0 g, 196 mmol) and 10% Pd/C (10 g) in EtOAc/THF (600 mL/75 mL) was subjected to hydrogenation conditions (1 atm) for 16 h at room temperature. The reaction mixture was filtered through celite and washed with MeOH. The filtrate was concentrated in vacuum to afford 64 (46.5 g, 96%) as a white solid: $^1$H NMR (400 MHz, CDCl3) δ 7.67 (d, J=9.4 Hz, 2H), 7.57-7.54 (m, 1H), 7.29 (dd, J=8.6, 1.8 Hz, 1H), 7.12 (dd, J=8.8, 2.5 Hz, 1H), 7.11-7.09 (m, 1H), 3.90 (s, 3H), 3.66 (s, 3H), 3.07 (t, J=7.7 Hz, 2H), 2.70 (t, J=7.7 Hz, 2H).

Preparation of Compound 66

To a solution of methyl ester 64 (46.5 g, 191 mmol) in THF/MeOH/H₂O (500 mL/500 mL/150 mL) was added NaOH (45.6 g, 114 mmol) and the reaction mixture was stirred at room temperature for 2 h. Solvent was removed and pH value was adjusted to 1 with 1 N aq HCl; white solid precipitated out. Solid was filtered, washed with water and dried under vacuum to afford acid 66 (42.5 g, 97%) as a white solid: $^1$H NMR (400 MHz, DMSO-d₆) δ 12.14 (brs, 1H), 7.73 (dd, J=9.5, 2.3 Hz, 2H), 7.64-7.61 (m, 1H), 7.35 (dd, J=8.5, 1.5 Hz, 1H), 7.26 (d, J=2.8 Hz, 1H), 7.12 9 (dd, J=9.1, 2.5 Hz, 1H), 3.85 (s, 3H), 2.94 (t, J=7.6 Hz, 2H), 2.60 (t, J=7.6 Hz, 2H).

Preparation of Compound 67

To a solution of compound 60 (39.3 g, 222 mmol) in dry THF (500 mL) was added n-butyl lithium (110 mL, 2M solution in cyclohexane) drop wise at −78° C. and the reaction mixture was stirred for 1 h to give a solution of compound 61. To another solution of compound 66 (42.5 g, 185 mmol) in dry THF (1000 mL) was added NMM (26.3 mL, 240 mmol) and PivCl (27.3 mL, 222 mmol) drop wise at −78° C. The reaction mixture was stirred for for 1 min at the same temperature, and then the prepared solution of compound 66 was added slowly at −78° C. The reaction mixture was stirred for another 10 min then brought to 0° C. and stirred for 1 h followed by at room temperature for 30 min, quenched with satd NH₄Cl, concentrated to remove THF, and partitioned between CH₂Cl₂ (1000 mL) and water (1000 mL). The aqueous layer was separated and extracted with CH₂Cl₂ (2×1000 mL). The combined organic extracts were dried over Na₂SO₄ and concentrated. The residue was purified by column chromatography (silica gel, CH₂Cl₂) to afford compound 67 (45.0 g, 63%) as a white solid: $^1$H NMR (400 MHz, CDCl3) δ 7.68 (d, J=8.6 Hz, 2H), 7.64-7.61 (m, 1H), 7.31 (dd, J=8.5, 1.8 Hz, 1H), 7.33-7.24 (m, 4H), 7.17-7.12 (m, 2H), 7.11-7.09 (m, 1H), 4.69-4.61 (m, 1H), 4.15 (d, J=2.4 Hz, 1H), 4.13 (s, 1H), 3.90 (s, 3H), 3.46-3.21 (m, 3H), 3.20-3.08 (m, 2H), 2.74 (dd, J=13.6, 9.4 Hz, 1H).

Preparation of Compound 68

To a solution of compound 67 (45.0 g, 116 mmol) in dry THF (700 mL) was added KHMDS (34.6 g, 174 mmol) portion wise at −78° C. After the resulting mixture was stirred for 30 min, trisyl azide (53.6 g, 174 mmol) was added and the reaction mixture was stirred for 5 min. Then acetic acid (69.6 mL, 1158 mmol) followed by tetramethyl ammonium acetate (30.9 g, 232 mmol) was added slowly at the same temperature. The reaction mixture was allowed to be warmed to 24° C., stirred for 16 h, quenched with satd NaHCO$_3$ (300 mL), concentrated to remove THF and extracted with CH$_2$Cl$_2$ (2×500 mL). The combined organic extracts were dried over Na$_2$SO$_4$ and concentrated. The residue was purified by column chromatography (silica gel, 10:90 EtOAc/Hexane followed by DCM) to afford compound 68 (31.0 g, 62%) as yellow solid1: $^1$H NMR (400 MHz, CDCl$_3$) δ 7.70 (d, J=9.1 Hz, 2H), 7.68-7.65 (m, 1H), 7.40 (dd, J=8.6, 1.8 Hz, 1H), 7.36-7.23 (m, 3H), 7.20 (d, J=1.8 Hz, 1H), 7.19-7.17 (m, 1H), 7.13 (dd, J=9.0, 2.6 Hz, 1H), 7.10 (d, J=2.4 Hz, 1H), 5.36 (dd, J=9.0, 6.0 Hz, 1H), 4.58-4.50 (m, 1H), 4.11 (dd, J=9.1, 2.6 Hz, 1H), 3.90 (s, 3H), 3.91 (t, J=8.6 Hz, 1H), 3.34 (dd, J=13.8, 6.5 Hz, 1H), 3.30 (dd, J=13.0, 3.5 Hz, 1H), 3.19 (dd, J=13.4, 8.6 Hz, 1H), 2.81 (dd, J=13.4, 9.5 Hz, 1H).

Preparation of Compound 69

To a solution of compound 68 (31.0 g, 72.1 mmol) in THF/H$_2$O (300 mL/100 mL) was added H$_2$O$_2$ (49 mL, 433 mmol) followed by LiOH (6.04 g, 144 mmol) portion wise at 0° C. The reaction mixture was stirred for 10 min at the same temperature followed by at rt for 1 hr then quenched with satd Na$_2$SO$_3$ (200 mL), concentrated under reduced pressure to remove THF and washed with CH$_2$Cl$_2$ (500 mL). The aqueous layer was acidified with 1N aq HCl and extracted with CH$_2$Cl$_2$ (2×500 mL). The combined organic extracts were dried over Na$_2$SO$_4$, concentrated and washed with MTBE to afford compound 69 (15.0 g, 82%) as an off-white solid: $^1$H NMR (400 MHz, MeOD-d$_3$) δ 7.70 (t, J=8.4 Hz, 2H), 7.66-7.63 (m, 1H), 7.35 (dd, J=8.6, 1.7 Hz, 1H), 7.19 (d, J=2.8 Hz, 1H), 7.10 (dd, J=9.1, 2.6 Hz, 1H), 4.25 (dd, J=8.6, 5.3 Hz, 1H), 3.88 (s, 3H), 3.29 (dd, J=13.9, 5.1 Hz, 1H), 3.10 (dd, J=14.3, 8.6 Hz, 1H).

Preparation of Compound 70

A suspension of compound 69 (15.0 g, 55.1 mmol) and 10% Pd/C (3.50 g) in AcOH/H$_2$O (300 mL/100 mL) was subjected to hydrogenation conditions (1 atm) for 3 h at room temperature. The reaction mixture was filtered through Celite and washed with AcOH/H$_2$O followed by MeOH. The filtrate was concentrated in vacuum to afford acetic salt 70 (14.0 g, 83%) as a yellow solid: $^1$H NMR (400 MHz, DMSO-d$_6$,TFA) δ 8.38-8.18 (m, 3H), 7.78 (dd, J=11.4, 8.1 Hz, 2H), 7.75-7.70 (m, 1H), 7.41 (dd, J=8.6, 1.6 Hz, 1H), 7.29 (d, J=2.3 Hz, 1H), 7.18 (dd, J=8.8, 2.4 Hz, 1H), 4.33-4.23 (m, 1H), 3.89 (s, 3H), 3.33 (dq, J=14.5, 5.9 Hz, 2H), 1.92 (s, 3H).

Preparation of Compound 71

To a solution of compound 70 (14.0 g, 45.9 mmol) in acetic acid (140 mL) was added hydro bromic acid (140 mL) drop wise at room temperature and the reaction mixture was refluxed for 3 h. The reaction mixture was cooled to room temperature and concentrated. The crude brown residue 71 (12.4 g, 87%) was directly used for the next step without any purification: $^1$H NMR (400 MHz, DMSO-d$_6$) δ 13.83 (brs, 1H), 9.71 (brs, 1H), 8.41 (brs, 1H), 8.25 (brs, 2H), 7.67 (dd, J=13.8, 8.7 Hz, 2H), 7.64-7.61 (m, 1H), 7.29 (dd, J=8.6, 1.7 Hz, 1H), 7.13-7.05 (m, 2H), 4.29-4.19 (m, 1H), 3.20 (t, J=5.5 Hz, 2H).

Preparation of Compound 72

Acetyl chloride (38.4 mL, 540 mmol) was added to dry methanol (400 mL) at 0° C. and then compound 71 (24.0 g, 77.2 mmol) was added. The reaction mixture was refluxed for 4 h and concentrated. The residue was partitioned between CH$_2$Cl$_2$ (500 mL) and saturated NaHCO$_3$ (300 mL). The aqueous layer was separated and extracted with CH$_2$Cl$_2$ (2×300 mL). The combined organic extracts were dried over Na$_2$SO$_4$ and concentrated to afford compound 72 (16.6 g, 88%) as white solid: $^1$H NMR (400 MHz, DMSO-d$_6$) δ 9.62 (brs, 1H), 7.67 (d, J=9.4 Hz, 1H), 7.58 (d, J=8.8 Hz, 1H), 7.53 (s, 1H), 7.22 (dd, J=8.2, 1.4 Hz, 1H), 7.09-7.06 (m, 1H), 7.04 (dd, J=8.8, 2.6 Hz, 1H), 3.67 (t, J=6.5 Hz, 1H), 3.57 (s, 3H), 2.97 (dd, J=13.5, 6.1 Hz, 1H), 2.86 (dd, J=13.2, 7.4 Hz, 1H), 1.90 (brs, 2H).

Preparation of Compound 73

To a solution of compound 72 (16.6 g, 67.8 mmol) in MeOH/H$_2$O (360 mL/120 mL) was added NaHCO$_3$ (22.8 g, 271 mmol) and Boc$_2$O (17.7 g, 81.3 mmol) at 0° C. The resulting mixture was allowed to warm to room temperature and stirred for 1 h. The reaction mixture was partitioned between CH$_2$Cl$_2$ (200 mL) and water (200 mL). The aqueous layer was separated and extracted with CH$_2$Cl$_2$ (2×400 mL). The combined organic extracts were washed with brine, dried over Na$_2$SO$_4$ and concentrated. FCC using 20% ethyl acetate-hexanes followed by CH$_2$Cl$_2$ gave the compound 73 (17.0 g, 73%) as a white solid: $^1$H NMR (400 MHz, CDCl$_3$) δ 7.60 (d, J=9.5 Hz, 1H), 7.51 (d, J=8.2 Hz, 1H), 7.49-7.43 (m, 1H), 7.15 (d, J=8.2 Hz, 1H), 7.09-6.99 (m, 2H), 6.31 (brs, 1H), 5.15-4.84 (m, 1H), 4.73-4.46 (m, 1H), 3.71 (s, 3H), 3.23 (dd, J=13.7, 5.3 Hz, 1H), 3.14 (dd, J=13.7, 5.5 Hz, 1H), 1.39 (s, 9H).

Preparation of Compound 74

To a solution of compound 73 (7.0 g, 20.3 mmol) in CH$_2$Cl$_2$ (300 mL) was added pyridine (16.5 mL, 203 mmol) was added triflate (5.11 mL, 30.4 mmol) at 0° C. and stirred at same temperature for 1 h followed by at room temperature for 2 h. After concentrated, the reaction mixture was partitioned between CH$_2$Cl$_2$ (300 mL) and water (200 mL). The aqueous layer was separated and extracted with CH$_2$Cl$_2$ (2×300 mL). The combined organic extracts were washed with brine, dried over Na$_2$SO$_4$ and concentrated to afford compound 74 (8.80 g, 91%) as a brown oil (pyridine present as confirmed by NMR). The reaction was monitored by using LC-MS, and product formation was confirmed by LM-MS data: $^1$H NMR (400 MHz, CDCl$_3$) 7.85 (d, J=9.2 Hz, 1H), 7.80 (d, J=8.7 Hz, 1H), 7.71 (d, J=2.7 Hz, 1H), 7.66-7.63 (m, 1H), 7.37 (ddd, J=10.0, 7.3, 2.0 Hz, 2H), 5.12-5.03 (m, 1H), 4.73-4.61 (m, 1H), 3.72 (s, 3H), 3.32 (dd, J=13.3, 5.3 Hz, 1H), 3.20 (dd, J=13.3, 6.2 Hz, 1H), 1.38 (s, 9H).

Preparation of Compound 75

Compound 74 (16.5 g, 34.6 mmol) and benzyl but-3-ynylcarbamate (17, 10.4 g, 51.9 mmol) in anhydrous CH$_3$CN (450 mL) was degassed with Argon for 10 min at rt, then added TEA (19.3 mL, 138 mmol), 10% (t-Bu)$_3$P in hexanes (13.9 mL, 6.91 mmol), and CuI (0.33 g, 1.72 mmol) at room temperature. The resulting mixture was degassed with Argon for 10 min and Pd(PPh$_3$)$_4$ (3.99 g, 3.45 mmol) was added rapidly in one portion. After degassed with Argon for 5 min, the resulting mixture was refluxed for 18 h. The reaction mixture was concentrated in vacuum and the residue was purified by column (silica gel, 75:25 hexanes/EA) to afford compound 75 (14.1 g, 77%) as a brown solid: $^1$H NMR (400 MHz, CDCl$_3$) δ 7.86 (brs, 1H), 7.68 (t, J=7.8 Hz, 2H), 7.53 (brs, 1H), 7.41 (dd, J=8.5, 1.6 Hz, 1H), 7.38-7.28 (m, 5H), 7.27-7.22 (m, 1H), 5.26-5.17 (m, 1H), 5.13 (s, 2H), 5.06-4.99 (m, 1H), 4.70-4.59 (m, 1H), 3.69 (s, 3H), 3.46 (q, J=6.7 Hz, 2H), 3.27 (dd, J=14.1, 5.9 Hz, 1H), 3.16 (dd, J=13.2, 6.2 Hz, 1H), 2.67 (t, J=6.6 Hz, 2H), 1.38 (s, 9H).

Preparation of Compound 76

To a solution of methyl ester 75 (12.1 g, 22.8 mmol) in THF/MeOH/H$_2$O (150 mL/150 mL/50 mL) was added NaOH (4.56 g, 114 mmol) and the reaction mixture was stirred at room temperature for 2 h. The pH value was adjusted to 9 with 1 N aq HCl and organic solvent was removed. The pH value of residue was adjusted to 5-6, and the suspension was partitioned between CH$_2$Cl$_2$ (500 mL) and water (200 mL). The aqueous layer was separated and extracted with CH$_2$Cl$_2$ (2×400 mL). The combined organic extracts were dried over Na$_2$SO$_4$ and concentrated to afford compound 76 (10.50 g, 89%) as a brown solid: $^1$H NMR (400 MHz, CD$_3$OD) δ 7.83 (s, 1H), 7.73-7.61 (m, 3H), 7.44-7.19 (m, 7H), 5.10 (s, 2H), 4.42-4.34 (m, 1H), 3.41-3.32 (m, 3H), 3.06 (dd, J=14.3, 9.3 Hz, 1H), 2.64 (t, J=7.0 Hz, 2H), 1.31 (s, 7H), 1.21 (s, 2H).

Preparation of Compound 77; SG-SJL-B-27

A suspension of 75 (2.0 g, 3.77 mmol) and 10% Pd/C (500 mg) in a mixture of EtOH (90 mL) and AcOH (10 mL) was degassed and then subjected to hydrogenation conditions (1 atm) for 16 h at room temperature. The reaction mixture was filtered through a plug of Celite and the plug was washed with MeOH. The filtrate was concentrated in vacuum to afford amine salt 77 (1.60 mg, 93%) as a white solid: $^1$H NMR (400 MHz, CD$_3$OD) 7.73 (d, J=8.5, 1H), 7.72 (d, J=8.7 Hz, 1H), 7.62 ((brs, 2H), 7.73 (ddd, J=10.0, 8.7, 2.7 Hz, 2H), 4.44 (dd, J=8.8, 5.6 Hz, 1H), 3.68 (s, 3H), 3.25 (dd, J=14.0, 6.6 Hz, 1H), 3.04 (dd, J=13.5, 9.2 Hz, 1H), 2.93 (t, J=7.4 Hz, 2H), 2.83 (t, J=7.4 Hz, 2H), 1.96 (s, 6H), 1.85-1.75 (m, 2H), 1.74-1.68 (m, 2H), 1.33 (s, 7H), 1.26 (s, 2H).

Preparation of Compound 78; SG-SJL-B-30

To a solution of amine salt 77 (1.60 g, 3.47 mmol) and methyl 3,5-diamino-6-chloropyrazine-2-carbonylcarbamimidothioate (13, 2.16 g, 5.56 mmol) in EtOH (40 mL) was added DIPEA (6.20 mL, 34.70 mmol) at room temperature. The reaction mixture was heated at 70° C. in a sealed tube for 1 h, then cooled to room temperature, and concentrated in vacuum. The residue was purified by column chromatography (silica gel, 80:18:2 CHCl$_3$/CH$_3$OH/NH$_4$OH) to afford guanidine 78 (1.24 g, 59%) as a yellow solid: $^1$H NMR (400 MHz, CD$_3$OD) δ 7.71 (dd, J=8.4, 2.8 Hz, 1H), 7.60 (brs, 2H), 7.34 (dd, J=8.5, 1.9 Hz, 1H), 7.30 (dd, J=8.7, 1.7 Hz, 1H), 4.45 (dd, J=8.9, 5.7 Hz, 1H), 3.68 (s, 3H), 3.28-3.26 (m, 1H), 3.25 (t, J=2.4 Hz, 1H), 3.22 (d, J=5.9 Hz, 1H), 3.04 (dd, J=14.0, 9.2 Hz, 1H), 2.82 (t, J=7.2 Hz, 2H), 1.86-1.77 (m, 2H), 1.73-1.63 (m, 2H), 1.32 (s, 7H), 1.23 (s, 2H).

Preparation of Compound 79; SG-SJL-B-32

A solution of methyl ester 78 (1.24 g, 2.00 mmol) in a mixture of THF (25 mL), methanol (25 mL) and water (10 mL) was added solid NaOH (324 mg, 8.00 mmol) and the reaction mixture was stirred at room temperature for 1 h. TLC of the reaction mixture showed completion of reaction then pH of the reaction mixture was brought to pH 9-10 by addition of 1 N HCl (aqueous) and organic solvent was removed. The pH of aq. part was adjusted to pH 5-6 and precipitated came out and extracted with dichloromethane. Aqueous part was extracted with CH$_2$Cl$_2$ (2×50 mL). Organic layers were combined, dried over Na$_2$SO$_4$, filtered, and concentrated. Yellow colored solid compound (79, 1.10 g, 92%) was dried under vacuum: $^1$H NMR ((400 MHz, CD$_3$OD) 7.70 (t, J=9.4, 2H), 7.61 (d, J=5.3 Hz, 2H), 7.33 (dd, J=8.4, 1.4 Hz, 2H), 4.38 (dd, J=8.4, 5.1 Hz, 1H), 3.05 (dd, J=14.1, 9.1 Hz, 1H), 2.84 (t, J=6.9 Hz, 2H), 3.35-3.34 (m, 3H), 1.88-1.79 (m, 2H), 1.76-1.67 (m, 2H), 1.32 (s, 7H), 1.21 (s, 2H).

Preparation of Compound 80—Hydrochloride salt of (S)-2-amino-3-(6-(4-(3-(3,5-diamino-6-chloropyrazine-2-carbonyl)guanidino)butyl)naphthalen-2-yl) propanoic acid 4 N HCl in dioxane (25 mL) was added to 79 (1.10 g, 1.83 mmol) in EtOH (5.0 mL) and reaction mixture was stirred at room temperature for 2 h. The solvent was removed, purified by reverse phase column (gold column) and residue was lyophilized to afford compound 80 (700 mg, 67%) as a yellow solid: $^1$H NMR (400 MHz, DMSO-d6) 10.48 (s, 1H), 9.24 (brs, 1H), 8.99-8.86 (m, 1H), 8.84-8.70 (m, 1H), 8.38 (brs, 3H), 7.80 (t, J=9.2 Hz, 2H), 7.73 (s, 1H), 7.69 (s, 1H), 7.45-7.35 (m, 4H), 4.25 (dd, J=11.4, 5.9 Hz, 1H), 3.34 (q, J=6.6 Hz, 2H), 3.27 (d, J=6.9 Hz, 2H), 2.79 (t, J=7.70 Hz, 2H), 1.79-1.67 (m, 2H), 1.65-1.54 (m, 2H).
$^1$H NMR ((400 MHz, CD$_3$OD) 7.82 (d, J=8.5 Hz, 1H), 7.78 (d, J=8.7 Hz, 1H), 7.73 (s, 1H), 7.68 (s, 1H), 7.40 (ddd, J=10.5, 8.6, 1.6 Hz, 2H), 4.33 (dd, J=7.7, 5.2 Hz, 1H), 3.46 (dd, J=14.9, 6.0 Hz, 1H), 3.37 (t, J=7.5 Hz, 2H), 3.33-3.29 (m, 1H), 2.87 (t, J=7.7 Hz, 2H), 1.90-1.80 (m, 2H), 1.79-1.71 (m, 2H).

11. Preparation of (S)-3,5-diamino-6-chloro-N—(N-(4-(6-(2,3-diamino-3-oxopropyl)naphthalen-2-yl) butyl)carbamimidoyl)pyrazine-2-carboxamide (84)

Scheme 12

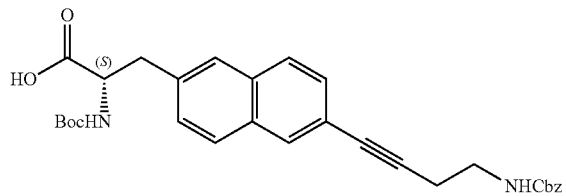

76 i-BCF, NMM
7N NH$_3$ in MeOH

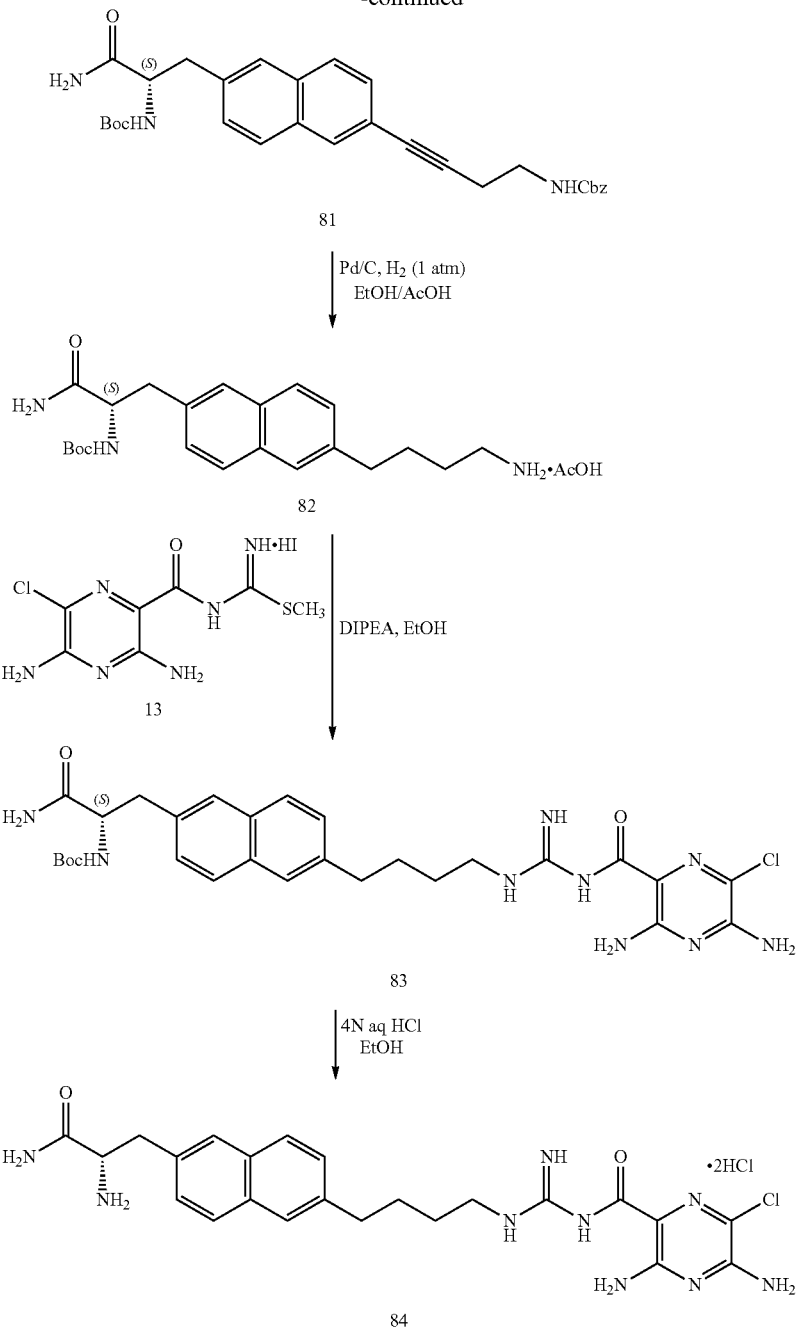

Preparation of Compound 81

A solution of acid 76 (2.0 g, 3.87 mmol) in THF (80 mL) was cooled to 0° C. in ice-bath, NMM (0.63 mL, 5.03 mmol) was added followed by dropwise i-BCF (0.63 mL, 5.80 mmol) and the reaction mixture was stirred at the same temperature for 2 h. NH$_3$ (7.0 N in methanol, 5.52 mL, 38.7 mmol) was added dropwise and the reaction mixture was stirred at the same temperature for a further 2 h. Reaction mixture was then brought to rt and stirred for 16 h. Organic solvent was removed. To this residue was added water and extracted with CH$_2$Cl$_2$ (3×100 mL). The organic layers were combined, dried over Na$_2$SO$_4$, filtered, and concentrated. The residue was purified by column chromatography (3% methanol in chloroform) to afford amide 81 (1.75 g, 88%) as a light yellow solid: $^1$H NMR (400 MHz, CD$_3$OD) 7.83 (s, 1H), 7.69 (d, J=8.1 Hz, 2H), 7.66 (s, 1H), 7.39 (dt, J=8.8, 1.9 Hz, 2H), 7.35-7.21 (m, 5H), 5.09 (s, 2H), 4.40 (dd, J=9.6, 5.8 Hz, 1H), 3.37 (t, J=6.9 Hz, 2H), 3.27 (dd, J=13.8, 5.2 Hz, 1H), 2.97 (dd, J=13.7, 9.4 Hz, 1H), 2.63 (t, J=7.0 Hz, 2H), 1.27 (s, 7H), 1.21 (s, 2H).

Preparation of Compound 82

A suspension of 81 (1.75 mg, 3.39 mmol) and 10% Pd/C (600 mg) in a mixture of EtOH (110 mL) and AcOH (15 mL) was degassed and then subjected to hydrogenation conditions (1 atm) for 12 h at room temperature. The reaction mixture was filtered through a plug of Celite and the plug was washed with MeOH. The filtrate was concentrated in vacuum to afford amine salt 82 as a white solid (1.40 g, 93%): $^1$H NMR (400 MHz, CD$_3$OD) 7.72 (dd, J=8.3, 5.6 Hz, 2H), 7.66 (s, 1H), 7.61 (s, 1H), 7.38 (dd, J=8.6, 1.3 Hz, 1H), 7.34 (dd, J=8.5, 1.5 Hz, 1H), 4.38 (dd, J=9.0, 5.0 Hz, 1H), 3.27 (dd, J=13.8, 5.0 Hz, 1H), 2.93 (t, J=7.9 Hz, 2H), 2.83 (t, J=7.5 Hz, 2H), 3.01-2.95 (m, 1H), 1.96 (s, 3H), 1.86-1.75 (m, 2H), 1.74-1.64 (m, 2H), 1.29 (s, 7H), 1.23 (s, 2H).

Preparation of Compound 83

To a solution of amine salt 82 (1.40 g, 3.15 mmol) and methyl 3,5-diamino-6-chloropyrazine-2-carbonylcarbamimidothioate (13, 1.96 g, 5.04 mmol) in EtOH (40 mL) was added DIPEA (5.64 mL, 31.5 mmol) at room temperature. The reaction mixture was heated at 70° C. in a sealed tube for 2 h, then cooled to room temperature, and concentrated in vacuum. The residue was purified by column chromatography (silica gel, 80:18:2 CHCl$_3$/CH$_3$OH/NH$_4$OH) to afford guanidine 83 (1.15 g, 61%) as a yellow solid: $^1$H NMR (400 MHz, CD$_3$OD) δ 7.70 (d, J=8.3 Hz, 2H), 7.64 (s, 1H), 7.60 (s, 1H), 7.34 (dt, J=8.9, 1.9 Hz, 2H), 4.38 (dd, J=9.0, 5.5 Hz, 1H), 3.28-3.20 (m, 3H), 2.96 (dd, J=9.6, 14.1 Hz, 1H), 2.81 (t, J=7.4 Hz, 2H), 1.85-1.76 (m, 2H), 1.70-1.61 (m, 2H), 1.27 (s, 7H), 1.20 (s, 2H).

Preparation of Compound the HCl Salt of (S)-3,5-diamino-6-chloro-N—(N-(4-(6-(2,3-diamino-3-oxopropyl)naphthalen-2-yl)butyl)carbamimidoyl)pyrazine-2-carboxamide (84)

4 N HCl in dioxane (25 mL) was added to 83 (1.15 g, 1.92 mmol) in EtOH (6.0 mL) and reaction mixture was stirred at room temperature for 2 h. The solvent was removed, purified by reverse phase column (gold column) and residue was lyophilized lyophilized to afford compound 84 (310 mg, 28%) as a yellow solid: H NMR (400 MHz, DMSO-d$_6$) 10.56 (s, 1H), 9.38 (t, J=5.5 Hz, 1H), 9.06-8.83 (m, 2H), 8.31 (brs, 3H), 8.02 (s, 1H), 7.79 (t, J=8.6 Hz, 2H), 7.73 (s, 1H), 7.69 (s, 1H), 7.51 (s, 1H), 7.46-7.36 (m, 4H), 4.06 (dd, J=11.5, 6.0 Hz, 1H), 3.37 (q, J=6.4 Hz, 2H), 3.27 (dd, J=6.6, 1.4 Hz, 1H), 3.18 (dd, J=13.7, 6.9 Hz, 1H), 2.79 (t, J=7.1 Hz, 2H), 1.79-1.69 (m, 2H), 1.64-1.54 (m, 2H).

$^1$H NMR (400 MHz, CD$_3$OD) 7.82 (d, J=8.4 Hz, 1H), 7.79 (d, J=8.7 Hz, 1H), 7.74 (s, 1H), 7.68 (s, 1H), 7.41 (td, J=8.1, 1.6 Hz, 2H), 4.18 (dd, J=8.1, 6.3 Hz, 1H), 3.42-3.34 (m, 3H), 3.21 (dd, J=14.1, 8.0 Hz, 1H), 2.86 (t, J=7.4 Hz, 2H), 1.91-1.80 (m, 2H), 1.79-1.71 (m, 2H).

12. Preparation of 3,5-diamino-N—(N-(4-(6-((S)-2-amino-3-(4-(3-(hexyl((2S,3R,4R,5R)-2,3,4,5,6-pentahydroxyhexyl)amino)propyl)phenylamino)-3-oxopropyl)naphthalen-2-yl)butyl)carbamimidoyl)-6-chloropyrazine-2-carboxamide (89)

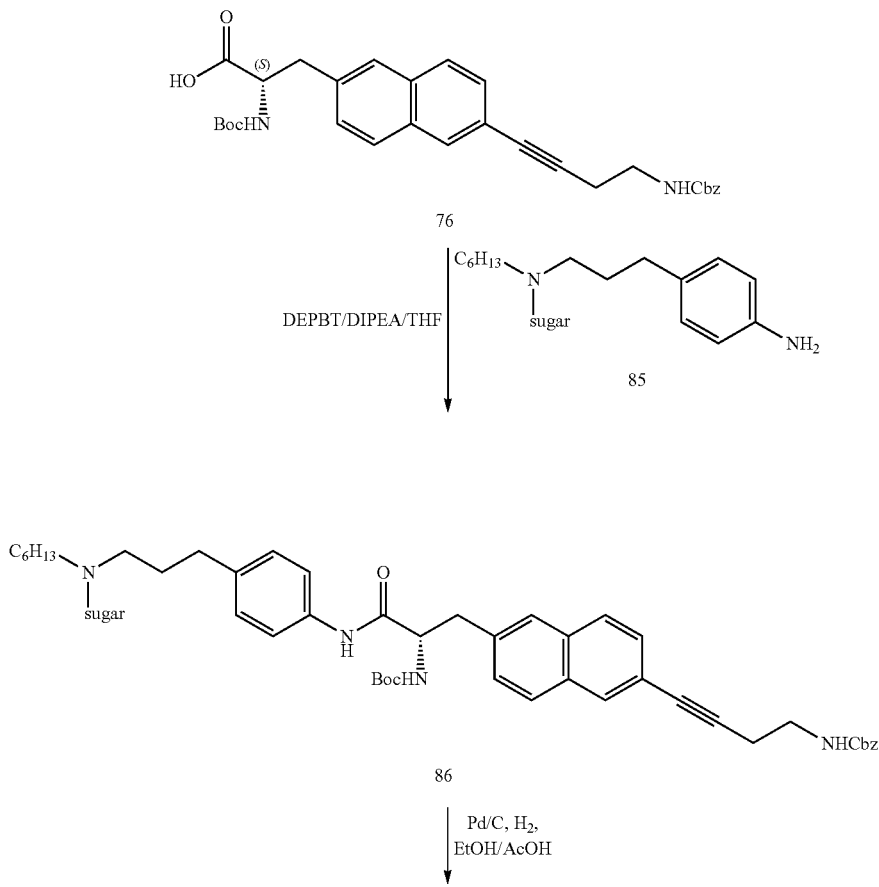

Scheme 13

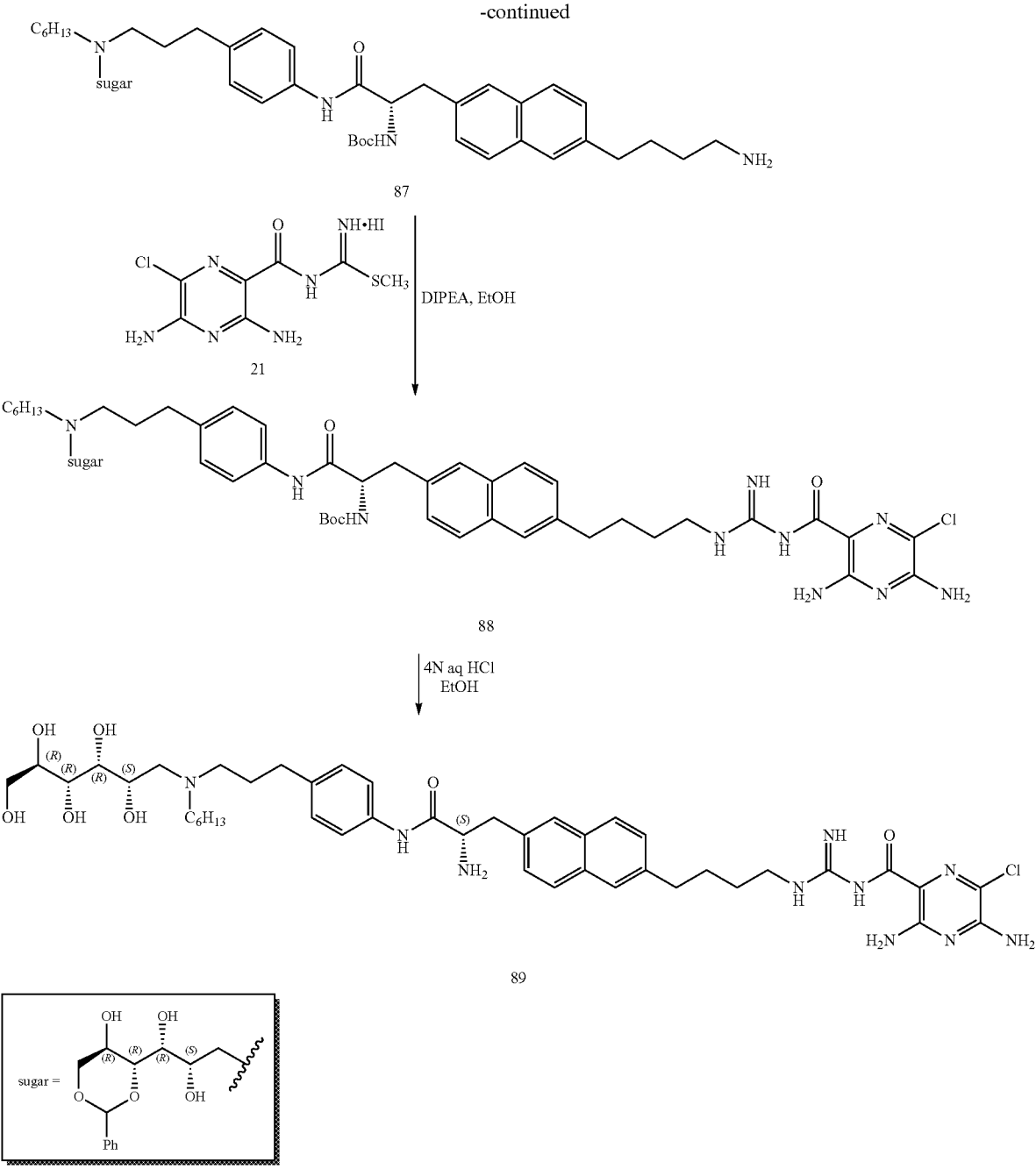

Preparation of Compound 86

To the compound 85 (1.10 g, 2.32 mmol) in THF (50 mL) were added DEPBT (766 mg, 2.56 mmol), 76 (1.00 g, 1.97 mmol) and DIPEA (1.0 mL, 5.91 mmol) successively and stirred at rt for 16 h. After the solvent was removed under reduced pressure, the residue was dissolved in CH$_2$Cl$_2$ (100 mL), quickly washed with saturated aqueous water (2×100 mL) and brine (50 mL), and dried over Na$_2$SO$_4$. The solvent was evaporated and the crude product purified by flash chromatography on silica gel (5% Methanol/CH$_2$Cl$_2$), yielding amide 86 as a yellow solid product (1.19 g, 57%): $^1$H NMR (400 MHz, CD$_3$OD): 7.82 (d, J=5.8 Hz, 2H), 7.73-7.61 (m, 4H), 7.51-7.43 (m, 2H), 7.39-7.19 (m, 10H), 7.05 (d, J=8.3 Hz, 2H), 5.52 (s, 1H), 5.10 (s, 2H), 4.51 (t, J=7.8 Hz, 1H), 4.31-4.25 (m, 1H), 4.24 (dd, J=11.0, 5.4 Hz, 1H), 4.01-3.91 (m, 2H), 3.88 (dd, J=5.5, 2.1 Hz, 1H), 3.76 (dd, J=9.3, 2.1 Hz, 1H), 3.61 (t, J=10.6 Hz, 1H), 3.37 (t, J=6.9 Hz, 2H), 3.12-3.00 (m, 1H), 2.74 (dd, J=13.2, 5.3 Hz, 1H), 2.64 (t, J=7.1 Hz, 2H), 2.57-2.37 (m, 7H), 1.74-1.64 (m, 2H), 1.31 (s, 9H), 1.29-1.16 (m, 8H), 0.86 (t, J=6.9 Hz, 3H).

Preparation of Compound 87

A suspension of 86 (1.19 g, mixture) and 10% Pd/C (220 mg) in a mixture of EtOH (110 mL) and AcOH (15 mL) was degassed and then subjected to hydrogenation conditions (1 atm) for 3 h at room temperature. The reaction mixture was filtered through a plug of Celite and the plug was washed with MeOH. The filtrate was concentrated in vacuum to afford amine salt 87 which was then neutralized with NaHCO₃ and crude product was purified by flash chromatography on silica gel (CMA, 80:18:2) yielding free amine 87 as a yellow solid (550 mg, 58%, over two steps): $^1$H NMR (400 MHz, CD$_3$OD) 7.71 (t, J=8.4 Hz, 2H), 7.62 (d, J=1.8 Hz, 1H), 7.49-7.45 (m, 3H), 7.40 (d, J=8.2 Hz, 2H), 7.36-7.28 (m, 5H), 7.09 (d, J=8.2 Hz, 2H), 5.55 (s, 1H), 4.51 (dd, J=15.6, 8.4 Hz, 1H), 4.25 (dd, J=10.6, 5.4 Hz, 1H), 4.17-4.03 (m, 2H), 3.98-3.90 (m, 2H), 3.81-3.74 (m, 1H), 3.63 (t, J=10.4 Hz, 1H), 3.27-3.20 (m, 1H), 3.09-2.98 (m, 5H), 2.93 (t, J=7.6 Hz, 2H), 2.83 (t, J=6.8 Hz, 2H), 2.61-2.54 (m, 2H), 1.95-1.86 (m, 2H), 1.85-1.75 (m, 2H), 1.74-1.65 (m, 2H), 1.57-1.47 (m, 2H), 1.39-1.19 (m, 7H), 1.33 (s, 9H), 0.88 (t, J=6.9 Hz, 3H).

Preparation of 88

To a solution of amine 87 (550 mg, 0.65 mmol) and methyl 3,5-diamino-6-chloropyrazine-2-carbonylcarbamimidothioate (21, 400 mg, 1.04 mmol) in EtOH (20 mL) was added DIPEA (1.15 mL, 6.44 mmol) at room temperature. The reaction mixture was heated at 70° C. in a sealed tube for 2 h, then cooled to room temperature, and concentrated in vacuum. The residue was purified by silica gel column chromatography (80:18:2 CHCl₃/CH₃OH/NH₄OH) followed by reverse phase column (Gold C18) to afford guanidine 88 (333 mg, 48%) as a yellow solid: $^1$H NMR (400 MHz, CD$_3$OD) 7.69 (dd, J=8.6, 3.5 Hz, 2H), 7.66 (s, 1H), 7.60 (s, 1H), 7.48-7.44 (m, 2H), 7.35 (ddd, J=10.4, 8.6, 1.6 Hz, 2H), 7.33-7.28 (m, 5H), 7.04 (d, J=8.3 Hz, 2H), 5.52 (s, 1H), 4.52-4.55 (m, 1H), 4.24 (dd, J=10.6, 5.4 Hz, 1H), 4.00-3.91 (m, 2H), 3.88 (dd, J=5.4, 2.0 Hz, 1H), 3.75 (dd, J=9.6, 2.2 Hz, 1H), 3.60 (t, J=10.6 Hz, 2H), 3.28-3.23 (m, 3H), 3.06 (dd, J=13.5, 8.3 Hz, 1H), 2.82 (t, J=7.0 Hz, 2H), 2.77 (dd, J=13.9, 5.6 Hz, 1H), 2.59-2.40 (m, 7H), 1.86-1.76 (m, 2H), 1.74-1.68 (m, 4H), 1.42-1.60 (m, 7H), 1.33 (s, 9H), 0.86 (t, J=7.1 Hz, 3H).

Preparation of the HCl Salt of 3,5-diamino-N—(N-(4-(6-((S)-2-amino-3-(4-(3-(hexyl((2S,3R,4R,5R)-2,3,4,5,6-pentahydroxyhexyl)amino)propyl)phenylamino)-3-oxopropyl)naphthalen-2-yl)butyl)carbamimidoyl)-6-chloropyrazine-2-carboxamide Compound (89)

4 N HCl in water (20 mL) was added to 88 (333 mg, 0.31 mmol) in ethanol (10 mL) and reaction mixture was stirred at rt for 2 h. Purified by reverse phase column (gold column) and residue was lyophilized to afford compound 89 (210 mg, 68%) as a yellow solid: $^1$H NMR (400 MHz, DMSO-d$_6$) 10.94 (brs, 1H), 9.29 (brs, 1H), 9.02-8.77 (m, 2H), 8.64-8.17 (m, 2H), 7.80-7.73 (m, 3H), 7.68 (s, 1H), 7.52 (d, J=8.8 Hz, 2H), 7.47 (dd, J=8.2, 1.0 Hz, 1H), 7.44-7.36 (m, 3H), 7.19 (d, J=8.6 Hz, 2H), 5.52-5.41 (m, 1H), 4.86-4.71 (m, 1H), 4.60 (d, J=5.4 Hz, 1H), 4.59-4.53 (m, 1H), 4.42 (t, J=5.8 Hz, 1H), 4.38 (t, J=7.0 Hz, 1H), 4.03-3.95 (m, 1H), 3.71-3.66 (m, 1H), 3.62-3.55 (m, 1H), 3.53-3.34 (m, 5H), 3.27 (d, J=7.7 Hz, 1H), 3.23 (d, J=7.4 Hz, 1H), 3.16-2.99 (m, 5H), 2.78 (t, J=7.4 Hz, 2H), 2.58 (t, J=7.9 Hz, 2H), 2.01-1.90 (m, 2H), 1.78-1.68 (m, 2H), 1.66-1.54 (m, 4H), 1.32-1.21 (m, 6H), 0.85 (t, J=6.6 Hz, 3H).
$^1$H NMR (400 MHz, CD$_3$OD) 7.79 (d, J=8.5 Hz, 1H), 7.77-7.73 (m, 2H), 7.67 (s, 1H), 7.47-7.37 (m, 4H), 7.21 (d, J=8.5 Hz, 2H), 4.30 (dd, J=7.7, 6.7 Hz, 1H), 4.12-4.05 (m, 1H), 3.82-3.74 (m, 1H), 3.71-3.61 (m, 2H), 3.49 (dd, J=14.0, 6.6 Hz, 1H), 3.47 (t, J=6.9 Hz, 2H), 3.33-3.27 (m, 3H), 3.26-3.13 (m, 4H), 2.86 (t, J=7.6 Hz, 2H), 2.73-2.64 (m, 2H), 2.10-2.00 (m, 2H), 1.89-1.80 (m, 2H), 1.79-1.72 (m, 2H), 1.71-1.63 (m, 2H), 1.40-1.30 (m, 6H), 0.91 (t, J=6.6 Hz, 3H).

13. Preparation of 3,5-diamino-N—(N-(4-(6-((S)-2-amino-3-(4-(3-(bis((2S,3R,4R,5R)-2,3,4,5,6-pentahydroxyhexyl)amino)propyl)phenylamino)-3-oxopropyl)naphthalen-2-yl)butyl)carbamimidoyl)-6-chloropyrazine-2-carboxamide (94)

Scheme 14

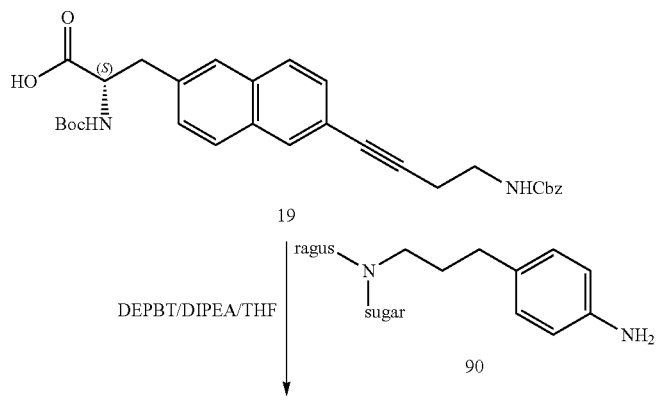

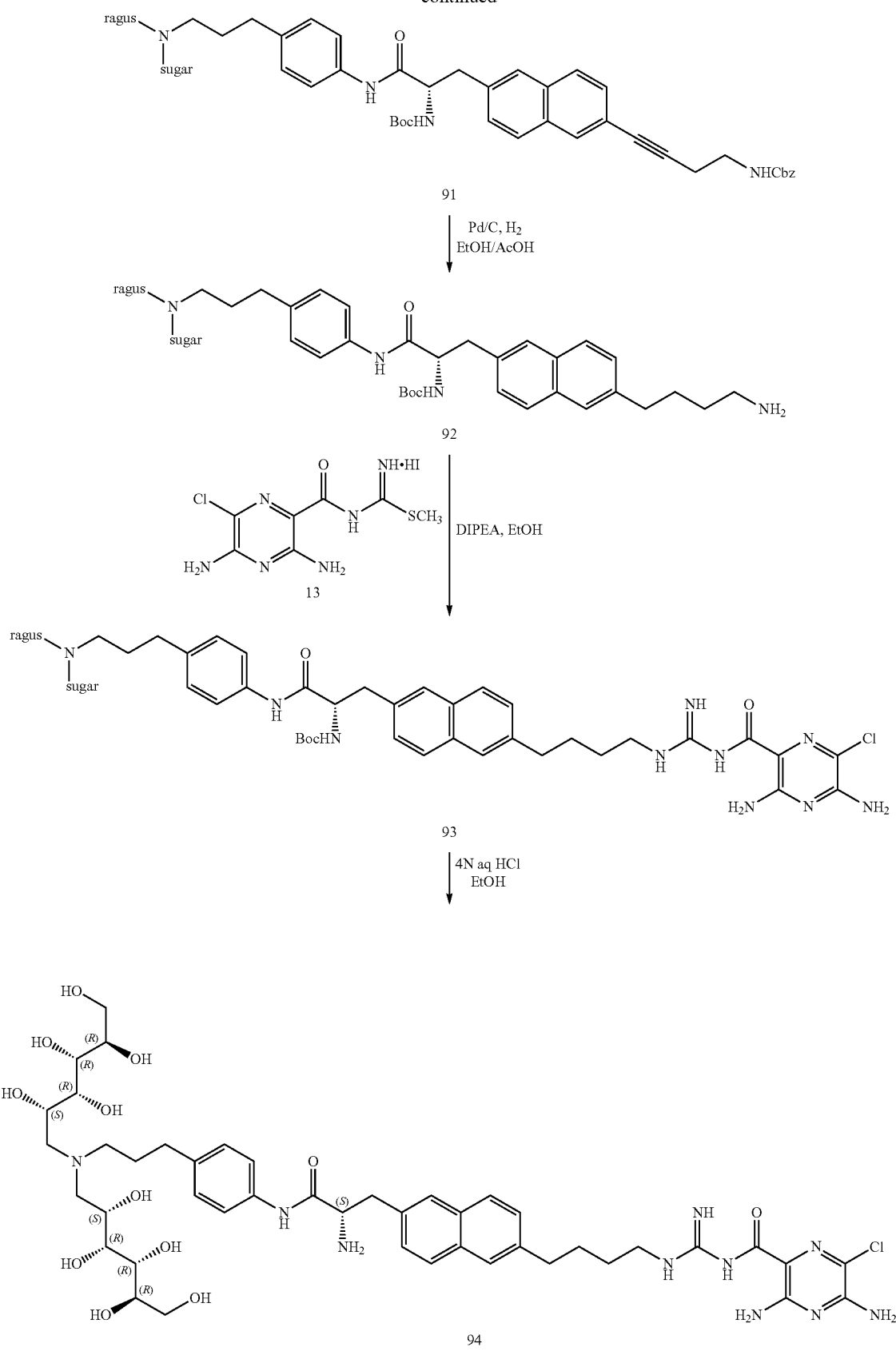

sugar = 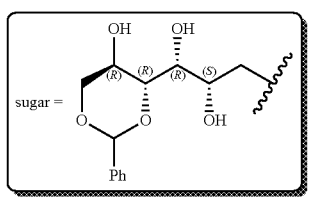

Preparation of Compound 91

To the compound 90 (484 mg, 0.91 mmol) in THF (30 mL) were added DEPBT (300 mg, 1.00 mmol), 19 (400 g, 0.77 mmol) and DIPEA (0.40 mL, 2.31 mmol) successively and stirred at rt for 16 h. After the solvent was removed under reduced pressure, the residue was dissolved in $CH_2Cl_2$ (100 mL), quickly washed with saturated aqueous water (2×100 mL) and brine (50 mL), and dried over $Na_2SO_4$. The solvent was evaporated and the crude product purified by flash chromatography on silica gel (5% Methanol/$CH_2Cl_2$), yielding amide 91 as a yellow solid product (600 mg, 76%, impure). Product formation was confirmed by LCMS.

Preparation of Compound 92

A suspension of 91 (600 mg, 0.59 mmol) and 10% Pd/C (200 mg) in a mixture of EtOH (90 mL) and AcOH (10 mL) was degassed and then subjected to hydrogenation conditions (1 atm) for 16 h at room temperature. The reaction mixture was filtered through a plug of Celite and the plug was washed with MeOH. The filtrate was concentrated in vacuum to afford amine salt 92 which was then neutralized with $NaHCO_3$ and crude product was purified by flash chromatography on silica gel (CMA, 80:18:2) yielding free amine 36 as a yellow solid (350 mg, 66%, impure): $^1$H NMR (400 MHz, $CD_3OD$) 7.71 (d, J=8.1 Hz, 2H), 7.68 (s, 1H), 7.61 (s, 2H), 7.43-7.37 (m, 2H), 7.34 (dd, J=8.3, 1.3 Hz, 1H), 7.16 (d, J=8.2 Hz, 2H), 4.69 (q, J=5.1 Hz, 2H), 4.50 (t, J=7.1 Hz, 1H), 4.13-4.06 (m, 2H), 4.05 (dd, J=11.0, 5.6 Hz, 2H), 3.83 (dd, J=4.8, 2.1 Hz, 2H), 3.81-3.73 (m, 2H), 3.51 (dd, J=9.5, 2.3 Hz, 2H), 3.38 (t, J=10.8 Hz, 2H), 3.13-3.03 (m, 6H), 2.93 (t, J=7.6 Hz, 2H), 2.82 (t, J=7.2 Hz, 2H), 2.74-2.57 (m, 2H), 2.04-1.95 (m, 2H), 1.84-1.75 (m, 3H), 1.74-1.63 (m, 3H), 1.33 (s, 9H), 1.25 (d, J=5.1 Hz, 6H).

Preparation of 93

To a solution of amine 92 (350 mg, 0.38 mmol) and methyl 3,5-diamino-6-chloropyrazine-2-carbonylcarbamimidothioate (13, 242 mg, 0.62 mmol) in EtOH (10 mL) was added DIPEA (0.67 mL, 3.80 mmol) at room temperature. The reaction mixture was heated at 70° C. in a sealed tube for 2 h, then cooled to room temperature, and concentrated in vacuum. The residue was purified by silica gel column chromatography (80:18:2 $CHCl_3$/$CH_3OH$/$NH_4OH$) followed by reverse phase column (Gold C18) to afford guanidine 93 (170 mg, 20% over three steps) as a yellow solid: 1H NMR (400 MHz, $CD_3OD$) 7.71 (d, J=8.2 Hz, 2H), 7.68 (s, 1H), 7.62 (s, 1H), 7.43 (d, J=8.2 Hz, 2H), 7.26 (ddd, J=10.6, 8.6, 1.3 Hz, 2H), 7.18 (d, J=8.2 Hz, 2H), 4.70 (q, J=0.5 Hz, 2H), 4.49 (t, J=7.8 Hz, 1H), 4.22-4.09 (m, 2H), 4.06 (dd, J=10.4, 5.1 Hz, 2H), 3.89-3.81 (m, 2H), 3.80-3.71 (m, 2H), 3.60-3.49 (m, 2H), 3.43-3.32 (m, 8H), 3.31-3.23 (m, 2H), 3.10-2.98 (m, 2H), 2.85 (t, J=6.9 Hz, 2H), 2.77-2.61 (m, 2H), 2.12-2.02 (m, 2H), 1.89-1.79 (m, 2H), 1.78-1.68 (m, 2H), 1.31 (s, 9H), 1.25 (d, J=5.1 Hz, 6H).

Preparation of the HCl Salt of 3,5-diamino-N—(N-(4-(6-((S)-2-amino-3-(4-(3-(bis((2S,3R,4R,5R)-2,3,4,5,6-pentahydroxyhexyl)amino)propyl)phenylamino)-3-oxopropyl)naphthalen-2-yl)butyl)carbamimidoyl)-6-chloropyrazine-2-carboxamide (94)

4 N HCl in water (20 mL) was added to 93 (170 mg, 0.15 mmol) in ethanol (5.0 mL) and reaction mixture was stirred at 40° C. for 2 h. The solvent was removed again 4N HCl was added and heated at 40° C. for another 2 h. This addition repeated two more times. Solvent was removed and purified by reverse phase column (gold column) and residue was lyophilized to afford compound 94 (80 mg, 50%) as a yellow solid: $^1$H NMR (400 MHz, DMSO-$d_6$) 10.74 (brs, 1H), 9.28-9.19 (m, 1H), 9.03-8.60 (m, 2H), 8.58-8.04 (m, 1H), 7.81-7.73 (m, 3H), 7.68 (s, 1H), 7.50 (d, J=8.4 Hz, 2H), 7.48-7.34 (m, 4H), 7.19 (d, J=9.0 Hz, 2H), 5.39-5.35 (m, 1H), 4.87-4.63 (m, 1H), 4.62-4.47 (m, 3H), 4.45-4.35 (m, 2H), 4.32-4.23 (m, 1H), 4.01-3.85 (m, 1H), 3.67 (d, J=4.6 Hz, 1H), 3.62-3.55 (m, 2H), 3.53-3.38 (m, 5H), 3.37-3.29 (m, 2H), 3.24-3.09 (m, 2H), 2.78 (t, J=7.2 Hz, 2H), 2.62-2.53 (m, 2H), 2.01-1.86 (m, 2H), 1.79-1.68 (m, 2H), 1.64-1.55 (m, 2H).

$^1$H NMR (400 MHz, $CD_3OD$) 7.78 (d, J=8.4 Hz, 1H), 7.75 (d, J=7.8 Hz, 1H), 7.73 (s, 1H), 7.66 (s, 1H), 7.42 (d, J=8.8 Hz, 2H), 7.39 (d, J=8.4 Hz, 2H), 7.21 (d, J=8.7 Hz, 2H), 4.16 (t, J=7.0 Hz, 1H), 4.13-4.05 (m, 2H), 3.81 (dd, J=4.7, 1.9 Hz, 2H), 3.77 (dd, J=10.6, 3.0 Hz, 2H), 3.72-3.61 (m, 6H), 3.44-3.30 (m, 10H), 2.86 (t, J=7.0 Hz, 2H), 2.76-2.61 (m, 2H), 2.11-2.01 (m, 2H), 1.89-1.80 (m, 2H), 1.79-1.72 (m, 2H).

14. Preparation of 3,5-diamino-N—(N-(4-(6-((S)-2-amino-3-oxo-3-(4-(3-((2S,3R,4R,5R)-2,3,4,5,6-pentahydroxyhexylamino)propyl)phenylamino)propyl)naphthalen-2-yl)butyl)carbamimidoyl)-6-chloropyrazine-2-carboxamide (99)
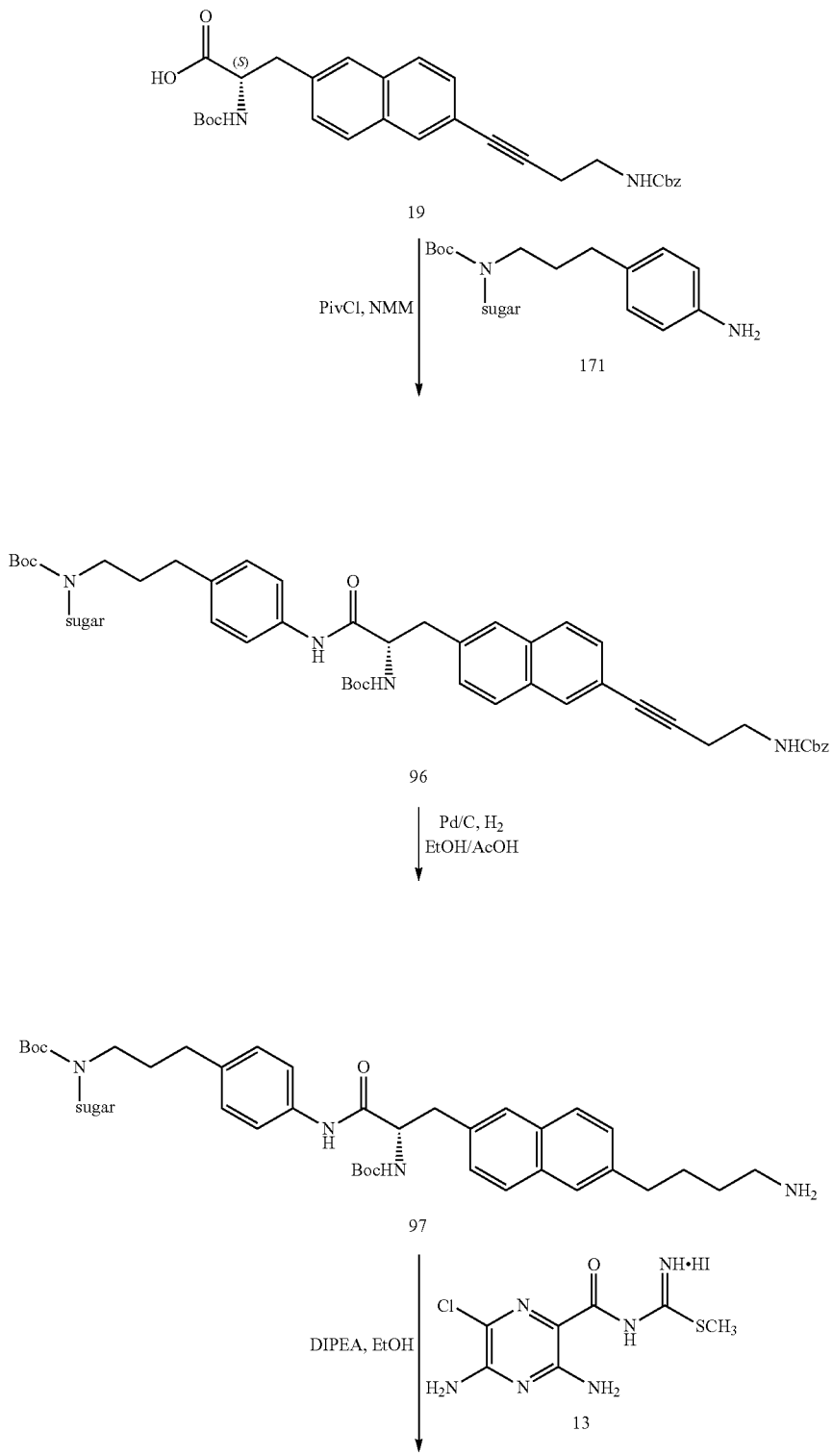
Scheme 15

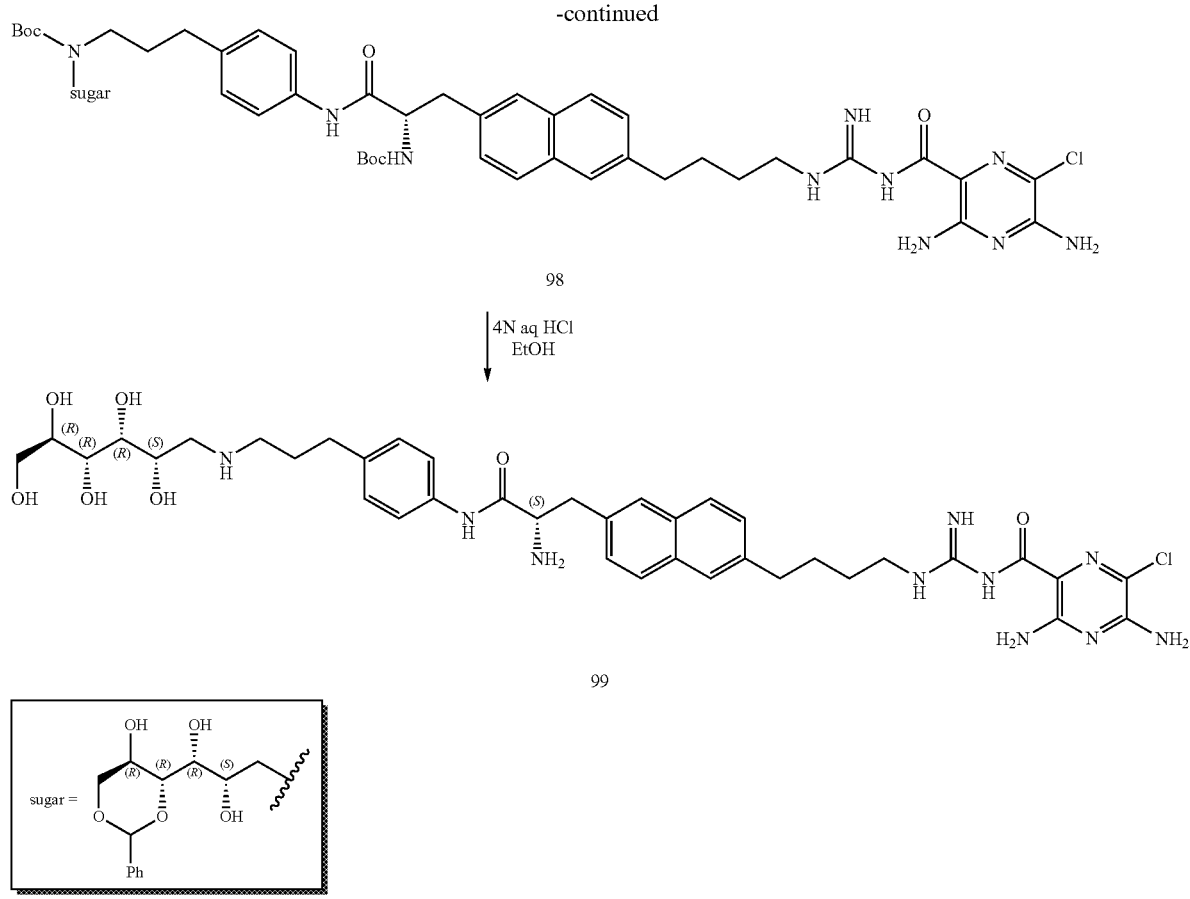

Preparation of Compound 96

A solution of acid 19 (1.17 g, 2.27 mmol) in THF (60 mL) was cooled to 0° C. in ice-bath, NMM (0.30 mL, 2.95 mmol) was added followed by PivCl (0.30 mL, 2.49 mmol) and the reaction mixture was stirred at the same temperature for 2 h. 34 (1.0 g, 2.27 mmol, 10 mL THF) of aniline 171 was added and the reaction mixture was stirred at the same temperature for a further 10 min. Reaction mixture was then brought to rt and stirred for 16 h. Organic solvent was removed. To this residue was added water and extracted with $CH_2Cl_2$ (3×100 mL). The organic layers were combined, dried over $Na_2SO_4$, filtered, and concentrated. The residue was purified by column chromatography (4% methanol in chloroform) to afford amide 96 (1.40 g, 66%, impure) as a light yellow solid. Product formation was confirmed by LCMS.

Preparation of Compound 97

A suspension of 96 (1.40 g, 1.50 mmol) and 10% Pd/C (300 mg) in a mixture of EtOH (120 mL) and AcOH (12 mL) was degassed and then subjected to hydrogenation conditions (1 atm) for 16 h at room temperature. The reaction mixture was filtered through a plug of Celite and the plug was washed with MeOH. The filtrate was concentrated in vacuum to afford amine salt 97 which was then neutralized with $NaHCO_3$ and crude product was purified by flash chromatography on silica gel (CMA, 80:18:2) yielding free amine 97 as a yellow solid (550 mg, 30%, over two steps): $^1$H NMR (400 MHz, $CD_3OD$) 7.74-7.65 (m, 3H), 7.59 (s, 1H), 7.41-7.29 (m, 4H), 7.11 (d, J=8.4 Hz, 2H), 4.69 (q, J=4.9 Hz, 1H), 4.50 (t, J=7.9 Hz, 1H), 4.04 (dd, J=10.4, 5.2 Hz, 1H), 4.02-3.94 (m, 1H), 3.79-3.71 (m, 1H), 3.70-3.63 (m, 1H), 3.54-3.39 (m, 3H), 3.26-(dd, J=13.6, 6.8 Hz, 1H), 3.07 (dd, J=13.1, 8.3 Hz, 1H), 2.79 (t, J=7.5 Hz, 2H), 2.75-2.67 (m, 2H), 2.55 (t, J=7.3 Hz, 2H), 1.91-1.80 (m, 2H), 1.79-1.69 (m, 2H), 1.62-1.52 (m, 2H), 1.50-1.37 (m, 12H), 1.33 (s, 9H), 1.25 (d, J=4.9 Hz, 3H).

Preparation of 98

To a solution of amine 97 (550 mg, 0.68 mmol) and methyl 3,5-diamino-6-chloropyrazine-2-carbonylcarbamimidothioate (13, 423 mg, 0.62 mmol) in EtOH (20 mL) was added DIPEA (1.21 mL, 6.80 mmol) at room temperature. The reaction mixture was heated at 70° C. in a sealed tube for 2 h, then cooled to room temperature, and concentrated in vacuum. The residue was purified by silica gel column chromatography (80:18:2 $CHCl_3/CH_3OH/NH_4OH$) followed by reverse phase column (Gold C18) to afford guanidine 98 (500 mg, 72%) as a yellow solid: $^1$H NMR (400 MHz, $CD_3OD$) 7.73-7.64 (m, 3H), 7.61 (s, 1H), 7.40-7.30 (m, 4H), 7.11 (d, J=8.5 Hz, 2H), 4.68 (d, J=4.9 Hz, 1H), 4.49 (t, J=7.2 Hz, 1H), 4.04 (dd, J=10.9, 5.5 Hz, 1H), 4.02-3.93 (m, 1H), 3.78-3.70 (m, 1H), 3.69-3.64 (m, 1H), 3.54-3.38 (m, 4H), 3.30-3.20 (m, 2H), 3.15-3.01 (m, 1H), 2.83 (t, J=7.4 Hz, 2H), 2.54 (t, J=7.3 Hz, 2H), 1.90-1.78 (m, 4H), 1.73-1.64 (m, 2H), 1.53-1.37 (m, 12H), 1.32 (s, 9H), 1.25 (d, J=4.9 Hz, 3H).

Preparation of the HCl Salt of 3,5-diamino-N—(N-(4-(6-((S)-2-amino-3-oxo-3-(4-(3-((2S,3R,4R,5R)-2,3,4,5,6-pentahydroxyhexylamino)propyl)phenylamino) propyl)naphthalen-2-yl)butyl)carbamimidoyl)-6-chloropyrazine-2-carboxamide (99)

4 N HCl in water (20 mL) was added to 98 (500 mg, 0.15 mmol) in ethanol (5.0 mL) and reaction mixture was stirred at 40° C. for 2 h. The solvent was removed again 4N HCl was added and heated at 40° C. for another 2 h. This addition repeated two more times. Solvent was removed purified by reverse phase column (gold column) and residue was lyophilized to afford compound 99 (206 mg, 50%) as a yellow solid: $^1$H NMR (400 MHz, DMSO-$d_6$) 11.0 (brs, 1H), 9.34 (brs, 1H), 9.09-8.25 (m, 6H), 7.82-7.73 (m, 2H), 7.68 (s, 1H), 7.53 (d, J=8.5 Hz, 2H), 7.49 (d, J=9.2 Hz, 1H), 7.41 (s, 2H), 7.39 (d, J=8.2 Hz, 2H), 7.17 (d, J=8.2 Hz, 2H), 5.39 (d, J=3.7 Hz, 1H), 4.80-4.70 (m, 1H), 4.62 (d, J=4.3 Hz, 1H), 4.60-4.54 (m, 1H), 4.46-4.36 (m, 2H), 3.96-3.88 (m, 1H), 3.71-3.65 (m, 1H), 3.62-3.54 (m, 1H), 3.51-3.35 (m, 5H), 3.09 (d, J=13.3 Hz, 1H), 2.94 (d, J=10.9 Hz, 1H), 2.87 (t, J=9.1 Hz, 2H), 2.78 (t, J=6.7 Hz, 2H), 2.60 (t, J=7.7 Hz, 2H), 2.00-1.86 (m, 2H), 1.85-1.67 (m, 2H), 1.65-1.53 (m, 2H).

$^1$H NMR (400 MHz, CD$_3$OD) 7.80 (d, J=9.5 Hz, 1H), 7.78-7.73 (m, 2H), 7.68 (s, 1H), 7.45-7.37 (m, 4H), 7.19 (d, J=7.1 Hz, 2H), 4.31 (t, J=6.3 Hz, 1H), 4.09-4.00 (m, 1H), 3.87-3.81 (m, 1H), 3.78 (d, J=11.4 Hz, 1H), 3.73-3.61 (m, 3H), 3.46 (dd, J=13.6, 6.3 Hz, 1H), 3.37 (t, J=6.8 Hz, 2H), 3.30-3.25 (m, 1H), 3.22-3.12 (m, 2H), 3.03 (t, J=7.9 Hz, 2H), 2.86 (t, J=6.8 Hz, 2H), 2.69 (t, J=7.4 Hz, 2H), 2.07-1.95 (m, 2H), 1.91-1.81 (m, 2H), 1.80-1.69 (m, 2H).

15. Preparation of (S)-3,5-diamino-N—(N-(4-(6-(2-amino-3-(4-(3-(dimethylamino)propyl)phenylamino)-3-oxopropyl)naphthalen-2-yl)butyl)carbamimidoyl)-6-chloropyrazine-2-carboxamide (103)

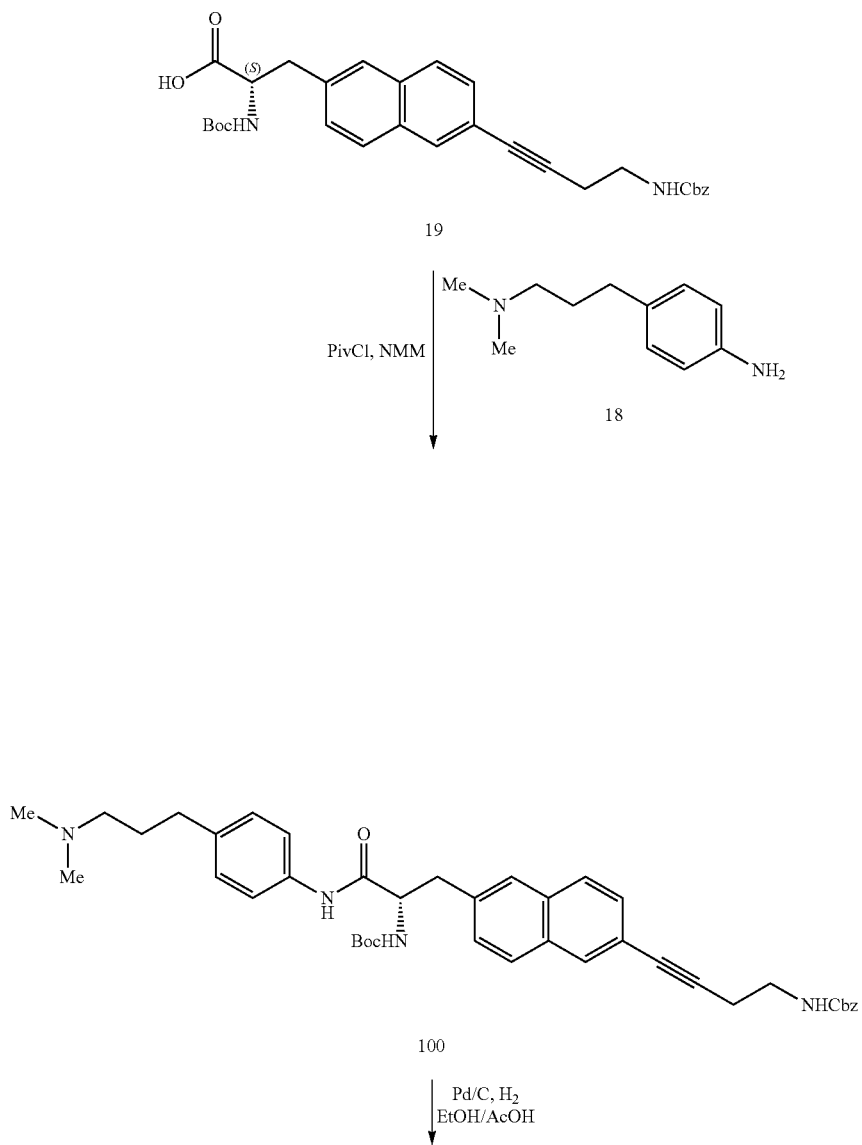

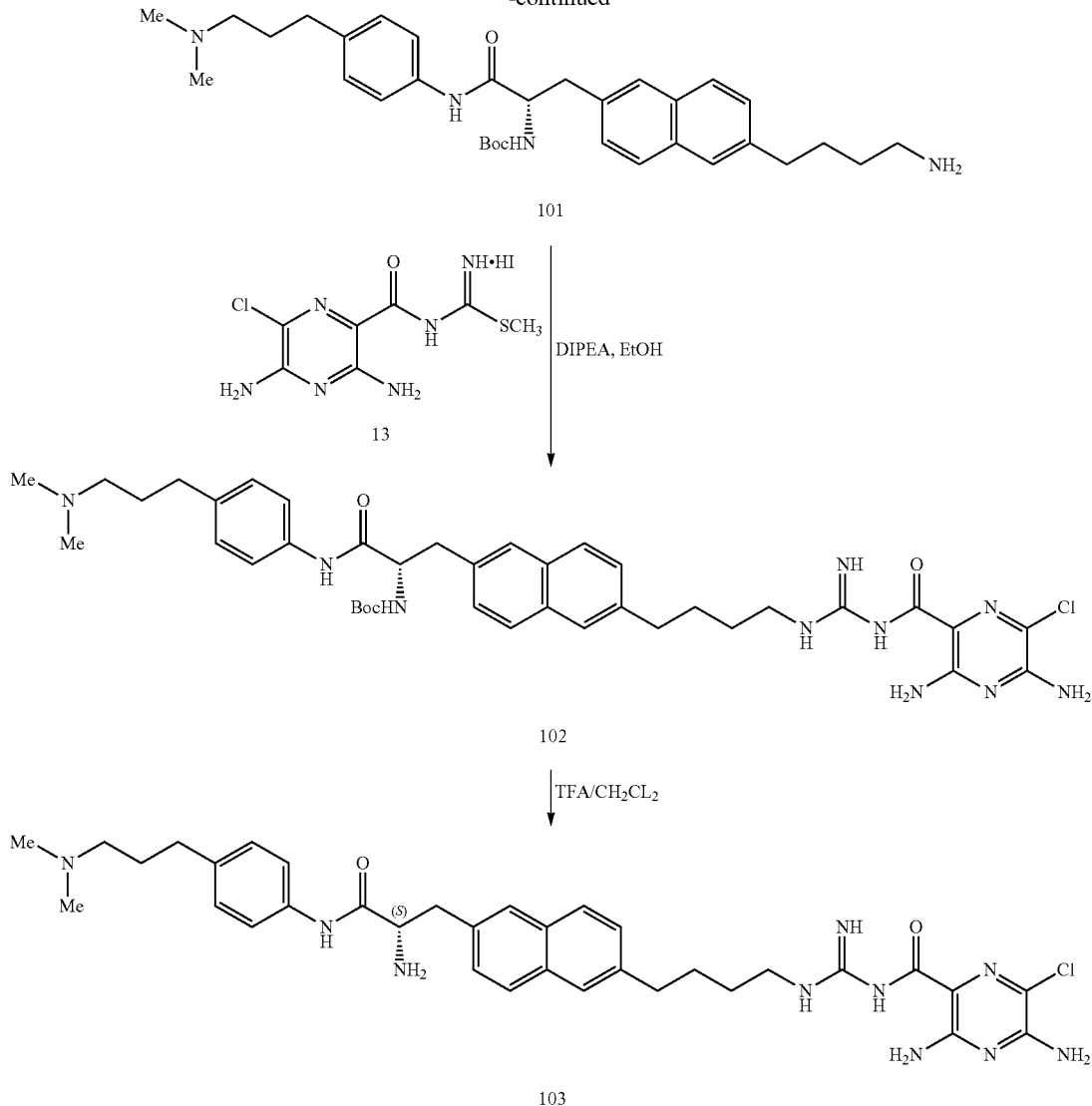

Preparation of Compound 100

A solution of acid 19 (1.75 g, 3.39 mmol) in THF (70 mL) was cooled to 0° C. in ice-bath, NMM (0.74 mL, 6.78 mmol) was added followed by PivCl (0.41 mL, 3.39 mmol) and the reaction mixture was stirred at the same temperature for 2 h. 18 (825 mg, 4.61 mmol, 10 mL THF) was added and the reaction mixture was stirred at the same temperature for a further 10 min. Reaction mixture was then brought to rt and stirred for 16 h. Organic solvent was removed. To this residue was added water and extracted with $CH_2Cl_2$ (3×100 mL). The organic layers were combined, dried over $Na_2SO_4$, filtered, and concentrated. The residue was purified by column chromatography (4% methanol in chloroform) to afford amide 100 (1.60 g, 71%) as a light yellow solid: $^1$H NMR (400 MHz, $CDCl_3$) 7.87 (s, 1H), 7.71 (d, J=8.5 Hz, 1H), 7.67 (d, J=8.5 Hz, 1H), 7.65-7.62 (m, 2H), 7.42 (dd, J=8.4, 1.9 Hz, 1H), 7.40-7.29 (m, 5H), 7.22 (d, J=8.6 Hz, 2H), 7.08 (d, J=8.4 Hz, 2H), 5.21-5.10 (m, 2H), 5.13 (s, 2H), 4.51 (q, J=7.6 Hz, 1H), 3.47 (q, J=6.5 Hz, 2H), 3.29 (d, J=6.9 Hz, 2H), 2.68 (t, J=6.7 Hz, 2H), 2.57 (t, J=7.9 Hz, 2H), 2.26 (ddt, J=11.5, 9.3, 2.5 Hz, 2H), 2.21 (s, 6H), 2.22-2.19 (m, 1H), 1.78-1.69 (m, 3H), 1.39 (s, 9H).

Preparation of Compound 101

A suspension of 100 (1.60 g, 2.30 mmol) and 10% Pd/C (400 mg) in a mixture of EtOH (130 mL) and AcOH (20 mL) was degassed and then subjected to hydrogenation conditions (1 atm) for 16 h at room temperature. The reaction mixture was filtered through a plug of Celite and the plug was washed with MeOH. The filtrate was concentrated in vacuum to afford amine salt 101 as a yellow solid (1.60 g, 99%): $^1$H NMR (400 MHz, $CD_3OD$) 7.71 (d, J=8.5 Hz, 2H), 7.68 (s, 1H), 7.61 (s, 1H), 7.42 (d, J=8.5 Hz, 2H), 7.39 (dd, J=8.5, 1.3 Hz, 1H), 7.33 (dd, J=8.5, 1.3 Hz, 1H), 7.16 (d, J=8.6 Hz, 2H), 4.50 (t, J=7.6 Hz, 1H), 3.28 (dd, J=14.0, 6.3 Hz, 1H), 3.07 (dd, J=13.3, 8.7 Hz, 1H), 3.05-2.98 (m, 2H), 2.93 (t, J=7.6 Hz, 2H), 2.82 (t, J=7.3 Hz, 2H), 2.78 (s, 6H), 2.65 (t, J=7.5 Hz, 2H), 2.06-1.96 (m, 2H), 1.93 (s, 6H), 1.86-1.75 (m, 2H), 1.74-1.64 (m, 2H), 1.33 (s, 9H).

Preparation of 102

To a solution of amine 101 (1.60 g, 2.30 mmol) and methyl 3,5-diamino-6-chloropyrazine-2-carbonylcarbamimidothioate (21, 1.60 g, 4.14 mmol) in EtOH (25 mL) was added DIPEA 4.1 mL, 23.0 mmol) at room temperature. The reaction mixture was heated at 70° C. in a sealed tube for 2 h, then cooled to room temperature, and concentrated in vacuum. The residue was purified by silica gel column chromatography (80:18:2 $CHCl_3/CH_3OH/NH_4OH$) to afford guanidine 102 (645 mg, 37% and 640 mg, 37% impure) as a yellow solid: $^1H$ NMR (400 MHz, $CD_3OD$) 7.70 (dd, J=9.0, 4.3 Hz, 2H), 7.66 (s, 1H), 7.61 (s, 1H), 7.39-7.31 (m, 4H), 7.11 (d, J=8.4 Hz, 2H), 4.48 (t, J=7.6 Hz, 1H), 3.30-3.22 (m, 3H), 3.06 (dd, J=13.8, 8.9 Hz, 1H), 2.83 (t, J=7.2 Hz, 2H), 2.57 (t, J=7.9 Hz, 2H), 2.32 (dd, J=10.5, 7.6 Hz, 2H), 2.23 (s, 6H), 1.86-1.74 (m, 4H), 1.73-1.64 (m, 2H), 1.32 (s, 9H).

Preparation of the HCl Salt of(S)-3,5-diamino-N—(N-(4-(6-(2-amino-3-(4-(3-(dimethylamino)propyl)phenylamino)-3-oxopropyl)naphthalen-2-yl)butyl)carbamimidoyl)-6-chloropyrazine-2-carboxamide (103)

TFA (10 mL) was added to 47 (545 mg, 0.71 mmol) in $CH_2Cl_2$ (15 mL) and reaction mixture was stirred at rt for 1 h. The solvent was removed again 1N HCl was added and solvent was removed, purified by reverse phase column (gold column) and residue was lyophilized to afford compound 48 (206 mg, 50%) as a yellow solid: $^1H$ NMR (400 MHz, DMSO-$d_6$) 11.02 (brs, 1H), 10.81-10.58 (m, 1H), 10.53 (s, 1H), 9.32 (s, 1H), 9.04-8.72 (m, 2H), 8.50 (brs, 3H), 7.82-7.73 (m, 3H), 7.68 (s, 1H), 7.53 (d, J=8.5 Hz, 2H), 7.48 (d, J=9.2 Hz, 1H), 7.45-7.35 (m, 3H), 7.18 (d, J=8.4 Hz, 2H), 4.45-4.35 (m, 1H), 3.74-3.45 (m, 1H), 3.27 (dd, J=14.7, 8.3 Hz, 1H), 3.03-2.93 (m, 2H), 2.78 (t, J=7.3 Hz, 2H), 2.70 (s, 6H), 2.58 (t, J=7.3 Hz, 2H), 2.02-1.88 (m, 2H), 1.79-1.66 (m, 2H), 1.64-1.54 (m, 2H).

$^1H$ NMR (400 MHz, $CD_3OD$) 7.80 (d, J=9.2 Hz, 1H), 7.78-7.73 (m, 2H), 7.67 (s, 1H), 7.47-7.38 (m, 4H), 7.20 (d, J=8.9 Hz, 2H), 4.33 (t, J=7.5 Hz, 1H), 3.46 (dd, J=13.6, 6.6 Hz, 1H), 3.37 (t, J=6.8 Hz, 2H), 3.36-3.26 (m, 3H), 2.87-2.83 (m, 2H), 2.87 (s, 6H), 2.68 (t, J=7.6 Hz, 2H), 2.07-1.97 (m, 2H), 1.89-1.80 (m, 2H), 1.80-1.71 (m, 2H).

16. Preparation of 3,5-diamino-N—(N-(4-(4-((S)-2-amino-3-(4-(3-(hexyl((2S,3R,4R,5R)-2,3,4,5,6-pentahydroxyhexyl)amino)propyl)phenylamino)-3-oxopropyl)-5,6,7,8-tetrahydronaphthalen-1-yl)butyl)carbamimidoyl)-6-chloropyrazine-2-carboxamide (123)

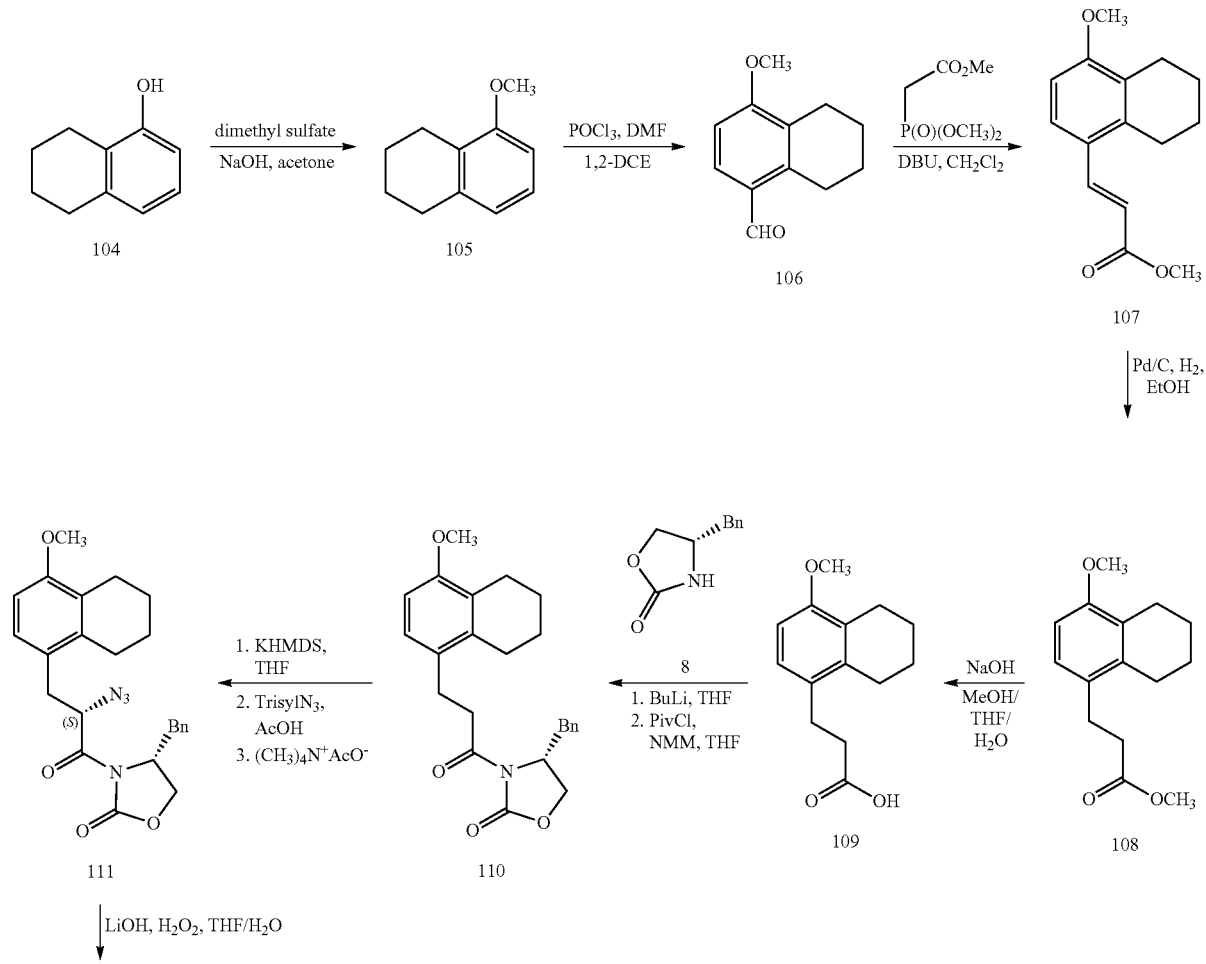

Scheme 17

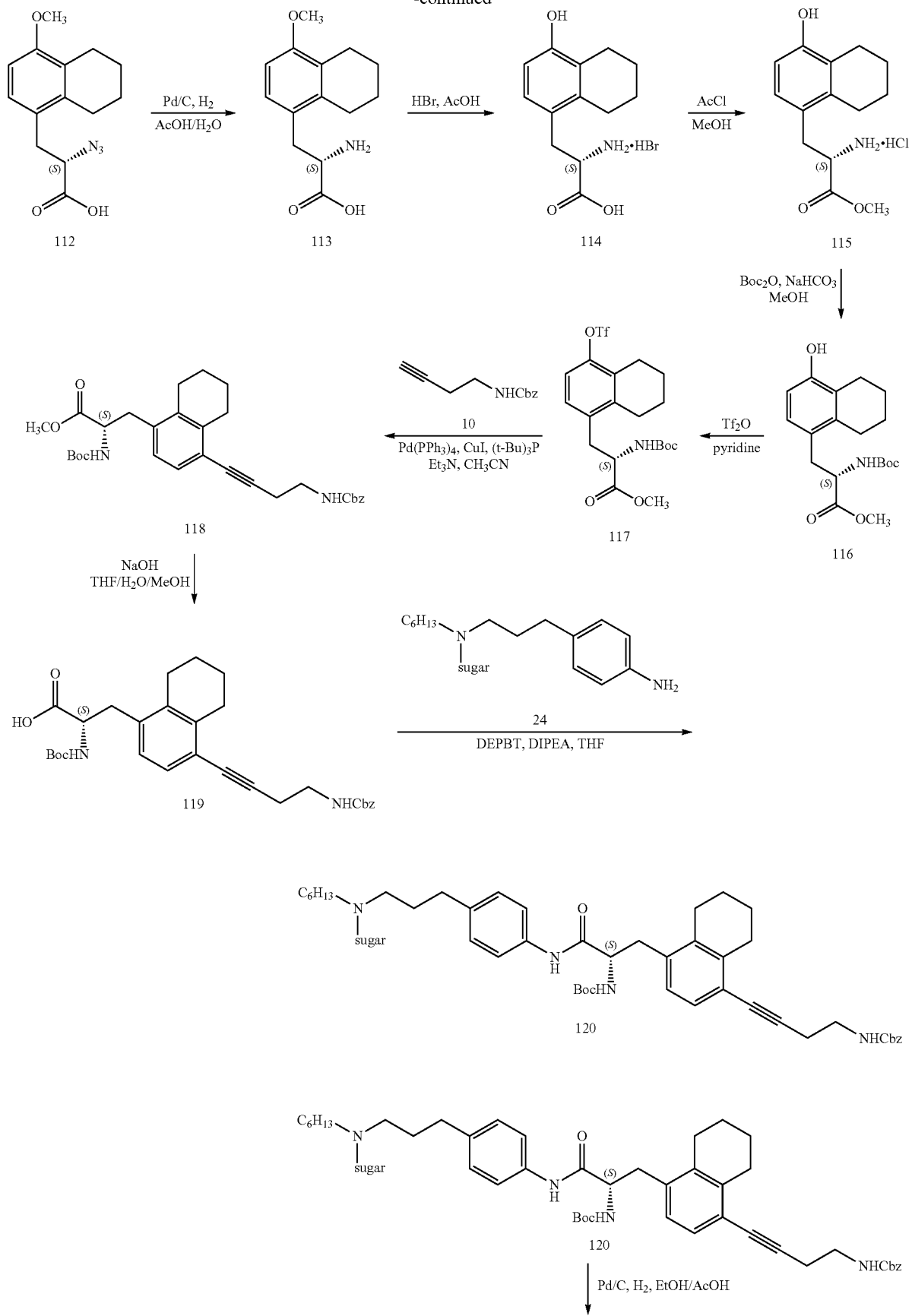

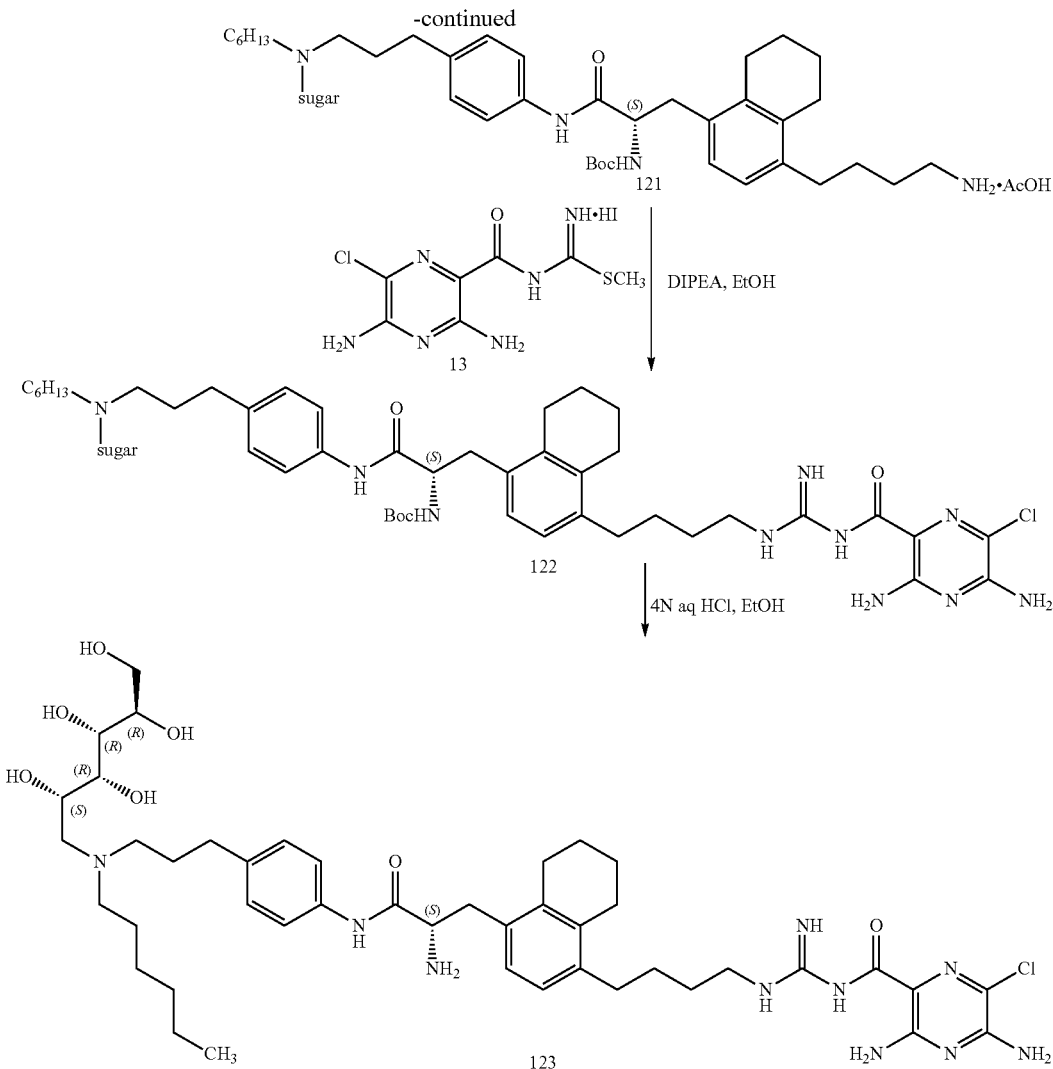

Preparation of Compound 105

A solution of 104 (100 g, 0.675 mmol) in dry THF (800 mL) was charged with NaOH (32.0 mg, 0.809 mmol) and dimethylsulfate (102 g, 0.809 mmol) dropwise at 0° C. The reaction mixture was stirred for 2 h at room temperature. THF was removed under reduced pressure, and the mixture was partitioned between $CH_2Cl_2$ (1.0 L) and water (1.0 L). The aqueous layer was separated and extracted with $CH_2Cl_2$ (2×1.0 L). The combined organic extracts were dried over $Na_2SO_4$ and concentrated. The residue was purified by column chromatography (silica gel, 100% $CH_2Cl_2$) to afford compound 105 (108.0 g, 90%) as a yellow liquid: $^1$H NMR (400 MHz, DMSO-$d_6$): δ 7.06 (t, J=7.85 Hz, 1H), 6.71 (d, J=7.25, 1H), 6.64 (t, J=7.7 Hz, 1H), 3.80 (s, 3H), 2.74 (t, J=2.75 Hz, 2H), 2.65 (t, J=2.65 Hz, 2H), 1.81-1.71 (m, 4H).

Preparation of Compound 106

A solution of dry DMF (71.45 ml, 0.923 mmol) was charged with $POCl_3$ (57.40 ml, 0.616 mmol) dropwise under nitrogen atmosphere at 0° C. The reaction mixture was stirred for 30 min at 0° C. A solution of 105 (50.0 g, 0.308 mmol) in dry 1,2-dichloromethane (500 mL) was added to the reaction mixture dropwise under nitrogen atmosphere at 0° C. After the addition was complete, the reaction mixture was heated at 80° C. for 6 h. The reaction mixture was quenched with cold $H_2O$ and partitioned between $CH_2Cl_2$ (1.0 L) and water (1.0 L). The aqueous layer was separated and extracted with $CH_2Cl_2$ (2×1.0 L). The combined organic extracts were dried over $Na_2SO_4$ and concentrated. The residue was purified by column chromatography (silica gel, 5% EA/Hexane) to afford compound 106 (35.0 g, 61%) as a yellow solid: $^1$H NMR (400 MHz, DMSO-$d_6$): δ 10.10 (s, 1H), 7.65 (d, J=7.81, 1H), 6.78 (d, J=7.47 Hz, 1H), 3.89 (s, 3H), 3.18 (t, J=5.80 Hz, 2H), 2.70 (t, J=4.64 Hz, 2H), 1.82-1.73 (m, 4H).

Preparation of Compound 107

A solution of trimethylphosphonoacetate (55.0 mL, 0.378 mmol) in 100 mL anhydrous $CH_2Cl_2$ cooled to 0° C. was charged with DBU (58.0 g, 0.380 mmol) and the mixture was stirred for 15 min. Aldehyde 106 (16.0 g, 0.084 mmol) in 50 mL $CH_2Cl_2$ was added dropwise. The reaction mixture was brought to room temperature, stirred for 16 h, and quenched with 100 mL of water. The mixture was partitioned, and the aqueous layer was extracted with $CH_2Cl_2$ (3×150 mL). The combined organics were washed with brine, dried (Na$_2$SO$_4$), filtered, and concentrated, and the residue was purified by silica-gel column chromatography (10:1 hexanes/ethyl acetate) to give the cis & trans-α,β-unsaturated ester 107 (15.0 g, 72%) as a white solid: $^1$H NMR (400 MHz, DMSO-d$_6$): δ 7.83 (d, J=14.7 Hz, 1H), 7.58 (d, J=8.3 Hz, 1H), 6.82 (d, J=8.4 Hz, 1H), 6.35 (d, J=15.2 Hz, 1H), 3.80 (s, 3H), 3.70 (s, 3H), 2.76 (t, J=5.7 Hz, 2H), 2.55 (t, J=5.4 Hz, 2H), 1.80-1.60 (m, 4H).

Preparation of Compound 108

A suspension of 107 (33.0 g, 0.134 mmol) and 10% Pd/C (15 g, 0.127) in EtOH (300 mL) was subjected to hydrogenation conditions (1 atm) for 3 h at room temperature. The reaction mixture was filtered through Celite and washed with MeOH. The filtrate was concentrated under vacuum to afford 108 (28.0 g, 90%) as a white solid: $^1$H NMR (400 MHz, CDCl$_3$): δ 7.65 (d, J=7.62, 1H), 6.78 (d, J=7.96 Hz, 1H), 4.06-4.11 (m, 1H), 3.78 (s, 3H), 2.86 (t, J=7.79 Hz, 2H), 2.69-2.64 (m, 4H), 2.57-2.51 (m, 2H), 1.79-1.74 (m, 4H).

Preparation of Compound 109

A solution of methyl ester 108 (28.0 g, 0.106 mmol) in THF/MeOH/H$_2$O (200 mL/200 mL/60 mL) was charged with NaOH (25.0 g, 0.625 mmol) and the reaction mixture was stirred at room temperature for 3 h. The solvent was removed and the pH was adjusted to 1 with 1 N aqueous HCl; a white solid precipitated and was filtered, washed with water, and dried under vacuum to afford acid 109 (25.5 g, 92%) as a white solid: $^1$H NMR (400 MHz, CDCl$_3$): δ 6.96 (d, J=7.29, 1H), 6.63 (d, J=6.86 Hz, 1H), 3.78 (s, 3H), 2.88 (t, J=7.29 Hz, 2H), 2.69-2.66 (m, 4H), 2.63-2.59 (m, 2H), 1.80-1.73 (m, 4H).

Preparation of Compound 110

A solution of 60 (13.70 g, 77.31 mmol) in dry THF (200 mL) was charged with n-butyllithium (45.07 mL, 90.08 mmol, 2M solution in cyclohexane) dropwise at −78° C., and the reaction mixture was stirred for 1 h to give a solution of lithium salt 61. Another solution of 109 (15.0 g, 64.37 mmol) in dry THF (200 mL) was charged with NMM (9.30 mL, 83.64 mmol) and PivCl (10.30 mL, 83.64 mmol) dropwise at −78° C. The reaction mixture was stirred for 30 min and warmed to −20° C. for 1 h, and the prepared solution of lithium salt was added slowly at −78° C. The reaction mixture was stirred for another 10 min, brought to 0° C. and stirred for 1 h, brought to room temperature and stirred for 30 min, quenched with saturated NH$_4$Cl, concentrated to remove THF, and partitioned between CH$_2$Cl$_2$ (300 mL) and water (100 mL). The aqueous layer was separated and extracted with CH$_2$Cl$_2$ (150 mL). The combined organic extracts were dried over Na$_2$SO$_4$ and concentrated. The residue was purified by column chromatography (silica gel, CH$_2$Cl$_2$) to afford compound 110 (15.0 g, 60%) as a white solid.

Preparation of Compound 111

A solution of 110 (15.0 g, 38.14 mmol) in dry THF (250 mL) was charged with KHMDS (13.70 g, 68.67 mmol) portionwise at −78° C. After the resulting mixture stirred for 30 min, trisyl azide (19.0 g, 61.40 mmol) was added and the reaction mixture was stirred for 5 min. Acetic acid (15.0 mL, 228 mmol) and tetramethylammonium acetate (30.9 g, 76.28 mmol) were added slowly at the same temperature. The reaction mixture was warmed to 24° C., stirred for 16 h, quenched with saturated NaHCO$_3$ (100 mL), concentrated to remove THF, and extracted with CH$_2$Cl$_2$ (300 mL). The combined organic extracts were dried over Na$_2$SO$_4$ and concentrated. The residue was purified by column chromatography (silica gel, 90:10 hexanes/EtOAc followed by DCM) to afford compound 111 (8.80 g, 54%) as a yellow solid: $^1$H NMR (400 MHz, CDCl$_3$): δ 7.36-7.30 (m, 3H), 7.23 (m, 1H), 7.20 (m, 1H), 7.16 (m, 1H), 7.01 (d, J=7.79 Hz, 1H), 6.60 (d, J=7.59 Hz, 2H), 5.35 (t, J=7.99, 2H), 4.89 (s, 1H), 4.58-4.51 (m, 1H), 4.13-4.10 (m, 3H), 3.93 (t, J=7.54, 1H), 3.77 (s, 3H), 3.33-3.27 (m, 3H), 2.71 (m, 2H), 2.63 (m, 2H), 1.78-1.75 (m, 5H), 1.58 (m, 2H).

Preparation of Compound 112

A solution of 111 (31.0 g, 72.1 mmol) in THF/H$_2$O (300 mL/100 mL) was charged with H$_2$O$_2$ (49 mL, 433 mmol) followed by LiOH (6.04 g, 144 mmol) portionwise at 0° C. The reaction mixture was stirred for 10 min at 0° C. and at room temperature for 1 h, quenched with saturated Na$_2$SO$_3$ (200 mL), concentrated under reduced pressure to remove THF, and washed with CH$_2$Cl$_2$ (500 mL). The aqueous layer was acidified with 1 N aqueous HCl and extracted with CH$_2$Cl$_2$ (2×500 mL). The combined organic extracts were dried over Na$_2$SO$_4$, concentrated, and washed with MTBE to afford compound 112 (15.0 g, 82%) as an off-white solid: $^1$H NMR (400 MHz, CD$_3$OD): δ 6.92 (d, J=7.7 Hz, 1H), 6.63 (d, J=8.0 Hz, 1H), 3.75 (s, 3H), 2.81 (t, J=7.8 Hz, 2H), 2.67 (t, J=6.0 Hz, 2H), 2.61 (t, J=5.7 Hz, 2H), 2.49-2.47 (m, 2H), 1.84-1.70 (m, 6H).

Preparation of Compound 113

A suspension of 112 (15.0 g, 55.1 mmol) and 10% Pd/C (3.50 g) in AcOH/H$_2$O (300 mL/100 mL) was subjected to hydrogenation conditions (1 atm) for 3 h at room temperature. The reaction mixture was filtered through Celite and washed with AcOH/H$_2$O followed by MeOH. The filtrate was concentrated under vacuum to afford acetic salt 113 (14.0 g, 83%) as a yellow solid.

Preparation of Compound 114

A solution of 113 (11.0 g, 44.1 mmol) in acetic acid (120 mL) was charged with hydrobromic acid (120 mL) dropwise at room temperature and the reaction mixture was refluxed for 3 h. The reaction mixture was cooled to room temperature and concentrated. The crude brown residue 114 (8.90 g, 80%) was directly used for the next step without any purification: $^1$H NMR (400 MHz, CDCl$_3$): δ 6.80 (d, J=7.85, 1H), 6.57 (d, J=7.21 Hz, 1H), 3.92-3.91 (m, 1H), 3.04-2.98 (m, 1H), 2.91-2.86 (m, 1H), 2.61 (m, 2H), 2.54-2.53 (m, 2H), 1.69-1.68 (m, 5H).

Preparation of Compound 115

Acetyl chloride (17.0 mL, 243 mmol) was added to dry methanol (300 mL) at 0° C. and 114 (8.90 g, 28.2 mmol) was added. The reaction mixture was refluxed for 4 h and concentrated. The residue was partitioned between CH$_2$Cl$_2$ (200 mL) and saturated NaHCO$_3$ (100 mL). The aqueous layer was separated and extracted with CH$_2$Cl$_2$ (200 mL). The combined organic extracts were dried over Na$_2$SO$_4$ and concentrated to afford compound 115 (7.30 g, 90%) as a white solid: ¹H NMR (400 MHz, CDCl₃): δ 6.81 (d, J=7.51, 1H), 6.59 (d, J=7.21 Hz, 1H), 4.12-4.11 (m, 1H), 3.75 (s, 1H), 3.31-3.30 (m, 2H), 2.70-2.67 (m, 2H), 2.63 (t, J=6.16 Hz, 2H).

Preparation of Compound 116

A solution of 115 (7.30 g, 25.60 mmol) in MeOH/H₂O (100 mL/60 mL) was charged with NaHCO₃ (12.0 g, 145 mmol) and Boc₂O (10.0 g, 45.8 mmol) at 0° C. The resulting mixture was warmed to room temperature and stirred for 1 h. The reaction mixture was partitioned between CH₂Cl₂ (100 mL) and water (50 mL). The aqueous layer was separated and extracted with CH₂Cl₂ (100 mL). The combined organic extracts were washed with brine, dried over Na₂SO₄, and concentrated. Flash-column chromatography using 20% ethyl acetate/hexanes followed by CH₂Cl₂ gave compound 116 (7.1 g, 81%) as a white solid: ¹H NMR (400 MHz, CDCl₃): δ 6.77 (d, J=7.36, 1H), 6.55 (d, J=7.86 Hz, 1H), 4.96-4.94 (m, 1H), 4.71 (s, 1H), 4.96-4.94 (m, 1H), 4.71 (s, 1H), 4.50-4.48 (m, 1H), 3.69 (s, 3H), 3.07-3.01 (m, 1H), 2.89-2.84 (m, 1H), 2.86 (m, 2H), 2.63 (m, 2H), 1.80-1.78 (m, 4H), 1.39 (s, 9H).

Preparation of Compound 117

A solution of 116 (7.0 g, 20.05 mmol) in CH₂Cl₂ (80 mL) was charged with pyridine (100 ml) and triflate (4.64 mL, 24.0 mmol) at 0° C., stirred for 1 h, and stirred at room temperature for 2 h. After concentration, the reaction mixture was partitioned between CH₂Cl₂ (150 mL) and water (70 mL). The aqueous layer was separated and extracted with CH₂Cl₂ (100 mL). The combined organic extracts were washed with brine, dried over Na₂SO₄, and concentrated to afford compound 117 (8.00 g, 83%) as a brown oil: ¹H NMR (400 MHz, CD₃OD): δ 8.81 (d, J=4.63 Hz, 5H), 8.56-8.51 (m, 2H), 8.02-7.99 (m, 4H), 7.11 (d, J=7.98 Hz, 1H), 7.03 (d, J=7.98, 1H), 4.39-4.35 (m, 1H), 3.68 (s, 3H), 3.19-3.14 (dd, 1H), 2.90-2.77 (m, 5H), 1.86-1.81 (m, 4H), 1.35 (s, 9H), 1.32-1.28 (m, 4H).

Preparation of Compound 118

Compound 117 (8.0 g, 16.6 mmol) and benzyl but-3-ynylcarbamate (10, 5.00 g, 24.9 mmol) in anhydrous CH₃CN (100 mL) were degassed with argon for 10 min at room temperature and charged with TEA (9.34 mL, 66.50 mmol), 10% (t-Bu)₃P in hexanes (7.0 mL, 3.32 mmol), and CuI (0.16 g, 0.84 mmol). The resulting mixture was degassed with argon for 10 min and Pd (PPh₃)₄ (2.00 g, 1.73 mmol) was added rapidly in one portion. After degassing with argon for 5 min, the resulting mixture was refluxed for 16 h. The reaction mixture was concentrated under vacuum and the residue was purified by column chromatography (silica gel, 75:25 hexanes/ethyl acetate) to afford compound 118 (4.50 g, 52%) as a brown solid: ¹H NMR (400 MHz, CD₃OD): δ 7.36-7.34 (m, 4H), 7.33-7.29 (m, 2H), 7.16 (d, J=7.63 Hz, 1H), 6.82 (d, J=7.02 Hz, 1H), 5.12-5.08 (m, 2H), 4.95 (d, J=7.88 Hz, 1H), 4.52-4.51 (m, 1H), 3.67 (s, 3H), 3.48-3.34 (m, 2H), 3.10-3.05 (dd, 1H), 2.84-2.83 (m, 2H), 2.68-2.65 (m, 4H), 1.81-1.76 (m, 4H), 1.39 (s, 9H).

Preparation of Compound 119

A solution of methyl ester 118 (4.50 g, 8.42 mmol) in THF/MeOH/H₂O (30 mL/30 mL/10 mL) was charged with NaOH (3.60 g, 90 mmol) and the reaction mixture was stirred at room temperature for 3 h. The pH value was adjusted to 9 with 1 N aqueous HCl and the organic solvent was removed. The pH value of the residue was adjusted to 5-6, and the suspension was partitioned between CH₂Cl₂ (100 mL) and water (50 mL). The aqueous layer was separated and extracted with CH₂Cl₂ (100 mL). The combined organic extracts were dried over Na₂SO₄ and concentrated to afford compound 119 (3.66 g, 85%) as a brown solid: ¹H NMR (400 MHz, CD₃OD): δ 7.28-7.24 (m, 5H), 7.05-7.03 (d, J=7.67 Hz, 1H), 6.89-6.87 (d, J=7.55 Hz, 1H), 5.04 (brs, J=7.02 Hz, 1H), 5.12-5.08 (m, 2H), 4.95 (d, J=7.88 Hz, 1H), 4.52-4.51 (m, 1H), 3.67 (s, 3H), 3.48-3.34 (m, 2H), 4.27-4.26 (m, 1H), 3.38-3.30 (m, 2H), 3.15-3.10 (m, 1H), 2.78-2.71 (m, 4H), 2.59 (d, J=5.95, 2H), 1.73-1.71 (m, 4H), 1.31 (s, 9H).

Preparation of Compound 120

Compound 119 (800 mg, 1.53 mmol) in THF (30 mL) was charged with DEPBT (845 mg, 2.56 mmol), 24 (700 mg, 2.33 mmol), and DIPEA (1.0 mL, 4.65 mmol) successively and stirred at room temperature for 16 h. After the solvent was removed under reduced pressure, the residue was dissolved in CH₂Cl₂ (50 mL), quickly washed with saturated aqueous water (50 mL) and brine (50 mL), and dried over Na₂SO₄. The solvent was evaporated and the crude product purified by flash chromatography on silica gel (6% methanol/CH₂Cl₂), yielding amide 120 (1.0 g) as a yellow solid: ¹H NMR (400 MHz, CDCl₃): δ 7.46-7.44 (m, 3H), 7.36-7.30 (m, 7H), 7.17 (d, J=7.2 Hz, 2H), 7.07 (d, J=7.5 Hz, 1H), 6.99-6.92 (m, 1H), 5.49 (s, 1H), 5.10 (s, 2H), 4.35-4.31 (m, 1H), 4.05-3.90 (m, 2H), 3.80-3.82 (m, 1H), 3.75-3.72 (m, 1H), 3.62 (t, J=9.9 Hz, 1H), 3.43 (t, J=5.7 Hz, 2H), 3.18-3.16 (m, 1H), 3.01-3.08 (m, 1H), 2.83-2.82 (m, 2H), 2.68-2.48 (m, 8H), 1.86-1.78 (m, 3H), 1.71-1.62 (m, 10H), 1.44 (s, 9H), 0.87 (t, J=6.3 Hz, 3H).

Preparation of Compound 121

A suspension of 120 (1.00 g, 1.01 mmol) and 10% Pd/C (600 mg) in a mixture of EtOH (50 mL) and AcOH (2 mL) was degassed and subjected to hydrogenation conditions (1 atm) for 12 h at room temperature. The reaction mixture was filtered through a plug of Celite and the plug was washed with MeOH. The filtrate was concentrated under vacuum to afford amine salt 121 as a white solid (700 mg, 80%): ¹H NMR (400 MHz, CDCl₃): δ 7.49-7.41 (m, 2H), 7.34-7.30 (m, 5H), 7.12-6.78 (m, 5H), 4.30-4.27 (m, 2H), 4.19-4.18 (m, 1H), 3.98-391 (m, 2H), 3.78-3.58 (m, 2H), 3.19-3.08 (m, 3H), 3.02-2.89 (m, 6H), 2.75-2.73 (m, 2H), 2.65-2.62 (m, 3H), 2.55-2.52 (m, 3H), 1.98-1.92 (m, 2H), 1.73-1.68 (m, 3H), 1.60-1.52 (m, 7H), 1.41 (s, 9H), 1.29-1.20 (m, 7H), 0.88-0.84 (m, 3H), 0.87 (t, J=6.4 Hz, 3H).

Preparation of Compound 122

A solution of amine salt 121 (700 mg, 0.81 mmol) and methyl 3,5-diamino-6-chloropyrazine-2-carbonylcarbamimidothioate (13, 680 mg, 1.75 mmol) in EtOH (20 mL) was charged with DIPEA (1.60 mL, 9.26 mmol) at room temperature. The reaction mixture was heated at 70° C. in a sealed tube for 2 h, cooled to room temperature, and concentrated under vacuum. The residue was purified by column chromatography (silica gel, 80:18:2 CHCl₃/CH₃OH/NH₄OH) to afford guanidine 122 (380 g, 48%) as a yellow solid: ¹H NMR (400 MHz, DMSO-d₆): δ 7.43-7.39 (m, 3H), 7.33-7.31 (m, 3H), 7.05 (d, J=6.69 Hz, 2H), 6.99-6.95 (m, 2H), 6.86 (d, J=7.59 Hz, 1H), 5.47 (s, 1H), 4.33-4.31 (m, 1H), 4.14-4.10 (m, 1H), 3.79-3.72 (m, 4H), 3.68-3.65 (m, 2H), 2.69-2.66 (m, 6H), 2.56-2.53 (m, 3H), 2.45-2.36 (m, 7H), 1.70 (m, 4H), 1.56 (m, 6H), 1.32 (s, 9H), 0.86 (t, J=7.0 Hz, 3H).

Preparation of the HCl Salt of 3,5-diamino-N—(N-(4-(4-((S)-2-amino-3-(4-(3-(hexyl((2S,3R,4R,5R)-2,3,4,5,6-pentahydroxyhexyl)amino)propyl)phenylamino)-3-oxopropyl)-5,6,7,8-tetrahydronaphthalen-1-yl)butyl)carbamimidoyl)-6-chloropyrazine-2-carboxamide (Compound 123)

4 N HCl in dioxane (15 mL) was added to 122 (350 g, 0.35 mmol) in EtOH (5.0 mL) and the reaction mixture was stirred at room temperature for 2 h. The solvent was removed, the mixture was purified by reverse-phase chromatography (Gold column), and the residue was lyophilized to give 110 mg (45%) of compound 123 as a yellow solid: $^1$H NMR (400 MHz, DMSO-d$_6$): δ 10.16 (s, 1H), 9.16 (brs, 1H), 8.51-8.34 (brs, 2H), 7.41 (t, J=8.1 Hz, 4H), 7.20 (d, J=8.6 Hz, 2H), 6.95-6.89 (q, 2H), 5.42 (brs, 1H), 4.42 (m, 1H), 4.53 (d, J=5.3 Hz, 2H), 4.42 (m, 1H), 4.01 (m, 1H), 3.93 (m, 1H), 3.60 (m, 1H), 3.50-3.38 (m, 4H), 3.08-3.03 (m, 6H), 2.72 (brs, 2H), 2.66-2.65 (m, 2H), 2.57 (m, 2H), 1.91-1.90 (m, 2H), 1.72-1.69 (m, 4H), 1.61-1.54 (m, 6H), 1.26 (s, 6H), 0.86 (t, J=7.0 Hz, 3H).
$^1$H NMR (400 MHz, D$_2$O): δ 7.08 (d, J=8.4 Hz, 2H), 7.04-6.98 (q, 2H), 6.92 (d, J=8.3 Hz, 2H), 4.06-4.02 (m, 2H), 3.78-3.69 (m, 3H), 3.62-3.54 (m, 2H), 3.25 (t, J=5.3 Hz, 1H), 3.19-3.14 (m, 3H), 3.10-3.04 (m, 4H), 2.66-2.54 (m, 7H), 1.90-1.86 (m, 2H), 1.65-1.58 (m, 5H), 1.50-1.40 (m, 4H), 1.19-1.18 (m, 6H), 0.78 (t, J=6.62).

17. Preparation of 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)-5,6,7,8-tetrahydronaphthalen-1-yl)butyl)carbamimidoyl)-6-chloropyrazine-2-carboxamide (127)

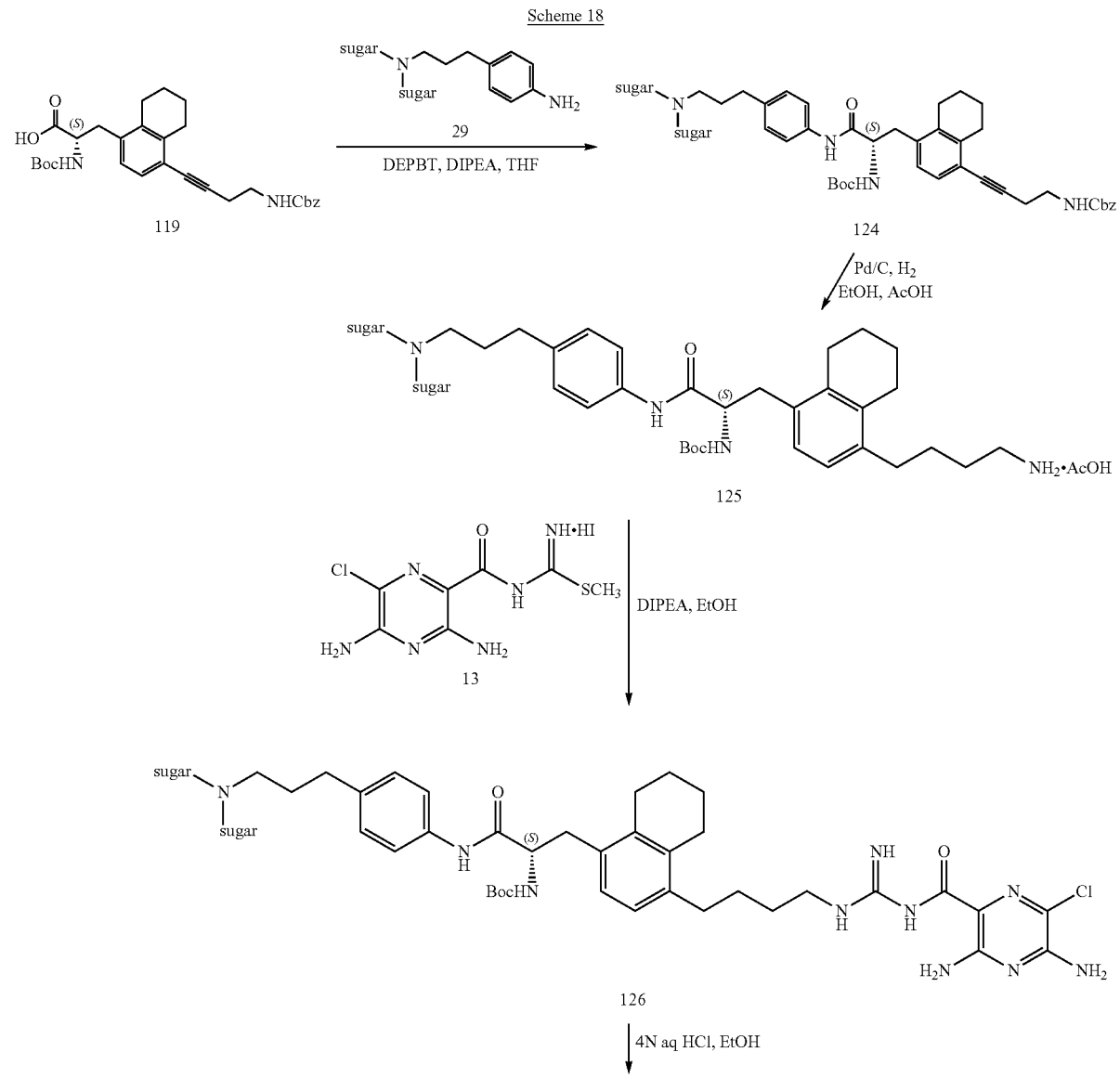

Scheme 18

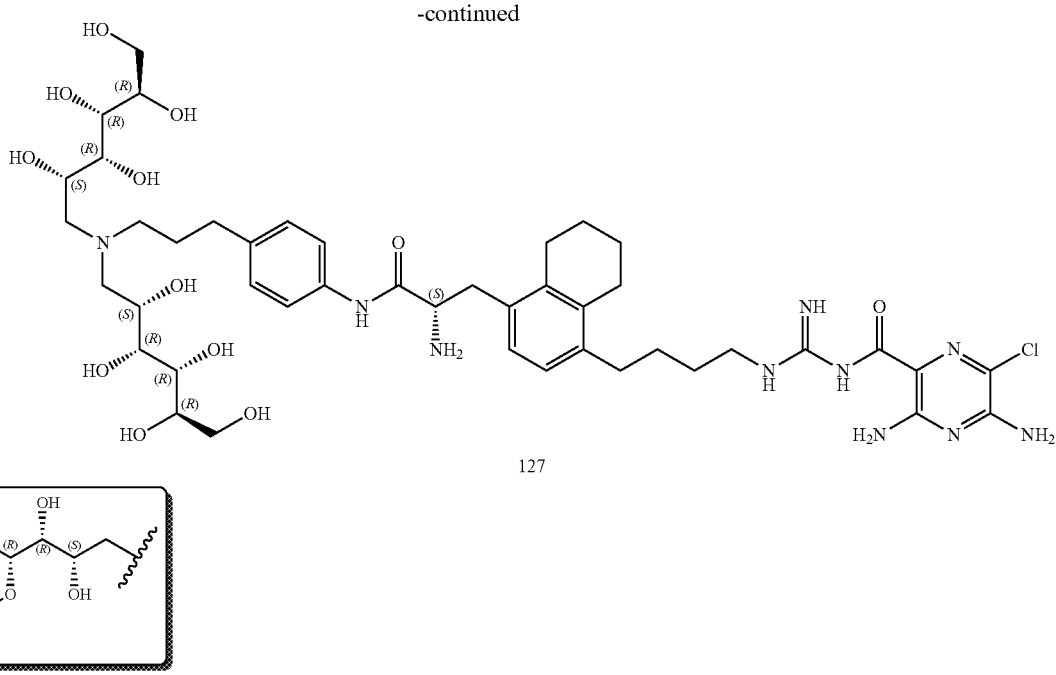

Preparation of Compound 124

The compound 119 (1.0 g, 1.92 mmol) in THF (30 mL) was charged with DEPBT (845 mg, 2.82 mmol), 29 (1.25 g, 1.91 mmol), and DIPEA (1.0 mL, 5.73 mmol) successively and stirred at room temperature for 16 h. After the solvent was removed under reduced pressure, the residue was dissolved in $CH_2Cl_2$ (50 mL), quickly washed with saturated aqueous water (50 mL) and brine (50 mL), and dried over $Na_2SO_4$. The solvent was evaporated and the crude product purified by flash chromatography on silica gel (5% methanol/$CH_2Cl_2$), yielding amide 124 [900 mg (mixture)] as a yellow solid.

Preparation of Compound 125

A suspension of 124 [900 mg (mixture), 0.77 mmol] and 10% Pd/C (600 mg) in a mixture of EtOH (50 mL) and AcOH (1.5 mL) was degassed and subjected to hydrogenation conditions (1 atm) for 12 h at room temperature. The reaction mixture was filtered through a plug of Celite and the plug was washed with MeOH. The filtrate was concentrated under vacuum to afford crude 125 (800 mg) as a colorless oil.

Preparation of Compound 126

A solution of crude 125 (800 mg) and methyl 3,5-diamino-6-chloropyrazine-2-carbonylcarbamimidothioate (13, 400 mg, 1.02 mmol) in EtOH (40 mL) was charged with DIPEA (1.10 mL, 6.38 mmol) at room temperature. The reaction mixture was heated at 70° C. in a sealed tube for 2 h, cooled to room temperature, and concentrated under vacuum. The residue was purified by column chromatography (silica gel, 80:18:2 $CHCl_3/CH_3OH/NH_4OH$) to afford guanidine 126 (285 mg, 12% over 3 steps) as a yellow solid: $^1$H NMR (400 MHz, DMSO-$d_6$): δ 7.44-7.42 (m, 4H), 7.30-7.28 (m, 6H), 7.22 (d, J=7.27 Hz, 2H), 6.96 (d, J=7.11 Hz, 2H), 6.91 (d, J=7.0 Hz, 2H), 6.86 (d, J=7.61 Hz, 2H), 5.47 (s, 2H), 4.33 (m, 1H), 4.23-4.19 (m, 2H), 3.97-3.91 (m, 4H), 3.84-3.82 (m, 2H), 3.71 (d, J=2.29 Hz, 1H), 3.69 (d, J=2.2 Hz, 1H), 3.58 (t, J=10.08 Hz, 2H), 3.06-3.00 (m, 1H), 2.91-2.86 (m, 1H), 2.76 (m, 2H), 2.71-2.68 (m, 4H), 2.61-2.55 (m, 4H), 2.44-2.35 (m, 4H), 1.74-1.60 (m, 10H), 1.38 (s, 9H).

Preparation of the HCl Salt of 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)-5,6,7,8-tetrahydronaphthalen-1-yl)butyl)carbamimidoyl)-6-chloropyrazine-2-carboxamide (Compound 127)

4 N HCl in dioxane (10 mL) was added to 126 (1.15 g, 0.23 mmol) in EtOH (3.0 mL) and the reaction mixture was stirred at room temperature for 2 h. The solvent was removed, the mixture was purified by reverse-phase chromatography (Gold column), and the residue was lyophilized to give 62 mg (32%) of compound 127: $^1$H NMR (400 MHz, DMSO-$d_6$): δ 10.39 (brs, 1H), 10.03 (brs, 1H), 8.91-8.82 (brs, 2H), 8.48 (brs, 2H), 7.42 (d, J=7.6 Hz, 4H), 7.18 (d, J=7.6 Hz, 2H), 6.96 (d, J=7.1, 1H), 6.89 (d, J=7.4, 1H), 5.44 (d, J=10.8, 2H), 4.81 (br, 2H), 4.59 (d, J=4.2, 2H), 4.55 (d, J=5.4 Hz, 2H), 4.42 (t, J=4.4, 2H), 4.11 (br, 1H), 4.00 (brs, 2H), 3.69-3.65 (m, 2H), 3.58 (m, 2H), 3.47 (m, 4H), 3.43-3.39 (m, 4H), 3.25-3.22 (m, 4H), 3.04 (d, J=6.3, 2H), 2.73 (m, 2H), 2.64 (m, 2H), 2.58-2.56 (m, 2H), 1.98 (m, 2H), 1.97 (m, 2H), 1.70-1.67 (m, 4H), 1.61-1.59 (m, 2H), 1.54-1.52 (m, 2H), 1.70-1.67 (m, 4H), 1.61-1.59 (m, 2H), 1.54-1.52 (m, 2H).

$^1$H NMR (400 MHz, $D_2O$): δ 7.10 (d, J=8.30 Hz, 2H), 7.02-6.90 (m, 2H), 6.91 (d, J=7.42 Hz, 2H), 4.07-3.92 (m, 5H), 3.77-3.70 (m, 8H), 3.62-3.55 (m, 5H), 4.07-3.95 (m, 5H), 3.74-3.56 (m, 8H), 3.60-3.55 (m, 5H), 3.30 (d, J=8.2 Hz, 5H), 3.20-3.16 (m, 7H), 2.60-2.51 (m, 10H), 1.97-1.95 (m, 3H), 1.61-1.59 (m, 7H), 1.49-1.45 (m, 2H).

18. Preparation of 3,5-diamino-N-(4-(4-((S)-2-amino-3-oxo-3-(4-(3-((2S,3R,4R,5R)-2,3,4,5,6-pentahydroxyhexylamino)propyl)phenylamino)propyl)-5,6,7,8-tetrahydronaphthalen-1-yl)butylcarbamoyl)-6-chloropyrazine-2-carboxamide (131)
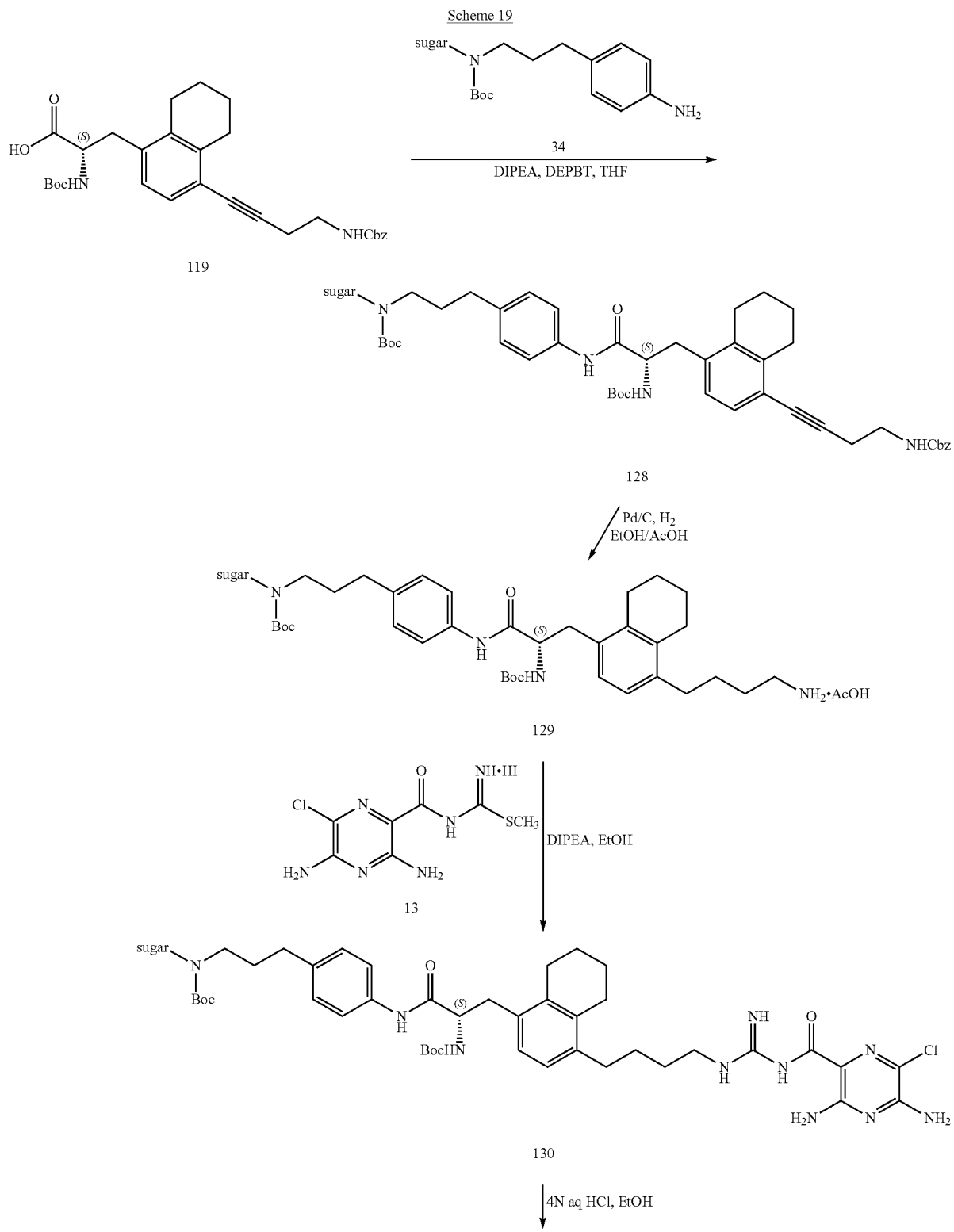

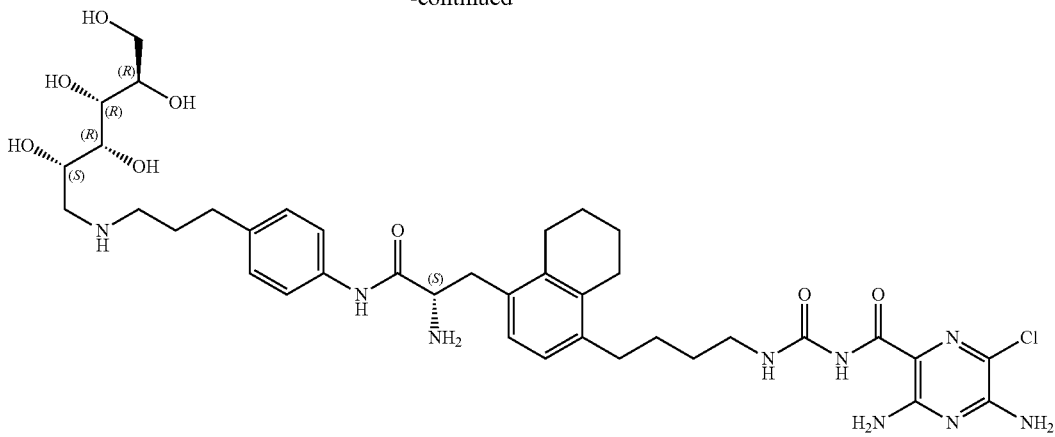

131

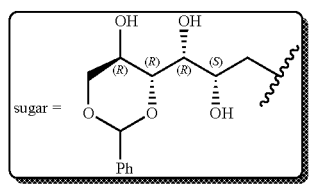

Preparation of Compound 128

The compound 119 (1.00 g, 1.92 mmol) in THF (30 mL) was charged with DEPBT (862 mg, 2.88 mmol), 34 (1.50 g, 2.98 mmol), and DIPEA (1.0 mL, 5.76 mmol) successively and stirred at room temperature for 16 h. After the solvent was removed under reduced pressure, the residue was dissolved in $CH_2Cl_2$ (50 mL), quickly washed with saturated aqueous water (30 mL) and brine (20 mL), and dried over $Na_2SO_4$. The solvent was evaporated and the crude product purified by flash chromatography on silica gel (6% methanol/$CH_2Cl_2$), yielding amide 128 (780 mg, 42%) as a yellow solid: $^1$H NMR (400 MHz, $CDCl_3$): δ 7.49 (m, 3H), 7.31-7.29 (m, 10H), 7.00-7.08 (m, 3H), 6.94 (d, J=7.4 Hz, 1H), 5.54 (m, 1H), 5.50-5.49 (m, 1H), 5.08 (s, 2H), 4.36 (m, 1H), 4.26-4.22 (m, 2H), 4.05 (m, 2H), 3.95-3.91 (m, 1H), 3.80 (m, 2H), 3.64-3.59 (m, 1H), 3.52-3.48 (m, 1H), 3.14-3.06 (m, 1H), 2.94-2.89 (m, 1H), 2.79 (d, J=16.12 Hz, 4H), 2.63 (t, J=5.98 Hz, 1H), 2.51 (t, J=6.9 Hz, 1H), 1.82-1.75 (m, 7H), 1.41 (s, 18H).

Preparation of Compound 129

A suspension of 128 (780 mg, 0.776 mmol) and 10% Pd/C (300 mg) in a mixture of EtOH (30 mL) and AcOH (1.0 mL) was degassed and subjected to hydrogenation conditions (1 atm) for 12 h at room temperature. The reaction mixture was filtered through a plug of Celite and the plug was washed with MeOH. The filtrate was concentrated under vacuum to afford amine salt 129 (720 mg, 85%) as a white solid: $^1$H NMR (400 MHz, $CDCl_3$): δ 7.49-7.46 (m, 2H), 7.32-7.30 (m, 5H), 7.08-7.06 (d, J=7.2 Hz, 1H), 6.88 (d, J=7.4 Hz, 1H), 5.53 (s, 1H), 4.34-4.33 (m, 1H), 4.25-4.21 (m, 1H), 4.03-4.02 (m, 1H), 3.96-3.89 (m, 1H), 3.78-3.76 (m, 1H), 3.71-3.69 (m, 1H), 3.60 (t, J=9.9 Hz, 1H), 3.48-3.46 (m, 1H), 3.09-3.04 (m, 1H), 2.89 (t, J=7.3 Hz, 3H), 2.79 (m, 2H), 2.69 (m, 2H), 2.58 (t, J=6.5 Hz, 2H), 2.51 (t, J=6.8 Hz, 2H), 1.84-1.77 (m, 6H), 1.67-1.66 (m, 2H), 1.61-1.57 (m, 2H), 1.41 (s, 18H).

Preparation of Compound 130

A solution of amine salt 129 (720 mg, 0.77 mmol) and methyl 3,5-diamino-6-chloropyrazine-2-carbonylcarbamimidothioate (13, 456 mg, 1.17 mmol) in EtOH (20 mL) was charged with DIPEA (1.12 mL, 6.24 mmol) at room temperature. The reaction mixture was heated at 70° C. in a sealed tube for 2 h, cooled to room temperature, and concentrated under vacuum. The residue was purified by column chromatography (silica gel, 80:18:2 $CHCl_3$/$CH_3OH$/$NH_4OH$) to afford guanidine 130 (380 mg, 45%) as a yellow solid: $^1$H NMR (400 MHz, $CDCl_3$): δ 7.48-7.46 (m, 2H), 7.30 (t, J=2.70 Hz, 5H), 7.08-7.06 (d, J=7.6 Hz, 2H), 6.93 (d, J=7.1 Hz, 1H), 6.88 (d, J=7.3 Hz, 1H), 5.53 (s, 1H), 4.34 (m, 1H), 4.25-4.21 (m, 1H), 4.04 (m, 1H), 3.96-3.90 (m, 1H), 3.79 (m, 2H), 3.60 (t, J=10.0 Hz, 1H), 3.50-3.46 (m, 1H), 3.25 (t, J=5.9 Hz, 3H), 3.07-3.02 (m, 1H), 2.92-2.87 (m, 1H), 2.77 (m, 2H), 2.69-2.67 (m, 2H), 2.58 (t, J=6.0 Hz, 2H), 2.48 (t, J=6.8 Hz, 2H), 1.82-1.74 (m, 6H), 1.67-1.64 (m, 5H), 1.40 (s, 18H).

Preparation of the HCl Salt of 3,5-diamino-N-(4-(4-((S)-2-amino-3-oxo-3-(4-(3-((2S,3R,4R,5R)-2,3,4,5,6-pentahydroxyhexylamino)propyl)phenylamino)propyl)-5,6,7,8-tetrahydronaphthalen-1-yl)butylcarbamoyl)-6-chloropyrazine-2-carboxamide (131)

4 N HCl in dioxane (25 mL) was added to 130 (350 mg, 0.35 mmol) in EtOH (5.0 mL) and the reaction mixture was stirred at room temperature for 2 h. The solvent was removed, the mixture was purified by reverse-phase chromatography (Gold column) and the residue was lyophilized to give compound 131 (125 mg, 48%) as a yellow solid: $^1$H NMR (400 MHz, $CD_3OD$): δ 7.35 (d, J=7.6, 2H), 7.18 (d, J=7.3, 2H), 6.99-6.98 (m, 2H), 4.07-4.03 (m, 2H), 3.83 (d, J=1.30, 1H), 3.82 (d, J=1.40 Hz, 1H), 3.78-3.75 (m, 1H), 3.68-3.66 (m, 3H), 3.36 (t, J=6.3, 2H), 3.18-3.15 (m, 4H), 3.04-3.00 (m, 2H), 2.76 (t, J=5.3 Hz, 2H), 2.69-2.61 (m, 5H), 2.00-1.97 (m, 2H), 1.77-1.73 (m, 5H), 1.69-1.65 (m, 3H).
$^1$H NMR (400 MHz, D$_2$O): δ 10.46 (s, 1H), 9.31 (br, 1H), 8.55 (br, 4H), 7.45 (d, J=6.6, 4H), 7.20 (d, J=7.62 Hz, 2H), 7.00 (d, J=6.6, 1H), 6.93 (d, J=6.6 Hz, 1H), 5.43 (d, J=3.8 Hz, 1H), 4.79 (d, J=5.38 1H), 4.64-4.63 (m, 2H), 4.46 (t, J=4.9 Hz, 1H), 4.15 (t, J=4.6 Hz, 1H), 3.96-3.94 (m, 1H), 3.71 (m, 1H), 3.64-3.61 (m, 1H), 3.51-3.45 (m, 3H), 2.96-2.92 (m, 3H), 2.78-2.77 (m, 2H), 2.68-2.65 (m, 2H), 2.62 (t, J=6.6 Hz, 2H), 1.95-1.94 (m, 2H), 1.76-1.15 (m, 8H).
19. Preparation of (S)-3,5-diamino-N—(N-(4-(4-(2-amino-3-(4-(3-(dimethylamino)propyl)phenylamino)-3-oxopropyl)-5,6,7,8-tetrahydronaphthalen-1-yl)butyl)carbamimidoyl)-6-chloropyrazine-2-carboxamide (135)
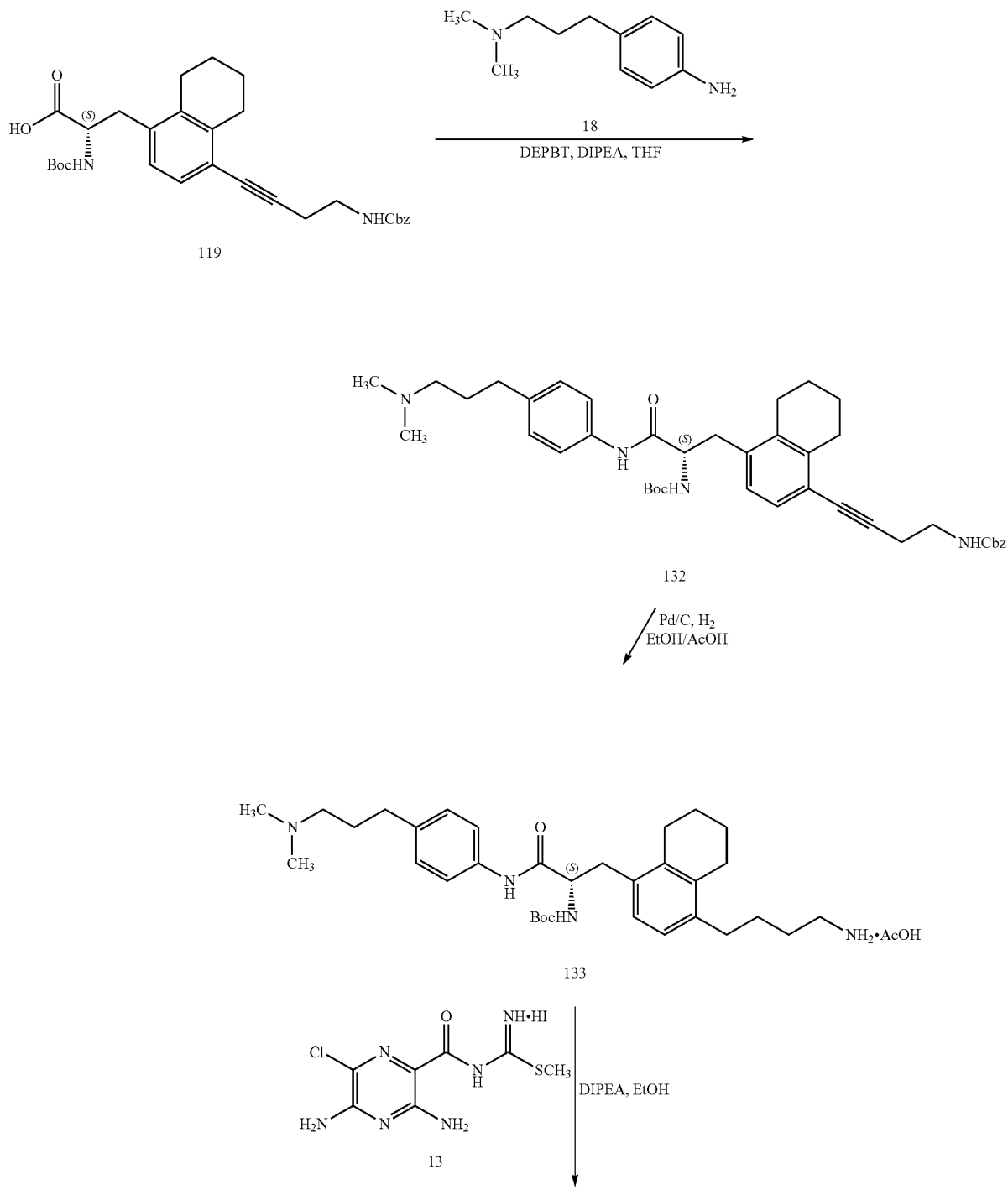

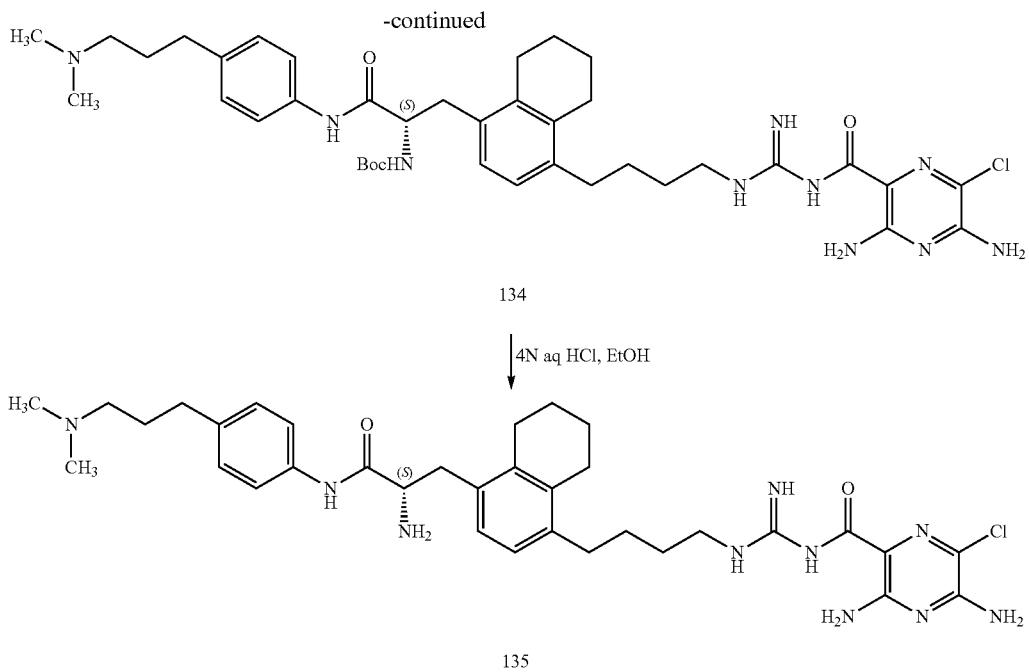

134

↓ 4N aq HCl, EtOH

135

Preparation of Compound 132

The compound 119 (700 mg, 1.34 mmol) in THF (30 mL) was charged with DEPBT (600 mg, 2.00 mmol), 18 (360 mg, 1.51 mmol), and DIPEA (0.80 mL, 4.03 mmol) successively and stirred at room temperature for 16 h. After the solvent was removed under reduced pressure, the residue was dissolved in $CH_2Cl_2$ (50 mL), quickly washed with saturated aqueous water (50 mL) and brine (50 mL), and dried over $Na_2SO_4$. The solvent was evaporated and the crude product purified by flash chromatography on silica gel (6% methanol/$CH_2Cl_2$), yielding amide 132 [800 mg (mixture)] as a yellow solid product: $^1$H NMR (400 MHz, DMSO-$d_6$): δ 8.13 (d, J=7.54 Hz, 1H), 8.03 (d, J=7.7 Hz, 1H), 7.89-7.85 (m, 1H), 7.71 (t, J=7.52 Hz, 1H), 7.64-7.59 (m, 2H), 7.44 (d, J=7.7 Hz, 2H), 7.33-7.30 (m, 6H), 7.12-7.06 (m, 3H), 7.0 (d, J=7.6 Hz, 1H), 5.02 (s, 2H), 2.70 (m, 4H), 2.63-2.61 (m, 5H), 2.45 (m, 5H), 1.83 (s, 6H), 1.69-1.65 (m, 3H), 1.33 (s, 9H).

Preparation of Compound 133

A suspension of 132 [800 mg (mixture), 1.01 mmol] and 10% Pd/C (350 mg) in a mixture of EtOH (30 mL) and AcOH (1 mL) was degassed and subjected to hydrogenation conditions (1 atm) for 12 h at room temperature. The reaction mixture was filtered through a plug of Celite and the plug was washed with MeOH. The filtrate was concentrated under vacuum and purified by column chromatography (silica gel, 80:18:2 $CHCl_3$/$CH_3OH$/$NH_4OH$) to afford compound 233 (500 mg, 67% over 2 steps) as a yellow solid: $^1$H NMR (400 MHz, DMSO-$d_6$): δ 7.31 (d, J=7.54 Hz, 2H), 7.12 (d, J=7.1 Hz, 2H), 6.93 (d, J=7.2 Hz, 1H), 6.88 (d, J=6.8 Hz, 1H), 4.32 (m, 1H), 3.08-3.03 (m, 1H), 2.91-2.86 (m, 1H), 2.77-2.76 (m, 4H), 2.69 (m, 2H), 2.60-2.55 (m, 4H), 2.35-2.31 (m, 2H), 1.82 (s, 6H), 1.58-1.57 (m, 4H), 1.40 (s, 9H).

Preparation of Compound 134

A solution of amine salt 133 (500 mg, 0.90 mmol) and methyl 3,5-diamino-6-chloropyrazine-2-carbonylcarbamimidothioate (13, 530 mg, 1.36 mmol) in EtOH (20 mL) was charged with DIPEA (1.30 mL, 7.25 mmol) at room temperature. The reaction mixture was heated at 70° C. in a sealed tube for 2 h, cooled to room temperature, and concentrated under vacuum. The residue was purified by column chromatography (silica gel, 80:18:2 $CHCl_3$/$CH_3OH$/$NH_4OH$) to afford guanidine 134 (285 mg, 42%) as a yellow solid: $^1$H NMR (400 MHz, DMSO-$d_6$): δ 7.29 (d, J=7.5 Hz, 2H), 7.10 (d, J=8.1 Hz, 2H), 6.94-6.87 (m, 2H), 4.33 (m, 1H), 3.27-3.24 (m, 2H), 3.07-3.00 (m, 1H), 2.92-2.87 (m, 1H), 2.76 (m, 2H), 2.70 (m, 2H), 2.61-2.54 (m, 4H), 2.35-2.31 (m, 2H), 2.22 (s, 6H), 1.80-1.72 (m, 5H), 1.69-1.62 (m, 4H), 1.39 (s, 9H).

Preparation of the HCl Salt of (S)-3,5-diamino-N—(N-(4-(4-(2-amino-3-(4-(3-(dimethylamino)propyl)phenylamino)-3-oxopropyl)-5,6,7,8-tetrahydronaphthalen-1-yl)butyl)carbamimidoyl)-6-chloropyrazine-2-carboxamide Compound 135

4 N HCl in dioxane (10 mL) was added to 134 (380 g, 0.35 mmol) in EtOH (5.0 mL) and the reaction mixture was stirred at room temperature for 2 h. The solvent was removed, the mixture was purified by reverse-phase chromatography (C18 Gold column), and the residue was lyophilized to afford compound 135 (125 mg, 49%) as a yellow solid: $^1$H NMR (400 MHz, DMSO-$d_6$): δ 10.69 (brs, 1H), 10.54-10.50 (d, J=16.7 Hz, 2H), 9.32 (t, J=4.8 Hz, 1H), 8.96 (brs, 1H), 8.86 (brs, 1H), 8.58 (brs, 3H), 7.42 (d, J=8.0 Hz, 4H), 7.18 (d, J=8.2 Hz, 2H), 6.96 (d, J=7.3 Hz, 1H), 6.88 (d, J=7.4 Hz, 1H), 4.15 (t, J=4.4 Hz, 1H), 3.36-3.32 (m, 2H), 3.09-3.06 (m, 2H), 3.00-2.95 (m, 2H), 2.74-2.73 (m, 1H), 2.22 (s, 6H), 2.64 (m, 2H), 2.57-2.56 (m, 2H), 1.94-1.90 (m, 2H), 1.70-1.67 (m, 3H), 1.62-1.58 (m, 2H), 1.54-1.52 (m, 2H).
$^1$H NMR (400 MHz, $D_2O$): δ 7.08 (d, J=7.7 Hz, 2H), 7.00-6.97 (q, 2H), 6.91 (d, J=8.1 Hz, 2H), 4.12-4.08 (q, 1H), 3.25 (t, J=5.2 Hz, 3H), 3.21-3.17 (m, 1H), 3.10 (t, J=9.8 Hz, 1H), 3.0-2.96 (m, 2H), 2.77 (s, 6H), 2.60-2.58 (m, 5H), 2.50-2.50 (m, 4H), 1.91-1.87 (m, 2H), 1.60-1.58 (m, 6H), 1.45-1.43 (m, 2H).

20. Preparation of (S)-2-amino-3-(4-(4-(3-(3,5-diamino-6-chloropyrazine-2-carbonyl)guanidino)butyl)-5,6,7,8-tetrahydronaphthalen-1-yl)propanoic acid (139)
Scheme 21
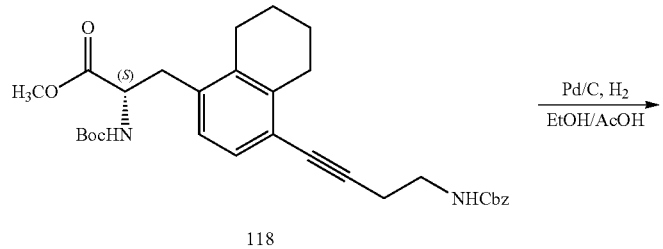
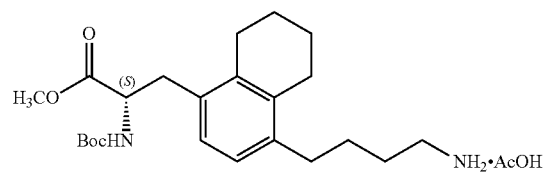
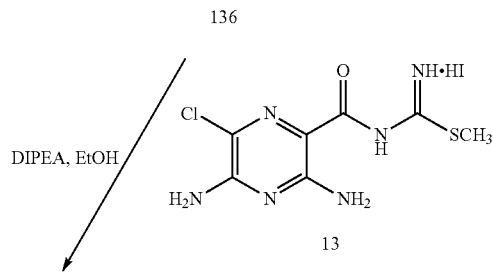
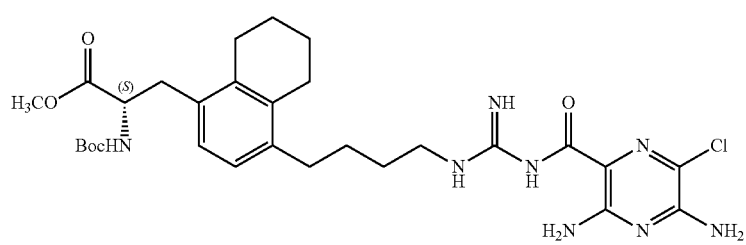

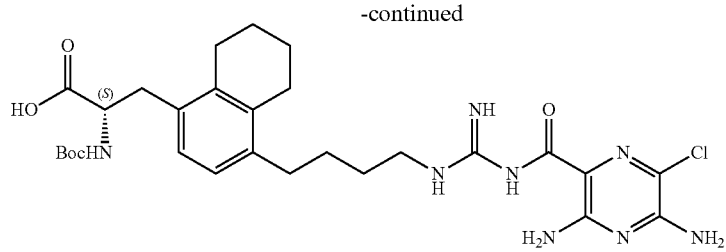

138

↓ 4N HCl in dioxane

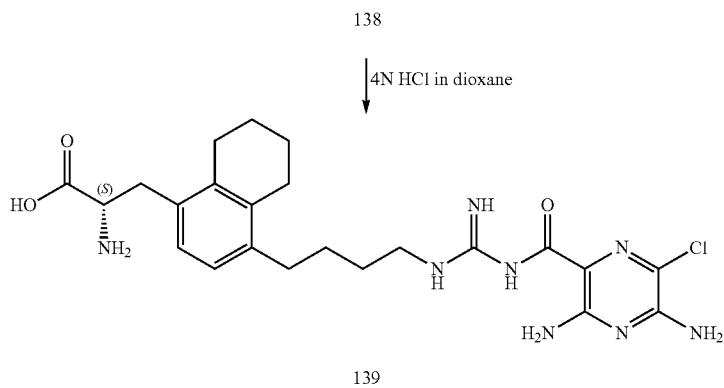

139

Preparation of Compound 136

A suspension of 118 (800 mg, 1.49 mmol) and 10% Pd/C (350 mg) in a mixture of EtOH (50 mL) and AcOH (1.0 mL) was degassed and subjected to hydrogenation conditions (1 atm) for 12 h at room temperature. The reaction mixture was filtered through a plug of Celite and the plug was washed with MeOH. The filtrate was concentrated under vacuum and purified by column chromatography (silica gel, 80:18:2 $CHCl_3/CH_3OH/NH_4OH$) to afford compound 136 (700 mg, 93%) as a yellow solid.

Preparation of Compound 137

A solution of amine salt 136 (700 mg, 1.50 mmol) and methyl 3,5-diamino-6-chloropyrazine-2-carbonylcarbamimidothioate (13, 880 mg, 2.26 mmol) in EtOH (30 mL) was charged with DIPEA (2.15 mL, 12.03 mmol) at room temperature. The reaction mixture was heated at 70° C. in a sealed tube for 2 h, cooled to room temperature, and concentrated under vacuum. The residue was purified by column chromatography (silica gel, 80:18:2 $CHCl_3/CH_3OH/NH_4OH$) to afford guanidine 137 (560 mg, 60%) as a yellow solid: $^1H$ NMR (400 MHz, $CD_3OD$); δ 6.95-6.85 (m, 2H), 4.32-4.28 (m, 1H), 3.72-3.67 (m, 2H), 3.34 (m, 3H), 3.22-3.16 (m, 2H), 3.08-3.03 (m, 1H), 2.73 (m, 4H), 2.62 (t, J=7.0 Hz, 1H), 1.81-1.78 (m, 4H), 1.74-1.72 (m, 2H), 1.68-1.60 (m, 2H), 1.36 (s, 9H), 1.34 (s, 5H).

Preparation of Compound 138

A solution of methyl ester 137 (560 mg, 0.907 mmol) in $THF/MeOH/H_2O$ (30 mL/30 mL/10 mL) was charged with NaOH (3.60 g, 7.25 mmol) and the reaction mixture was stirred at room temperature for 3 h. The pH value was adjusted to 9 with 1 N aqueous HCl and the organic solvent was removed. The pH value of the residue was adjusted to 5-6, and the suspension was partitioned between $CH_2Cl_2$ (100 mL) and water (50 mL). The aqueous layer was separated and extracted with $CH_2Cl_2$ (100 mL). The combined organic extracts were dried over $Na_2SO_4$ and concentrated to afford compound 138 (420 mg, 78%) as a brown solid: $^1H$ NMR (400 MHz, DMSO-$d_6$); δ 6.93 (d, J=6.7 Hz, 1H), 6.84 (d, J=7.35 Hz, 1H), 6.70 (s, 3H), 3.93 (m, 1H), 3.16 (m, 5H), 2.98-2.94 (m, 1H), 2.74-2.64 (m, 6H), 1.70 (m, 5H), 1.55 (m, 5H), 1.31 (s, 9H), 1.16-1.06 (m, 2H).

Preparation of the HCl Salt of (S)-2-amino-3-(4-(4-(3-(3,5-diamino-6-chloropyrazine-2-carbonyl)guanidino)butyl)-5,6,7,8-tetrahydronaphthalen-1-yl)propanoic acid Compound 139

4 N HCl in dioxane (10 mL) was added to 138 (420 mg, 0.69 mmol) in EtOH (5.0 mL) and the reaction mixture was stirred at room temperature for 2 h. The solvent was removed, the mixture was purified by reverse-phase chromatography (C18 Gold column), and the residue was lyophilized to afford compound 139 as a yellow solid (200 mg, 49%): $^1H$ NMR (400 MHz, DMSO-$d_6$); δ 10.56 (brs, 1H), 9.36 (t, J=4.7 Hz, 1H), 8.9-8.8 (brs, 2H), 6.98-6.93 (m, 2H), 3.95-3.92 (m, 2H), 3.38-3.35 (m, 2H), 3.04 (d, J=7.0 Hz, 2H), 2.67-2.66 (m, 4H), 2.56-2.55 (m, 2H), 1.72-1.70 (m, 4H), 1.63-1.56 (m, 4H).

$^1H$ NMR (400 MHz, $D_2O$); δ 7.43 (brs, 2H), 6.94 (d, J=7.2 Hz, 1H), 6.87 (d, J=7.1 Hz, 1H), 3.41 (t, J=6.0 Hz, 2H), 3.28-3.26 (m, 4H), 3.11 (d, 1H), 3.08 (m, 1H), 2.66-2.64 (m, 6H), 1.67-1.57 (m, 8H).

21. Chiral Synthesis of 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (33)
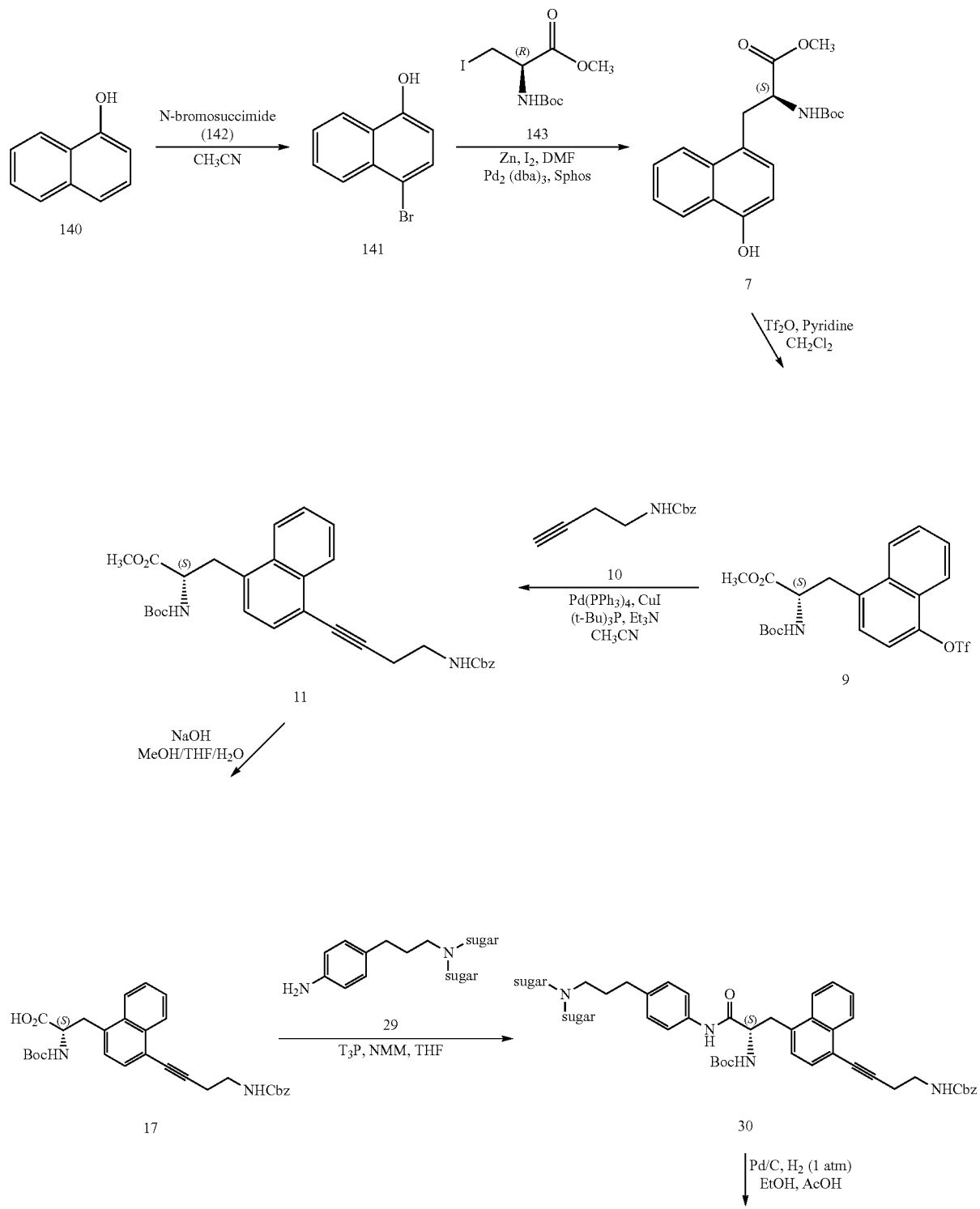
Scheme 22

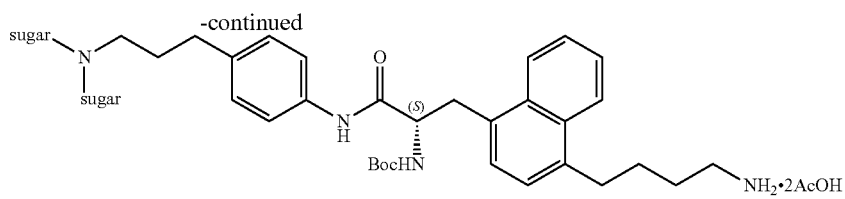

31

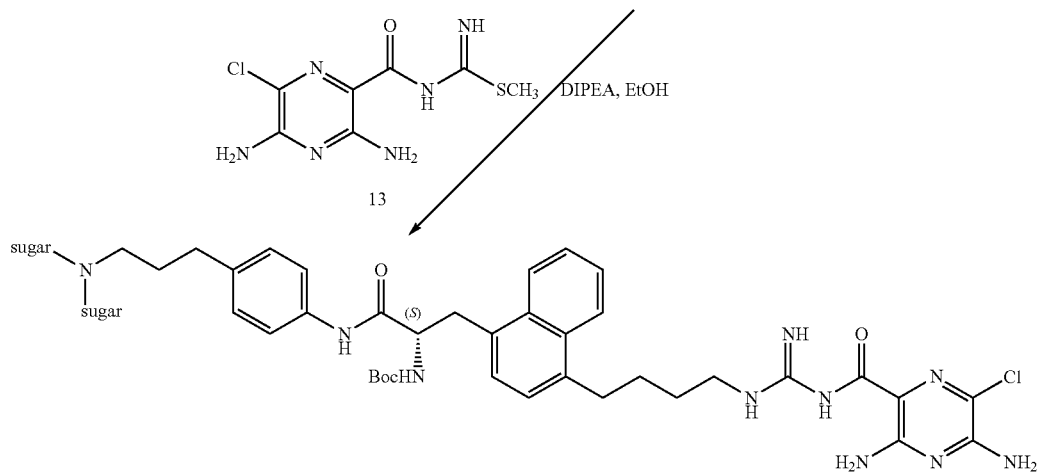

32

4N aq HCl, EtOH

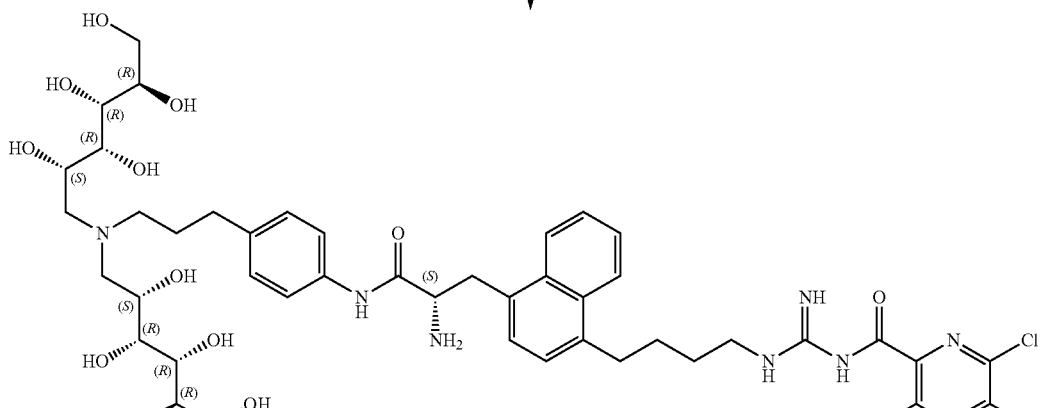

33

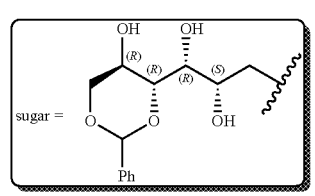

Preparation of Compound 141

To a solution of 1-naphthol (140, 10.0 g, 69.4 mmol) in acetonitrile (70.0 mL) was added several portions of NBS (142, 12.3 g, 69.4 mmol) over a period of 30 min. The resulting mixture was stirred at room temperature for 4 h, concentrated under vacuum, followed by addition of water (200 mL) and ethyl acetate (200 mL). The aqueous layer was separated and extracted with ethyl acetate (2×200 mL). The combined organic extracts were washed with brine, dried over $Na_2SO_4$ and concentrated. The residue was purified by column chromatography (silica gel, 4:1 hexanes/EtOAc) to afford desired compound 141 (9.50 g, 61%) as a white solid: $^1$H NMR (400 MHz, DMSO-$d_6$) δ 10.49 (s, 1H), 8.20 (dd, J=8.3, 0.5 Hz, 1H), 8.02 (d, J=8.3 Hz, 1H), 7.66 (dd, J=8.4, 1.4 Hz, 1H), 7.64 (d, J=8.1 Hz, 1H), 7.55 (ddd, J=8.2, 7.7, 1.1 Hz, 1H), 6.83 (d, J=8.2 Hz, 1H).

Preparation of Compound 7

Zinc dust (7.03 g, 107.6 mmol) was added to a flame-dried, nitrogen-purged side arm round-bottomed flask. Anhydrous DMF (50.0 mL) was added via syringe, followed by a catalytic amount of iodine (1.00 g, 3.94 mmol). The resulting mixture was observed to undergo a colour change from colorless to yellow and back to colourless. Protected iodoalanine 143 (11.8 g, 35.9 mmol) was added in one portion, followed by a catalytic amount of iodine (1.00 g, 3.94 mmol) and stirred at room temperature for 30 min; successful zinc insertion is accompanied by a mild exotherm. The solution of organozinc reagent was allowed to cool to room temperature before $Pd_2dba_3$ (821 mg, 0.89 mmol), SPhos (736 mg, 1.79 mmol), and aryl bromide 141 (8.00 g, 35.9 mmol) were added and the mixture was heated at 50° C. for 16 h, under a positive pressure of nitrogen. The reaction mixture was allowed to cool to room temperature. Saturated $NH_4Cl$ solution (300 mL) and EtOAc (300 mL) were added, and then the mixture was filtered through Celite and washed with EtOAc (100 mL). The aqueous layer was separated and extracted with EtOAc (2×300 mL). The combined organic extracts were washed with brine, dried over $Na_2SO_4$ and concentrated under vacuum. Crude product was purified by column chromatography (silica gel, 4:1 hexanes/EtOAc) to afford desired compound 7 (4.60 g, 37%) as a yellow solid: $^1$H NMR (400 MHz, CDCl$_3$, mixture of rotamers) δ 8.23 (d, J=8.3 Hz, 1H), 7.99 (d, J=8.6 Hz, 1H), 7.54 (t, J=8.04 Hz, 1H), 7.48 (ddd, J=8.3, 6.9, 1.3 Hz, 1H), 7.08 (d, J=7.8 Hz, 1H), 6.70 (d, J=7.6 Hz, 1H), 6.57 (br s, 0.2H), 6.45 (br s, 0.2H), 5.91 (br s, 0.65H), 5.05 (d, J=7.7 Hz, 0.75H), 4.89 (br s, 0.25H), 4.68 (q, J=6.8 Hz, 0.7H), 4.56 (br s, 0.2H), 3.73 (s, 0.7H), 3.62 (s, 2.3H), 3.49 (dd, J=14.0, 5.9 Hz, 0.8H), 3.89 (dd, J=14.0, 7.2 Hz, 0.7H), 3.05 (br s, 0.2H), 1.39 (s, 7.5H), 1.09 (s, 2.5H).

Preparation of Compound 9

To a solution of compound 7 (7.60 g, 21.8 mmol) in $CH_2Cl_2$ (150 mL) was added pyridine (18.0 mL) and $Tf_2O$ (9.19 g, 32.6 mmol) at 0° C. The resulting mixture was stirred at room temperature for 2 h, concentrated under vacuum and partitioned between $CH_2Cl_2$ (100 mL) and water (50 mL). The aqueous layer was separated and extracted with $CH_2Cl_2$ (2×50 mL). The combined organic extracts were washed with brine, dried over $Na_2SO_4$ and concentrated to afford compound 9 (11.0 g, crude) as a brown oil. The crude product was directly used for the next step without further purification: $^1$H NMR (400 MHz, CDCl$_3$, mixture of rotamers) δ 8.19-8.07 (m, 2H), 7.69-7.64 (m, 2H), 7.38 (d, J=8.1 Hz, 1H), 7.28 (d, J=7.9 Hz, 1H), 5.12-5.06 (br s, 1H), 4.78-4.67 (m, 1H), 3.68-3.46 (m, 5H), 1.39 (s, 8H), 1.25 (s, 1H).

Preparation of Compound 11

The solution of compound 9 (11.0 g, 21.8 mmol) and benzyl but-3-ynylcarbamate 10 (6.56 g, 32.6 mmol) in anhydrous acetonitrile (100 mL) was degassed for 10 min under Argon atmosphere followed by addition of TEA (11.9 mL, 87.0 mmol), 10% (t-Bu)$_3$P in hexanes (8.80 mL, 4.35 mmol) and CuI (207 mg, 1.08 mmol) at room temperature. The resulting mixture was degassed with Argon for another 10 min and Pd(PPh$_3$)$_4$ (2.51 g, 2.17 mmol) was added in one portion. After degassing with argon for 5 min, the resulting mixture was refluxed for 16 h. The reaction mixture was concentrated in vacuum and the residue was purified by column chromatography (silica gel, 2:3 hexanes/EtOAc) to afford compound 11 (7.00 g, 61% over two steps) as a brown oil: $^1$H NMR (400 MHz, CDCl$_3$, mixture of rotamers) δ 8.33 (dd, J=8.9, 1.9 Hz, 1H), 8.07 (dd, J=9.0, 1.7 Hz, 1H), 7.59-7.49 (m, 3H), 7.39-7.27 (m, 5H), 7.19 (d, J=7.3 Hz, 1H), 5.24-5.16 (m, 1H), 5.12 (s, 2H), 5.08-4.99 (m, 1H), 4.69 (q, J=6.7 Hz, 1H), 3.59 (s, 3H), 3.57-3.40 (m, 4H), 2.79 (t, J=6.4 Hz, 2H), 1.39 (s, 7.5H), 1.11 (s, 1.5H).

Preparation of Compound 17

To a solution of methyl ester 11 (7.00 g, 13.2 mmol) in THF (200 mL), methanol (200 mL) and water (75.0 mL) was added solid NaOH (16.0 g, 79.2 mmol). The resulting mixture was stirred at room temperature for 1 h until TLC showed the reaction was completed. 1 N hydrochloric acid was added to adjust pH of reaction mixture to 10. After concentrated; water (100 mL) was added and pH was adjusted to 5-6. The resulting precipitate was extracted with $CH_2Cl_2$ (2×250 mL). Organic layers were combined, dried over $Na_2SO_4$, filtered, concentrated and triturated with MTBE to afford compound 17 (5.00 g, 75%) as a white solid: $^1$H NMR (400 MHz, CD$_3$OD; mixture of rotamers) δ 8.33 (d, J=8.2 Hz, 1H), 8.28-8.20 (m, 1H), 7.59-7.45 (m, 3H), 7.38-7.21 (m, 6H), 5.09 (s, 2H), 4.55-4.45 (m, 1H), 3.76-3.66 (m, 1H), 3.44 (t, J=6.7 Hz, 2H), 3.28-3.20 (m, 1H), 2.76 (t, J=6.7 Hz, 2H), 1.29 (s, 6H), 0.82 (s, 3H).

Preparation of Compound 30

To a solution of compound 17 (4.60 g, 8.91 mmol) in THF (160 mL) were added T$_3$P (50% in ethyl acetate, 10.7 mL) and NMM (4.89 mL, 44.5 mmol) successively. After stirring at room temperature for 10 min, amine 29 (6.11 g, 9.33 mmol) was added and the reaction mixture was stirred at room temperature for 16 h. After the solvent was removed, the residue was dissolved in $CH_2Cl_2$ (100 mL), quickly washed with saturated NH$_4$Cl, saturated NaHCO$_3$ and brine, dried over Na$_2$SO$_4$ and concentrated. The residue was purified by column chromatography (silica gel, 9:1 $CH_2Cl_2$/MeOH) to afford amide 30 (6.60 g, 64%) as an off-white solid: $^1$H NMR (400 MHz, CDCl3) δ 8.33 (dd, J=9.0, 1.7 Hz, 1H), 8.17 (d, J=7.3 Hz, 1H), 7.62-7.47 (m, 4H), 7.42 (dd, J=7.7, 4.1 Hz, 4H), 7.37-7.28 (m, 11H), 7.09-6.95 (m, 4H), 5.46 (s, 2H), 5.33 (br s, 1H), 5.22 (t, J=5.8 Hz, 1H), 5.11 (s, 2H), 4.63-4.51 (m, 1H), 4.27 (dd, J=10.8, 5.4 Hz, 2H), 4.02-3.84 (m, 6H), 3.71 (t, J=4.5 Hz, 6H impurities), 3.57 (t, J=10.6 Hz, 2H), 3.54-3.45 (m, 4H), 2.82-2.60 (m, 6H), 2.59-2.45 (m, 3H), 2.44-2.36 (m, 4H), 1.82-1.69 (m, 2H), 1.38 (s, 9H).

Preparation of Compound 31

A suspension of 30 (7.26 g, 6.20 mmol) and 10% Pd/C (1.50 g) in EtOH/AcOH (240 mL/40.0 mL) was degassed by bubbling with Argon using syringe for 10 min and then subjected to hydrogenation conditions (1 atm) for 16 h at room temperature. The reaction mixture was filtered through Celite and washed with MeOH. The filtrate was concentrated in vacuum and triturated with MTBE to afford amine salt 31 (7.06 g, 98%) as a brown solid: $^1$H NMR (400 MHz, CD$_3$OD, mixture of rotamers) δ 8.24 (dd, J=7.2, 2.0 Hz, 1H), 8.09 (d, J=7.0 Hz, 1H), 7.59-7.22 (m, 2H), 7.49-7.41 (m, 4H), 7.39-7.22 (m, 10H), 6.95 (d, J=8.5 Hz, 2H), 5.51 (s, 2H), 4.55 (t, J=7.2 Hz, 1H), 4.24 (dd, J=10.7, 5.4 Hz, 2H), 4.19-4.10 (m, 2H), 3.99-3.88 (m, 4H), 3.83-3.73 (m, 8H, impurities), 3.61 (t, J=10.5, Hz, 2H), 3.59-3.52 (m, 1H), 3.45-3.36 (m, 1H), 3.19-3.02 (m, 4H), 2.93-2.81 (m, 8H), 2.54.2.39 (m, 2H), 1.95 (s, 6H), 1.88-1.80 (m, 2H), 1.80-1.65 (m, 4H), 1.36 (s, 7H), 1.09 (s, 2H).

Preparation of 32

To a solution of 31 (7.06 g, 6.18 mmol) in EtOH (50.0 mL) was added DIPEA (8.80 mL, 49.4 mmol) followed by methyl 3,5-diamino-6-chloropyrazine-2-carbonylcarbamimidothioate (13, 3.84 g, 9.88 mmol) at room temperature. The reaction mixture was heated at 70° C. for 2 h, cooled to room temperature and concentrated under vacuum. The residue was purified twice by column chromatography (silica gel, 80:18:2 CHCl$_3$/CH$_3$OH/NH$_4$OH) to afford compound 32 (2.50 g, 33%) as a yellow solid: $^1$H NMR (400 MHz, CD$_3$OD, mixture of rotamers) δ 8.22 (d, J=9.3 Hz, 1H), 8.08 (d, J=7.8 Hz, 1H), 7.56-7.47 (m, 4H), 7.43 (dd, J=7.4, 3.6 Hz, 4H), 7.33-7.14 (m, 10H), 6.94 (d, J=8.0 Hz, 2H), 5.47 (s, 2H), 4.53 (t, J=7.7 Hz, 1H), 4.22 (dd, J=10.8, 5.4 Hz, 2H), 3.99-3.89 (m, 4H), 3.84 (dd, J=5.5, 2.3 Hz, 2H), 3.70 (dd, J=9.2, 2.2 Hz, 2H), 3.59 (t, J=10.8 Hz, 2H), 3.54-3.46 (m, 1H), 3.47-3.38 (m, 1H), 3.22 (t, J=6.4 Hz, 2H), 3.11-3.02 (m, 2H), 2.70 (dd, J=13.5, 4.6 Hz, 2H), 2.61 (dd, J=13.6, 8.9, 2H), 2.57-2.47 (m, 2H), 2.46-2.34 (m, 2H), 1.84-1.73 (m, 2H), 1.72-1.61 (m, 4H), 1.36 (s, 7H), 1.12 (s, 2H).

Preparation of the HCl Salt of 3,5-diamino-N—(N-(4-(4-((S)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (33)

To a solution of 32 (2.50 g, 2.02 mmol) in EtOH (30.0 mL) was added 4 N hydrochloric acid (80.0 mL). The resulting mixture was stirred at room temperature for 2 h. The solvent was removed, purified by reverse phase column and lyophilized to afford compound 33 (1.82 g, 85%) as a yellow hygroscopic solid: $^1$H NMR (400 MHz, DMSO-d$_6$) δ 10.61 (s, 1H), 10.59 (s, 1H), 9.41 (t, J=5.2 Hz, H), 9.01 (br s, 1H), 8.96 (br s, 1H), 8.81 (br s, 2H), 8.77 (br s, 2H), 8.44-8.37 (m, 1H), 8.16-8.10 (m, 1H), 7.61-7.52 (m, 2H), 7.41 (d, J=8.6 Hz, 2H), 7.35 (d, J=7.5 Hz, 1H), 7.27 (d, J=7.3 Hz, 1H), 7.17 (d, J=8.5 Hz, 2H), 4.28 (q, J=7.4 Hz, 1H), 4.09-3.99 (m, 2H), 3.75-3.65 (m, 3H), 3.58 (dd, J=11.0, 2.6 Hz, 2H), 3.55-3.31 (m, 10H), 3.30-3.13 (m, 4H), 3.32-3.00 (m, 2H), 2.63-2.53 (m, 2H), 2.05-1.92 (m, 2H), 1.78-1.61 (m, 4H).

$^1$H NMR (400 MHz, CD$_3$OD): δ 9.25 (t, J=5.9 Hz, 0.5H), 8.26-8.21 (m, 1H), 8.17-8.12 (m, 1H), 7.60-7.54 m, 2H), 7.38 (d, J=7.2 Hz, 1H), 7.32 (d, J=7.2 Hz, 1H), 7.25 (d, J=8.6 Hz, 2H), 7.15 (d, J=8.6 Hz, 2H), 4.31 (t, J=8.1 Hz, 1H), 4.21-4.14 (m, 1H), 4.13-4.08 (m, 1H), 3.85-3.80 (m, 2H), 3.79 (d, J=2.9 Hz, 1H), 3.76 (d, J=3.2 Hz, 1H), 3.73-3.62 (m, 8H), 3.51-3.34 (m, 8H), 3.15 (t, J=6.8 Hz, 2H), 2.73-2.57 (m, 2H), 2.15-1.98 (m, 2H), 1.91-1.73 (m, 4H).

22. Preparation of (2R,2'R,3R,3'R,4R,4'R,5S,5'S)-6,6'-(3-(4-aminophenyl)propylazanediyl)dihexane-1,2,3,4,5-pentaol (29)

Scheme 23

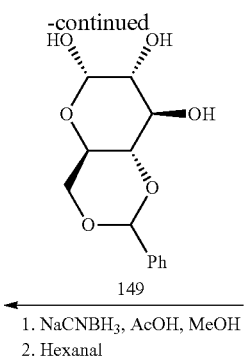

149

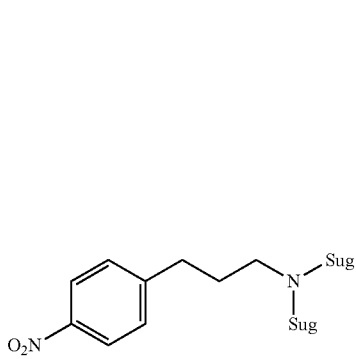

150

1. NaCNBH₃, AcOH, MeOH
2. Hexanal

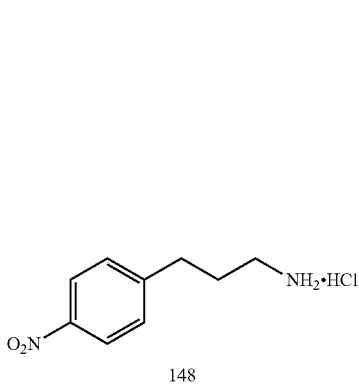

148

H₂, Pd/C
EtOH

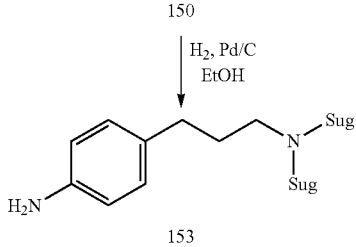

153

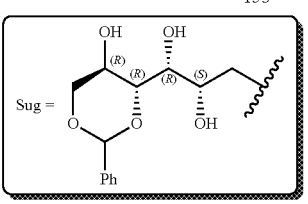

Preparation of Compound 145

To a solution of compound 144 (8.80 g, 154.1 mmol) in CH₂Cl₂ (150 mL) was added TEA (32.2 mL, 231.2 mmol) and Boc₂O (40.4 g, 185.3 mmol) at 0° C. The reaction mixture was continued to be stirred at 0° C. for 0.5 h, allowed to be warmed to room temperature and stirred for 5 h. Then the mixture was partitioned between CH₂Cl₂ (150 mL) and water (150 mL). The aqueous layer was separated and extracted with CH₂Cl₂ (2×150 mL). The combined organic extracts were washed with brine, dried over Na₂SO₄, concentrated to afford desired compound 145 (22.0 g, 91%) as a colorless oil. ¹H NMR (400 MHz, CDCl₃): δ 5.90-5.77 (m, 1H), 5.17 (dq, J=17.1, 1.7 Hz, 1H), 5.10 (dq, J=10.4, 1.4 Hz, 1H), 4.64 (brs, 1H), 3.74 (t, J=5.2 Hz, 2H), 1.45 (s, 9H).

Preparation of Compound 147

To a solution of compound 145 (14.0 g, 89.12 mmol) in anhydrous THF (150 mL) was added 9-BBN (0.5 M in THF, 270 mL, 133.8 mmol) under argon. After the reaction mixture was stirred for 2 h at room temperature, compound 146 (17.7 g, 71.3 mmol), Pd(PPh₃)₂Cl₂ (3.12 g, 4.45 mmol), and 1 N aq NaOH (150 mL) were added at room temperature. The resulting mixture was stirred for additional 1 h. After solvent removed; the residue was partitioned between EtOAc (200 mL) and water (200 mL). The aqueous layer was separated and extracted with EtOAc (2×200 mL). The combined organic extracts were washed with brine, dried over Na₂SO₄ and concentrated under vacuum. The crude product was purified by column chromatography (silica gel, 4:1 hexanes/EtOAc) to afford compound 147 (8.00 g, 43%) as a brown solid: ¹H NMR (400 MHz, CDCl₃) δ 8.14 (d, J=8.9 Hz, 2H), 7.34 (d, J=8.9 Hz, 2H), 4.56 (br s, 1H), 3.17 (q, J=6.2 Hz, 2H), 2.75 (t, J=7.7 Hz, 2H), 1.89-1.79 (m, 2H), 1.44 (s, 9H).

Preparation of Compound 148

Compound 147 (8.00 g, 28.6) was dissolved in 4 N HCl in dioxane (50.0 mL) at room temperature and the solution was stirred for 1 h. The reaction mixture was concentrated under vacuum and the residue was triturated with MTBE to afford compound 148 (4.00 g, 65%) as a brown solid: ¹H NMR (400 MHz, CD₃OD) δ 8.19 (d, J=8.7 Hz, 2H), 7.50 (d, J=8.7 Hz, 2H), 2.98 (t, J=7.4 Hz, 2H), 2.86 (t, J=7.6 Hz, 2H), 2.07-1.97 (m, 2H).

Preparation of Compound 150

To a solution of compound 148 (4.00 g, 18.5 mmol) and triol 149 (24.8 g, 92.5 mmol) in MeOH (150 mL) was added AcOH (11.1 mL, 185 mmol) and the reaction mixture was stirred at room temperature for 10 min. After NaCNBH₃ (5.83 g, 92.5 mmol) was added, the solution was continued to be stirred at room temperature for 24 h. Additional compound 149 (4.0 equiv), AcOH (4.0 equiv) and NaCNBH₃ (4.0 equiv) were added over 4 days. Then hexanal (2.0 equiv), AcOH (2.0 equiv) and NaCNBH₃ (2.0 equiv) were added. The solution was further stirred at room temperature for 1 h. After removal of solvent, the residue was neutralized with saturated NaHCO₃ and the residue was partitioned between EtOAc (200 mL) and water (200 mL). The aqueous layer was separated and extracted with CH₂Cl₂ (2×300 mL). The combined organic extracts were dried over Na₂SO₄ and concentrated under vacuum. The residue was purified by column chromatography (silica gel, 9:1 CH₂Cl₂/

MeOH, 80:18:2 CHCl₃/MeOH/NH₄OH) to afford compound 150 (6.50 g, 52%) as an off-white solid. Additional 4.00 g of material from impure fractions was isolated and purified by reverse phase column to afford 1.50 g (12%) of pure compound 150 (total 7.70 g, 64%): $^1$H NMR (400 MHz, CD₃OD) δ 8.03 (d, J=8.7 Hz, 2H), 7.50-7.41 (m, 4H), 7.35-7.23 (m, 8H), 5.48 (s, 2H), 4.22 (dd, J=10.6, 5.3 Hz, 2H), 3.99-3.91 (m, 4H), 3.85 (dd, J=5.5, 2.4 Hz, 2H), 3.70 (dd, J=9.5, 2.4 Hz, 2H), 3.59 (t, J=10.6 Hz, 2H), 2.73 (dd, J=13.6, 4.5 Hz, 2H), 2.67-2.50 (m, 6H), 1.83-1.71 (m, 2H).

Preparation of (2R,2'R,3R,3'R,4R,4'R,5S,5'S)-6,6'-(3-(4-aminophenyl)propylazanediyl) dihexane-1,2,3,4,5-pentaol (Compound 153)

A suspension of compound 150 (6.50 g, 9.50 mmol) and 10% Pd/C (1.30 g) in EtOH (150 mL) was degassed by bubbling with Argon using syringe for 10 min then stirred at rt under hydrogen atmosphere (balloon, 1 atm) for 6 h at room temperature. The reaction mixture was filtered through celite and washed with MeOH. The filtrate was concentrated in vacuum to afford 153 (6.01 g, 97%) as an off-white solid: $^1$H NMR (400 MHz, CD₃OD): δ 7.49-7.42 (m, 4H), 7.35-7.26 (m, 6H), 6.82 (d, J=8.4 Hz, 2H), 6.60 (d, J=8.4 Hz, 2H), 5.48 (s, 2H), 4.22 (dd, J=10.8, 5.9 Hz, 2H), 3.98-3.89 (m, 4H), 3.83 (dd, J=5.7, 2.3 Hz, 2H), 3.69 (dd, J=13.2, 3.4 Hz, 2H), 3.62-3.55 (m, 3H), 2.71 (dd, J=13.2, 3.4 Hz, 2H), 2.65-2.48 (m, 3H), 2.45-2.29 (m, 2H), 1.74-1.63 (m, 2H).

23. Preparation of 3,5-diamino-N—(N-(4-(4-((R)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (152)

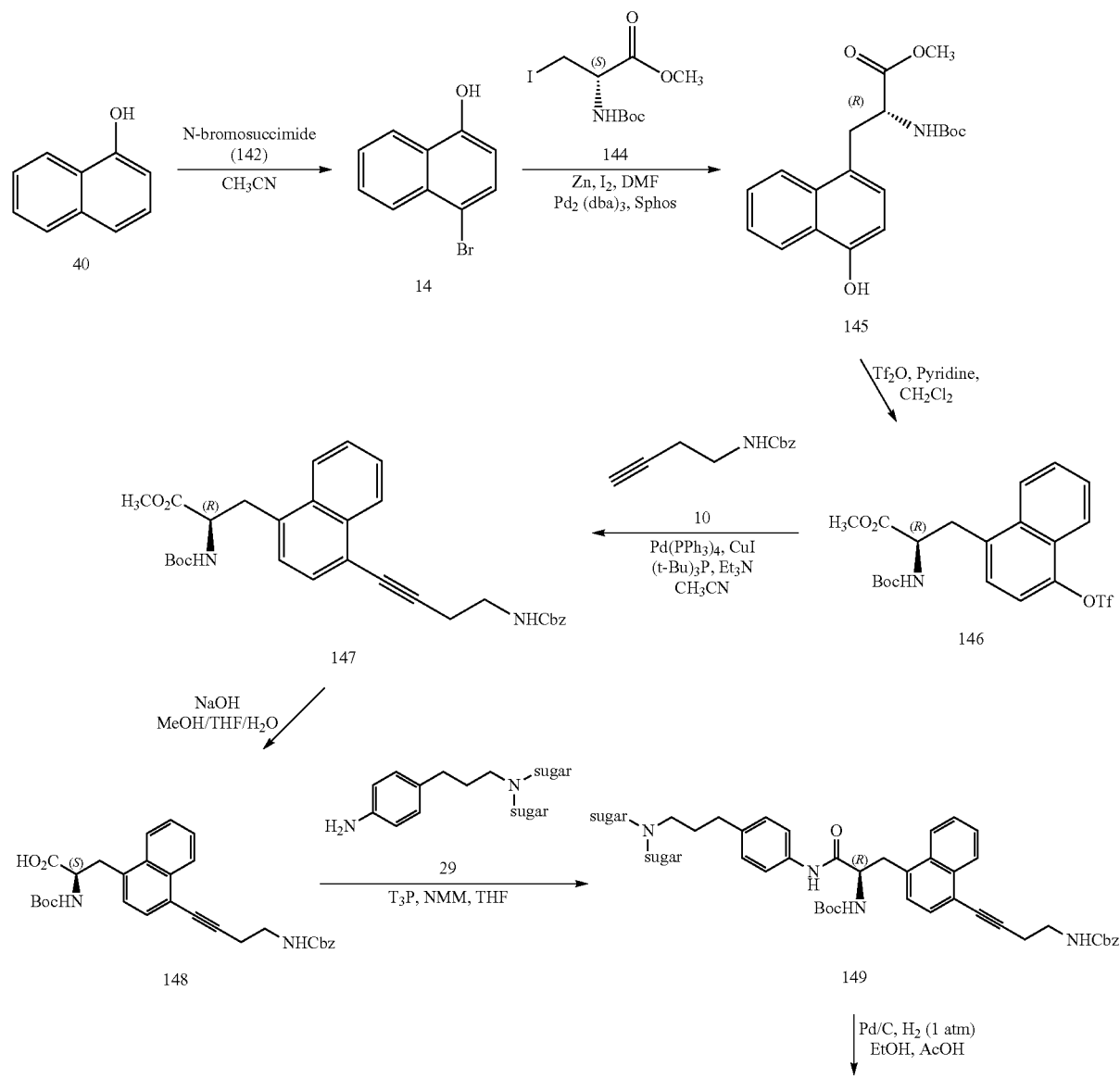

Scheme 24

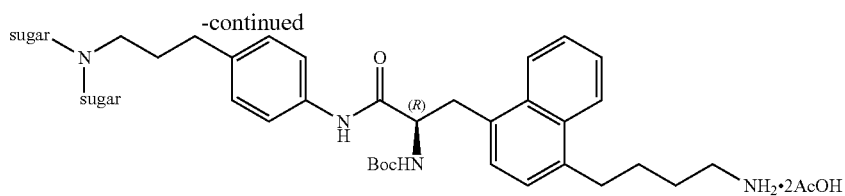

150

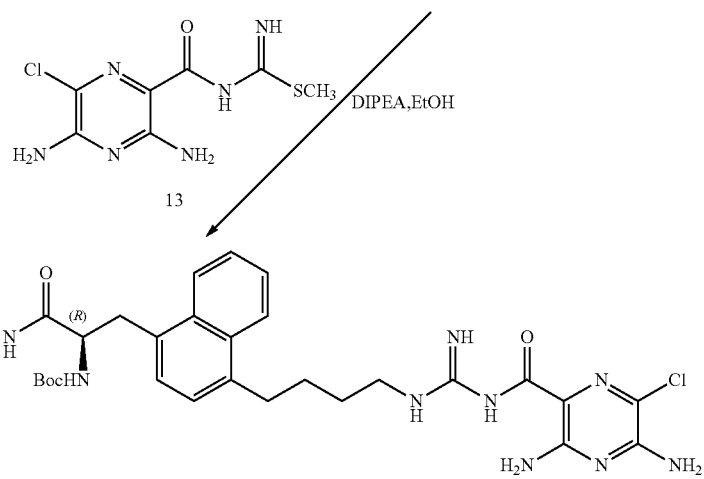

151

↓ 4N aq HCl, EtOH

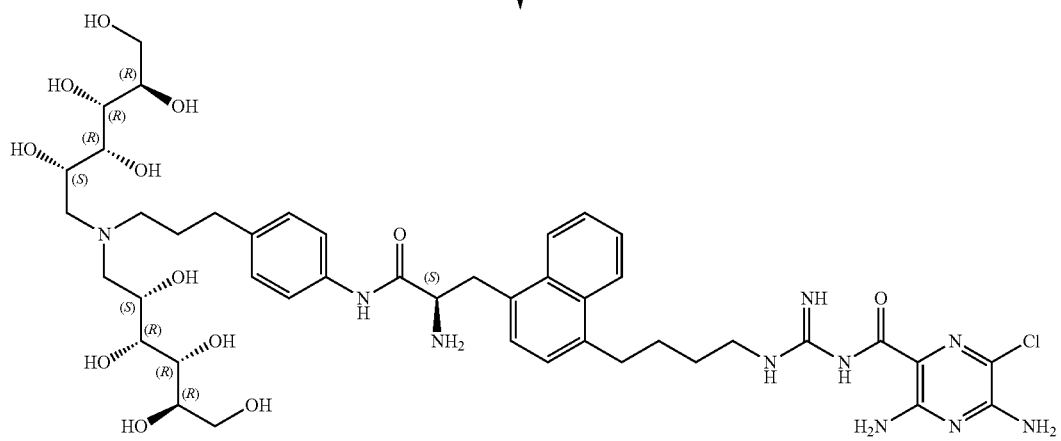

152

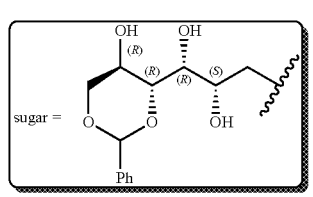

Preparation of Compound 14

To a solution of 1-naphthol (1, 10.0 g, 69.4 mmol) in acetonitrile (70.0 mL) was added several portions of NBS (142, 12.3 g, 69.4 mmol) over a period of 30 min. The resulting mixture was stirred at room temperature for 4 h, concentrated under vacuum, followed by addition of water (200 mL) and ethyl acetate (200 mL). The aqueous layer was separated and extracted with ethyl acetate (2×200 mL). The combined organic extracts were washed with brine, dried over $Na_2SO_4$ and concentrated. The residue was purified by crystallization (heptane/EtOAc) to afford desired compound 14 (6.0 g, 39%) as a white solid. $^1$H NMR (400 MHz, DMSO-d$_6$): δ 10.49 (s, 1H), 8.20 (dd, J=8.3, 0.5 Hz, 1H), 8.02 (d, J=8.3 Hz, 1H), 7.66 (dd, J=8.4, 1.4 Hz, 1H), 7.64 (d, J=8.1 Hz, 1H), 7.55 (ddd, J=8.2, 7.7, 1.1 Hz, 1H), 6.83 (d, J=8.2 Hz, 1H).

Preparation of Compound 145

Zinc dust (4.76 g, 72.9 mmol) was added to a flame-dried, nitrogen-purged side arm round-bottomed flask. Anhydrous DMF (25.0 mL) was added via syringe, followed by a catalytic amount of iodine (677 mg, 2.67 mmol). The resulting mixture was observed to undergo a colour change from colorless to yellow and back to colourless. Protected iodoalanine 114 (8.00 g, 24.3 mmol) was added in one portion, followed by a catalytic amount of iodine (677 mg, 2.67 mmol) and stirred at room temperature for 30 min; successful zinc insertion is accompanied by a mild exotherm. The solution of organozinc reagent was allowed to cool to room temperature before Pd2(dba)$_3$ (556 mg, 0.60 mmol), SPhos (498 mg, 1.21 mmol), and aryl bromide 14 (5.40 g, 24.3 mmol) were added and the mixture was heated at 50° C. for 16 h, under a positive pressure of nitrogen. The reaction mixture was allowed to cool to room temperature. Saturated NH$_4$Cl solution (300 mL) and EtOAc (300 mL) were added, and then the mixture was filtered through Celite and washed with EtOAc (100 mL). The aqueous layer was separated and extracted with EtOAc (2×300 mL). The combined organic extracts were washed with brine, dried over Na$_2$SO$_4$ and concentrated under vacuum. Crude product was purified by column chromatography (silica gel, 4:1 hexanes/EtOAc) to afford desired compound 145 (3.10 g, 37%) as a yellow solid. $^1$H NMR (400 MHz, CDCl$_3$, mixture of rotamers): δ 8.23 (d, J=8.3 Hz, 1H), 7.99 (d, J=8.6 Hz, 1H), 7.54 (t, J=8.04 Hz, 1H), 7.48 (ddd, J=8.3, 6.9, 1.3 Hz, 1H), 7.08 (d, J=7.8 Hz, 1H), 6.70 (d, J=7.6 Hz, 1H), 5.98 (brs, 0.3H), 5.59 (br s, 0.7H), 5.03 (d, J=7.7 Hz, 0.85H), 4.84 (br s, 0.15H), 4.68 (q, J=6.8 Hz, 1H), 3.76-3.68 (m, 1H), 3.62 (s, 3H), 3.54-3.33 (m, 2H), 1.39 (s, 7H), 1.09 (s, 2H).

Preparation of Compound 146

To a solution of compound 145 (3.07 g, 8.90 mmol) in CH$_2$Cl$_2$ (75.0 mL) was added pyridine (7.25 mL, 88.9 mmol) and Tf$_2$O (2.24 mL, 13.3 mmol) at 0° C. The resulting mixture was stirred at room temperature for 2 h, concentrated under vacuum and partitioned between CH$_2$Cl$_2$ (100 mL) and water (50 mL). The aqueous layer was separated and extracted with CH$_2$Cl$_2$ (2×50 mL). The combined organic extracts were washed with brine, dried over Na$_2$SO$_4$ and concentrated to afford compound 146 (4.20 g, crude) as a brown oil. The crude product was directly used for the next step without further purification. $^1$H NMR (400 MHz, CDCl$_3$, mixture of rotamers): δ 8.19-8.07 (m, 2H), 7.69-7.64 (m, 2H), 7.38 (d, J=8.1 Hz, 1H), 7.28 (d, J=7.9 Hz, 1H), 5.12-5.06 (br s, 1H), 4.78-4.67 (m, 1H), 3.68-3.46 (m, 5H), 1.39 (s, 8H), 1.25 (s, 1H).

Preparation of Compound 147

The solution of compound 6 (4.20 g, 8.80 mmol, crude) and benzyl but-3-ynylcarbamate 7 (2.65 g, 13.2 mmol) in anhydrous acetonitrile (50.0 mL) was degassed for 10 min under Argon atmosphere followed by addition of TEA (4.81 mL, 35.2 mmol), 10% (t-Bu)$_3$P in hexanes (3.56 mL, 1.76 mmol) and CuI (84 mg, 0.44 mmol) at room temperature. The resulting mixture was degassed with Argon for another 10 min and Pd(PPh$_3$)$_4$ (1.01 g, 0.88 mmol) was added in one portion. After degassing with argon for 5 min, the resulting mixture was refluxed for 18 h. The reaction mixture was concentrated in vacuum and the residue was purified by column chromatography (silica gel, 2:3 hexanes/EtOAc) to afford compound 147 (3.20 g, 67% over two steps) as a brown oil. $^1$H NMR (400 MHz, CDCl$_3$, mixture of rotamers): δ 8.33 (dd, J=8.9, 1.9 Hz, 1H), 8.07 (dd, J=9.0, 1.7 Hz, 1H), 7.59-7.49 (m, 3H), 7.39-7.27 (m, 5H), 7.19 (d, J=7.3 Hz, 1H), 5.24-5.16 (m, 1H), 5.12 (s, 2H), 5.08-4.99 (m, 1H), 4.69 (q, J=6.7 Hz, 1H), 3.59 (s, 3H), 3.57-3.40 (m, 4H), 2.79 (t, J=6.4 Hz, 2H), 1.39 (s, 7.5H), 1.11 (s, 1.5H).

Preparation of Compound 148

To a solution of methyl ester 147 (3.10 g, 5.84 mmol) in THF (60 mL), methanol (60 mL) and water (20.0 mL) was added solid NaOH (1.40 g, 35.09 mmol). The resulting mixture was stirred at room temperature for 2 h until TLC showed the reaction was completed. 1 N hydrochloric acid was added to adjust pH of reaction mixture to 10. After concentrated; water (100 mL) was added and pH was adjusted to 5-6. The resulting precipitate was extracted with CH$_2$Cl$_2$ (2×200 mL). Organic layers were combined, dried over Na$_2$SO$_4$, filtered, concentrated and triturated with MTBE to afford compound 148 (3.00 g, 99%) as a white solid. $^1$H NMR (400 MHz, CD$_3$OD; mixture of rotamers): δ 8.33 (d, J=8.2 Hz, 1H), 8.28-8.20 (m, 1H), 7.59-7.45 (m, 3H), 7.38-7.21 (m, 6H), 5.09 (s, 2H), 4.55-4.45 (m, 1H), 3.76-3.66 (m, 1H), 3.44 (t, J=6.7 Hz, 2H), 3.28-3.20 (m, 1H), 2.76 (t, J=6.7 Hz, 2H), 1.29 (s, 6H), 0.82 (s, 3H).

Preparation of Compound 149

To a solution of compound 148 (800 mg, 1.55 mmol) in THF (30 mL) were added T$_3$P (50% in ethyl acetate, 1.86 mL) and NMM (0.85 mL, 7.75 mmol) successively. After stirring at room temperature for 10 min, amine 29 (1.01 g, 1.55 mmol) was added and the reaction mixture was stirred at room temperature for 1 h. After the solvent was removed, the residue was dissolved in CH$_2$Cl$_2$ (100 mL), quickly washed with saturated NH$_4$Cl, saturated NaHCO$_3$ and brine, dried over Na$_2$SO$_4$ and concentrated. The residue was purified by column chromatography (silica gel, 9:1 CH$_2$Cl$_2$/MeOH) to afford amide 149 (1.20 g, 67%) as an off-white solid. $^1$H NMR (400 MHz, CDCl3): δ 8.35 (d, J=8.0, 1.7 Hz, 1H), 8.19 (d, J=8.5 Hz, 1H), 7.60-7.52 (m, 2H), 7.50 (d, J=7.3 Hz, 2H), 7.45-7.39 (m, 5H), 7.37-7.28 (m, 11H), 7.08-6.96 (m, 3H), 5.47 (s, 2H), 5.33-5.17 (m, 2H), 5.12 (s, 2H), 4.59-4.48 (m, 1H), 4.29 (dd, J=10.8, 5.4 Hz, 2H), 4.07-4.00 (m, 2H), 3.99-3.91 (m, 4H), 3.78-3.68 (m, 3H), 3.59 (t, J=10.6 Hz, 2H), 3.55-3.46 (m, 4H), 2.95-2.82 (m, 2H), 2.81-2.69 (m, 4H), 2.68-2.57 (m, 1H), 2.56-2.44 (m, 3H), 2.43-2.38 (m, 1H), 1.85-1.69 (m, 2H), 1.38 (s, 9H).

Preparation of Compound 150

A suspension of 149 (1.15 g, 1.00 mmol) and 10% Pd/C (230 mg) in EtOH/AcOH (80.0 mL/20.0 mL) was degassed by bubbling with Argon using syringe for 10 min and then subjected to hydrogenation conditions (1 atm) for 16 h at room temperature. The reaction mixture was filtered through Celite and washed with MeOH. The filtrate was concentrated in vacuum and triturated with MTBE to afford amine salt 150 (1.12 g, 97%) as a brown solid. $^1$H NMR (400 MHz, CD$_3$OD, mixture of rotamers): δ 8.25 (dd, J=7.2, 2.0 Hz, 1H), 8.09 (d, J=7.0 Hz, 1H), 7.59-7.51 (m, 2H), 7.48-7.41

(m, 4H), 7.37-7.21 (m, 10H), 6.94 (d, J=8.5 Hz, 2H), 5.52 (s, 2H), 4.54 (t, J=7.2 Hz, 1H), 4.24 (dd, J=10.7, 5.4 Hz, 2H), 4.16-4.08 (m, 2H), 3.97-3.88 (m, 4H), 3.75-3.70 (m, 2H), 3.62 (t, J=10.5, Hz, 2H), 3.60-3.51 (m, 1H), 3.28-3.15 (m, 2H), 3.14-2.95 (m, 4H), 2.89 (t, J=7.4 Hz, 2H), 2.73-2.67 (m, 1H), 2.54-2.39 (m, 2H), 1.95 (s, 6H), 1.88-1.64 (m, 8H), 1.36 (s, 7.5H), 1.09 (s, 1.5H).

Preparation of 151

To a solution of 150 (1.05 g, 0.92 mmol) in EtOH (15.0 mL) was added DIPEA (1.30 mL, 7.35 mmol) followed by methyl 3,5-diamino-6-chloropyrazine-2-carbonylcarbamimidothioate (13, 573 mg, 1.47 mmol) at room temperature. The reaction mixture was heated at 70° C. for 2 h, cooled to room temperature and concentrated under vacuum. The residue was purified twice by column chromatography (silica gel, 80:18:2 CHCl$_3$/CH$_3$OH/NH$_4$OH) to afford compound 151 (410 mg, 36%) as a yellow solid. $^1$H NMR (400 MHz, CD$_3$OD, mixture of rotamers): δ 8.22 (d, J=8.4 Hz, 1H), 8.09 (d, J=8.2 Hz, 1H), 7.56-7.48 (m, 2H), 7.47-7.40 (m, 4H), 7.33-7.25 (m, 6H), 7.22 (d, J=7.5 Hz, 2H), 7.16 (d, J=7.8 Hz, 2H), 6.94 (d, J=8.1 Hz, 2H), 5.47 (s, 2H), 4.53 (t, J=8.1 Hz, 1H), 4.22 (dd, J=10.8, 5.4 Hz, 2H), 3.99-3.89 (m, 4H), 3.84 (dd, J=5.5, 2.1 Hz, 2H), 3.70 (dd, J=9.1, 2.0 Hz, 2H), 3.59 (t, J=10.8 Hz, 2H), 3.53-3.47 (m, 1H), 3.46-3.39 (m, 1H), 3.26-3.17 (m, 2H), 3.12-3.04 (m, 2H), 2.70 (dd, J=13.2, 4.0 Hz, 2H), 2.60 (dd, J=13.0, 8.2 Hz, 2H), 2.57-2.49 (m, 2H), 2.47-2.33 (m, 2H), 1.84-1.73 (m, 2H), 1.72-1.61 (m, 4H), 1.37 (s, 7H), 1.12 (s, 2H).

Synthesis of 3,5-diamino-N—(N-(4-(4-((R)-2-amino-3-(4-(3-(bis((2S,3R,4R,5R)-2,3,4,5,6-pentahydroxyhexyl)amino)propyl)phenylamino)-3-oxopropyl)naphthalen-1-yl)butyl)carbamimidoyl)-6-chloropyrazine-2-carboxamide (152)

To a solution of 151 (480 mg, 0.42 mmol) in EtOH (5.0 mL) was added 4 N hydrochloric acid (25.0 mL). The resulting mixture was stirred at room temperature for 2 h. The solvent was removed, purified by reverse phase column and lyophilized to afford compound 152 (300 mg, 71%) as a yellow hygroscopic solid. $^1$H NMR (400 MHz, DMSO-d$_6$): δ 10.57 (brs, 1H), 10.55 (brss, 1H), 9.35 (t, J=6.0 Hz, 1H), 9.04-8.84 (m, 2H), 8.81-8.66 (m, 4H), 8.42-8.36 (m, 1H), 8.16-8.10 (m, 1H), 7.61-7.53 (m, 2H), 7.41 (d, J=8.6 Hz, 2H), 7.35 (d, J=7.5 Hz, 1H), 7.28 (d, J=7.8 Hz, 1H), 7.17 (d, J=9.0 Hz, 2H), 4.32-4.23 (m, 1H), 4.08-3.97 (m, 2H), 3.75-3.30 (m, 13H), 3.29-3.15 (m, 4H), 3.14-2.97 (m, 2H), 2.64-2.53 (m, 2H), 2.05-1.92 (m, 2H), 1.79-1.60 (m, 4H).
$^1$H NMR (400 MHz, CD$_3$OD): δ 8.25-8.21 (m, 1H), 8.18-8.13 (m, 1H), 7.59-7.53 (m, 2H), 7.38 (d, J=7.3 Hz, 1H), 7.32 (d, J=7.3 Hz, 1H), 7.26 (d, J=8.8 Hz, 2H), 7.15 (d, J=8.5 Hz, 2H), 4.30 (t, J=7.3 Hz, 1H), 4.20-4.14 (m, 1H), 4.13-4.08 (m, 1H), 3.84-3.80 (m, 2H), 3.79-3.75 (m, 2H), 3.72-3.61 (m, 8H), 3.51-3.34 (m, 8H), 3.15 (t, J=7.3 Hz, 2H), 2.74-2.58 (m, 2H), 2.13-1.98 (m, 2H), 1.91-1.73 (m, 4H).
HRMS calculated for C$_{44}$H$_{64}$ClN$_{10}$O$_{12}$ [M+Na]$^+$, 959.4418 and found 959.4394.

24. Preparation of Intermediate 18

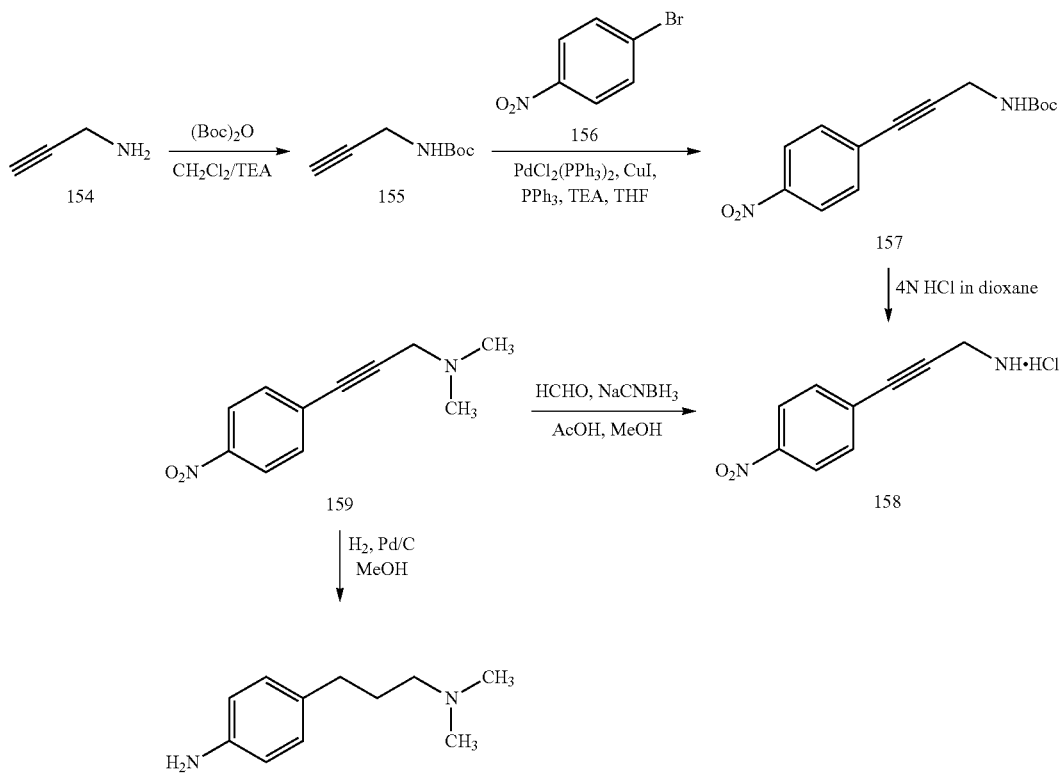

Scheme 25

Preparation of Compound 155

To a solution of compound 154 (500 mg, 9.00 mmol) in $CH_2Cl_2$ (50 mL) was added TEA (1.63 mL, 11.7 mmol) and $Boc_2O$ (2.16 g, 9.90 mmol) at 0° C. The reaction mixture was continued to be stirred at 0° C. for 0.5 h, allowed to be warmed to room temperature and stirred for 3 h. Then the mixture was partitioned between $CH_2Cl_2$ (50 mL) and water (50 mL). The aqueous layer was separated and extracted with $CH_2Cl_2$ (2×50 mL). The combined organic extracts were washed with brine, dried over $Na_2SO_4$, concentrated, the residue was purified by column chromatography (silica gel, 2:3 hexanes/EtOAc) to afford desired compound 155 (1.20 g, 86%) as a colorless oil. $^1$H NMR (300 MHz, $CDCl_3$): δ 4.70 (br s, 1H), 3.91 (dd, J=5.3, 2.2 Hz, 2H), 2.21 (t, J=2.7 Hz, 1H), 1.45 (s, 9H).

Preparation of Compound 157

The solution of compound 155 (1.00 g, 6.45 mmol) and 156 (1.30 g, 6.45 mmol) in anhydrous THF (15 mL) was degassed for 10 min under Argon atmosphere followed by addition of TEA (3.53 mL, 25.8 mmol), $PPh_3$ (424 mg, 1.61 mmol) and CuI (246 mg, 1.29 mmol) at room temperature. The resulting mixture was degassed with Argon for another 10 min and $Pd(PPh_3)_4$ (7.45 g, 6.45 mmol) was added in one portion. After degassing with argon for 5 min, the resulting mixture was refluxed for 16 h. The reaction mixture was concentrated in vacuum and the residue was purified by column chromatography (silica gel, 2:3 hexanes/EtOAc) to afford compound 157 (750 mg, 42%) as a brown oil. $^1$H NMR (400 MHz, $CDCl_3$): δ 8.17 (d, J=9.2 Hz, 2H), 7.55 (d, J=9.2 Hz, 2H), 4.79 (brs, 1H), 4.18 (d, J=6.0 Hz, 2H), 1.47 (s, 9H).

Preparation of Compound 158

Compound 157 (2.00 g, 7.24) was dissolved in 4 N HCl in dioxane (20.0 mL) at room temperature and the solution was stirred for 2 h. The reaction mixture was concentrated under vacuum and the residue was triturated with MTBE to afford compound 158 (1.25 g, 82%) as a brown solid. $^1$H NMR (300 MHz, $CD_3OD$): δ 8.26 (d, J=9.2 Hz, 2H), 7.72 (d, J=9.2 Hz, 2H), 4.09 (s, 2H).

Preparation of Compound 159

To a solution of compound 158 (100 mg, 0.47 mmol) and formaldehyde solution in water (30%, 1.40 mL, 1.41 mmol) in MeOH (3.0 mL) was added AcOH (0.09 mL, 1.41 mmol) and the reaction mixture was stirred at room temperature for 30 min. After $NaCNBH_3$ (88 mg, 1.41 mmol) was added, the solution was continued to be stirred at room temperature for 16 h. Additional formaldehyde solution in water (30%, 0.92 mL, 0.94 mmol), AcOH (0.09 mL, 1.41 mmol) and $NaCNBH_3$ (88 mg, 1.41 mmol) were added and stirred for another 16 h. After removal of solvent, the residue was neutralized with saturated $NaHCO_3$ and the residue was partitioned between EtOAc (30 mL) and water (30 mL). The aqueous layer was separated and extracted with $CH_2Cl_2$ (2×40 mL). The combined organic extracts were dried over $Na_2SO_4$ and concentrated under vacuum. The residue was purified by column chromatography (silica gel, 9:1 $CH_2Cl_2$/MeOH, 80:18:2 $CHCl_3$/MeOH/$NH_4OH$) to afford compound 159 (50 g, 52%) as an off-white oil. $^1$H NMR (300 MHz, $CD_3OD$): δ 8.17 (d, J=9.0 Hz, 2H), 7.57 (d, J=9.0 Hz, 2H), 3.50 (s, 2H), 2.37 (s, 6H).

Preparation of Compound 18

A suspension of compound 159 (100 mg, 0.49 mmol) and 10% Pd/C (40 mg) in MeOH (3.0 mL) was degassed with Argon for 10 min then stirred under hydrogen atmosphere (balloon, 1 atm) for 3 h at room temperature. The reaction mixture was filtered through celite and washed with MeOH. The filtrate was concentrated in vacuum and triturated with $CH_2Cl_2$/hexane to afford 18 (48 mg, 55%) as a white crystal: $^1$H NMR (300 MHz, $CDCl_3$): δ 6.96 (d, J=8.3 Hz, 2H), 6.60 (d, J=8.3 Hz, 2H), 3.47 (br s, 2H), 2.53 (t, J=7.8 Hz, 2H), 2.26 (dd, J=8.7, 7.2 Hz, 2H), 2.22 (s, 6H), 1.77-1.67 (m, 2H).

Preparation of Intermediate 29

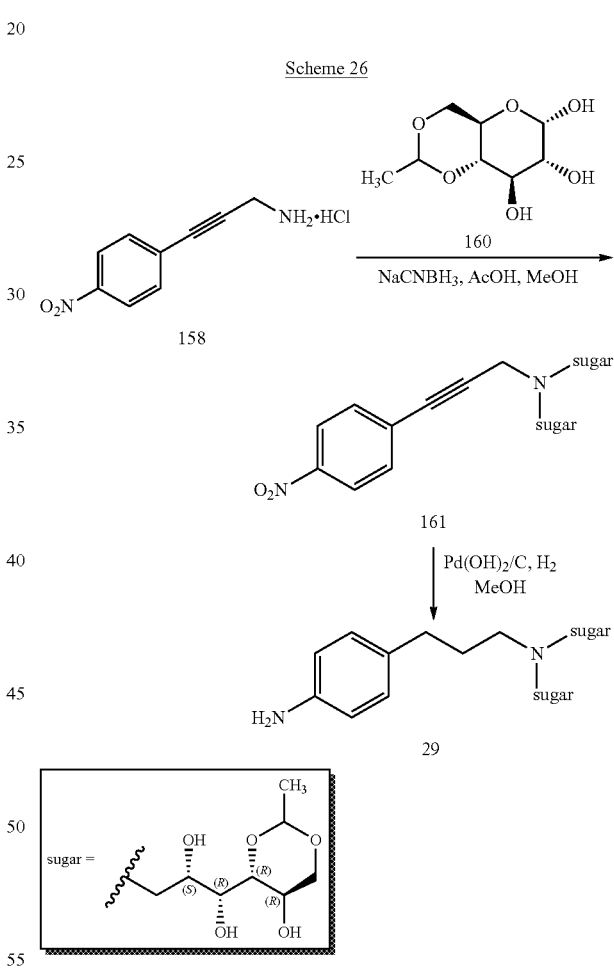

Scheme 26

Preparation of Compound 161

To a solution of compound 158 (4.00 g, 18.9 mmol) and triol 160 (11.7 g, 56.6 mmol) in MeOH (50 mL) was added AcOH (3.40 mL, 56.6 mmol) and the reaction mixture was stirred at room temperature for 30 min. After $NaCNBH_3$ (3.55 g, 56.6 mmol) was added, the solution was continued to be stirred at room temperature for 16 h. Additional compound 160 (11.7 g, 56.6 mmol), AcOH (3.40 mL, 56.6 mmol) and $NaCNBH_3$ (3.55 g, 56.6 mmol) were added the solution was continued to be stirred at room temperature for 16 h. After removal of solvent, the residue was neutralized with saturated NaHCO$_3$ and the residue was partitioned between CH$_2$Cl$_2$ (10 mL) and water (10 mL). The aqueous layer was separated and extracted with CH$_2$Cl$_2$ (2×10 mL). The combined organic extracts were dried over Na$_2$SO$_4$ and

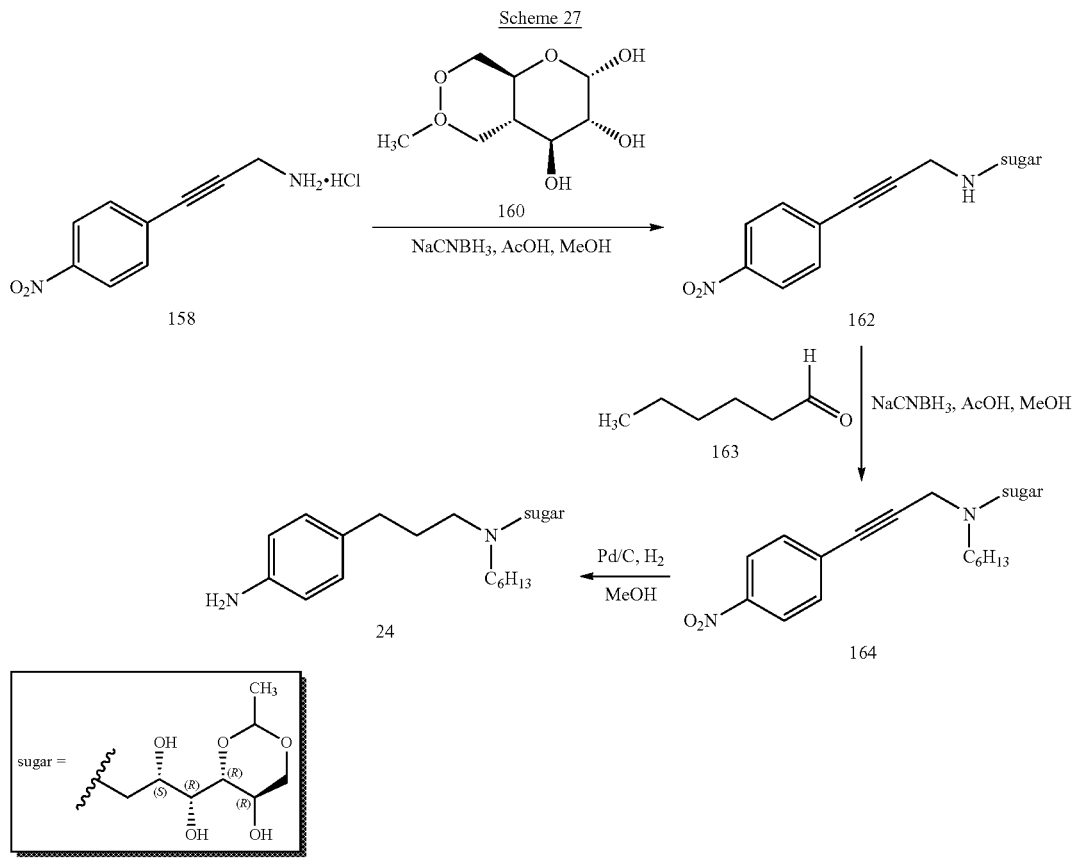

concentrated under vacuum. The residue was purified by column chromatography (silica gel, 9:1 CH$_2$Cl$_2$/MeOH, 80:18:2 CHCl$_3$/MeOH/NH$_4$OH) to afford compound 29 (700 mg, 7.0%) as an off-white solid. $^1$H NMR (300 MHz, CD$_3$OD): δ 8.21 (d, J=8.8 Hz, 2H), 7.66 (d, J=8.8 Hz, 2H), 4.68 (q, J=5.1 Hz, 2H), 4.04 (dd, J=10.8, 5.4 Hz, 2H), 3.99-3.93 (m, 2H), 3.86-3.74 (m, 6H), 3.54 (dd, J=9.8, 2.3 Hz, 2H), 3.36 (t, J=10.7 Hz, 2H), 2.87 (dd, J=13.3, 4.9 Hz, 2H), 2.74 (dd, J=13.3, 7.8 Hz, 2H), 1.25 (d, J=5.1 Hz, 6H).

Preparation of Compound 29

A suspension of compound 161 (500 mg, 0.90 mmol) and 10% Pd(OH)$_2$/C (215 mg) in EtOH (230 mL) was degassed by bubbling with Argon using syringe for 10 min then stirred under hydrogen atmosphere (balloon, 1 atm) for 2 h at room temperature. The reaction mixture was filtered through celite and washed with MeOH. The filtrate was concentrated in vacuum and residue was purified by column chromatography (silica gel, 9:1 CH$_2$Cl$_2$/MeOH, 80:18:2 CHCl$_3$/MeOH/NH$_4$OH) to afford compound 29 (264 mg, 55%) as an off-white solid. $^1$H NMR (400 MHz, CD$_3$OD): δ 6.97 (d, J=8.6 Hz, 2H), 6.67 (d, J=8.6 Hz, 2H), 4.71 (q, J=5.1 Hz, 2H), 4.06 (dd, J=10.6, 5.3 Hz, 2H), 4.13-4.05 (m, 2H), 3.81 (dd, J=5.0, 2.3 Hz, 2H), 3.80-3.72 (m, 2H), 3.51 (dd, J=9.6, 2.4 Hz, 2H), 3.33-3.23 (m, 2H), 3.38 (t, J=10.7 Hz, 2H), 2.83-2.54 (m, 6H), 1.85-1.69 (m, 2H), 1.26 (d, J=5.1 Hz, 6H).

Preparation of Intermediate 24

Preparation of Compound 162

To a solution of compound 158 (200 mg, 0.94 mmol) and triol 160 (194 mg, 0.94 mmol) in MeOH (2.0 mL) was added AcOH (0.17 mL, 2.82 mmol) and the reaction mixture was stirred at room temperature for 30 min. After NaCNBH$_3$ (148 mg, 2.35 mmol) was added, the solution was continued to be stirred at room temperature for 16 h. Additional compound 160 (0.2 equiv), AcOH (3.0 equiv) and NaCNBH$_3$ (1.0 equiv) were added the solution was continued to be stirred at room temperature for 16 h. After removal of solvent, the residue was neutralized with saturated NaHCO$_3$ and the residue was partitioned between CH$_2$Cl$_2$ (10 mL) and water (10 mL). The aqueous layer was separated and extracted with CH$_2$Cl$_2$ (2×10 mL). The combined organic extracts were dried over Na$_2$SO$_4$ and concentrated under vacuum. The residue was purified by column chromatography (silica gel, 9:1 CH$_2$Cl$_2$/MeOH, 80:18:2 CHCl$_3$/MeOH/NH$_4$OH) to afford compound 162 (95 mg, 28%) as an off-white solid. $^1$H NMR (400 MHz, CD$_3$OD): δ 8.24 (d, J=9.1 Hz, 2H), 7.69 (d, J=9.1 Hz, 2H), 4.70 (q, J=5.1 Hz, 1H), 4.09-4.02 (m, 2H), 4.00 (d, J=2.1 Hz, 2H), 3.83 (dd, J=5.1, 2.3 Hz, 1H), 3.81-3.71 (m, 1H), 3.53 (dd, J=9.3, 2.3 Hz, 1H), 3.38 (t, J=11.0 Hz, 1H), 3.21-3.07 (m, 2H), 1.25 (d, J=5.1 Hz, 3H).

Preparation of Compound 164

To a solution of compound 162 (95 mg, 0.26 mmol) and hexanal 163 (52 mg, 0.51 mmol), AcOH (0.05 mL, 0.78 mmol) and NaCNBH$_3$ (41 mg, 0.65 mmol) were added. The solution was stirred at room temperature for 16 h. After removal of solvent, the residue was neutralized with saturated NaHCO$_3$ and the residue was partitioned between EtOAc (10 mL) and water (10 mL). The aqueous layer was separated and extracted with CH$_2$Cl$_2$ (2×10 mL). The combined organic extracts were dried over Na$_2$SO$_4$ and concentrated under vacuum. The residue was purified by column chromatography (silica gel, 9:1 CH$_2$Cl2/MeOH, 80:18:2 CHCl$_3$/MeOH/NH$_4$OH) to afford compound 164 (70 mg, 59%) as an off-white solid. $^1$H NMR (400 MHz, CDCl$_3$): δ 8.18 (d, J=8.9 Hz, 2H), 7.56 (d, J=8.9 Hz, 2H), 4.70 (q, J=5.0 Hz, 1H), 4.15 (dd, J=10.4, 5.2 Hz, 1H), 4.01-3.89 (m, 2H), 3.83 (dd, J=3.8, 2.7 Hz, 1H), 3.77 (brs, 1H), 3.70 (brs, 1H), 3.64 (t, J=6.2 Hz, 1H), 3.56 (dd, J=9.2, 4.0 Hz, 1H), 3.41 (t, J=10.8 Hz, 1H), 2.87 (dd, J=13.2, 4.3 Hz, 1H), 2.78-2.68 (m, 2H), 2.63-2.55 (m, 1H), 1.75-1.43 (m, 4H), 1.34 (d, J=5.0 Hz, 3H), 1.32-1.25 (m, 6H), 0.89 (t, J=6.6 Hz, 3H).

Preparation of Compound 24

A suspension of compound 164 (1.70 g, 3.77 mmol) and 10% Pd/C (200 mg) in MeOH (40 mL) was degassed with Argon for 10 min then stirred under hydrogen atmosphere (balloon, 1 atm) for 2 h at room temperature. The reaction mixture was filtered through celite and washed with MeOH. The filtrate was concentrated in vacuum and residue was purified by column chromatography (silica gel, 9:1 CH$_2$Cl$_2$/MeOH, 80:18:2 CHCl$_3$/MeOH/NH$_4$OH) to afford compound 24 (1.20 g, 76%) as an off-white solid. $^1$H NMR (300 MHz, CDCl$_3$): δ 6.96 (d, J=8.9 Hz, 2H), 6.62 (d, J=8.9 Hz, 2H), 4.68 (q, J=5.0 Hz, 1H), 4.14 (dd, J=11.0, 5.5 Hz, 1H), 3.92-3.81 (m, 2H), 3.72 (dd, J=3.8, 2.4 Hz, 1H), 3.50 (dd, J=9.1, 4.0 Hz, 1H), 3.40 (t, J=10.5 Hz, 1H), 2.76-2.38 (m, 10H), 1.81-1.64 (m, 3H), 1.48-1.36 (m, 2H), 1.33 (d, J=5.0 Hz, 3H), 1.30-1.20 (m, 6H), 0.88 (t, J=6.6 Hz, 3H).

Preparation of Intermediate 85

Scheme 28

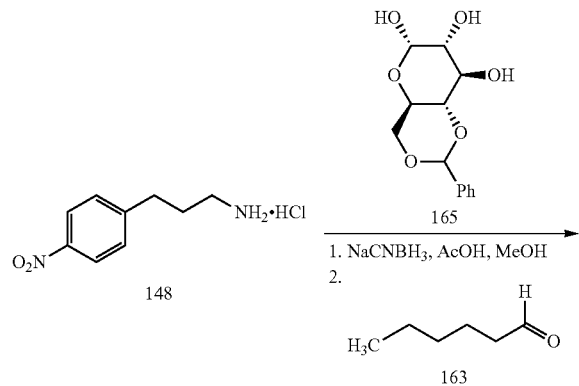

Preparation of Compound 166

To a solution of compound 148 (4.60 g, 21.3 mmol) and triol 165 (17.1 g, 63.9 mmol) in MeOH (100 mL) was added AcOH (12.1 mL, 63.9 mmol) and the reaction mixture was stirred at room temperature for 10 min. After NaCNBH$_3$ (4.00 g, 63.9 mmol) was added, the solution was continued to be stirred at room temperature for 6 h. Then hexanal 163 (5.10 mL, 42.6 mmol) and NaCNBH$_3$ (2.60 g, 42.6 mmol) were added. The solution was further stirred at room temperature for 2 h. After removal of solvent, the residue was neutralized with saturated NaHCO$_3$ and the residue was partitioned between EtOAc (200 mL) and water (200 mL). The aqueous layer was separated and extracted with CH$_2$Cl$_2$ (2×300 mL). The combined organic extracts were dried over Na$_2$SO$_4$ and concentrated under vacuum. The residue was purified by column chromatography (silica gel, 9:1 CH$_2$Cl$_2$/MeOH, 80:18:2 CHCl$_3$/MeOH/NH$_4$OH) to afford compound 166 (6.90 g, 64%) as an off-white solid. $^1$H NMR (400 MHz, CD$_3$OD): δ 8.12 (d, J=8.6 Hz, 2H), 7.51-7.43 (m, 2H), 7.38 (d, J=8.6 Hz, 2H), 7.37-7.27 (m, 3H), 5.55 (s, 1H), 4.24 (dd, J=11.5, 5.5 Hz, 1H), 4.18-4.01 (m, 1H), 4.00-3.94 (m, 1H), 3.93-3.89 (m, 1H), 3.77 (dd, J=9.3, 1.8 Hz, 1H), 3.61 (t, J=10.7 Hz, 1H), 3.13-2.77 (m, 6H), 2.71 (t, J=7.5 Hz, 2H), 1.99-1.85 (m, 2H), 1.55-1.42 (m, 2H), 1.38-1.18 (m, 6H), 0.87 (t, J=7.0 Hz, 3H).

Preparation of Compound 85

A suspension of compound 166 (800 mg, 1.55 mmol) and 10% Pd/C (300 mg) in EtOH (40 mL) was degassed by bubbling with Argon using syringe for 10 min then stirred at room temperature under hydrogen atmosphere (balloon, 1 atm) for 2 h at room temperature. The reaction mixture was filtered through celite and washed with MeOH. The filtrate was concentrated in vacuum to afford 85 (700 mg, 93%) as an off-white solid. $^1$H NMR (400 MHz, CD$_3$OD): δ 7.52-7.42 (m, 2H), 7.38-7.25 (m, 3H), 6.88 (d, J=8.4 Hz, 2H), 6.63 (d, J=8.4 Hz, 2H), 5.53 (s, 1H), 4.24 (dd, J=10.8, 5.5 Hz, 1H), 4.05-3.84 (m, 3H), 3.76 (dd, J=9.6, 1.8 Hz, 1H), 3.61 (t, J=10.8 Hz, 1H), 2.93 (dd, J=13.6, 5.0 Hz, 1H), 2.79 (dd, J=13.4, 9.0 Hz, 1H), 2.73-2.60 (m, 4H), 2.42 (t, J=8.0

Hz, 2H), 1.88-1.68 (m, 2H), 1.48-1.36 (m, 2H), 1.33-1.14 (m, 6H), 0.87 (t, J=7.0 Hz, 3H).

Preparation of Intermediate 34

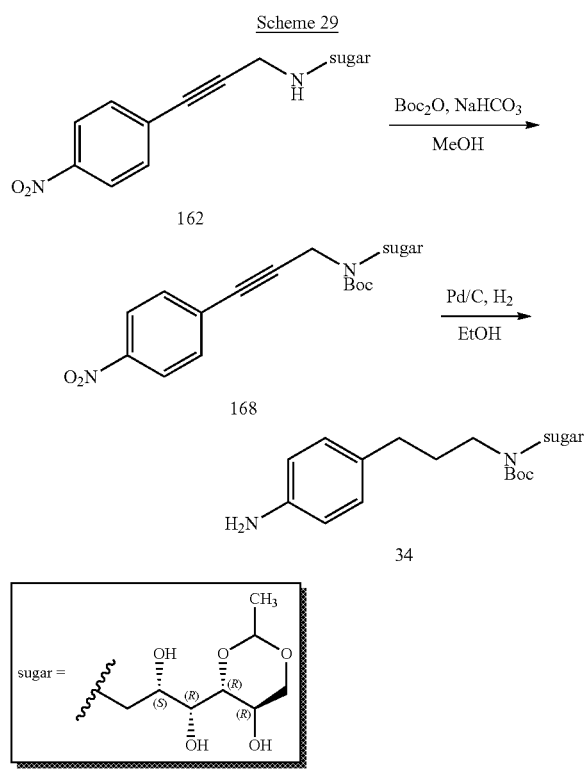

Preparation of Compound 168

A solution of 162 (534 mg, 1.45 mmol) in MeOH (30 mL) and was charged with saturated NaHCO$_3$ solution in water (5.0 ml) at 0° C. and stirred for 10 min. (Boc)$_2$O (350 mg, 1.60 m mmol) was then added and the reaction mixture was stirred for 3 h at the same temperature, brought to room temperature, and stirred for another 30 min. The mixture was concentrated, the residue was dissolved in CH$_2$Cl$_2$ (100 mL), and the solution was washed with water (100 mL) and brine (50 mL). The organic layer was dried over Na$_2$SO$_4$, filtered, concentrated and residue was purified by column chromatography (silica gel, 9:1 CH$_2$Cl$_2$/MeOH, 8:2 CHCl$_3$/MeOH) to afford compound 168 (435 mg, 64%) as an off-white solid. $^1$H NMR (400 MHz, CDCl$_3$): δ 8.18 (d, J=8.7 Hz, 2H), 7.56 (d, J=8.7 Hz, 2H), 4.72 (q, J=5.1 Hz, 1H), 4.41-4.35 (m, 2H), 4.16 (dd, J=10.8, 5.5 Hz, 1H), 4.15-4.04 (m, 1H), 3.93-3.83 (m, 1H), 3.81-3.76 (m, 1H), 3.66-3.53 (m, 4H), 3.40 (t, J=11.0 Hz, 1H), 3.25-3.12 (m, 1H), 3.08-2.96 (m, 1H), 1.49 (s, 9H), 1.32 (d, J=5.1 Hz, 3H).

Preparation of Compound 34

A suspension of compound 168 (80 mg, 0.21 mmol) and 10% Pd/C (40 mg) in EtOH (10 mL) was degassed by bubbling with Argon using syringe for 10 min then stirred under hydrogen atmosphere (balloon, 1 atm) for 2 h at room temperature. The reaction mixture was filtered through celite and washed with MeOH. The filtrate was concentrated in vacuum to afford 34 (82 mg, 89%) as an off-white solid. $^1$H NMR (400 MHz, CDCl$_3$): δ 6.96 (d, J=8.1 Hz, 2H), 6.62 (d, J=8.1 Hz, 2H), 4.69 (q, J=5.1 Hz, 1H), 4.15 (dd, J=10.8, 5.5 Hz, 1H), 4.13-4.09 (m, 1H), 4.01-3.93 (m, 1H), 3.89-3.78 (m, 1H), 3.75-3.68 (m, 1H), 3.62-3.43 (m, 4H), 3.40 (t, J=11.3 Hz, 1H), 3.35 (dd, J=13.5, 4.0 Hz, 1H), 3.26 (t, J=7.9 Hz, 1H), 3.23-3.13 (m, 1H), 2.48 (t, J=7.8 Hz, 2H), 1.86-1.76 (m, 2H), 1.43 (s, 9H), 1.33 (d, J=5.1 Hz, 3H).

Preparation of Intermediate 171

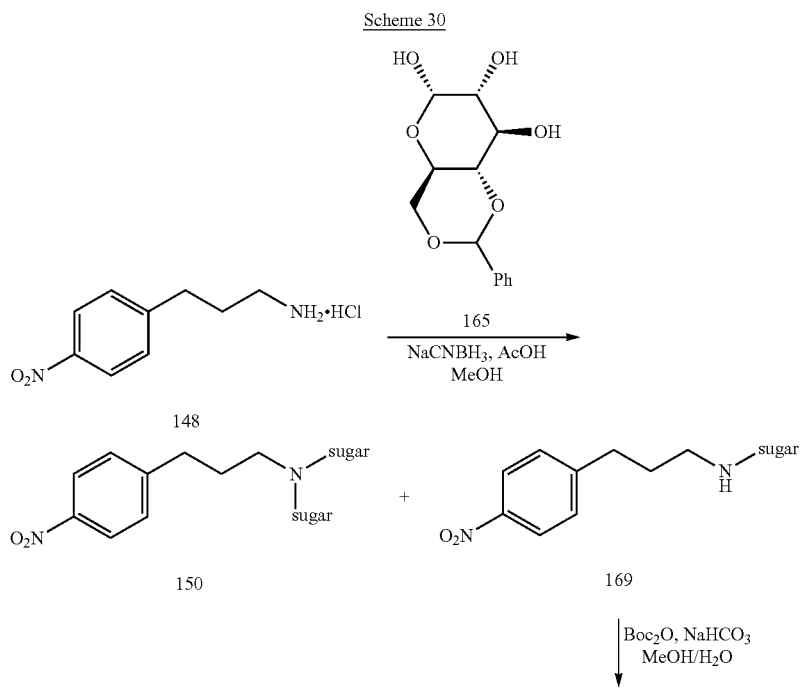

-continued

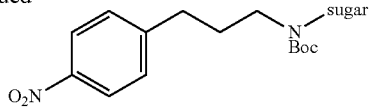

170

Pd/C, H₂
EtOH

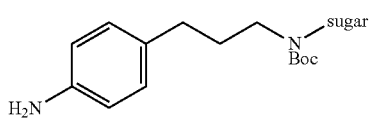

171

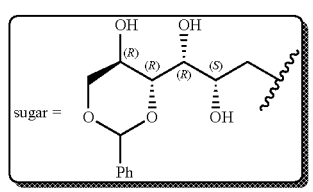

To a solution of compound 148 (6.40 g, 29.6 mmol) and triol 165 (11.9 g, 44.5 mmol) in MeOH (300 mL) was added AcOH (5.32 mL, 88.8 mmol) and the reaction mixture was stirred at room temperature for 30 min. After NaCNBH₃ (3.73 g, 59.2 mmol) was added, the solution was continued to be stirred at room temperature for 16 h. Additional compound 165 (11.9 g, 44.5 mmol), AcOH (5.32 mL, 88.8 mmol) and NaCNBH₃ (3.73 g, 59.2 mmol) were added the solution was continued to be stirred at room temperature for 14 h. Additional compound 165 (7.93 g, 29.6 mmol), AcOH (3.55 mL, 59.2 mmol) and NaCNBH₃ (2.80 g, 44.4 mmol) were added the solution was continued to be stirred at room temperature for 10 h. After removal of solvent, the residue was neutralized with saturated NaHCO₃ and the residue was partitioned between CH₂Cl₂ (100 mL) and water (100 mL). The aqueous layer was separated and extracted with CH₂Cl₂ (2×100 mL). The combined organic extracts were dried over Na₂SO₄ and concentrated under vacuum. Challenging purification encountered by column chromatography (silica gel, 9:1 CH₂Cl₂/MeOH, 80:18:2 CHCl₃/MeOH/NH₄OH) to afford compound 150 and 169 (20 g, mixture). The mixture was directly used for next step.

Preparation of Compound 170

A solution of 150 and 169 (20.0 g, mixture) in MeOH (120 mL) and water (40 mL) was charged with saturated NaHCO₃ (9.99 g, 118.4 mmol) at 0° C. and stirred for 10 min. (Boc)₂O (9.69 g, 44.4 mmol) was added and the reaction mixture was stirred for 10 min at the same temperature, brought to room temperature, and stirred for another 2 h. The mixture was concentrated, the residue was dissolved in CH₂Cl₂ (100 mL), and the solution was washed with water (100 mL) and brine (50 mL). The organic layer was dried over Na₂SO₄, filtered, concentrated and residue was purified by column chromatography (silica gel, 9:1 CH₂Cl₂/MeOH, 8:2 CHCl₃/MeOH) to afford compound 150 (1.50 g) and 170 (4.50 g) as an off-white solid. ESI-MS m/z 529 [$C_{27}H_{32}N_2O_9$+H]⁺.

Preparation of Compound 171

A suspension of compound 170 (4.20 g, 7.92 mmol) and 10% Pd/C (500 mg) in EtOH (100 mL) and AcOH (10 mL) was degassed with Argon for 10 min then stirred under hydrogen atmosphere (balloon, 1 atm) for 16 h at room temperature. The reaction mixture was filtered through celite and washed with MeOH. The filtrate was concentrated in vacuum, neutralized with Na₂CO₃ and residue was purified by column chromatography (silica gel, 9:1 CH₂Cl₂/MeOH, 8:2 CHCl₃/MeOH) to afford compound 172 (2.70 g, 68%) as an off-white solid. ¹H NMR (400 MHz, CD₃OD): δ 7.52-7.44 (m, 2H), 7.36-7.29 (m, 3H), 6.89 (d, J=8.3 Hz, 2H), 6.64 (d, J=8.3 Hz, 2H), 5.54 (s, 1H), 4.23 (dd, J=11.9, 5.9 Hz, 1H), 4.10-3.97 (m, 1H), 3.97-3.89 (m, 1H), 3.81-3.75 (m, 1H), 3.74-3.69 (m, 1H), 3.60 (t, J=10.9 Hz, 1H), 3.48 (dd, J=14.1, 4.6 Hz, 1H), 3.28-3.22 (m, 3H), 2.41 (t, J=7.5 Hz, 2H), 1.83-1.71 (m, 2H), 1.41 (s, 9H).

Preparation of Intermediate 39

Scheme 31

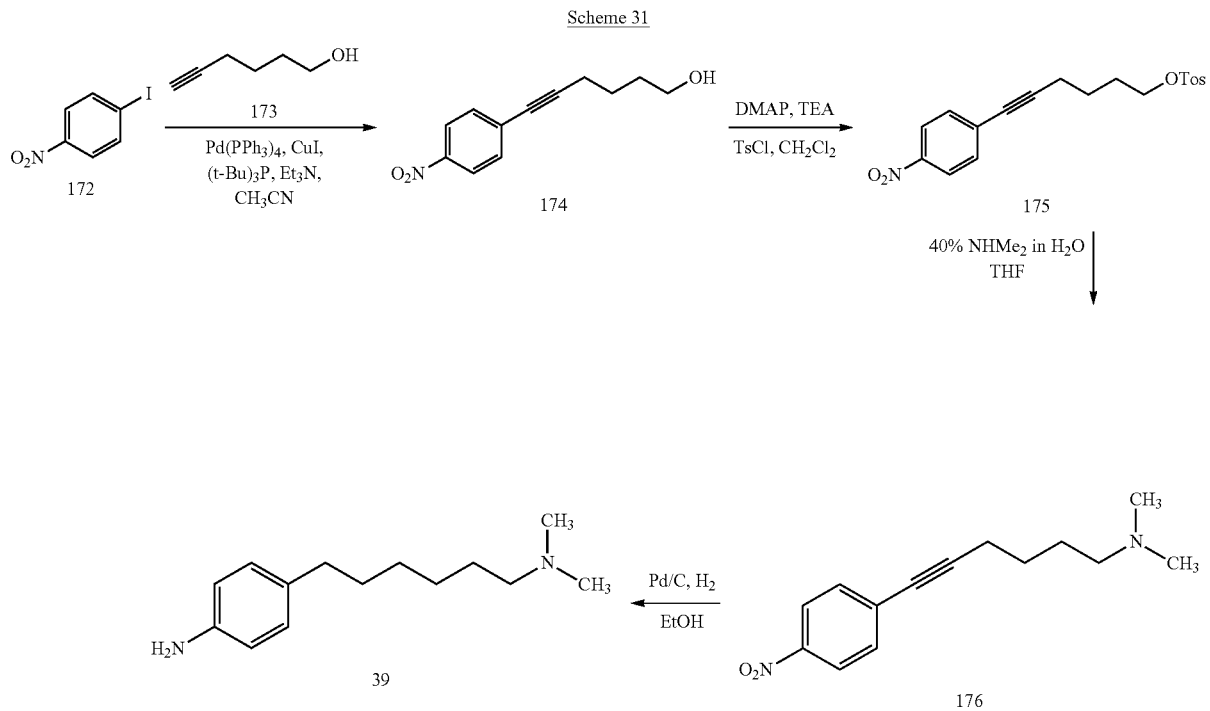

The solution of compound 17 (30.0 g, 121 mmol) and 173 (14.2 g, 145 mmol) in anhydrous acetonitrile (300 mL) was degassed for 10 min under Argon atmosphere followed by addition of TEA (67 mL, 484 mmol), 10% (t-Bu)$_3$P in hexanes (49.0 mL, 24.2 mmol) and CuI (1.15 g, 6.05 mmol) at room temperature. The resulting mixture was degassed with Argon for another 10 min and Pd(PPh$_3$)$_4$ (14.0 g g, 12.1 mmol) was added in one portion. After degassing with argon for 5 min, the resulting mixture was heated at 50° C. for 16 h. The reaction mixture was concentrated in vacuum and the residue was purified by column chromatography (silica gel, 2:3 hexanes/EtOAc) to afford compound 174 (15.0 g, 58%) as a brown oil. $^1$H NMR (400 MHz, CDCl$_3$) δ 8.14 (d, J=8.8 Hz, 2H), 7.50 (d, J=8.8 Hz, 2H), 3.71 (t, J=6.4 Hz, 2H), 2.50 (t, J=6.8 Hz, 2H), 1.80-1.70 (m, 4H), 1.70-1.65 (m, 1H).

Preparation of Compound 175

To a solution of compound 174 (15.0 g, 67.9 mmol) in anhydrous CH$_2$Cl$_2$ (50 mL) was added Et$_3$N (28.0 mL, 203.7 mmol) and DMAP (4.12 g, 33.9 mmol) under argon at 0° C. After the reaction mixture was stirred for 5 min at same temperature, TsCl (32.5 g, 170 mmol), was added at 0° C. The resulting mixture was stirred for additional 4 h at room temperature. After solvent removed; the residue was partitioned between CH$_2$Cl$_2$ (250 mL) and water (150 mL). The aqueous layer was separated and extracted with CH$_2$Cl$_2$ (2×250 mL). The combined organic extracts were washed with brine, dried over Na$_2$SO$_4$ and concentrated under vacuum. The residue was purified by column chromatography (silica gel, hexanes/EtOAc) to afford compound 175 (15.0 g, 60%) as a brown oil. $^1$H NMR (400 MHz, CDCl$_3$): δ δ 8.15 (d, J=8.8 Hz, 2H), 7.79 (d, J=8.8 Hz, 2H), 7.50 (d, J=8.8 Hz, 2H), 7.34 (d, J=8.8 Hz, 2H), 4.10 (t, J=6.4 Hz, 2H), 2.44 (t, J=7.0 Hz, 2H), 2.44 (s, 3H), 1.90-1.79 (m, 2H), 1.75-1.61 (m, 2H).

Preparation of Compound 176

To a solution of compound 175 (5.00 g, 12.9 mmol, crude) in THF (10 mL) was added NHMe$_2$ in water (30%, 50.0 mL) and then stirred at rt in seal tube for 3 h. After solvent removed; the residue was partitioned between CH$_2$Cl$_2$ (100 mL) and water (100 mL). The aqueous layer was separated and extracted with CH$_2$Cl$_2$ (2×100 mL). The combined organic extracts were washed with brine, dried over Na$_2$SO$_4$ and concentrated under vacuum. The crude product was purified by column chromatography (silica gel) to afford compound 176 (400 mg, 13%) as a yellow sticky solid. 1H NMR (400 MHz, CDCl$_3$): δ 8.15 (d, J=7.3 Hz, 2H), 7.51 (d, J=7.3 Hz, 2H), 2.48 (t, J=6.6 Hz, 2H), 2.30 (t, J=5.7 Hz, 2H), 2.23 (s, 6H), 1.70-1.61 (m, 4H).

Preparation of Compound 39

A suspension of compound 176 (400 mg, 1.62 mmol) and 10% Pd/C (50 mg) in EtOH (50 mL) was degassed by bubbling with Argon using syringe for 10 min then stirred at room temperature under hydrogen atmosphere (balloon, 1 atm) for 16 h at room temperature. The reaction mixture was filtered through celite and washed with MeOH. The filtrate was concentrated in vacuum to afford 39 (300 mg, 84%) as a brown sticky solid. $^1$H NMR (400 MHz, CD$_3$OD): δ 6.91 (d, J=7.5 Hz, 2H), 6.65 (d, J=7.5 Hz, 2H), 2.47 (t, J=7.0 Hz, 2H), 2.30 (dd, J=8.4, 6.5 Hz, 2H), 2.23 (s, 6H), 1.60-1.52 (m, 2H), 1.51-1.41 (m, 2H), 1.38-1.27 (m, 4H).

31 Preparation of Intermediate 44

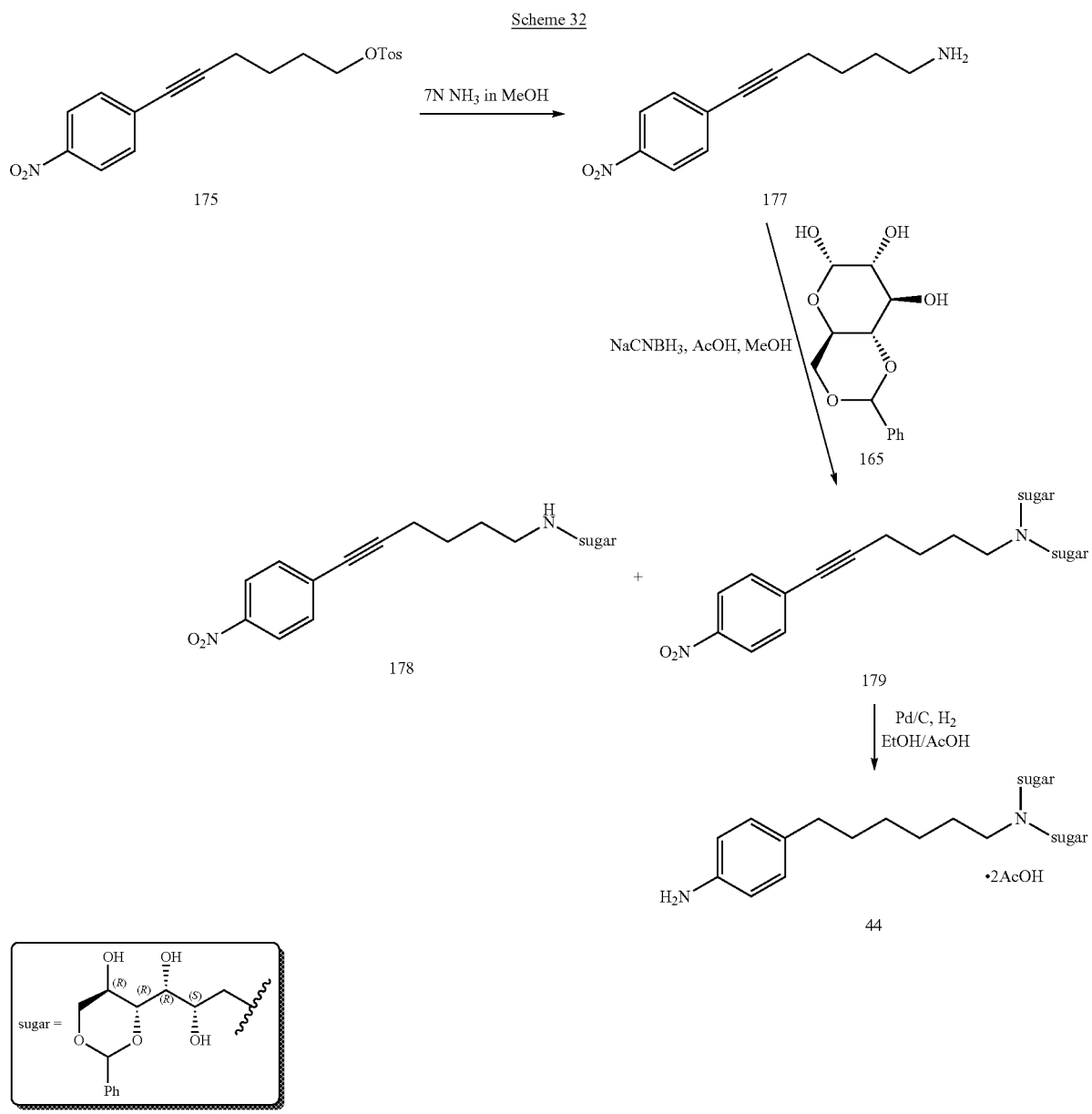

Preparation of Compound 177

Solution of compound 175 (6.00 g, 16.0 mmol) in 7 N NH$_3$ in methanol (150 mL) was heated at 30° C. in seal tube for 5 h. Temperature raised to 40° C. and stirred for 16 h then again temperature raised to 60° C. and stirred for 4 h. After solvent removed; the residue was partitioned between CH$_2$Cl$_2$ (100 mL) and water (100 mL). The aqueous layer was separated and extracted with CH$_2$Cl$_2$ (2×100 mL). The combined organic extracts were washed with brine, dried over Na$_2$SO$_4$ and concentrated under vacuum. The crude product was purified by column chromatography (silica gel, 9:1 CH$_2$Cl$_2$/MeOH) to afford compound 177 (1.48 g, 43%) as yellow oil. $^1$H NMR (400 MHz, CDCl$_3$): δ 8.16 (d, J=8.4 Hz, 2H), 7.39 (d, J=8.4 Hz, 2H), 3.61 (t, J=5.6 Hz, 2H), 2.08-2.05 (m, 2H), 1.65-1.53 (m, 4H).

Preparation of Compounds 178 and 179

To a solution of compound 177 (1.38 g, 6.33 mmol) and triol 165 (2.03 g, 7.59 mmol) in MeOH (10 mL) was added AcOH (0.6 mL, 9.49 mmol) and the reaction mixture was stirred at room temperature for 30 min. After NaCNBH$_3$ (800 mg, 12.7 mmol) was added, the solution was continued to be stirred at room temperature for 16 h. Additional compound 165 (2.55 g, 9.49 mmol), AcOH (0.80 mL, 12.7 mmol) and NaCNBH$_3$ (1.19 g, 18.9 mmol) were added the solution was continued to be stirred at room temperature for 16 h. Additional compound 165 (2.55 g, 9.49 mmol), AcOH (0.80 mL, 12.7 mmol) and NaCNBH$_3$ (1.19 g, 18.9 mmol) were added the solution was continued to be stirred at room temperature for 16 h. After removal of solvent, the residue was neutralized with saturated NaHCO₃ and the residue was partitioned between CH₂Cl₂ (10 mL) and water (10 mL). The aqueous layer was separated and extracted with CH₂Cl₂ (2×10 mL). The combined organic extracts were dried over Na₂SO₄ and concentrated under vacuum. The residue was purified by column chromatography (silica gel, 9:1 CH₂Cl₂/MeOH, 80:18:2 CHCl₃/MeOH/NH₄OH) to afford compound 179 (2.28 g, 51%) as an off-white solid. ¹H NMR (300 MHz, CD₃OD): δ 8.14 (d, J=9.0 Hz, 2H), 7.54 (d, J=9.0 Hz, 2H), 7.47-7.44 (m, 4H), 7.34-7.30 (m, 6H), 5.48 (s, 2H), 4.24-4.19 (m, 2H), 3.99-3.94 (m, 4H), 3.86-3.84 (m, 2H), 3.73-3.69 (m, 2H), 3.57 (t, J=10.8 Hz, 4H), 3.35-3.25 (m, 4H), 2.33 (d, J=6.9 Hz, 2H), 1.61-1.51 (m, 4H).

A mixture of 178/179 (900 mg) was isolated as well and was directly used for next step (SG-GHC-G-106).

Preparation of Compound 44

A suspension of compound 179 (2.26 g, 3.11 mmol) and 10% Pd/C (100 mg) in a mixture of EtOH (50 mL) and AcOH (10 mL) was degassed with Argon for 10 min then stirred under hydrogen atmosphere (balloon, 1 atm) for 16 h at room temperature. The reaction mixture was filtered through celite and washed with MeOH. The filtrate was concentrated in vacuum to afford 44 (1.90 g, 80%) as a brown solid. ¹H NMR (400 MHz, CD₃OD): δ 7.46-7.44 (m, 4H), 7.33-7.31 (m, 6H), 6.89 (d, J=8.4 Hz, 2H), 6.65 (d, J=8.4 Hz, 2H), 5.51 (s, 2H), 4.26-4.14 (m, 2H), 3.93-3.90 (m, 2H), 3.76-3.73 (m, 4H), 3.63-3.58 (m, 4H), 3.35-3.25 (m, 2H), 3.10-3.00 (m, 2H), 2.41 (t, J=7.2 Hz, 2H), 1.47-1.45 (m, 4H), 1.16-1.12 (m, 4H).

Preparation of Intermediate 49

Scheme 33

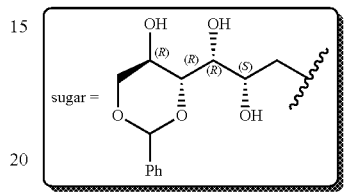

178

Boc₂O, NaHCO₃
———————→
MeOH/H₂O

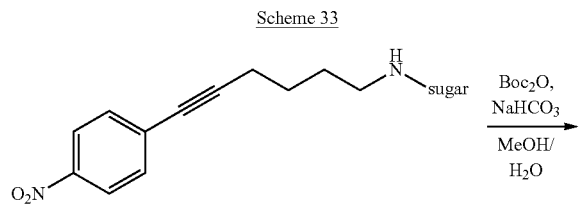

180

Pd/C, H₂
EtOH/AcOH
↓

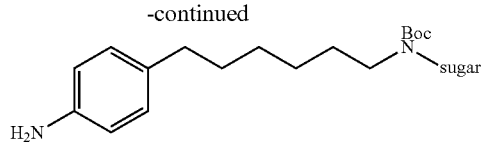

49

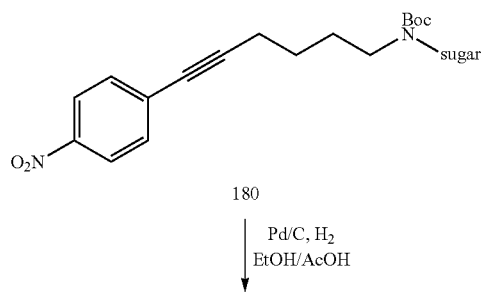

Preparation of Compound 180

A solution of 178 (900 mg, mixture, apox. 2.0 mmol) in a mixture of MeOH (20 mL) and water (10 mL) a and was charged with NaHCO₃ (672 mg, 4.0 mmol) at 0° C. and stirred for 10 min. (Boc)₂O (524 mg, 2.40 mmol) was added and the reaction mixture was stirred for 1 h at the same temperature, brought to room temperature, and stirred for another 4 h. The mixture was concentrated, the residue was dissolved in CH₂Cl₂ (100 mL), and the solution was washed with water (100 mL) and brine (50 mL). The organic layer was dried over Na₂SO₄, filtered, concentrated and residue was purified by column chromatography (silica gel, 9:1 CH₂Cl₂/MeOH, 8:2 CHCl₃/MeOH) to afford compound 180 (780 mg, 64%) as an off-white solid. ¹H NMR (300 MHz, CD₃OD): δ 8.16 (d, J=9.0 Hz, 2H), 7.55 (d, J=9.0 Hz, 2H), 7.50-7.47 (m, 2H), 7.34-7.30 (m, 3H), 5.53 (s, 1H), 4.25-4.20 (m, 1H), 4.10 (br s, 1H), 3.94-3.91 (m, 1H), 3.80-3.48 (m, 4H), 3.35-3.25 (m, 3H), 2.46 (t, J=6.9 Hz, 2H), 1.70-1.49 (m, 4H), 1.43 (s, 9H).

Preparation of Compound 49

A suspension of compound 180 (780 mg, 1.36 mmol) and 10% Pd/C (50 mg) in a mixture of EtOH (10 mL) and AcOH (2.0 mL) was degassed by bubbling with Argon using syringe for 10 min then stirred at rt under hydrogen atmosphere (balloon, 1 atm) for 4 h at room temperature. The reaction mixture was neutralized with Na₂CO₃, filtered through celite and washed with MeOH. The filtrate was concentrated in vacuum to afford 49 (625 g, 84%) as a white solid. ¹H NMR (300 MHz, CD₃OD): δ 7.50-7.46 (m, 2H), 7.32-7.30 (m, 3H), 6.90 (d, J=8.4 Hz, 2H), 6.66 (d, J=8.4 Hz, 2H), 5.53 (s, 1H), 4.25-4.20 (m, 1H), 4.04 (br s, 1H), 3.94-3.89 (m, 1H), 3.77-3.43 (m, 4H), 3.35-3.25 (m, 3H), 2.45 (t, J=7.5 Hz, 2H), 1.52-1.47 (m, 4H), 1.42 (s, 9H), 1.27-1.24 (m, 4H).

Preparation of Intermediate 54

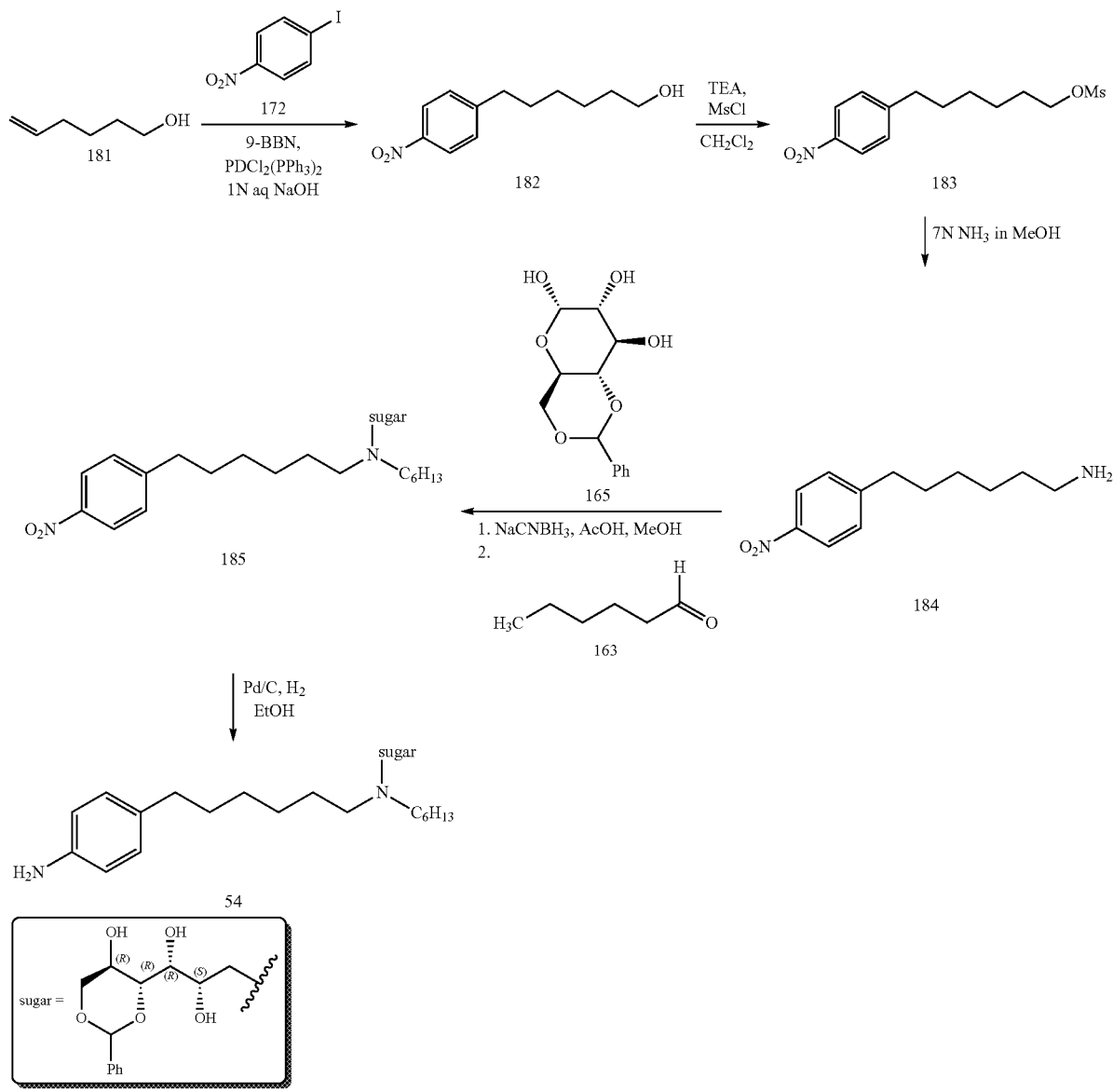

Preparation of Compound 182

To a solution of compound 181 (1.60 g, 16.00 mmol) in anhydrous THF (40 mL) was added 9-BBN (0.5 M in THF, 80 mL, 40.0 mmol) under argon. After the reaction mixture was stirred for 2 h at room temperature, compound 172 (3.17 g, 12.8 mmol), Pd(PPh$_3$)$_2$Cl$_2$ (561 mg, 0.80 mmol), and 1 N aq NaOH (24 mL) were added at room temperature. The resulting mixture was stirred for additional 1 h. After solvent removed; the residue was partitioned between EtOAc (100 mL) and water (100 mL). The aqueous layer was separated and extracted with EtOAc (2×100 mL). The combined organic extracts were washed with brine, dried over Na$_2$SO$_4$ and concentrated under vacuum. The crude product was purified by column chromatography (silica gel, 4:1 hexanes/EtOAc) to afford compound 182 (1.20 g, 34%) as a brown solid. $^1$H NMR (400 MHz, CDCl$_3$): δ 8.13 (d, J=9.0 Hz, 2H), 7.31 (d, J=9.0 Hz, 2H), 3.64 (t, J=6.7 Hz, 2H), 2.71 (t, J=7.8 Hz, 2H), 1.73-1.46 (m, 4H), 1.43-1.31 (m, 4H).

Preparation of Compound 183

To a solution of compound 182 (1.20 g, 5.38 mmol) in anhydrous CH$_2$Cl$_2$ (20 mL) was added Et$_3$N (7.32 mL, 53.8 mmol) under argon at 0° C. After the reaction mixture was stirred for 5 min at same temperature, Mesyl chloride (0.62 mL, 8.07 mmol), was added at 0° C. The resulting mixture was stirred for additional 2 h at rt. After solvent removed; the residue was partitioned between CH$_2$Cl$_2$ (50 mL) and water (50 mL). The aqueous layer was separated and extracted with CH$_2$Cl$_2$ (2×50 mL). The combined organic extracts were washed with brine, dried over Na$_2$SO$_4$ and concentrated under vacuum. The crude product 183 (3.00 g, crude) was directly used for the next step.

Preparation of Compound 184

Solution of compound 183 (3.00 g, 5.38 mmol, crude) in 7 N $NH_3$ in methanol (30.0 mL) was heated at 60° C. in seal tube for 2 h. After solvent removed; the residue was partitioned between $CH_2Cl_2$ (100 mL) and water (100 mL). The aqueous layer was separated and extracted with $CH_2Cl_2$ (2×100 mL). The combined organic extracts were washed with brine, dried over $Na_2SO_4$ and concentrated under vacuum. The crude product was purified by column chromatography (silica gel) to afford compound 184 (390 mg, 33%, over two steps) as a yellow oil. $^1H$ NMR (400 MHz, $CD_3OD$): δ 8.14 (d, J=9.0 Hz, 2H), 7.42 (d, J=9.0 Hz, 2H), 2.75 (t, J=7.8 Hz, 2H), 2.67 (t, J=7.3 Hz, 2H), 1.72-1.63 (m, 2H), 1.53-1.46 (m, 2H), 1.42-1.35 (m, 4H).

Preparation of Compound 185

To a solution of compound 184 (620 mg, 2.79 mmol) and triol165 (938 mg, 3.49 mmol) in MeOH (30 mL) was added AcOH (1.16 mL, 27.8 mmol) and the reaction mixture was stirred at room temperature for 10 min. After $NaCNBH_3$ (526 mg, 8.37 mmol) was added, the solution was continued to be stirred at room temperature for 16 h. Additional compound 165 (0.3 equiv), AcOH (10 equiv) and $NaCNBH_3$ (1.0 equiv) were added over 16 h. Then hexanal 163 (0.96 mL, 8.37 mmol), AcOH (1.00 mL) and $NaCNBH_3$ (526 mg, 8.37 mmol) were added. The solution was further stirred at room temperature for 2 h. After removal of solvent, the residue was neutralized with saturated $NaHCO_3$ and the residue was partitioned between EtOAc (100 mL) and water (100 mL). The aqueous layer was separated and extracted with $CH_2Cl_2$ (2×100 mL). The combined organic extracts were dried over $Na_2SO_4$ and concentrated under vacuum. The residue was purified by column chromatography (silica gel, 9:1 $CH_2Cl_2$/MeOH, 80:18:2 $CHCl_3$/MeOH/$NH_4OH$) to afford compound 185 (950 g, 61%) as an off-white oil. $^1H$ NMR (400 MHz, $CDCl_3$): δ 8.02 (d, J=8.7 Hz, 2H), 7.48-7.42 (m, 3H), 7.37-7.34 (m, 2H), 7.31 (d, J=8.7 Hz, 2H), 5.54 (s, 1H), 4.46-4.40 (m, 1H), 4.30 (dd, J=11.6, 6.6 Hz, 1H), 4.03 (t, J=4.0 Hz, 1H), 3.97 (dd, J=10.5, 5.4 Hz, 1H), 3.88 (dd, J=9.4, 4.0 Hz, 1H), 3.65 (t, J=10.4 Hz, 1H), 3.11-3.00 (m, 4H), 2.69 (t, J=7.8 Hz, 2H), 2.00 (s, 1H), 1.70-1.55 (m, 6H), 1.37-1.30 (m, 4H), 1.29-1.20 (m, 8H), 0.87 (t, J=7.1 Hz, 3H).

Preparation of Compound 54

A suspension of compound 185 (950 g, 1.70 mmol) and 10% Pd/C (300 mg) in EtOH (100 mL) was degassed with Argon for 10 min then stirred under hydrogen atmosphere (balloon, 1 atm) for 3 h at room temperature. The reaction mixture was filtered through celite and washed with MeOH. The filtrate was concentrated in vacuum to afford 54 (790 mg, 88%) as yellow oil. $^1H$ NMR (400 MHz, $CD_3OD$): δ 7.51-7.44 (m, 2H), 7.35-7.29 (m, 3H), 6.90 (d, J=8.5 Hz, 2H), 6.65 (d, J=8.5 Hz, 2H), 5.54 (s, 1H), 4.24 (dd, J=10.8, 5.4 Hz, 1H), 4.08-4.02 (m, 1H), 4.00-3.92 (m, 1H), 3.91 (dd, J=5.6, 1.8 Hz, 1H), 3.78 (dd, J=9.6, 1.8 Hz, 1H), 3.61 (t, J=10.9 Hz, 1H), 3.01 (dd, J=13.7, 5.4 Hz, 1H), 2.91 (dd, J=12.1, 8.1 Hz, 1H), 2.82-2.71 (m, 4H), 2.45 (t, J=7.5 Hz, 2H), 1.59-1.42 (m, 6H), 1.37-1.13 (m, 10H), 0.89 (t, J=7.1 Hz, 3H).

Several assays may be used to characterize the compounds of the present invention. Representative assays are discussed below.

In Vitro Measure of Sodium Channel Blocking Activity and Reversibility

One assay used to assess mechanism of action and/or potency of the compounds of the present invention involves the determination of lumenal drug inhibition of airway epithelial sodium currents measured under short circuit current ($I_{SC}$) using airway epithelial monolayers mounted in Ussing chambers. Cells obtained from freshly excised human, dog, sheep or rodent airways are seeded onto porous 0.4 micron Snapwell™ Inserts (CoStar), cultured at air-liquid interface (ALI) conditions in hormonally defined media, and assayed for sodium transport activity ($I_{SC}$) while bathed in Krebs Bicarbonate Ringer (KBR) in Using chambers. All test drug additions are to the lumenal bath with half-log dose addition protocols (from $1\times10^{-11}$ M to $3\times10^{-5}$ M), and the cumulative change in $I_{SC}$ (inhibition) recorded. All drugs are prepared in dimethyl sulfoxide as stock solutions at a concentration of $1\times10^{-2}$ M and stored at −20° C. Eight preparations are typically run in parallel; two preparations per run incorporate amiloride and/or benzamil as positive controls. After the maximal concentration ($5\times10^{-5}$ M) is administered, the lumenal bath is exchanged three times with fresh drug-free KBR solution, and the resultant $I_{SC}$ measured after each wash for approximately 5 minutes in duration. Reversibility is defined as the percent return to the baseline value for sodium current after the third wash. All data from the voltage clamps are collected via a computer interface and analyzed off-line.

Dose-effect relationships for all compounds are considered and analyzed by the Prism 3.0 program. $IC_{50}$ values, maximal effective concentrations, and reversibility are calculated and compared to amiloride and benzamil as positive controls. The potency of the sodium channel blocking activity of representative compounds relative to amiloride in freshly excised cell from canine airways is shown in Table 1.

TABLE 1

Inhibition of Short-Circuit Current by Compound (Ia) in canine bronchial epithelial cells ($IC_{50}$ nM)

| Compound Number | Potency of Sodium Channel Blockade $IC_{50}$ nM |
|---|---|
| Amiloride | 773 |
| 23 | 20.7 |
| 38 | 25.4 |
| 28 | 7.4 |
| 33 | 21.8 |
| 16 | 79.6 |
| 103 | 17.9 |
| 99 | 7.6 |
| 94 | 21.2 |
| 80 | 19.4 |
| 135 | 5.2 |
| 131 | 6.0 |
| 123 | 2.3 |
| 127 | 8.6 |
| 139 | 73.7 |
| 43 | 50.1 |
| 53 | 15.5 |
| 58 | 10.6 |
| 48 | 47 |

Assay 2. Mucociliary Clearance (MCC) Studies in Sheep

The animal model that has been used most often to measure changes in MCC is the sheep model. The effect of compounds for enhancing mucociliary clearance (MCC) can be measured using an in vivo model described by Sabater et al., Journal of Applied Physiology, 1999, pp. 2191-2196, incorporated herein by reference.

In these studies, adult sheep were restrained and nasally intubated with an endotracheal tube. Aerosolized test articles were administered over 10-15 minutes to sheep. Radiolabeled $^{99m}$Tc-sulfur colloid (TSC, 3.1 mg/mL; containing approximately 20 mCi) was then administered at a specified time four or eight hours after test article. The radiolabeled aerosol was administered through the endotracheal tube for about 5 minutes. The sheep were then extubated, and total radioactive counts in the lung were measured every 5 minutes for a 1-hour observation period. The rate of radiolabel clearance from the lung is representative of the MCC rate in the animal. The advantage of this system is that it closely simulates the human lung environment. The model also allows for the collection of simultaneous PK/PD information through plasma and urine sampling over the test period. There are also several techniques to measure the drug concentrations on the airway surface during the MCC measurements. These include the collection of exhaled breath condensates or a filter paper method to obtain ASL via bronchoscopy.

The ovine model described above was used to evaluate the in vivo effects (efficacy/durability) of aerosol-delivered test agent on MCC. Treatments consisting of either 4 mL of test agent or test agent in combination with HS were tested. To determine if combining HS with test agent enhanced MCC, HS was administered immediately following test agent administration. Test solutions were aerosolized using a Raindrop nebulizer at a flowrate of eight liters per minute and connected to a dosimetry system consisting of a solenoid valve and a source of compressed air (20 psi). The deposited dose of drug in sheep lungs after an aerosol administration using the Raindrop nebulizer is estimated to be 8-15% of the dose. Using a Raindrop nebulizer, radiolabeled TSC was administered over approximately 3 minutes either 4 or 8 hours after drug treatment to evaluate efficacy/durability. Radioactive counts were measured in a central region in the right lung at 5 min intervals for one hour with a gamma camera. Three methods of analysis were utilized, 1) initial rate of clearance (slope) over the first 30 min fitted using linear regression 2) area under the curve for % clearance over time over one hour, and 3) the maximum clearance obtained in one hour.

The effect of Compound 33 at 0.24 nmol/kg (3 μM) was tested and compared to vehicle (4 mL sterile H$_2$O) on sheep MCC four hour post-dosing (FIG. 1). The analyses of effects are shown in Table A. Compound 33 enhanced MCC compared to vehicle control.

TABLE A

MCC in Sheep at 4 h Post-dose of Compound 33 or Vehicle

| Compound 33 Dose | Initial Slope (4.0-4.5 h) | AUC (% Cl-h) | Maximum Clearance |
|---|---|---|---|
| 0.24 nmol/kg (3 μM) | 37.5* (4) | 17.4* (4) | 30.0* (4) |
| Vehicle (H$_2$O) 4 mL | 17.2 ± 6.8 (8) | 7.3 ± 1.5 (8) | 12.2 ± 2.9 (8) |

Figure 2:
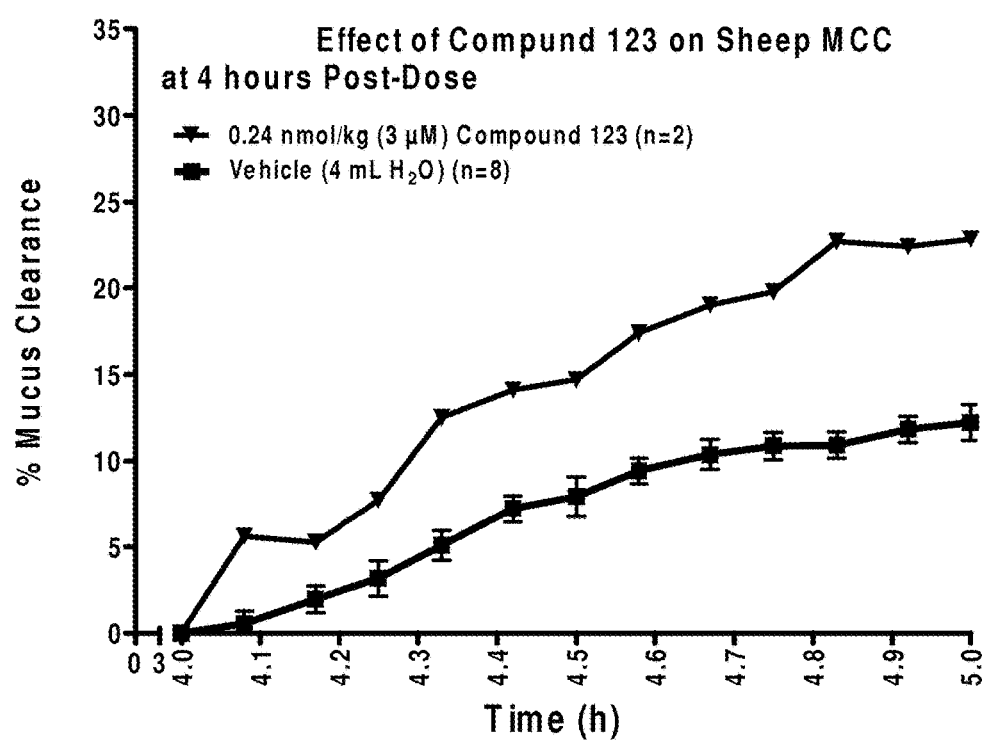
FIG. 2 is a plot of the effect of Compound 123 on Sheep MCC at 4 hours post-dose.
Figure 3:
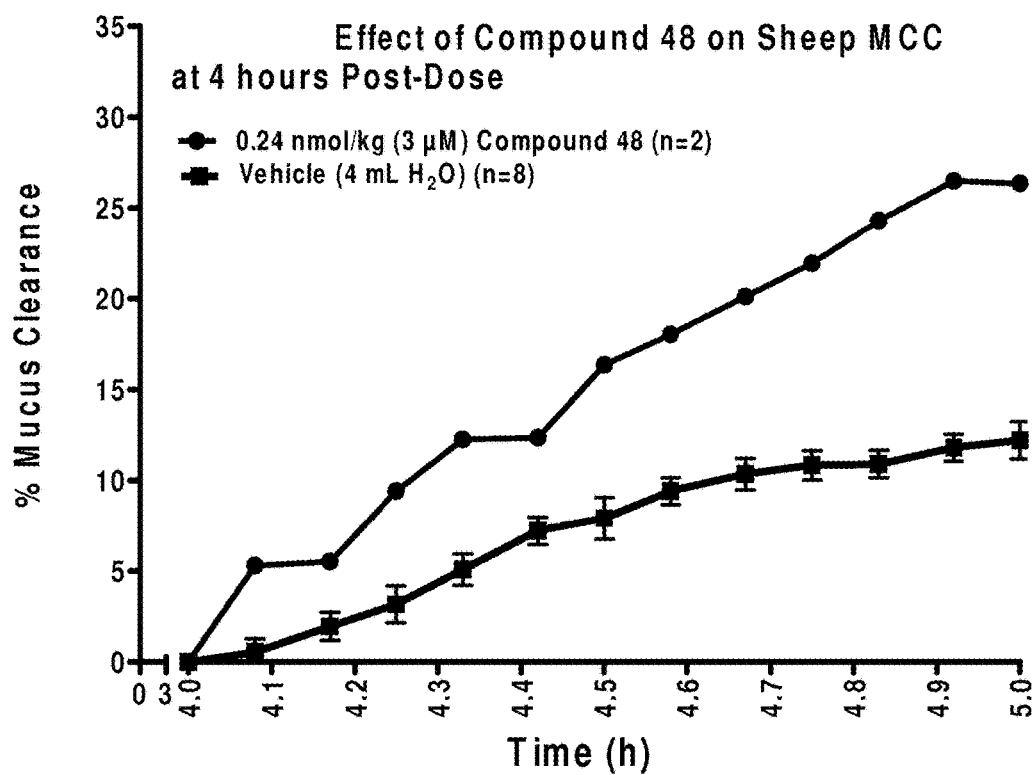
FIG. 3 is a plot of the effect of Compound 48 on Sheep MCC at 4 hours post-dose.

Tables B and C along with FIGS. 2 and 3 demonstrate that other compounds of this invention similarly enhance MCC compared to vehicle (see e.g., Compounds 123 and 48)

TABLE B

MCC in Sheep at 4 h Post-dose of Compound 123 or Vehicle

| Compound 123 Dose | Initial Slope (4.0-4.5 h) | AUC (% Cl-h) | Maximum Clearance |
|---|---|---|---|
| 0.24 nmol/kg (3 μM) | 29.2* (2) | 14.4* (2) | 22.8* (2) |
| Vehicle (H$_2$O) 4 mL | 17.2 ± 6.8 (8) | 7.3 ± 1.5 (8) | 12.2 ± 2.9 (8) |

TABLE C

MCC in Sheep at 4 h Post-dose of Compound 48 or Vehicle

| Compound 48 Dose | Initial Slope (4.0-4.5 h) | AUC (% Cl-h) | Maximum Clearance |
|---|---|---|---|
| 0.24 nmol/kg (3 μM) | 29.8* (2) | 15.4* (2) | 26.7* (2) |
| Vehicle (H$_2$O) 4 mL | 17.2 ± 6.8 (8) | 7.3 ± 1.5 (8) | 12.2 ± 2.9 (8) |

Figure 4:
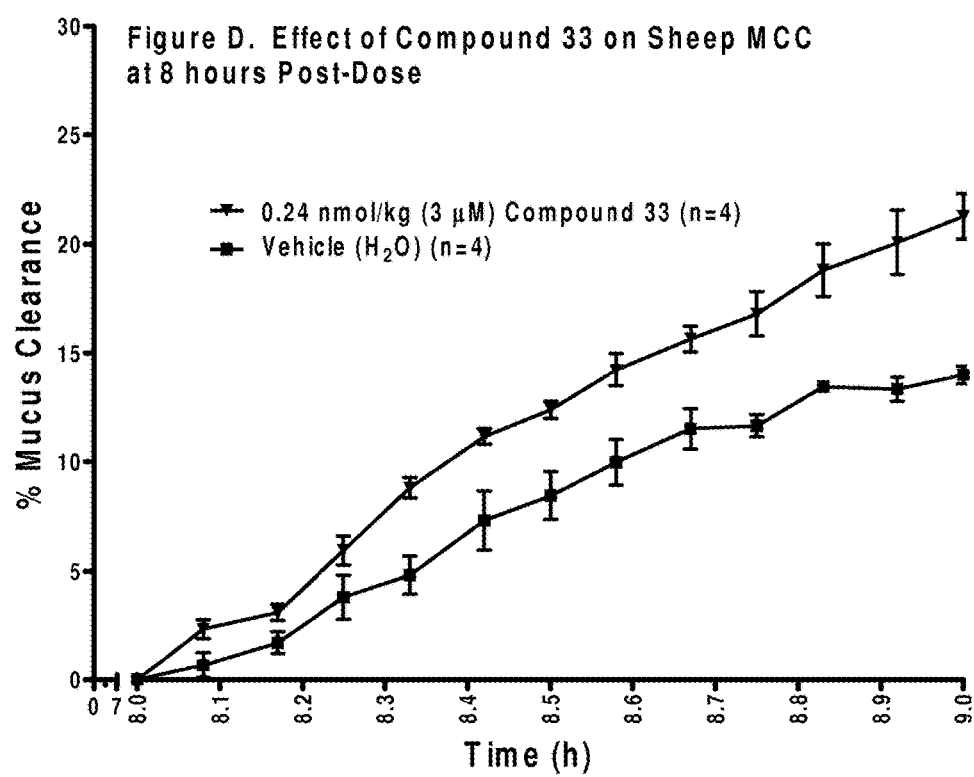
FIG. 4 is a plot of the effect of Compound 33 on Sheep MCC at 8 hours post-dose.
Figure 5:
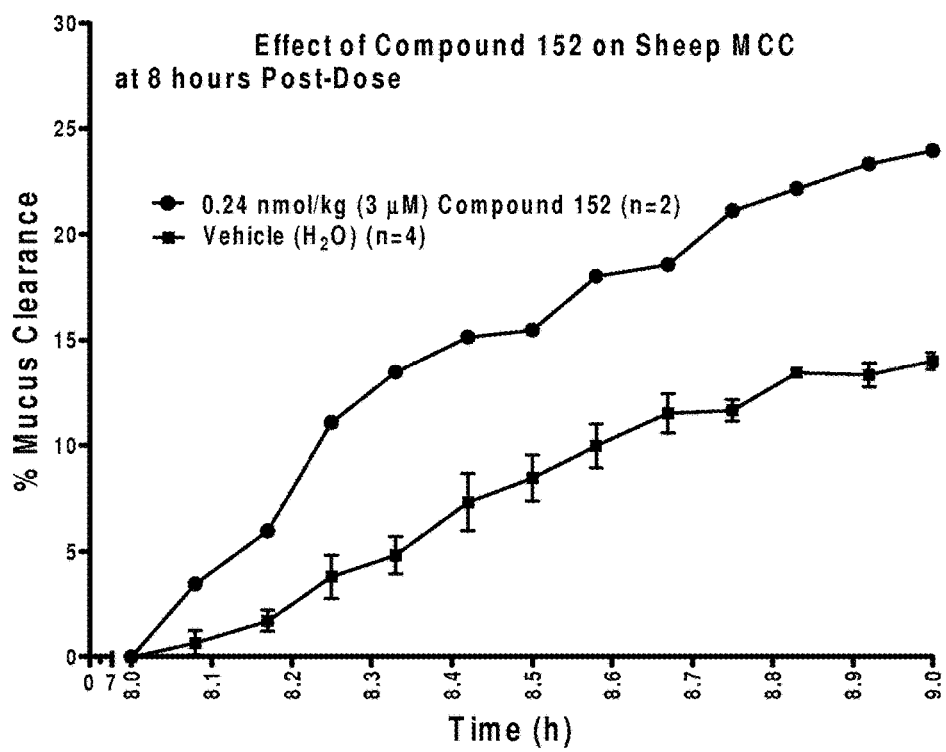
FIG. 5 is a plot of the effect of Compound 152 on Sheep MCC at 8 hours post-dose.

To determine whether compounds of this invention have enhance duration of action, they were tested at 8 hours post dose. Tables D and E along with FIGS. 4 and 5 clearly show enhanced duration action of MCC vs. vehicle for Compounds 33 and 152.

TABLE D

MCC in Sheep at 8 h Post-dose of Compound 33 or Vehicle

| Compound 33 Dose | Initial Slope (8.0-8.5 h) | AUC (% Cl-h) | Maximum Clearance |
|---|---|---|---|
| 0.24 nmol/kg (3 μM) | 25.8* (4) | 11.7* (4) | 21.4* (4) |
| Vehicle (H$_2$O) 4 mL | 17.2 ± 6.8 (8) | 7.3 ± 1.5 (8) | 12.2 ± 2.9 (8) |

TABLE E

MCC in Sheep at 8 h Post-dose of Compound 152 or Vehicle

| Compound 152 Dose | Initial Slope (8.0-8.5 h) | AUC (% Cl-h) | Maximum Clearance |
|---|---|---|---|
| 0.24 nmol/kg (3 μM) | 37.5* (4) | 17.4* (4) | 30.0* (4) |
| Vehicle (H$_2$O) 4 mL | 17.2 ± 6.8 (8) | 7.3 ± 1.5 (8) | 12.2 ± 2.9 (8) |

Figure 6:
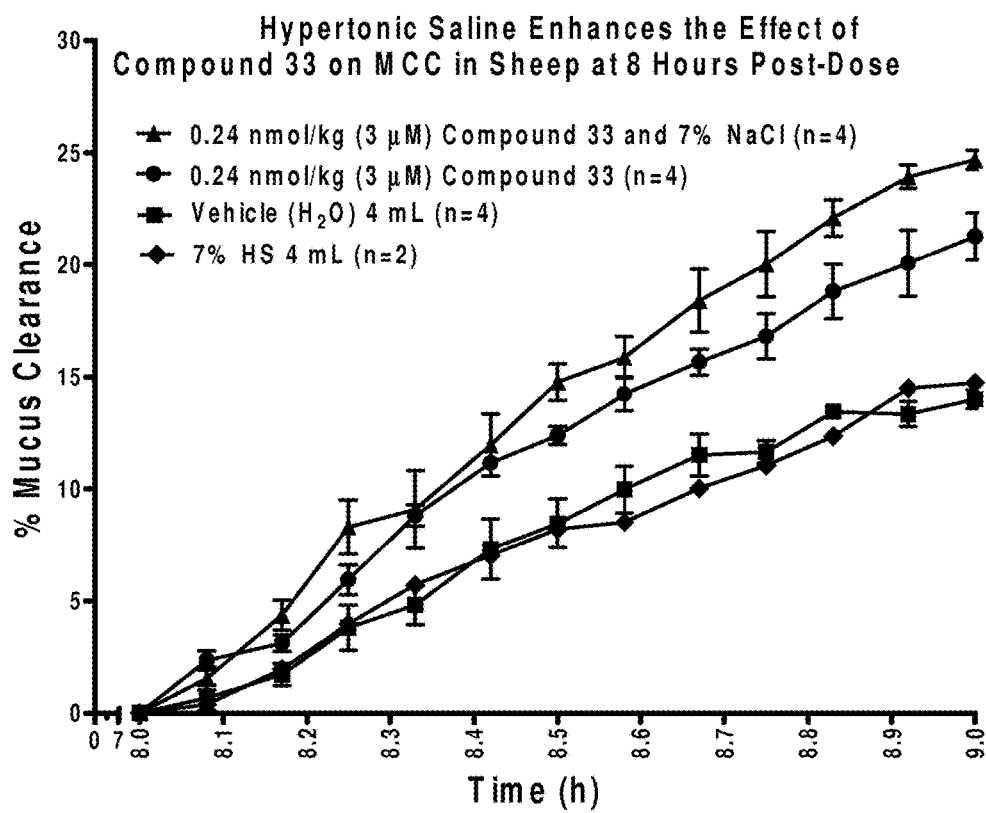
FIG. 6 is a plot of the enhancement of Compound 33 on Sheep MCC at 8 hours post-dose by hypertonic saline.

To determine whether HS increases the MCC effect of Compound 33, 7% HS was dosed immediately following 0.24 nmol/kg of Compound 33 and MCC was assessed eight hours after the combined dosing (FIG. 6). HS increased the effect of Compound 33 on MCC as shown in FIG. 6.

Assay 3. Airway Surface Liquid Drug (ASL) Clearance and Metabolism by Human Airway Epithelium The disappearance of 33 from the apical surface and airway epithelial metabolism were assessed in human bronchial epithelial (HBE) cells (Table 3). In these experiments 25 μL of a 25 μM solution of ENaC blocker was added to the apical surface of HBE cells grown at an air/liquid interface, and the drug and metabolite concentration in the apical and basolateral compartment was measured over 2 h by UPLC.

TABLE G

Apical Disappearance and Metabolism of Compound 33

| Compound | % of Initial Drug Mass on Apical Side (Parent and metabolite, 2 h) | % of Apical Mass as Metabolites (2 h) | % of Initial Apical Mass on Basolateral Side (2 h) | % on Basolateral Side as Metabolites (2 h) |
|---|---|---|---|---|
| 33 | 44.8 ± 18% | 4% | 1.1 ± 0.45% | 32% |

Values represent the mean ± SD

COMPARATIVE EXAMPLES

The present compounds of formula (I) are more potent and/or absorbed less rapidly from mucosal surfaces, especially airway surfaces, compared to known sodium channel blockers, such as amiloride and third generation compounds such as Comparative Example 1 described below. Therefore, the compounds of formula (I) have a longer half-life on mucosal surfaces compared to these know compounds as evidenced by the data shown in Table G. The disappearance of Compound 33 from the apical surface and airway epithelial metabolism were assessed in HBE and compared to Comparative Example 1 (Table H). In these experiments 25 μL of a 25 μM solution of ENaC blocker was added to the apical surface of HBE cells grown at an air/liquid interface, and the drug concentration in the apical and basolateral compartment was measured over 2 h by UPLC. After 2 h incubation of the compounds of this present invention on the apical surface (37° C.), Compound 33 was mostly unmetabolized on the apical side. Conversely, most of Comparative Example 1 was eliminated from the apical side with 83% metabolized to the less active carboxylic acid, (S)-2-amino-3-(4-(4-(3-(3,5-diamino-6-chloropyrazine-2-carbonyl)guanidino)butyl) phenoxy)propanoic acid, structure below.

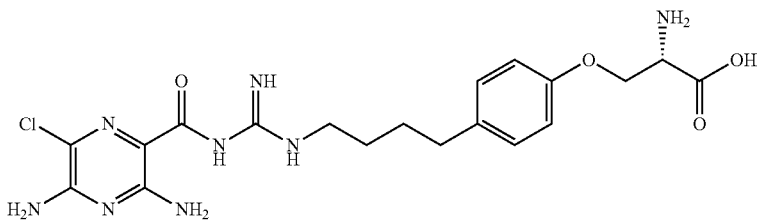 [SMILES: N=C(NCCCCc1ccc(OC[C@H](N)C(=O)O)cc1)NC(=O)c1nc(Cl)c(N)nc1N]

TABLE H

Apical Disappearance and Metabolism of Compound 33 vs. Comparative Example 1 in HBE

| Compound | % of Initial Drug Mass on Apical Side (Parent and metabolite, 2 h) | % of Apical Mass as Metabolites (2 h) | % of Initial Apical Mass on Basolateral Side (2 h) | % on Basolateral Side as Metabolites (2 h) |
|---|---|---|---|---|
| 33 | 44.8 ± 18% | 4% | 1.1 ± 0.45% | 32% |
| Comparative Example 1 | 41.6 ± 7.6% (8% Parent) | 83.0 ± 3.5% | 8.3 ± 0.2 (1% Parent) | 94.7 ± 1.0% |

Values represent the mean ± SD

Comparative Example 1 is claimed, described or within the disclosures of WO 2003/070182 (U.S. Pat. Nos. 6,858,615; 7,186,833; 7,189,719; 7,192,960; and 7,332,496), as sodium channel blockers having useful medicinal properties and can be prepared by methods described therein and others known in the art.

Comparative Example 1

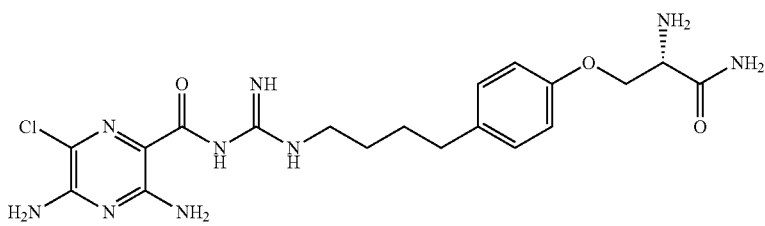

(S)-3,5-diamino-6-chloro-N-(N-(4-(4-(2,3-diamino-3-oxopropoxy)phenyl)butyl)carbamimidoyl)pyrazine-2-carboxamide The compound of Comparative Example 1 can be seen on page 15 of US 2005/0080093 and as Compound 2 on page 90 of WO 2008/031048, and as Compound 2 on pages 42-43 of WO 2008/031028. In order to have useful activity in treating Cystic Fibrosis and C.O.P.D a compound must have properties that will cause enhancement of mucociliary clearance (MCC) at doses that do not elevate plasma potassium which will eventually lead to hyperkalemia, a serious and dangerous condition, upon multiple dosing. It must therefore be avoided in this class of compounds, which are known to elevate plasma potassium if they are significantly excreted by the kidney. In order to evaluate this potential, it is beneficial to have MCC activity in vivo and not cause elevation of plasma potassium at the useful dose. One model to assess this is the sheep MCC model described below.

Figure 7:
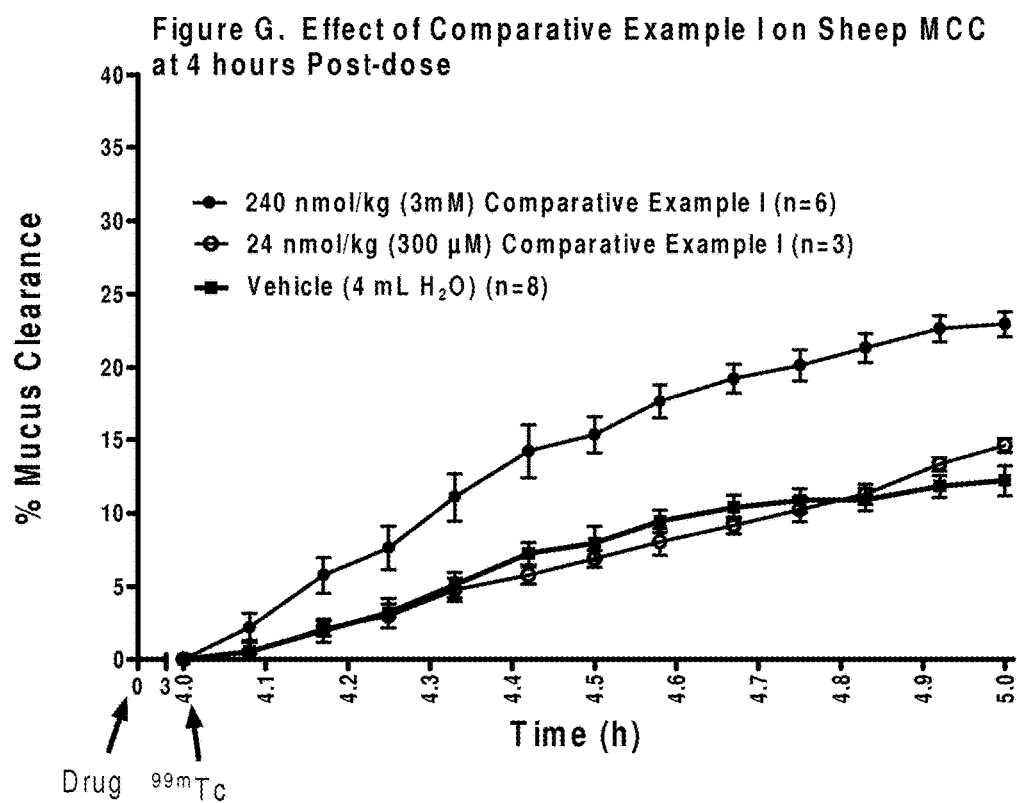
FIG. 7 is a plot of the effect of Comparative Example I on sheep MCC at 4 hrs post-dose.

As can be seen from the Table I and FIG. 7 the $ED_{50}$ for Comparative Example 1 in the sheep MCC model is approximately 240 nmol/kg (3 mM) using three different measures (slope, AUC and Maximum Clearance). At this dose, which would be a clinically active dose, Comparative Example 1 causes a rise in plasma potassium (FIG. 8) which on repeat dosing will lead to hyperkalemia. Thus, Comparative Example I is unacceptable for human use while Compound (Ia) produces a safe and effective MCC with a benefit to risk ratio greater than 1000 in this model.

TABLE I

MCC in Sheep at 4 h Post-dose of vehicle, Comparative Example 1 or Compound 33

| Dose | Initial Slope (4.0-4.5 h) | AUC (% Cl × h) | Maximum Clearance |
|---|---|---|---|
| Comparative Example 1 240 nmol/kg (3 mM) | 32.2 ± 7.3* (6) | 14.1 ± 2.2* (6) | 22.9 ± 2.1* (6) |
| Comparative Example 1 24 nmol/kg (300 μM) | 14.5 ± 1.3 (3) | 6.9 ± 1.0 (3) | 14.6 ± 0.9 (3) |
| Compound 33 0.240 nmol/kg (30 μM) | 37.5* (4) | 17.4* (4) | 30.0* (4) |
| Vehicle H₂O (4 mL) | 17.2 ± 6.8 (8) | 7.3 ± 1.5 (8) | 12.2 ± 2.9 (8) |

FIG. 1 graphs the percentage mucus clearance over time by Compound 33 and Comparative Example 1, as described in the MCC model above. An even greater percentage mucus clearance was provided by Compound 33 at a 1000-fold lower dose than seen with Comparative Example 1. Thus, Compound 33 provided a maximal effect in a clinically relevant dose range free of potassium elevations.

Figure 8:
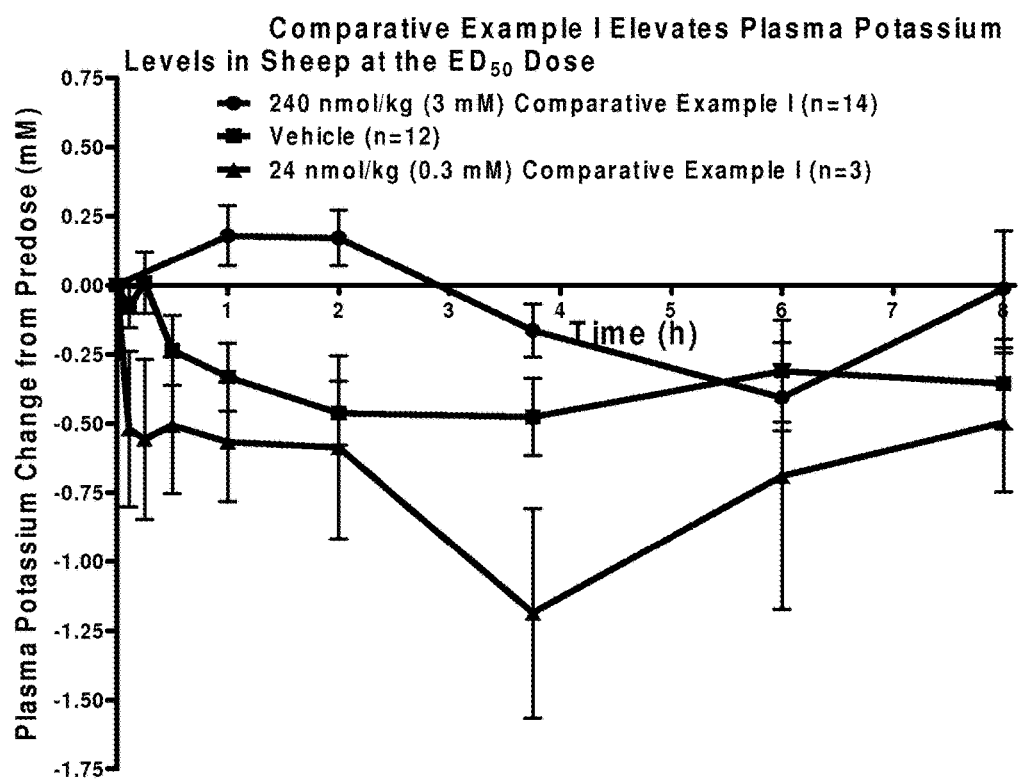
FIG. 8 is a plot of the effect of Comparative Example 1 on sheep plasma potassium levels.
Figure 9:
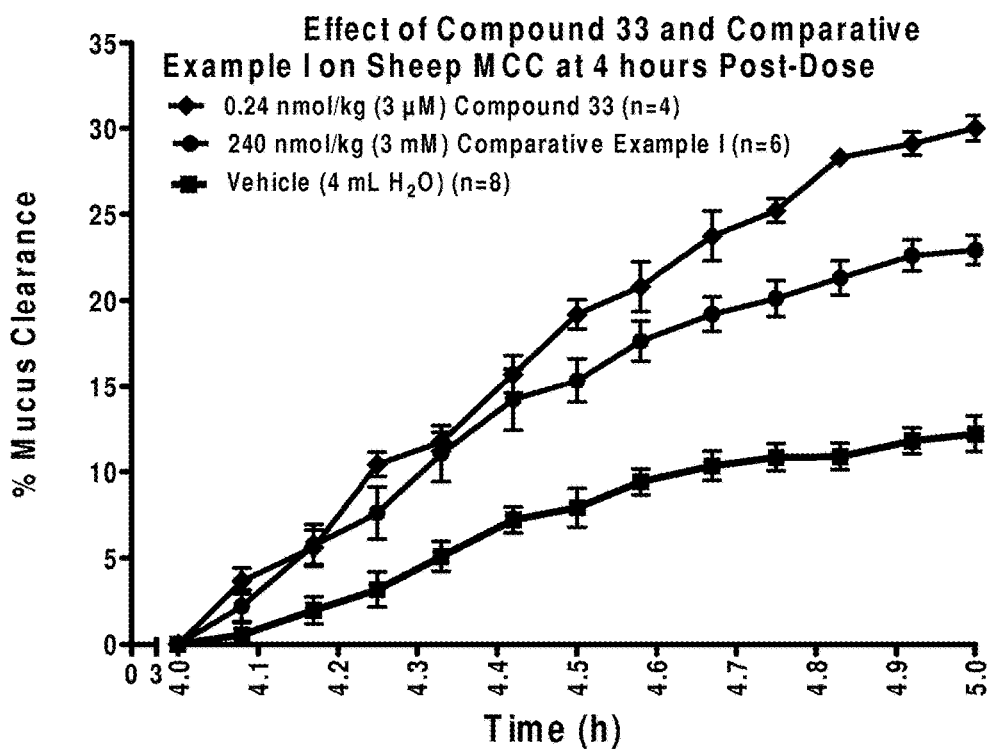
FIG. 9 is a plot comparing the activity of Comparative Example 1 and Compound 33 on sheep MCC at 4 h Post-dose.
Figure 10:
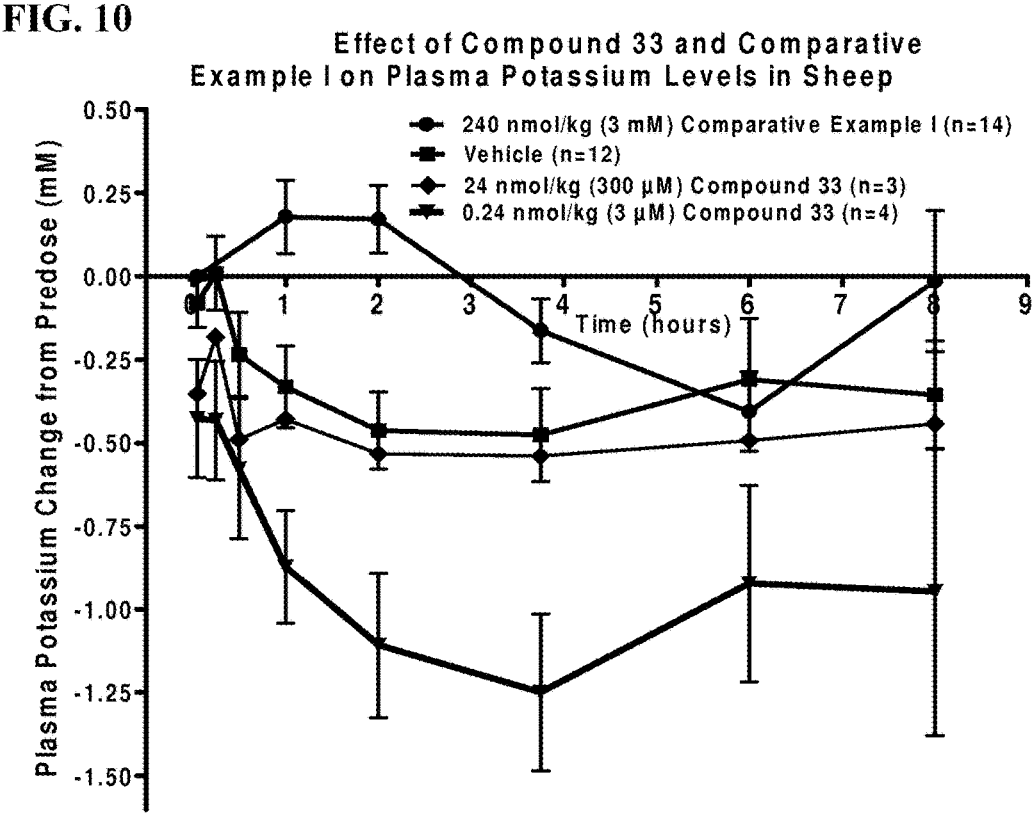
FIG. 10 is a plot comparing the effect on sheep Plasma $K^+$ levels of Comparative Example 1 and Compound 33.
Figure 11:
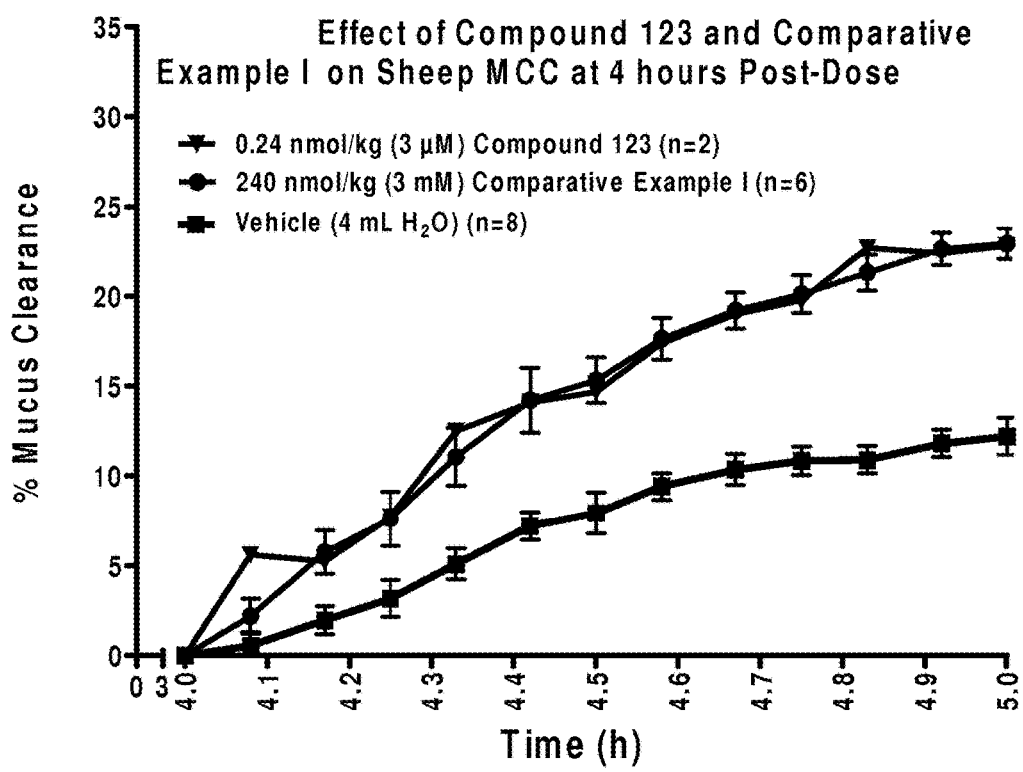
FIG. 11 is a plot comparing the activity of Comparative Example 1 and Compound 123 on sheep MCC at 4 h Post-dose.
Figure 12:
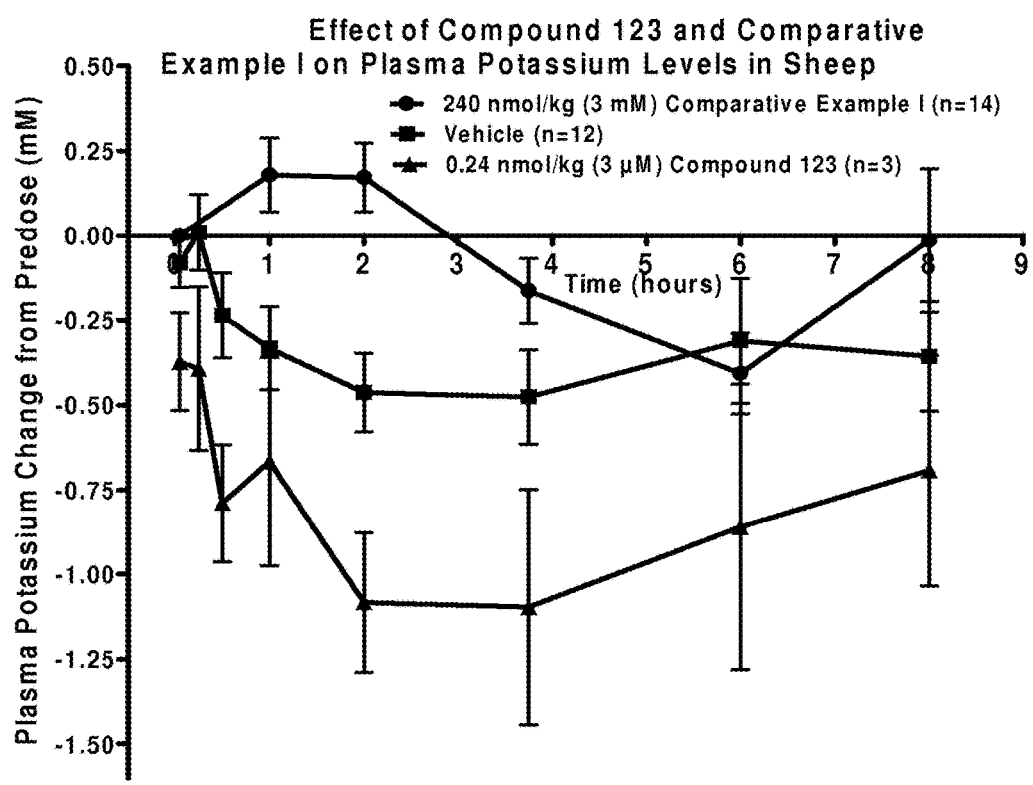
FIG. 12 is a plot comparing the effect on sheep Plasma $K^+$ levels of Comparative Example 1 and Compound 123.
Figure 13:
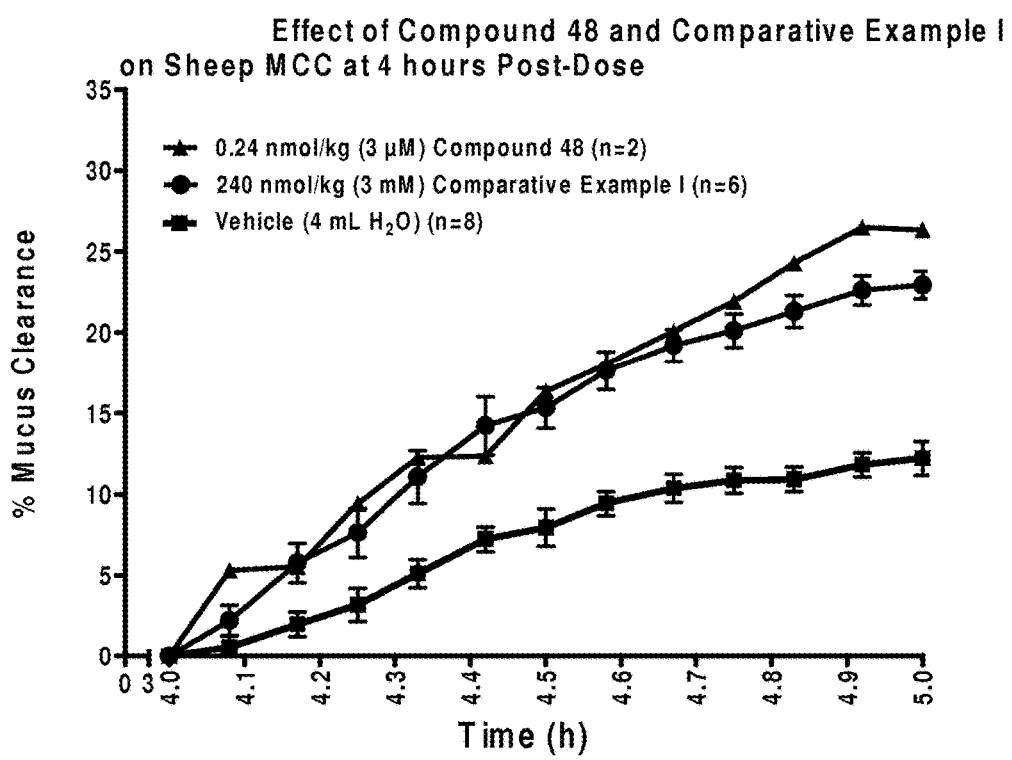
FIG. 13 is a plot comparing the activity of Comparative Example 1 and Compound 48 on sheep MCC at 4 h Post-dose.
Figure 14:
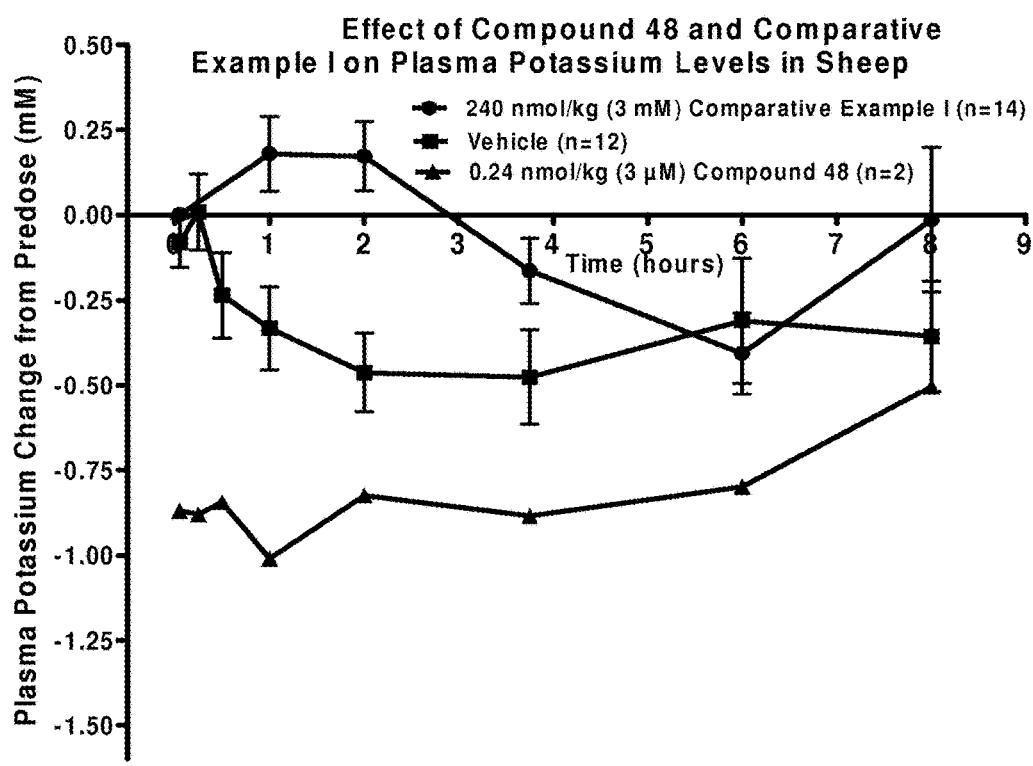
FIG. 14 is a plot comparing the effect on sheep Plasma $K^+$ levels of Comparative Example 1 and Compound 48.

FIG. 10 illustrates the significant increase in plasma potassium levels at an efficacious dose seen in the plasma of the sheep receiving Comparative Example 1 in the MCC study. Compound 33 is more than 1000 times more potent in sheep MCC than Comparative Example 1 with no elevation of Plasma K at doses as high as 24 nmol/kg (1000 times the ED50 dose), whereas Comparative Example 1 has elevations of plasma K at the approximate ED50 dose of 3 mM (FIGS. 7 and 8). This again demonstrates the unique and unexpected potency and safety advantage of Compound 33 as seen in Table J with a Therapeutic Index of more than 1,000 times greater renal safety than Comparative Example 1.

TABLE J

| | Therapeutic Ratio (Benefit/Risk) | | |
|---|---|---|---|
| | MCC Highest Submaximal Dose | Top Dose in Sheep with no Elevation of Plasma Potassium | Therapeutic Ratio |
| Comparative Example 1 | 240 nmol/kg (3 mM) | 24 nmol/kg (300 μM) | 0.1 |
| 33 | <0.24 nmol/kg (3 μM) | 24 nmol/kg (300 μM) | >100 |
| Ratio | >1,000 | 1 | >1,000 |

Other compounds of this invention have similar safety and efficacy advantages over know compounds as exemplified in FIGS. 11, 12, 13 and 14.

That which is claimed is:

1. A method for treating reversible or irreversible airway obstruction, chronic obstructive pulmonary disease (COPD), asthma, bronchiectasis, acute bronchitis, chronic bronchitis, post-viral cough, cystic fibrosis, emphysema, pneumonia, panbronchiolitis, transplant-associate bronchiolitis, or ventilator-associated tracheobronchitis in a subject, or for preventing ventilator-associated pneumonia in a subject, the method comprising administering to the subject a compound of Formula (I):

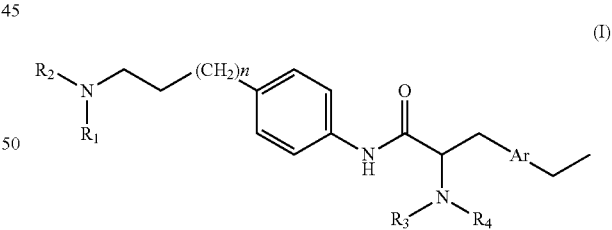

(I)

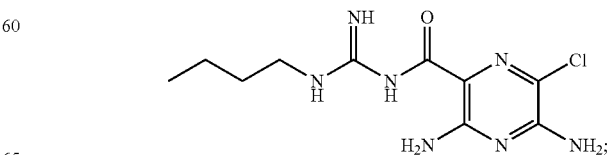

or a pharmaceutically acceptable salt thereof, wherein:

Ar is selected from:

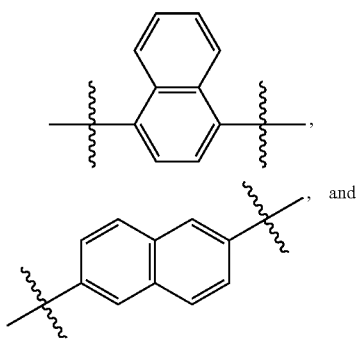, and

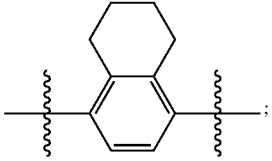;

n is an integer selected from 0, 1, 2, 3, 4, 5, and 6;

$R^1$ is selected from hydrogen, $C_1$-$C_8$ alkyl, and polyhydroxylated alkyl groups having from 3 to 8 carbon atoms;

$R^2$ is hydrogen or a polyhydroxylated alkyl group having from 3 to 8 carbon atoms; and $R^3$ and $R^4$ are each, independently, hydrogen or $C_1$-$C_3$ alkyl.

2. The method of claim 1, wherein the compound is of the formula:

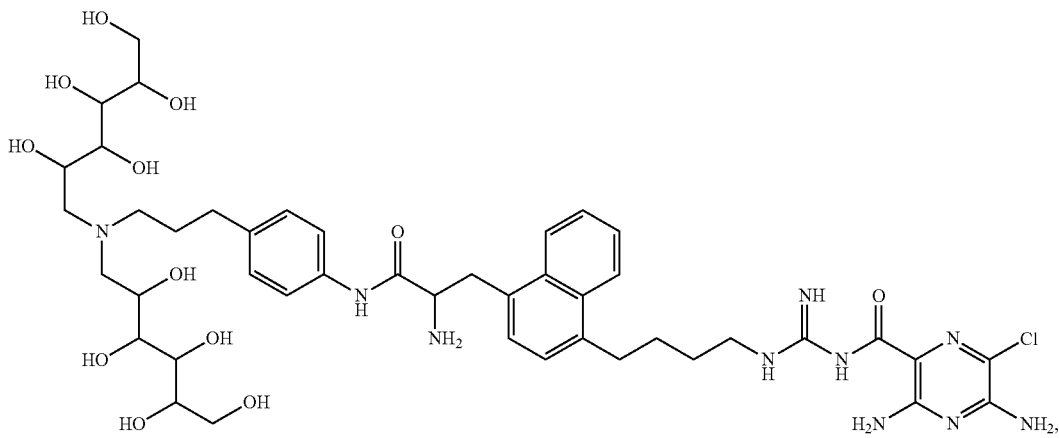 [SMILES: N=C(NCCCCc1ccc(CC(N)C(=O)Nc2ccc(CCCN(CC(O)C(O)C(O)C(O)CO)CC(O)C(O)C(O)C(O)CO)cc2)c2ccccc12)NC(=O)c1nc(Cl)c(N)nc1N]

or a pharmaceutically acceptable salt thereof.

3. The method of claim 2, wherein the compound is:

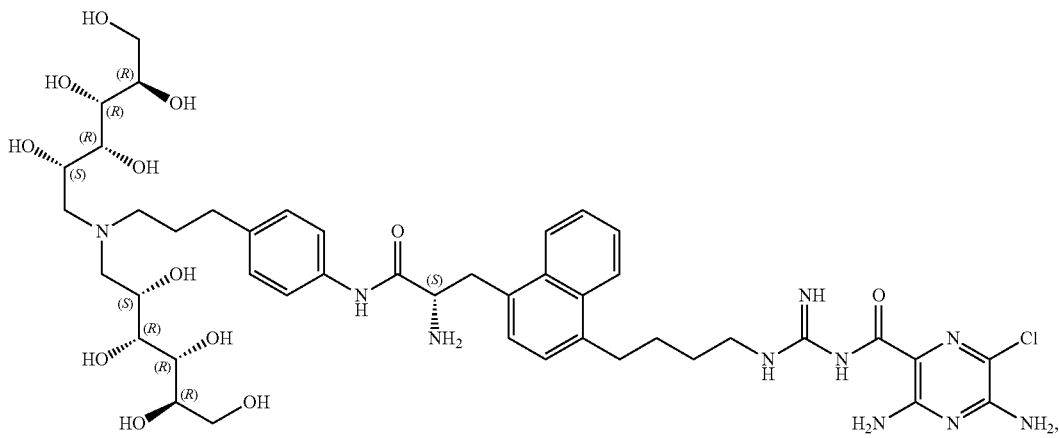

or a pharmaceutically acceptable salt thereof.

4. The method of claim 1, wherein the compound is of Formula (II):

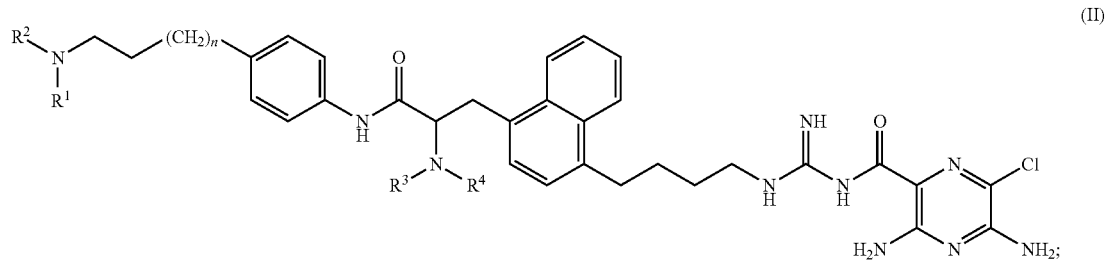

(II)

or a pharmaceutically acceptable salt thereof, wherein:

n is an integer selected from 1, 2, 3, 4, 5, and 6;

$R^1$ is selected from hydrogen, $C_1$-$C_8$ alkyl, and polyhydroxylated alkyl groups having from 3 to 8 carbon atoms;

$R^2$ is hydrogen or a polyhydroxylated alkyl group having from 3 to 8 carbon atoms; and $R^3$ and $R^4$ are each, independently, hydrogen or $C_1$-$C_3$ alkyl.

5. The method of claim 4, wherein the compound is selected from the group consisting of:

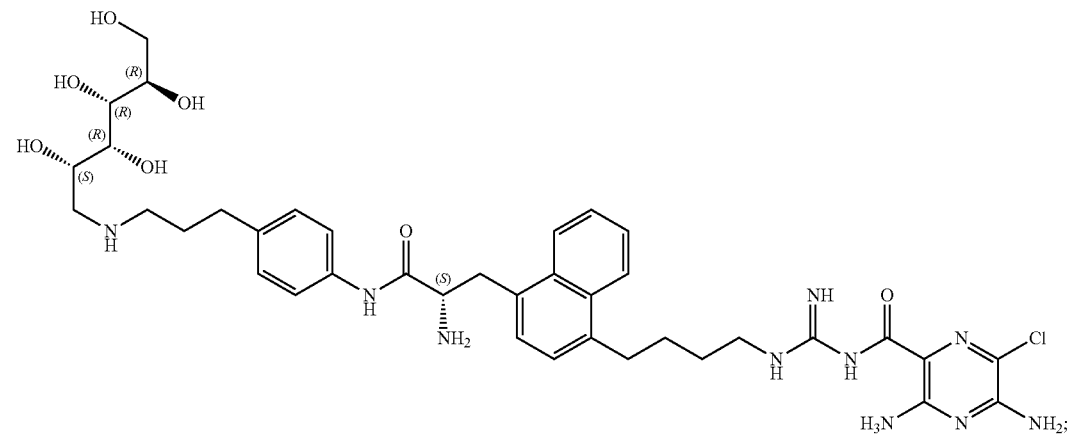

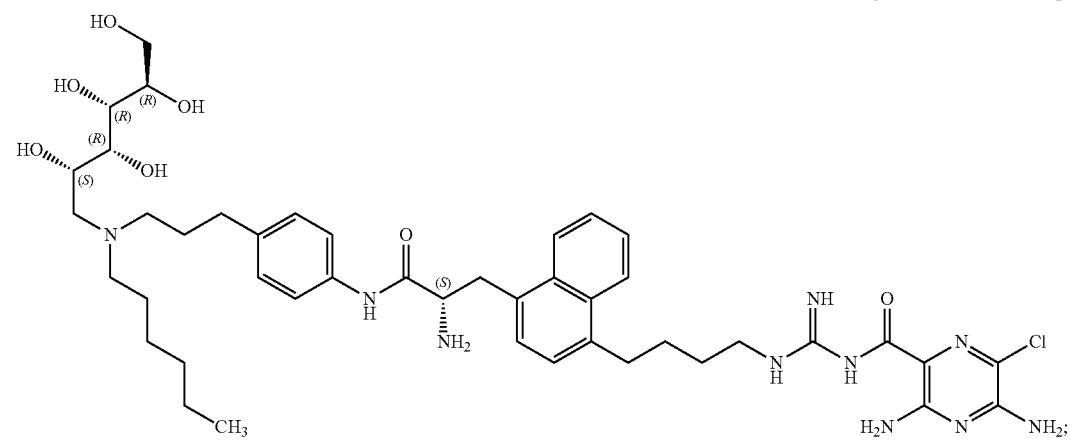

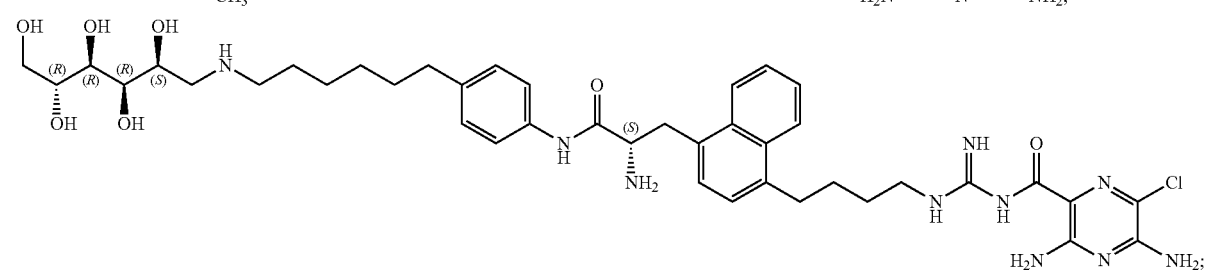

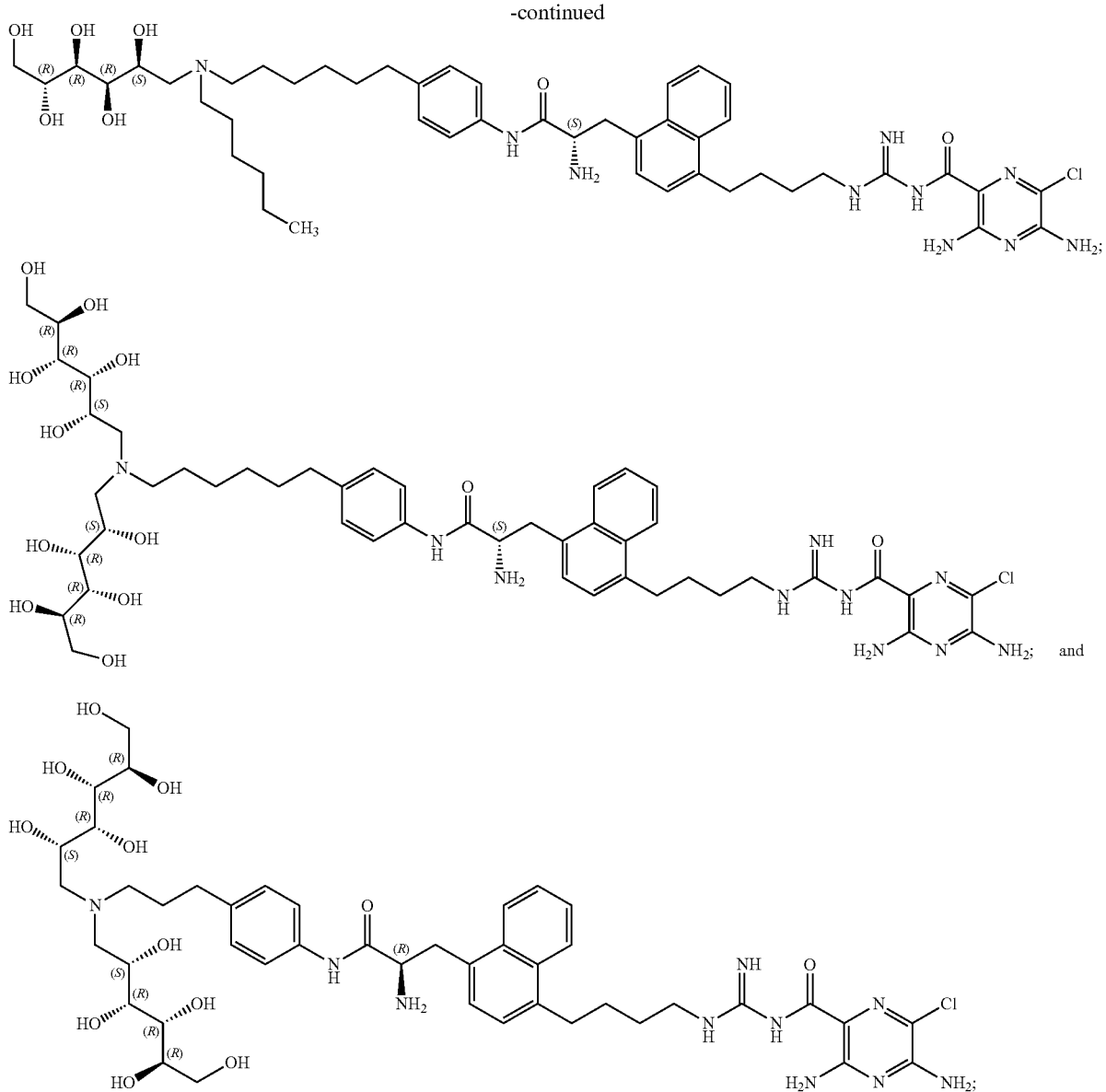
and pharmaceutically acceptable salts thereof.
6. The method of claim 1, wherein the compound is of Formula (III):
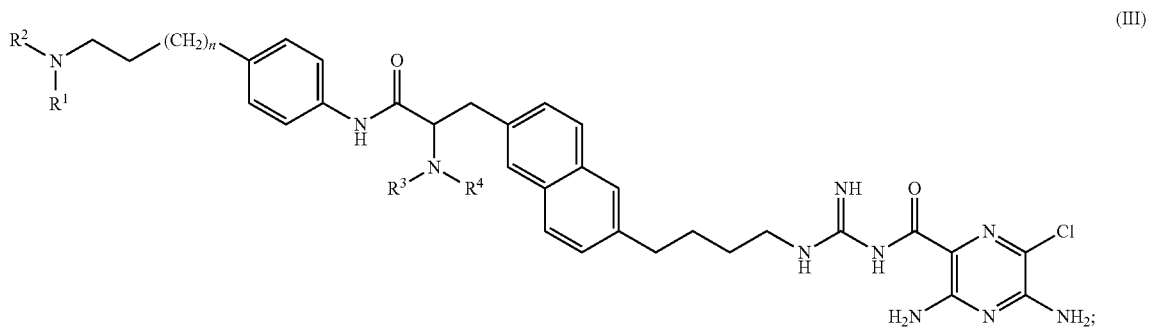

or a pharmaceutically acceptable salt thereof, wherein:

n is an integer selected from 1, 2, 3, 4, 5, and 6;

$R^1$ is selected from hydrogen, $C_1$-$C_8$ alkyl, and polyhydroxylated alkyl groups having from 3 to 8 carbon atoms;

$R^2$ is hydrogen or a polyhydroxylated alkyl group having from 3 to 8 carbon atoms; and $R^3$ and $R^4$ are each, independently, hydrogen or $C_1$-$C_3$ alkyl.

7. The method of claim 6, wherein the compound is selected from the group consisting of:

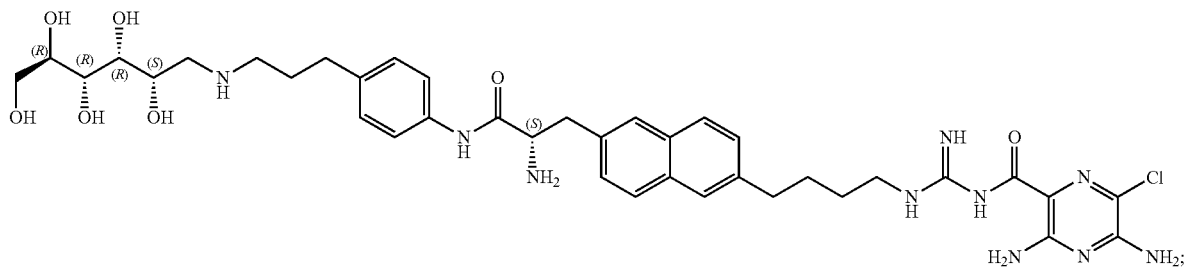

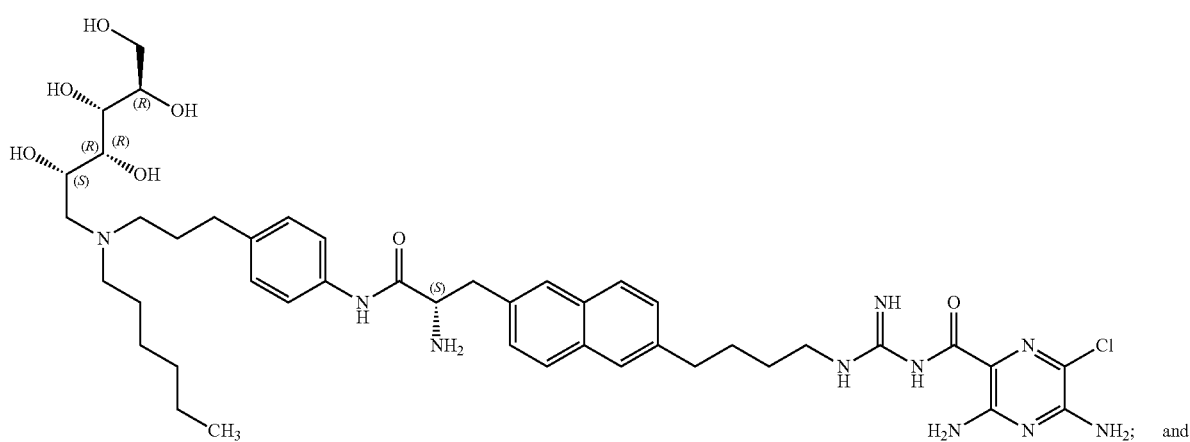

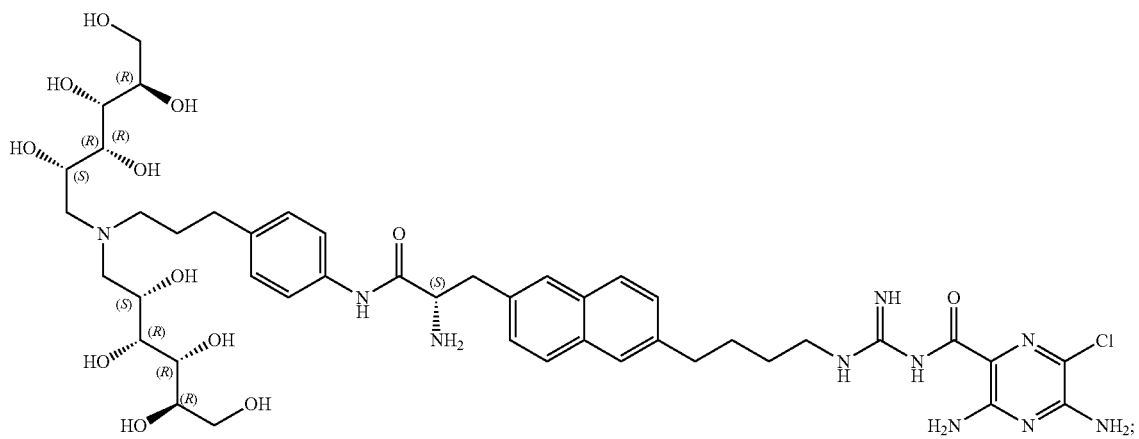

and pharmaceutically acceptable salts thereof.

8. The method of claim 1, wherein the compound is of Formula (IV):

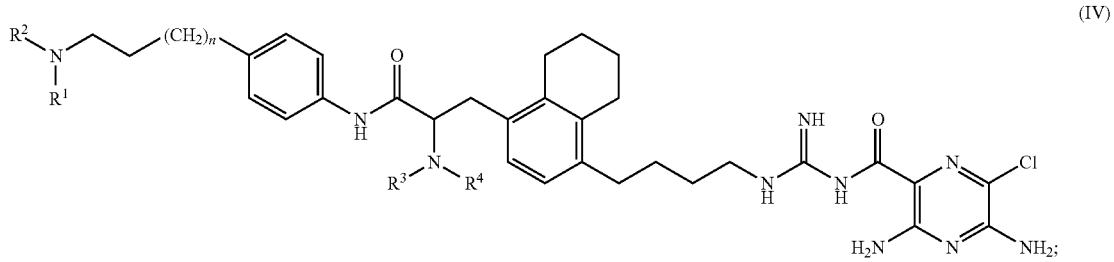

or a pharmaceutically acceptable salt thereof, wherein:

n is an integer selected from 1, 2, 3, 4, 5, and 6;

$R^1$ is selected from hydrogen, $C_1$-$C_8$ alkyl, and polyhydroxylated alkyl groups having from 3 to 8 carbon atoms;

$R^2$ is hydrogen or a polyhydroxylated alkyl group having from 3 to 8 carbon atoms; and $R^3$ and $R^4$ are each, independently, hydrogen or $C_1$-$C_3$ alkyl.

9. The method of claim 8, wherein the compound is selected from the group consisting of:

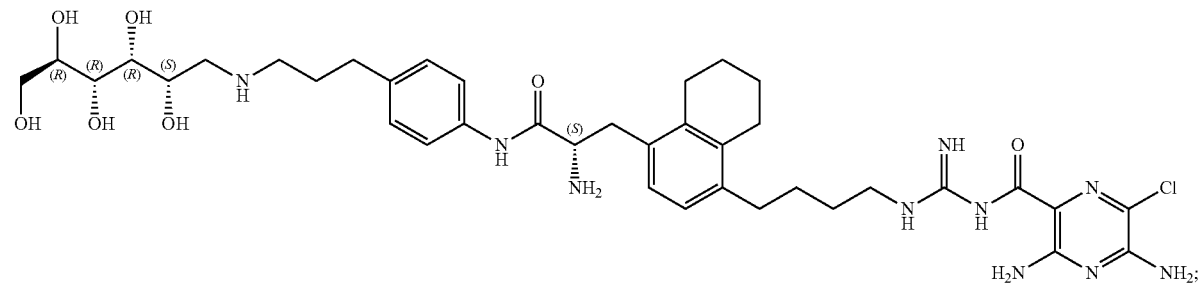

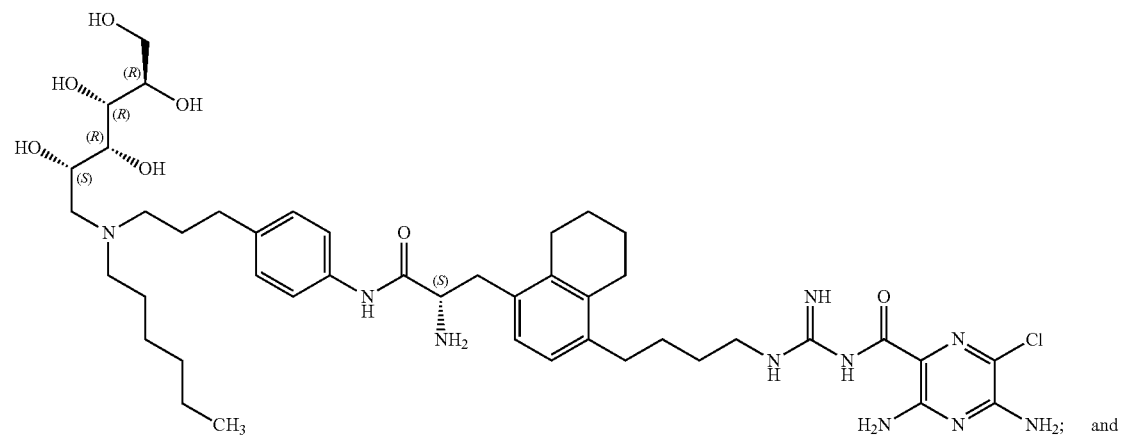

and

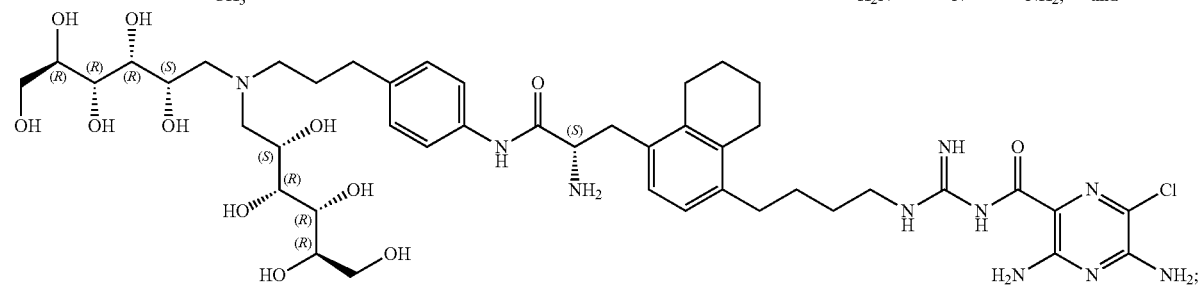

and pharmaceutically acceptable salts thereof.

10. The method of claim 1, for treating reversible or irreversible airway obstruction, chronic obstructive pulmonary disease (COPD), asthma, bronchiectasis, acute bronchitis, chronic bronchitis, post-viral cough, cystic fibrosis, emphysema, pneumonia, panbronchiolitis, transplant-associate bronchiolitis, or ventilator-associated tracheobronchitis in a subject.

11. The method of claim 1, for treating bronchiectasis, wherein the bronchiectasis is due to a condition other than cystic fibrosis.

12. The method of claim 1, wherein the subject is a human.

13. The method of claim 3, for treating cystic fibrosis in a subject.

14. The method of claim 3, for treating chronic obstructive pulmonary disease (COPD) in a subject.

15. The method of claim 3, for treating bronchiectasis in a subject.

16. A method for treating reversible or irreversible airway obstruction, chronic obstructive pulmonary disease (COPD), asthma, bronchiectasis, acute bronchitis, chronic bronchitis, post-viral cough, cystic fibrosis, emphysema, pneumonia, panbronchiolitis, transplant-associate bronchiolitis, or ventilator-associated tracheobronchitis in a subject, or for preventing ventilator-associated pneumonia in a subject, the method comprising administering to the subject a compound of one of the following formulae:

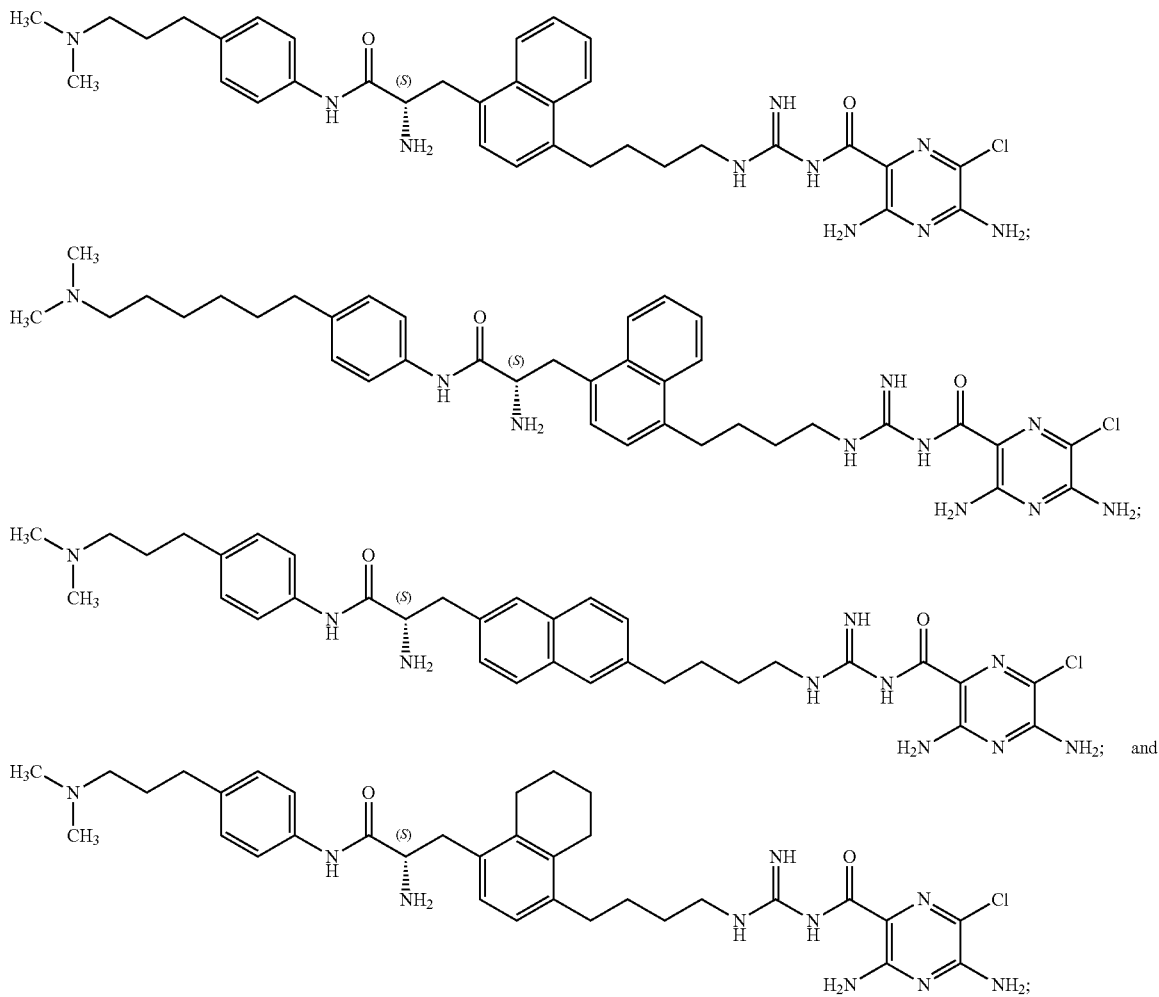

and pharmaceutically acceptable salts thereof.

17. The method of claim 16, for treating bronchiectasis, wherein the bronchiectasis is due to a condition other than cystic fibrosis.

18. The method of claim 16, wherein the subject is a human.

19. The method of claim 16, for treating cystic fibrosis in a subject.

20. The method of claim 16, for treating chronic obstructive pulmonary disease (COPD) in a subject.

21. The method of claim 16, for treating bronchiectasis in a subject.

* * * * *